United States Patent
Moeller

(10) Patent No.: US 9,725,721 B2
(45) Date of Patent: Aug. 8, 2017

(54) OLIGOMERS WITH IMPROVED OFF-TARGET PROFILE

(71) Applicant: MIRRX THERAPEUTICS, Vejle (DK)

(72) Inventor: Thorleif Moeller, Odense SOE (DK)

(73) Assignee: MIRRX THERAPEUTICS, Vejle (DK)

( * ) Notice: Subject to any disclaimer, the term of this patent is extended or adjusted under 35 U.S.C. 154(b) by 0 days.

(21) Appl. No.: 14/431,212

(22) PCT Filed: Sep. 26, 2013

(86) PCT No.: PCT/DK2013/050308
§ 371 (c)(1),
(2) Date: Mar. 25, 2015

(87) PCT Pub. No.: WO2014/048441
PCT Pub. Date: Apr. 3, 2014

(65) Prior Publication Data
US 2016/0145620 A1 May 26, 2016

Related U.S. Application Data

(60) Provisional application No. 61/705,668, filed on Sep. 26, 2012.

(30) Foreign Application Priority Data

Sep. 26, 2012 (DK) ................................. 2012 00587

(51) Int. Cl.
C07H 21/04 (2006.01)
C07H 21/02 (2006.01)
C12N 15/113 (2010.01)
C12N 15/11 (2006.01)

(52) U.S. Cl.
CPC ........ *C12N 15/1131* (2013.01); *C12N 15/111* (2013.01); *C12N 15/113* (2013.01); *C12N 2310/11* (2013.01); *C12N 2310/113* (2013.01); *C12N 2310/315* (2013.01); *C12N 2310/321* (2013.01); *C12N 2310/3231* (2013.01); *C12N 2310/341* (2013.01); *C12N 2320/53* (2013.01)

(58) Field of Classification Search
CPC ........................... C12N 15/113; C12N 2310/11
See application file for complete search history.

(56) References Cited

FOREIGN PATENT DOCUMENTS

| | | |
|---|---|---|
| WO | WO 2005/061710 A1 | 7/2005 |
| WO | WO 2007/031081 A2 | 3/2007 |
| WO | WO 2008/061537 A2 | 5/2008 |
| WO | WO 2008/074328 | 6/2008 |
| WO | WO 2008/151639 A2 | 12/2008 |
| WO | WO 2009/068033 | 6/2009 |
| WO | WO 2009/090182 A1 | 7/2009 |
| WO | WO 2010/122538 A1 | 10/2010 |
| WO | WO 2011/115818 | 9/2011 |
| WO | WO 2011/115818 A1 | 9/2011 |
| WO | WO 2011/117353 A1 | 9/2011 |

OTHER PUBLICATIONS

International Search Report dated Dec. 18, 2013 for corresponding International Patent Application No. PCT/DK2013/050308, filed Sep. 26, 2013, 4 pages.
International Preliminary Report on Patentability dated Dec. 11, 2014 for corresponding International Patent Application No. PCT/DK2013/050308, filed Sep. 26, 2013, 6 pages.
Takagi-Sato, M. et al., "Fine-Tuning of ENA® Gapmers as Antisense Oligonucleotides for Sequence-Specific Inhibition", Oligonucleotides, 2007, vol. 17, No. 3, pp. 291-301.
Lennox et al., "Chemical modification and design of anti-miRNA oligonucleotides," Gener Therapy (2011)pp. 1111-1120.
Stanley T. Crooke: "Principles, Strategies and Applications", Antisense Drug Technology, $2^{nd}$ Edition, 2007, p. 93.
Third Party Observation filed in related European Patent Application No. 13842025.2, dated Apr. 12, 2017, 15 pages.
Jens Kurreck et al.: "Design of antisense oligonucleotides stabilized by locked nucleic acids," Nucleic Acids Research, 2002, vol. 30, No. 9, pp. 1911-1918.

*Primary Examiner* — Amy Bowman
(74) *Attorney, Agent, or Firm* — Merchant & Gould

(57) ABSTRACT

The present invention provides oligomers that binds RNA that consists of a lower affinity region and a higher affinity region, wherein the monomers in the higher affinity region increases the melting temperature (i.e. affinity) of the oligomer base paired to RNA more than the monomers used in the lower affinity region, wherein said increase in melting temperature is relatively to the alternative use of DNA monomers of the same (base) sequence. The oligomers of the invention are useful for binding to target RNA such as mRNA and non-coding RNA and have the advantage that they will be less prone to off-target binding via the lower affinity region than via the higher affinity region.

7 Claims, 3 Drawing Sheets

On-target binding with various oligomer designs

A

B

C

SEQUENCE LISTING

<160> NUMBER OF SEQ ID NOS: 2042

<210> SEQ ID NO 1
<211> LENGTH: 22
<212> TYPE: RNA
<213> ORGANISM: Homo Sapiens

<400> SEQUENCE: 1
aagaugugga aaaauuggaa uc                                                22

<210> SEQ ID NO 2
<211> LENGTH: 22
<212> TYPE: RNA
<213> ORGANISM: Homo Sapiens

<400> SEQUENCE: 2
cagugguuuu acccuauggu ag                                                22

<210> SEQ ID NO 3
<211> LENGTH: 23
<212> TYPE: RNA
<213> ORGANISM: Homo Sapiens

<400> SEQUENCE: 3
caggcaguga cuguucagac guc                                               23

<210> SEQ ID NO 4
<211> LENGTH: 23
<212> TYPE: RNA
<213> ORGANISM: Homo Sapiens

<400> SEQUENCE: 4
aagaagagac ugagucaucg aau                                               23

<210> SEQ ID NO 5
<211> LENGTH: 22
<212> TYPE: RNA
<213> ORGANISM: Homo Sapiens

<400> SEQUENCE: 5
cucuagaggg aagcgcuuuc ug                                                22

<210> SEQ ID NO 6
<211> LENGTH: 21
<212> TYPE: RNA
<213> ORGANISM: Homo Sapiens

```
<400> SEQUENCE: 6
uuucugucuu uucuggucca g                                          21

<210> SEQ ID NO 7
<211> LENGTH: 23
<212> TYPE: RNA
<213> ORGANISM: Homo Sapiens

<400> SEQUENCE: 7
guuugcacgg gugggccuug ucu                                        23

<210> SEQ ID NO 8
<211> LENGTH: 22
<212> TYPE: RNA
<213> ORGANISM: Homo Sapiens

<400> SEQUENCE: 8
aaagaccgug acuacuuuug ca                                         22

<210> SEQ ID NO 9
<211> LENGTH: 18
<212> TYPE: RNA
<213> ORGANISM: Homo Sapiens

<400> SEQUENCE: 9
aaaaguacuu gcggauuu                                              18

<210> SEQ ID NO 10
<211> LENGTH: 22
<212> TYPE: RNA
<213> ORGANISM: Homo Sapiens

<400> SEQUENCE: 10
uguaaacauc cccgacugga ag                                         22

<210> SEQ ID NO 11
<211> LENGTH: 24
<212> TYPE: RNA
<213> ORGANISM: Homo Sapiens

<400> SEQUENCE: 11
ugggcgaggg gugggcucuc agag                                       24

<210> SEQ ID NO 12
<211> LENGTH: 20
<212> TYPE: RNA
<213> ORGANISM: Homo Sapiens

<400> SEQUENCE: 12
accaggaggc ugaggccccu                                            20

<210> SEQ ID NO 13
<211> LENGTH: 22
<212> TYPE: RNA
<213> ORGANISM: Homo Sapiens

<400> SEQUENCE: 13
cucuagaggg aagcacuuuc ug                                         22

<210> SEQ ID NO 14
<211> LENGTH: 22
<212> TYPE: RNA
<213> ORGANISM: Homo Sapiens
```

```
<400> SEQUENCE: 14
aggacugauc cucucgggca gg                                              22

<210> SEQ ID NO 15
<211> LENGTH: 21
<212> TYPE: RNA
<213> ORGANISM: Homo Sapiens

<400> SEQUENCE: 15
ucaccugagc ucccgugccu g                                               21

<210> SEQ ID NO 16
<211> LENGTH: 24
<212> TYPE: RNA
<213> ORGANISM: Homo Sapiens

<400> SEQUENCE: 16 acuggggcu uucgggcucu gcgu                                             24

<210> SEQ ID NO 17
<211> LENGTH: 21
<212> TYPE: RNA
<213> ORGANISM: Homo Sapiens

<400> SEQUENCE: 17
agaaggccuu uccaucucug u                                               21

<210> SEQ ID NO 18
<211> LENGTH: 22
<212> TYPE: RNA
<213> ORGANISM: Homo Sapiens

<400> SEQUENCE: 18
caggcacggg agcucaggug ag                                              22

<210> SEQ ID NO 19
<211> LENGTH: 21
<212> TYPE: RNA
<213> ORGANISM: Homo Sapiens

<400> SEQUENCE: 19
aaagugcuuc cuuuuagagg g                                               21

<210> SEQ ID NO 20
<211> LENGTH: 23
<212> TYPE: RNA
<213> ORGANISM: Homo Sapiens

<400> SEQUENCE: 20
accuggaccc agcguagaca aag                                             23

<210> SEQ ID NO 21
<211> LENGTH: 23
<212> TYPE: RNA
<213> ORGANISM: Homo Sapiens

<400> SEQUENCE: 21
uaggcagugu cauuagcuga uug                                             23

<210> SEQ ID NO 22
<211> LENGTH: 22
<212> TYPE: RNA
```

<213> ORGANISM: Homo Sapiens

<400> SEQUENCE: 22
uauacaaggg caagcucucu gu                    22

<210> SEQ ID NO 23
<211> LENGTH: 23
<212> TYPE: RNA
<213> ORGANISM: Homo Sapiens

<400> SEQUENCE: 23
uugaagagga ggugcucugu agc                   23

<210> SEQ ID NO 24
<211> LENGTH: 22
<212> TYPE: RNA
<213> ORGANISM: Homo Sapiens

<400> SEQUENCE: 24
gaaagcgcuu cccuuugcug ga                    22

<210> SEQ ID NO 25
<211> LENGTH: 22
<212> TYPE: RNA
<213> ORGANISM: Homo Sapiens

<400> SEQUENCE: 25
ugaggcuaau gcacuacuuc ac                    22

<210> SEQ ID NO 26
<211> LENGTH: 19
<212> TYPE: RNA
<213> ORGANISM: Homo Sapiens

<400> SEQUENCE: 26
ucuaggcugg uacugcuga                        19

<210> SEQ ID NO 27
<211> LENGTH: 22
<212> TYPE: RNA
<213> ORGANISM: Homo Sapiens

<400> SEQUENCE: 27
cuuagcaggu uguauuauca uu                    22

<210> SEQ ID NO 28
<211> LENGTH: 20
<212> TYPE: RNA
<213> ORGANISM: Homo Sapiens

<400> SEQUENCE: 28
gagacagguu caugcugcua                       20

<210> SEQ ID NO 29
<211> LENGTH: 23
<212> TYPE: RNA
<213> ORGANISM: Homo Sapiens

<400> SEQUENCE: 29
caaagugcuu acagugcagg uag                   23

<210> SEQ ID NO 30
<211> LENGTH: 21

-continued

<212> TYPE: RNA
<213> ORGANISM: Homo Sapiens

<400> SEQUENCE: 30
cugggcucgg gacgcgcggc u                                              21

<210> SEQ ID NO 31
<211> LENGTH: 22
<212> TYPE: RNA
<213> ORGANISM: Homo Sapiens

<400> SEQUENCE: 31
aaucugagaa ggcgcacaag gu                                             22

<210> SEQ ID NO 32
<211> LENGTH: 22
<212> TYPE: RNA
<213> ORGANISM: Homo Sapiens

<400> SEQUENCE: 32
uugcauaugu aggauguccc au                                             22

<210> SEQ ID NO 33
<211> LENGTH: 23
<212> TYPE: RNA
<213> ORGANISM: Homo Sapiens

<400> SEQUENCE: 33
cuggcggagc ccauuccaug cca                                            23

<210> SEQ ID NO 34
<211> LENGTH: 21
<212> TYPE: RNA
<213> ORGANISM: Homo Sapiens

<400> SEQUENCE: 34
guuagggcca acaucucuug g                                              21

<210> SEQ ID NO 35
<211> LENGTH: 22
<212> TYPE: RNA
<213> ORGANISM: Homo Sapiens

<400> SEQUENCE: 35
uaguggauga ugcacucugu gc                                             22

<210> SEQ ID NO 36
<211> LENGTH: 23
<212> TYPE: RNA
<213> ORGANISM: Homo Sapiens

<400> SEQUENCE: 36
auggccaaaa cugcaguuau uuu                                            23

<210> SEQ ID NO 37
<211> LENGTH: 23
<212> TYPE: RNA
<213> ORGANISM: Homo Sapiens

<400> SEQUENCE: 37
uaagugcuuc cauguuuuag uag                                            23

<210> SEQ ID NO 38

```
<211> LENGTH: 24
<212> TYPE: RNA
<213> ORGANISM: Homo Sapiens

<400> SEQUENCE: 38
uucuccaaaa gaaagcacuu ucug                                              24

<210> SEQ ID NO 39
<211> LENGTH: 22
<212> TYPE: RNA
<213> ORGANISM: Homo Sapiens

<400> SEQUENCE: 39
uauugcacuc gucccggccu cc                                                22

<210> SEQ ID NO 40
<211> LENGTH: 20
<212> TYPE: RNA
<213> ORGANISM: Homo Sapiens

<400> SEQUENCE: 40
guggguuggg gcgggcucug                                                   20

<210> SEQ ID NO 41
<211> LENGTH: 21
<212> TYPE: RNA
<213> ORGANISM: Homo Sapiens

<400> SEQUENCE: 41
accugaauua ccaaaagcuu u                                                 21

<210> SEQ ID NO 42
<211> LENGTH: 22
<212> TYPE: RNA
<213> ORGANISM: Homo Sapiens

<400> SEQUENCE: 42
gacucacuca caggauugug ca                                                22

<210> SEQ ID NO 43
<211> LENGTH: 22
<212> TYPE: RNA
<213> ORGANISM: Homo Sapiens

<400> SEQUENCE: 43
caggucgucu ugcagggcuu cu                                                22

<210> SEQ ID NO 44
<211> LENGTH: 23
<212> TYPE: RNA
<213> ORGANISM: Homo Sapiens

<400> SEQUENCE: 44
agcuucuuua cagugcugcc uug                                               23

<210> SEQ ID NO 45
<211> LENGTH: 22
<212> TYPE: RNA
<213> ORGANISM: Homo Sapiens

<400> SEQUENCE: 45
ucguaucaga gauuccagac ac                                                22
```

-continued

```
<210> SEQ ID NO 46
<211> LENGTH: 20
<212> TYPE: RNA
<213> ORGANISM: Homo Sapiens

<400> SEQUENCE: 46
uuggccaugg ggcugcgcgg                                              20

<210> SEQ ID NO 47
<211> LENGTH: 23
<212> TYPE: RNA
<213> ORGANISM: Homo Sapiens

<400> SEQUENCE: 47
augcuacucg gaaaucccac uga                                          23

<210> SEQ ID NO 48
<211> LENGTH: 22
<212> TYPE: RNA
<213> ORGANISM: Homo Sapiens

<400> SEQUENCE: 48
cuacuucuac cuguguuauc au                                           22

<210> SEQ ID NO 49
<211> LENGTH: 21
<212> TYPE: RNA
<213> ORGANISM: Homo Sapiens

<400> SEQUENCE: 49
ccaggcucug cagugggaac u                                            21

<210> SEQ ID NO 50
<211> LENGTH: 22
<212> TYPE: RNA
<213> ORGANISM: Homo Sapiens

<400> SEQUENCE: 50
gaugguugac cagagagcac ac                                           22

<210> SEQ ID NO 51
<211> LENGTH: 21
<212> TYPE: RNA
<213> ORGANISM: Homo Sapiens

<400> SEQUENCE: 51
gugggauuuc ugaguagcau c                                            21

<210> SEQ ID NO 52
<211> LENGTH: 23
<212> TYPE: RNA
<213> ORGANISM: Homo Sapiens

<400> SEQUENCE: 52
gugcuucauc guaauuaacc uua                                          23

<210> SEQ ID NO 53
<211> LENGTH: 22
<212> TYPE: RNA
<213> ORGANISM: Homo Sapiens

<400> SEQUENCE: 53
guagcaccuu gcaggauaag gu                                           22
```

```
<210> SEQ ID NO 54
<211> LENGTH: 19
<212> TYPE: RNA
<213> ORGANISM: Homo Sapiens

<400> SEQUENCE: 54
aagugugcag ggcacuggu                                              19

<210> SEQ ID NO 55
<211> LENGTH: 22
<212> TYPE: RNA
<213> ORGANISM: Homo Sapiens

<400> SEQUENCE: 55
acuguugcua auaugcaacu cu                                          22

<210> SEQ ID NO 56
<211> LENGTH: 22
<212> TYPE: RNA
<213> ORGANISM: Homo Sapiens

<400> SEQUENCE: 56
ugaucucacc gcugccuccu uc                                          22

<210> SEQ ID NO 57
<211> LENGTH: 22
<212> TYPE: RNA
<213> ORGANISM: Homo Sapiens

<400> SEQUENCE: 57
agagguugcc cuuggugaau uc                                          22

<210> SEQ ID NO 58
<211> LENGTH: 20
<212> TYPE: RNA
<213> ORGANISM: Homo Sapiens

<400> SEQUENCE: 58
aaaguagcug uaccauuugc                                             20

<210> SEQ ID NO 59
<211> LENGTH: 17
<212> TYPE: RNA
<213> ORGANISM: Homo Sapiens

<400> SEQUENCE: 59
ccaguuuucc caggauu                                                17

<210> SEQ ID NO 60
<211> LENGTH: 21
<212> TYPE: RNA
<213> ORGANISM: Homo Sapiens

<400> SEQUENCE: 60
ucauccucgu cucccucccca g                                          21

<210> SEQ ID NO 61
<211> LENGTH: 22
<212> TYPE: RNA
<213> ORGANISM: Homo Sapiens

<400> SEQUENCE: 61
ucaccugacc ucccaugccu gu                                          22
```

```
<210> SEQ ID NO 62
<211> LENGTH: 25
<212> TYPE: RNA
<213> ORGANISM: Homo Sapiens

<400> SEQUENCE: 62
aaaggauucu gcugucgguc ccacu                                          25

<210> SEQ ID NO 63
<211> LENGTH: 20
<212> TYPE: RNA
<213> ORGANISM: Homo Sapiens

<400> SEQUENCE: 63
agagguauag ggcaugggaa                                                20

<210> SEQ ID NO 64
<211> LENGTH: 20
<212> TYPE: RNA
<213> ORGANISM: Homo Sapiens

<400> SEQUENCE: 64
ucucuucauc uaccccccag                                                20

<210> SEQ ID NO 65
<211> LENGTH: 18
<212> TYPE: RNA
<213> ORGANISM: Homo Sapiens

<400> SEQUENCE: 65
cucugggaaa ugggacag                                                  18

<210> SEQ ID NO 66
<211> LENGTH: 20
<212> TYPE: RNA
<213> ORGANISM: Homo Sapiens

<400> SEQUENCE: 66
uaaagagccc uguggagaca                                                20

<210> SEQ ID NO 67
<211> LENGTH: 22
<212> TYPE: RNA
<213> ORGANISM: Homo Sapiens

<400> SEQUENCE: 67
acacagugcu ucauccacua cu                                             22

<210> SEQ ID NO 68
<211> LENGTH: 21
<212> TYPE: RNA
<213> ORGANISM: Homo Sapiens

<400> SEQUENCE: 68
cgagccucaa gcaagggacu u                                              21

<210> SEQ ID NO 69
<211> LENGTH: 24
<212> TYPE: RNA
<213> ORGANISM: Homo Sapiens

<400> SEQUENCE: 69
```
acaaagugcu ucccuuuaga gugu                                          24

<210> SEQ ID NO 70
<211> LENGTH: 22
<212> TYPE: RNA
<213> ORGANISM: Homo Sapiens

<400> SEQUENCE: 70
agcaguguuu guuuugccca ca                                            22

<210> SEQ ID NO 71
<211> LENGTH: 22
<212> TYPE: RNA
<213> ORGANISM: Homo Sapiens

<400> SEQUENCE: 71
caaauaauac cacagugggu gu                                            22

<210> SEQ ID NO 72
<211> LENGTH: 22
<212> TYPE: RNA
<213> ORGANISM: Homo Sapiens

<400> SEQUENCE: 72
gggggucccc ggugcucgga uc                                            22

<210> SEQ ID NO 73
<211> LENGTH: 21
<212> TYPE: RNA
<213> ORGANISM: Homo Sapiens

<400> SEQUENCE: 73
cacagcaagu guagacaggc a                                             21

<210> SEQ ID NO 74
<211> LENGTH: 24
<212> TYPE: RNA
<213> ORGANISM: Homo Sapiens

<400> SEQUENCE: 74
ggugggaugg agagaaggua ugag                                          24

<210> SEQ ID NO 75
<211> LENGTH: 22
<212> TYPE: RNA
<213> ORGANISM: Homo Sapiens

<400> SEQUENCE: 75
ccaccucccc ugcaaacguc ca                                            22

<210> SEQ ID NO 76
<211> LENGTH: 22
<212> TYPE: RNA
<213> ORGANISM: Homo Sapiens

<400> SEQUENCE: 76
cucgugggcu cuggccacgg cc                                            22

<210> SEQ ID NO 77
<211> LENGTH: 22
<212> TYPE: RNA
<213> ORGANISM: Homo Sapiens

<400> SEQUENCE: 77
aaagugcauc cuuuuagagg uu                                              22

<210> SEQ ID NO 78
<211> LENGTH: 22
<212> TYPE: RNA
<213> ORGANISM: Homo Sapiens

<400> SEQUENCE: 78
gcuacuucac aacaccaggg cc                                              22

<210> SEQ ID NO 79
<211> LENGTH: 24
<212> TYPE: RNA
<213> ORGANISM: Homo Sapiens

<400> SEQUENCE: 79
ugcccaugcc auacuuugc cuca                                             24

<210> SEQ ID NO 80
<211> LENGTH: 22
<212> TYPE: RNA
<213> ORGANISM: Homo Sapiens

<400> SEQUENCE: 80
uucacaagga ggugucauuu au                                              22

<210> SEQ ID NO 81
<211> LENGTH: 21
<212> TYPE: RNA
<213> ORGANISM: Homo Sapiens

<400> SEQUENCE: 81
aucacauugc cagggauuuc c                                               21

<210> SEQ ID NO 82
<211> LENGTH: 22
<212> TYPE: RNA
<213> ORGANISM: Homo Sapiens

<400> SEQUENCE: 82
uuuggacaga aaacacgcag gu                                              22

<210> SEQ ID NO 83
<211> LENGTH: 23
<212> TYPE: RNA
<213> ORGANISM: Homo Sapiens

<400> SEQUENCE: 83
uguagagcag ggagcaggaa gcu                                             23

<210> SEQ ID NO 84
<211> LENGTH: 20
<212> TYPE: RNA
<213> ORGANISM: Homo Sapiens

<400> SEQUENCE: 84
cuguaugccc ucaccgcuca                                                 20

<210> SEQ ID NO 85
<211> LENGTH: 22
<212> TYPE: RNA
<213> ORGANISM: Homo Sapiens

```
<400> SEQUENCE: 85
uuggggaaac ggccgcugag ug                                              22

<210> SEQ ID NO 86
<211> LENGTH: 22
<212> TYPE: RNA
<213> ORGANISM: Homo Sapiens

<400> SEQUENCE: 86
cuggacugag ccgugcuacu gg                                              22

<210> SEQ ID NO 87
<211> LENGTH: 21
<212> TYPE: RNA
<213> ORGANISM: Homo Sapiens

<400> SEQUENCE: 87
cgggggcggg gccgaagcgc g                                               21

<210> SEQ ID NO 88
<211> LENGTH: 22
<212> TYPE: RNA
<213> ORGANISM: Homo Sapiens

<400> SEQUENCE: 88
aaucauacag ggacauccag uu                                              22

<210> SEQ ID NO 89
<211> LENGTH: 22
<212> TYPE: RNA
<213> ORGANISM: Homo Sapiens

<400> SEQUENCE: 89
accugucugu ggaaaggagc ua                                              22

<210> SEQ ID NO 90
<211> LENGTH: 21
<212> TYPE: RNA
<213> ORGANISM: Homo Sapiens

<400> SEQUENCE: 90
ucacuccucu ccucccgucu u                                               21

<210> SEQ ID NO 91
<211> LENGTH: 17
<212> TYPE: RNA
<213> ORGANISM: Homo Sapiens

<400> SEQUENCE: 91
cgcgccgggc ccggguu                                                    17

<210> SEQ ID NO 92
<211> LENGTH: 22
<212> TYPE: RNA
<213> ORGANISM: Homo Sapiens

<400> SEQUENCE: 92
uuucuucuua gacauggcaa cg                                              22

<210> SEQ ID NO 93
<211> LENGTH: 22
<212> TYPE: RNA
<213> ORGANISM: Homo Sapiens
```

```
<400> SEQUENCE: 93
ugggucuuug cgggcgagau ga                                          22

<210> SEQ ID NO 94
<211> LENGTH: 17
<212> TYPE: RNA
<213> ORGANISM: Homo Sapiens

<400> SEQUENCE: 94
gcugggcgag gcuggca                                                17

<210> SEQ ID NO 95
<211> LENGTH: 22
<212> TYPE: RNA
<213> ORGANISM: Homo Sapiens

<400> SEQUENCE: 95
ugagaacuga auuccauggg uu                                          22

<210> SEQ ID NO 96
<211> LENGTH: 23
<212> TYPE: RNA
<213> ORGANISM: Homo Sapiens

<400> SEQUENCE: 96
uggaguccag gaaucugcau uuu                                         23

<210> SEQ ID NO 97
<211> LENGTH: 17
<212> TYPE: RNA
<213> ORGANISM: Homo Sapiens

<400> SEQUENCE: 97
ggauggagga ggggucu                                                17

<210> SEQ ID NO 98
<211> LENGTH: 19
<212> TYPE: RNA
<213> ORGANISM: Homo Sapiens

<400> SEQUENCE: 98
agguugacau acguuuccc                                              19

<210> SEQ ID NO 99
<211> LENGTH: 22
<212> TYPE: RNA
<213> ORGANISM: Homo Sapiens

<400> SEQUENCE: 99
gagagcagug uguuugccu gg                                           22

<210> SEQ ID NO 100
<211> LENGTH: 22
<212> TYPE: RNA
<213> ORGANISM: Homo Sapiens

<400> SEQUENCE: 100
aucgggaaug ucguguccgc cc                                          22

<210> SEQ ID NO 101
<211> LENGTH: 22
<212> TYPE: RNA
```

```
<213> ORGANISM: Homo Sapiens

<400> SEQUENCE: 101
uuguggcugg ucaugaggcu aa                                    22

<210> SEQ ID NO 102
<211> LENGTH: 21
<212> TYPE: RNA
<213> ORGANISM: Homo Sapiens

<400> SEQUENCE: 102
aagcauucuu ucauugguug g                                     21

<210> SEQ ID NO 103
<211> LENGTH: 21
<212> TYPE: RNA
<213> ORGANISM: Homo Sapiens

<400> SEQUENCE: 103
uauucagaaa ggugccaguc a                                     21

<210> SEQ ID NO 104
<211> LENGTH: 24
<212> TYPE: RNA
<213> ORGANISM: Homo Sapiens

<400> SEQUENCE: 104
aauuuggUUU cugaggcacu uagu                                  24

<210> SEQ ID NO 105
<211> LENGTH: 23
<212> TYPE: RNA
<213> ORGANISM: Homo Sapiens

<400> SEQUENCE: 105
augagacuca uguaaaacau cuu                                   23

<210> SEQ ID NO 106
<211> LENGTH: 21
<212> TYPE: RNA
<213> ORGANISM: Homo Sapiens

<400> SEQUENCE: 106
cuauacaauc uacugucuuu c                                     21

<210> SEQ ID NO 107
<211> LENGTH: 22
<212> TYPE: RNA
<213> ORGANISM: Homo Sapiens

<400> SEQUENCE: 107
ugguugacca uagaacaugc gc                                    22

<210> SEQ ID NO 108
<211> LENGTH: 18
<212> TYPE: RNA
<213> ORGANISM: Homo Sapiens

<400> SEQUENCE: 108 aggggcggg cuccggcg                                          18

<210> SEQ ID NO 109
<211> LENGTH: 23
```

<212> TYPE: RNA
<213> ORGANISM: Homo Sapiens

<400> SEQUENCE: 109
aguggaugau ggagacucgg uac                                              23

<210> SEQ ID NO 110
<211> LENGTH: 23
<212> TYPE: RNA
<213> ORGANISM: Homo Sapiens

<400> SEQUENCE: 110
aguuuugcag guuugcaucc agc                                              23

<210> SEQ ID NO 111
<211> LENGTH: 21
<212> TYPE: RNA
<213> ORGANISM: Homo Sapiens

<400> SEQUENCE: 111
aguggcaaag ucuuuccaua u                                                21

<210> SEQ ID NO 112
<211> LENGTH: 23
<212> TYPE: RNA
<213> ORGANISM: Homo Sapiens

<400> SEQUENCE: 112
uaauccuugc uaccugggug aga                                              23

<210> SEQ ID NO 113
<211> LENGTH: 22
<212> TYPE: RNA
<213> ORGANISM: Homo Sapiens

<400> SEQUENCE: 113
ugcggggcua gggcuaacag ca                                               22

<210> SEQ ID NO 114
<211> LENGTH: 22
<212> TYPE: RNA
<213> ORGANISM: Homo Sapiens

<400> SEQUENCE: 114
ccucccacac ccaaggcuug ca                                               22

<210> SEQ ID NO 115
<211> LENGTH: 22
<212> TYPE: RNA
<213> ORGANISM: Homo Sapiens

<400> SEQUENCE: 115
agggaaggag gcuuggucuu ag                                               22

<210> SEQ ID NO 116
<211> LENGTH: 22
<212> TYPE: RNA
<213> ORGANISM: Homo Sapiens

<400> SEQUENCE: 116
ccuauucuug auuacuuguu uc                                               22

<210> SEQ ID NO 117

```
<211> LENGTH: 23
<212> TYPE: RNA
<213> ORGANISM: Homo Sapiens

<400> SEQUENCE: 117
ccuccguguu accuguccuc uag                                              23

<210> SEQ ID NO 118
<211> LENGTH: 22
<212> TYPE: RNA
<213> ORGANISM: Homo Sapiens

<400> SEQUENCE: 118
ucugugagac caaagaacua cu                                               22

<210> SEQ ID NO 119
<211> LENGTH: 22
<212> TYPE: RNA
<213> ORGANISM: Homo Sapiens

<400> SEQUENCE: 119
caaucagcaa guauacugcc cu                                               22

<210> SEQ ID NO 120
<211> LENGTH: 22
<212> TYPE: RNA
<213> ORGANISM: Homo Sapiens

<400> SEQUENCE: 120
guugggacaa gaggacgguc uu                                               22

<210> SEQ ID NO 121
<211> LENGTH: 22
<212> TYPE: RNA
<213> ORGANISM: Homo Sapiens

<400> SEQUENCE: 121
uuugugaccu gguccacuaa cc                                               22

<210> SEQ ID NO 122
<211> LENGTH: 18
<212> TYPE: RNA
<213> ORGANISM: Homo Sapiens

<400> SEQUENCE: 122
cagcaguccc uccccug                                                     18

<210> SEQ ID NO 123
<211> LENGTH: 21
<212> TYPE: RNA
<213> ORGANISM: Homo Sapiens

<400> SEQUENCE: 123
ugaggagauc gucgagguug g                                                21

<210> SEQ ID NO 124
<211> LENGTH: 21
<212> TYPE: RNA
<213> ORGANISM: Homo Sapiens

<400> SEQUENCE: 124
ucucaguaag uggcacucug u                                                21
```

```
<210> SEQ ID NO 125
<211> LENGTH: 22
<212> TYPE: RNA
<213> ORGANISM: Homo Sapiens

<400> SEQUENCE: 125
cucaaguagu cugaccaggg ga                                              22

<210> SEQ ID NO 126
<211> LENGTH: 21
<212> TYPE: RNA
<213> ORGANISM: Homo Sapiens

<400> SEQUENCE: 126
uaaaacugca guuauuuuug c                                               21

<210> SEQ ID NO 127
<211> LENGTH: 21
<212> TYPE: RNA
<213> ORGANISM: Homo Sapiens

<400> SEQUENCE: 127
gcagcccagc ugaggccucu g                                               21

<210> SEQ ID NO 128
<211> LENGTH: 22
<212> TYPE: RNA
<213> ORGANISM: Homo Sapiens

<400> SEQUENCE: 128
uuccuaugca uauacuucuu ug                                              22

<210> SEQ ID NO 129
<211> LENGTH: 22
<212> TYPE: RNA
<213> ORGANISM: Homo Sapiens

<400> SEQUENCE: 129
cucucuacug acuugcaaca ua                                              22

<210> SEQ ID NO 130
<211> LENGTH: 21
<212> TYPE: RNA
<213> ORGANISM: Homo Sapiens

<400> SEQUENCE: 130
acucggcugc gguggacaag u                                               21

<210> SEQ ID NO 131
<211> LENGTH: 18
<212> TYPE: RNA
<213> ORGANISM: Homo Sapiens

<400> SEQUENCE: 131
ugggagcugg acuacuuc                                                   18

<210> SEQ ID NO 132
<211> LENGTH: 20
<212> TYPE: RNA
<213> ORGANISM: Homo Sapiens

<400> SEQUENCE: 132
acuggacuug gagucagaaa                                                 20
```

```
<210> SEQ ID NO 133
<211> LENGTH: 23
<212> TYPE: RNA
<213> ORGANISM: Homo Sapiens

<400> SEQUENCE: 133
caggcagaag ugggcugac agg                                              23

<210> SEQ ID NO 134
<211> LENGTH: 22
<212> TYPE: RNA
<213> ORGANISM: Homo Sapiens

<400> SEQUENCE: 134
caguuaucac agugcugaug cu                                              22

<210> SEQ ID NO 135
<211> LENGTH: 21
<212> TYPE: RNA
<213> ORGANISM: Homo Sapiens

<400> SEQUENCE: 135
agguagaaug aggccugaca u                                               21

<210> SEQ ID NO 136
<211> LENGTH: 21
<212> TYPE: RNA
<213> ORGANISM: Homo Sapiens

<400> SEQUENCE: 136
ccuguugaag uguaaucccc a                                               21

<210> SEQ ID NO 137
<211> LENGTH: 23
<212> TYPE: RNA
<213> ORGANISM: Homo Sapiens

<400> SEQUENCE: 137
agggaaaaaa aaaaggauuu guc                                             23

<210> SEQ ID NO 138
<211> LENGTH: 22
<212> TYPE: RNA
<213> ORGANISM: Homo Sapiens

<400> SEQUENCE: 138
accgaagacu gugcgcuaau cu                                              22

<210> SEQ ID NO 139
<211> LENGTH: 27
<212> TYPE: RNA
<213> ORGANISM: Homo Sapiens

<400> SEQUENCE: 139
accuucuugu auaagcacug ugcuaaa                                         27

<210> SEQ ID NO 140
<211> LENGTH: 20
<212> TYPE: RNA
<213> ORGANISM: Homo Sapiens

<400> SEQUENCE: 140
ggggagcugu ggaagcagua                                                 20
```

<210> SEQ ID NO 141
<211> LENGTH: 22
<212> TYPE: RNA
<213> ORGANISM: Homo Sapiens

<400> SEQUENCE: 141
aauccacgcu gagcuuggca uc                                              22

<210> SEQ ID NO 142
<211> LENGTH: 17
<212> TYPE: RNA
<213> ORGANISM: Homo Sapiens

<400> SEQUENCE: 142
gagacugggg ugggggcc                                                   17

<210> SEQ ID NO 143
<211> LENGTH: 22
<212> TYPE: RNA
<213> ORGANISM: Homo Sapiens

<400> SEQUENCE: 143
aaaaguaauu gugguuuugg cc                                              22

<210> SEQ ID NO 144
<211> LENGTH: 18
<212> TYPE: RNA
<213> ORGANISM: Homo Sapiens

<400> SEQUENCE: 144
ugcuuccuuu cagagggu                                                   18

<210> SEQ ID NO 145
<211> LENGTH: 22
<212> TYPE: RNA
<213> ORGANISM: Homo Sapiens

<400> SEQUENCE: 145
uauagggauu ggagccgugg cg                                              22

<210> SEQ ID NO 146
<211> LENGTH: 21
<212> TYPE: RNA
<213> ORGANISM: Homo Sapiens

<400> SEQUENCE: 146
cgccugccca gcccuccugc u                                               21

<210> SEQ ID NO 147
<211> LENGTH: 22
<212> TYPE: RNA
<213> ORGANISM: Homo Sapiens

<400> SEQUENCE: 147
agacugacgg cuggaggccc au                                              22

<210> SEQ ID NO 148
<211> LENGTH: 19
<212> TYPE: RNA
<213> ORGANISM: Homo Sapiens

<400> SEQUENCE: 148
agcagggcug gggauugca 19

<210> SEQ ID NO 149
<211> LENGTH: 22
<212> TYPE: RNA
<213> ORGANISM: Homo Sapiens

<400> SEQUENCE: 149
cucuagaggg aagcgcuuuc ug 22

<210> SEQ ID NO 150
<211> LENGTH: 18
<212> TYPE: RNA
<213> ORGANISM: Homo Sapiens

<400> SEQUENCE: 150
acguuggcuc ugguggug 18

<210> SEQ ID NO 151
<211> LENGTH: 20
<212> TYPE: RNA
<213> ORGANISM: Homo Sapiens

<400> SEQUENCE: 151
gcucggacug agcagguggg 20

<210> SEQ ID NO 152
<211> LENGTH: 23
<212> TYPE: RNA
<213> ORGANISM: Homo Sapiens

<400> SEQUENCE: 152
ucugcacugu gaguuggcug gcu 23

<210> SEQ ID NO 153
<211> LENGTH: 22
<212> TYPE: RNA
<213> ORGANISM: Homo Sapiens

<400> SEQUENCE: 153
uccuucauuc caccggaguc ug 22

<210> SEQ ID NO 154
<211> LENGTH: 19
<212> TYPE: RNA
<213> ORGANISM: Homo Sapiens

<400> SEQUENCE: 154
ugucucugcu gggguuucu 19

<210> SEQ ID NO 155
<211> LENGTH: 19
<212> TYPE: RNA
<213> ORGANISM: Homo Sapiens

<400> SEQUENCE: 155
gagccaguug gacaggagc 19

<210> SEQ ID NO 156
<211> LENGTH: 22
<212> TYPE: RNA
<213> ORGANISM: Homo Sapiens

<400> SEQUENCE: 156

-continued ugaguauuac auggccaauc uc                                          22

<210> SEQ ID NO 157
<211> LENGTH: 20
<212> TYPE: RNA
<213> ORGANISM: Homo Sapiens

<400> SEQUENCE: 157
aaaagcuggg uugagagggu                                             20

<210> SEQ ID NO 158
<211> LENGTH: 21
<212> TYPE: RNA
<213> ORGANISM: Homo Sapiens

<400> SEQUENCE: 158
uuggagggug uggaagacau c                                           21

<210> SEQ ID NO 159
<211> LENGTH: 21
<212> TYPE: RNA
<213> ORGANISM: Homo Sapiens

<400> SEQUENCE: 159
gugucuuuug cucugcaguc a                                           21

<210> SEQ ID NO 160
<211> LENGTH: 23
<212> TYPE: RNA
<213> ORGANISM: Homo Sapiens

<400> SEQUENCE: 160
aggucugcau ucaaaucccc aga                                         23

<210> SEQ ID NO 161
<211> LENGTH: 21
<212> TYPE: RNA
<213> ORGANISM: Homo Sapiens

<400> SEQUENCE: 161
ucccuacccc uccacucccc a                                           21

<210> SEQ ID NO 162
<211> LENGTH: 24
<212> TYPE: RNA
<213> ORGANISM: Homo Sapiens

<400> SEQUENCE: 162
ugccuggguc ucuggccugc gcgu                                        24

<210> SEQ ID NO 163
<211> LENGTH: 23
<212> TYPE: RNA
<213> ORGANISM: Homo Sapiens

<400> SEQUENCE: 163
uguuucgggg cucauggccu gug                                         23

<210> SEQ ID NO 164
<211> LENGTH: 21
<212> TYPE: RNA
<213> ORGANISM: Homo Sapiens

```
<400> SEQUENCE: 164
ucuggcugug cuguaaugca g                                        21

<210> SEQ ID NO 165
<211> LENGTH: 23
<212> TYPE: RNA
<213> ORGANISM: Homo Sapiens

<400> SEQUENCE: 165
ggcaggaggg cugugccagg uug                                      23

<210> SEQ ID NO 166
<211> LENGTH: 22
<212> TYPE: RNA
<213> ORGANISM: Homo Sapiens

<400> SEQUENCE: 166
cuauuaagga cauuugugau uc                                       22

<210> SEQ ID NO 167
<211> LENGTH: 22
<212> TYPE: RNA
<213> ORGANISM: Homo Sapiens

<400> SEQUENCE: 167
uuuguucguu cggcucgcgu ga                                       22

<210> SEQ ID NO 168
<211> LENGTH: 21
<212> TYPE: RNA
<213> ORGANISM: Homo Sapiens

<400> SEQUENCE: 168
caaaacguga ggcgcugcua u                                        21

<210> SEQ ID NO 169
<211> LENGTH: 22
<212> TYPE: RNA
<213> ORGANISM: Homo Sapiens

<400> SEQUENCE: 169
aacaucacug caagucuuaa ca                                       22

<210> SEQ ID NO 170
<211> LENGTH: 21
<212> TYPE: RNA
<213> ORGANISM: Homo Sapiens

<400> SEQUENCE: 170
agagauuggu agaaaucagg u                                        21

<210> SEQ ID NO 171
<211> LENGTH: 22
<212> TYPE: RNA
<213> ORGANISM: Homo Sapiens

<400> SEQUENCE: 171
ugucuacauu aaugaaaaga gc                                       22

<210> SEQ ID NO 172
<211> LENGTH: 24
<212> TYPE: RNA
<213> ORGANISM: Homo Sapiens
```

```
<400> SEQUENCE: 172
aaauauauau auauauguac guau                                              24

<210> SEQ ID NO 173
<211> LENGTH: 23
<212> TYPE: RNA
<213> ORGANISM: Homo Sapiens

<400> SEQUENCE: 173
gugaguggga gccccagugu gug                                               23

<210> SEQ ID NO 174
<211> LENGTH: 23
<212> TYPE: RNA
<213> ORGANISM: Homo Sapiens

<400> SEQUENCE: 174
uaaauuucac cuuucugaga agg                                               23

<210> SEQ ID NO 175
<211> LENGTH: 22
<212> TYPE: RNA
<213> ORGANISM: Homo Sapiens

<400> SEQUENCE: 175
aucuaaaugc agcaugccag uc                                                22

<210> SEQ ID NO 176
<211> LENGTH: 21
<212> TYPE: RNA
<213> ORGANISM: Homo Sapiens

<400> SEQUENCE: 176
guuccugcug aacugagcca g                                                 21

<210> SEQ ID NO 177
<211> LENGTH: 22
<212> TYPE: RNA
<213> ORGANISM: Homo Sapiens

<400> SEQUENCE: 177
agggaagggg acgagggguug gg                                               22

<210> SEQ ID NO 178
<211> LENGTH: 19
<212> TYPE: RNA
<213> ORGANISM: Homo Sapiens

<400> SEQUENCE: 178
ccgccugagc uagcugugg                                                    19

<210> SEQ ID NO 179
<211> LENGTH: 22
<212> TYPE: RNA
<213> ORGANISM: Homo Sapiens

<400> SEQUENCE: 179
agcaaggcgg caucucucug au                                                22

<210> SEQ ID NO 180
<211> LENGTH: 22
<212> TYPE: RNA
```

```
<213> ORGANISM: Homo Sapiens

<400> SEQUENCE: 180
ugcccugccu guuucuccu uu                                            22

<210> SEQ ID NO 181
<211> LENGTH: 21
<212> TYPE: RNA
<213> ORGANISM: Homo Sapiens

<400> SEQUENCE: 181 gagguuggg gaggauuugc u                                             21

<210> SEQ ID NO 182
<211> LENGTH: 18
<212> TYPE: RNA
<213> ORGANISM: Homo Sapiens

<400> SEQUENCE: 182
ccaguguggc ucagcgag                                                18

<210> SEQ ID NO 183
<211> LENGTH: 21
<212> TYPE: RNA
<213> ORGANISM: Homo Sapiens

<400> SEQUENCE: 183
aaaggugcuc aaauuagaca u                                            21

<210> SEQ ID NO 184
<211> LENGTH: 21
<212> TYPE: RNA
<213> ORGANISM: Homo Sapiens

<400> SEQUENCE: 184
gcaggacagg cagaagugga u                                            21

<210> SEQ ID NO 185
<211> LENGTH: 22
<212> TYPE: RNA
<213> ORGANISM: Homo Sapiens

<400> SEQUENCE: 185
ugucaguuug ucaaauaccc ca                                           22

<210> SEQ ID NO 186
<211> LENGTH: 19
<212> TYPE: RNA
<213> ORGANISM: Homo Sapiens

<400> SEQUENCE: 186
cggcgcgacc ggcccgggg                                               19

<210> SEQ ID NO 187
<211> LENGTH: 21
<212> TYPE: RNA
<213> ORGANISM: Homo Sapiens

<400> SEQUENCE: 187
cauaaaguag aaagcacuac u                                            21

<210> SEQ ID NO 188
<211> LENGTH: 24
```

```
<212> TYPE: RNA
<213> ORGANISM: Homo Sapiens

<400> SEQUENCE: 188
ugggcuaagg gagaugauug ggua                                    24

<210> SEQ ID NO 189
<211> LENGTH: 22
<212> TYPE: RNA
<213> ORGANISM: Homo Sapiens

<400> SEQUENCE: 189
ccucaccauc ccuucugccu gc                                      22

<210> SEQ ID NO 190
<211> LENGTH: 21
<212> TYPE: RNA
<213> ORGANISM: Homo Sapiens

<400> SEQUENCE: 190 gggggggaugu gcaugcuggu u                                      21

<210> SEQ ID NO 191
<211> LENGTH: 21
<212> TYPE: RNA
<213> ORGANISM: Homo Sapiens

<400> SEQUENCE: 191
cggggcagcu caguacagga u                                       21

<210> SEQ ID NO 192
<211> LENGTH: 22
<212> TYPE: RNA
<213> ORGANISM: Homo Sapiens

<400> SEQUENCE: 192
uuuaacaugg ggguaccugc ug                                      22

<210> SEQ ID NO 193
<211> LENGTH: 22
<212> TYPE: RNA
<213> ORGANISM: Homo Sapiens

<400> SEQUENCE: 193
aaacuaauau acccauauuc ug                                      22

<210> SEQ ID NO 194
<211> LENGTH: 21
<212> TYPE: RNA
<213> ORGANISM: Homo Sapiens

<400> SEQUENCE: 194
uuuugcaccu uuuggaguga a                                       21

<210> SEQ ID NO 195
<211> LENGTH: 22
<212> TYPE: RNA
<213> ORGANISM: Homo Sapiens

<400> SEQUENCE: 195
uggcagugua uuguuagcug gu                                      22

<210> SEQ ID NO 196
```

```
<211> LENGTH: 24
<212> TYPE: RNA
<213> ORGANISM: Homo Sapiens

<400> SEQUENCE: 196
agggcuggac ucagcggcgg agcu                                          24

<210> SEQ ID NO 197
<211> LENGTH: 22
<212> TYPE: RNA
<213> ORGANISM: Homo Sapiens

<400> SEQUENCE: 197
ugagugauug auagcuaugu uc                                            22

<210> SEQ ID NO 198
<211> LENGTH: 22
<212> TYPE: RNA
<213> ORGANISM: Homo Sapiens

<400> SEQUENCE: 198
ucagcaggca ggcuggugca gc                                            22

<210> SEQ ID NO 199
<211> LENGTH: 24
<212> TYPE: RNA
<213> ORGANISM: Homo Sapiens

<400> SEQUENCE: 199
agauguaugg aaucuguaua uauc                                          24

<210> SEQ ID NO 200
<211> LENGTH: 22
<212> TYPE: RNA
<213> ORGANISM: Homo Sapiens

<400> SEQUENCE: 200
acuccagccc cacagccuca gc                                            22

<210> SEQ ID NO 201
<211> LENGTH: 22
<212> TYPE: RNA
<213> ORGANISM: Homo Sapiens

<400> SEQUENCE: 201
gagcaaugua gguagacugu uu                                            22

<210> SEQ ID NO 202
<211> LENGTH: 21
<212> TYPE: RNA
<213> ORGANISM: Homo Sapiens

<400> SEQUENCE: 202
acaaggugug caugccugac c                                             21

<210> SEQ ID NO 203
<211> LENGTH: 23
<212> TYPE: RNA
<213> ORGANISM: Homo Sapiens

<400> SEQUENCE: 203
gcaaagcaca cggccugcag aga                                           23
```

<210> SEQ ID NO 204
<211> LENGTH: 22
<212> TYPE: RNA
<213> ORGANISM: Homo Sapiens

<400> SEQUENCE: 204
gcccaaaggu gaauuuuuug gg                                              22

<210> SEQ ID NO 205
<211> LENGTH: 22
<212> TYPE: RNA
<213> ORGANISM: Homo Sapiens

<400> SEQUENCE: 205
gggaggugug aucucacacu cg                                              22

<210> SEQ ID NO 206
<211> LENGTH: 18
<212> TYPE: RNA
<213> ORGANISM: Homo Sapiens

<400> SEQUENCE: 206
ccagaggugg ggacugag                                                   18

<210> SEQ ID NO 207
<211> LENGTH: 17
<212> TYPE: RNA
<213> ORGANISM: Homo Sapiens

<400> SEQUENCE: 207
acucagucau ggucauu                                                    17

<210> SEQ ID NO 208
<211> LENGTH: 22
<212> TYPE: RNA
<213> ORGANISM: Homo Sapiens

<400> SEQUENCE: 208
agggacggga cgcggugcag ug                                              22

<210> SEQ ID NO 209
<211> LENGTH: 22
<212> TYPE: RNA
<213> ORGANISM: Homo Sapiens

<400> SEQUENCE: 209
caaauucgua ucuagggaa ua                                               22

<210> SEQ ID NO 210
<211> LENGTH: 22
<212> TYPE: RNA
<213> ORGANISM: Homo Sapiens

<400> SEQUENCE: 210
uccugucuuu ccuuguugga gc                                              22

<210> SEQ ID NO 211
<211> LENGTH: 22
<212> TYPE: RNA
<213> ORGANISM: Homo Sapiens

<400> SEQUENCE: 211
cagggaaaug ggaagaacua ga                                              22

```
<210> SEQ ID NO 212
<211> LENGTH: 20
<212> TYPE: RNA
<213> ORGANISM: Homo Sapiens

<400> SEQUENCE: 212
agagaugaag cgggggggcg                                              20

<210> SEQ ID NO 213
<211> LENGTH: 18
<212> TYPE: RNA
<213> ORGANISM: Homo Sapiens

<400> SEQUENCE: 213
gggugagggc aggugguu                                                18

<210> SEQ ID NO 214
<211> LENGTH: 22
<212> TYPE: RNA
<213> ORGANISM: Homo Sapiens

<400> SEQUENCE: 214
uggaagggag aagagcuuua au                                           22

<210> SEQ ID NO 215
<211> LENGTH: 22
<212> TYPE: RNA
<213> ORGANISM: Homo Sapiens

<400> SEQUENCE: 215
caucuuaccg gacagugcug ga                                           22

<210> SEQ ID NO 216
<211> LENGTH: 21
<212> TYPE: RNA
<213> ORGANISM: Homo Sapiens

<400> SEQUENCE: 216
cugacuguug ccguccucca g                                            21

<210> SEQ ID NO 217
<211> LENGTH: 20
<212> TYPE: RNA
<213> ORGANISM: Homo Sapiens

<400> SEQUENCE: 217
aaaggcauaa aaccaagaca                                              20

<210> SEQ ID NO 218
<211> LENGTH: 23
<212> TYPE: RNA
<213> ORGANISM: Homo Sapiens

<400> SEQUENCE: 218
uuuguaugga uaugugugug uau                                          23

<210> SEQ ID NO 219
<211> LENGTH: 22
<212> TYPE: RNA
<213> ORGANISM: Homo Sapiens

<400> SEQUENCE: 219
cuauacaacc uacugccuuc cc                                           22
```

<210> SEQ ID NO 220
<211> LENGTH: 22
<212> TYPE: RNA
<213> ORGANISM: Homo Sapiens

<400> SEQUENCE: 220
ugcccugugg acucaguucu gg                                              22

<210> SEQ ID NO 221
<211> LENGTH: 21
<212> TYPE: RNA
<213> ORGANISM: Homo Sapiens

<400> SEQUENCE: 221
cggcggggac ggcgauuggu c                                               21

<210> SEQ ID NO 222
<211> LENGTH: 22
<212> TYPE: RNA
<213> ORGANISM: Homo Sapiens

<400> SEQUENCE: 222
uccauuacac uacccugccu cu                                              22

<210> SEQ ID NO 223
<211> LENGTH: 17
<212> TYPE: RNA
<213> ORGANISM: Homo Sapiens

<400> SEQUENCE: 223
uaagugcuuc caugcuu                                                    17

<210> SEQ ID NO 224
<211> LENGTH: 23
<212> TYPE: RNA
<213> ORGANISM: Homo Sapiens

<400> SEQUENCE: 224
gugccaccuu aacugcagcc aau                                             23

<210> SEQ ID NO 225
<211> LENGTH: 20
<212> TYPE: RNA
<213> ORGANISM: Homo Sapiens

<400> SEQUENCE: 225
ucguuugccu uuucugcuu                                                  20

<210> SEQ ID NO 226
<211> LENGTH: 21
<212> TYPE: RNA
<213> ORGANISM: Homo Sapiens

<400> SEQUENCE: 226
uucgcgggcg aaggcaaagu c                                               21

<210> SEQ ID NO 227
<211> LENGTH: 22
<212> TYPE: RNA
<213> ORGANISM: Homo Sapiens

<400> SEQUENCE: 227

-continued ugcuggggc cacaugagug ug                                                22

<210> SEQ ID NO 228
<211> LENGTH: 22
<212> TYPE: RNA
<213> ORGANISM: Homo Sapiens

<400> SEQUENCE: 228
cucgggcgga ggugguugag ug                                               22

<210> SEQ ID NO 229
<211> LENGTH: 22
<212> TYPE: RNA
<213> ORGANISM: Homo Sapiens

<400> SEQUENCE: 229
gcugcgcuug gauuucgucc cc                                               22

<210> SEQ ID NO 230
<211> LENGTH: 21
<212> TYPE: RNA
<213> ORGANISM: Homo Sapiens

<400> SEQUENCE: 230
uugccauaca uagacuuuau u                                                21

<210> SEQ ID NO 231
<211> LENGTH: 21
<212> TYPE: RNA
<213> ORGANISM: Homo Sapiens

<400> SEQUENCE: 231
cuguacaggc cacugccuug c                                                21

<210> SEQ ID NO 232
<211> LENGTH: 22
<212> TYPE: RNA
<213> ORGANISM: Homo Sapiens

<400> SEQUENCE: 232
gaaaucaagc gugggugaga cc                                               22

<210> SEQ ID NO 233
<211> LENGTH: 21
<212> TYPE: RNA
<213> ORGANISM: Homo Sapiens

<400> SEQUENCE: 233
ucacgcggag agauggcuuu g                                                21

<210> SEQ ID NO 234
<211> LENGTH: 22
<212> TYPE: RNA
<213> ORGANISM: Homo Sapiens

<400> SEQUENCE: 234
ugagaccucu gguucugag cu                                                22

<210> SEQ ID NO 235
<211> LENGTH: 23
<212> TYPE: RNA
<213> ORGANISM: Homo Sapiens

<400> SEQUENCE: 235
acuuaaacgu ggauguacuu gcu                                          23

<210> SEQ ID NO 236
<211> LENGTH: 22
<212> TYPE: RNA
<213> ORGANISM: Homo Sapiens

<400> SEQUENCE: 236
acugcauuau gagcacuuaa ag                                           22

<210> SEQ ID NO 237
<211> LENGTH: 23
<212> TYPE: RNA
<213> ORGANISM: Homo Sapiens

<400> SEQUENCE: 237
ugugcaaauc uaugcaaaac uga                                          23

<210> SEQ ID NO 238
<211> LENGTH: 22
<212> TYPE: RNA
<213> ORGANISM: Homo Sapiens

<400> SEQUENCE: 238
agcgagguug cccuuuguau au                                           22

<210> SEQ ID NO 239
<211> LENGTH: 20
<212> TYPE: RNA
<213> ORGANISM: Homo Sapiens

<400> SEQUENCE: 239
ccccagggcg acgcggcggg                                              20

<210> SEQ ID NO 240
<211> LENGTH: 22
<212> TYPE: RNA
<213> ORGANISM: Homo Sapiens

<400> SEQUENCE: 240
accugagguu gugcauuucu aa                                           22

<210> SEQ ID NO 241
<211> LENGTH: 22
<212> TYPE: RNA
<213> ORGANISM: Homo Sapiens

<400> SEQUENCE: 241
cacacacugc aauuacuuuu gc                                           22

<210> SEQ ID NO 242
<211> LENGTH: 18
<212> TYPE: RNA
<213> ORGANISM: Homo Sapiens

<400> SEQUENCE: 242
aggcugggcu gggacgga                                                18

<210> SEQ ID NO 243
<211> LENGTH: 22
<212> TYPE: RNA
<213> ORGANISM: Homo Sapiens

```
<400> SEQUENCE: 243
uauugcacau uacuaaguug ca                                              22

<210> SEQ ID NO 244
<211> LENGTH: 22
<212> TYPE: RNA
<213> ORGANISM: Homo Sapiens

<400> SEQUENCE: 244
uucuggauaa caugcugaag cu                                              22

<210> SEQ ID NO 245
<211> LENGTH: 22
<212> TYPE: RNA
<213> ORGANISM: Homo Sapiens

<400> SEQUENCE: 245
aggagcuagc caggcauaug ca                                              22

<210> SEQ ID NO 246
<211> LENGTH: 22
<212> TYPE: RNA
<213> ORGANISM: Homo Sapiens

<400> SEQUENCE: 246
agguguuauc cuauccauuu gc                                              22

<210> SEQ ID NO 247
<211> LENGTH: 19
<212> TYPE: RNA
<213> ORGANISM: Homo Sapiens

<400> SEQUENCE: 247
ggagauggag guugcagug                                                  19

<210> SEQ ID NO 248
<211> LENGTH: 22
<212> TYPE: RNA
<213> ORGANISM: Homo Sapiens

<400> SEQUENCE: 248
uucuagauga gagauauaua ua                                              22

<210> SEQ ID NO 249
<211> LENGTH: 22
<212> TYPE: RNA
<213> ORGANISM: Homo Sapiens

<400> SEQUENCE: 249
aauucccuug uagauaaccc gg                                              22

<210> SEQ ID NO 250
<211> LENGTH: 22
<212> TYPE: RNA
<213> ORGANISM: Homo Sapiens

<400> SEQUENCE: 250 cagugggccag agcccugcag ug                                             22

<210> SEQ ID NO 251
<211> LENGTH: 22
<212> TYPE: RNA
<213> ORGANISM: Homo Sapiens
```

```
<400> SEQUENCE: 251
aauguggacu ggugugacca aa                                        22

<210> SEQ ID NO 252
<211> LENGTH: 23
<212> TYPE: RNA
<213> ORGANISM: Homo Sapiens

<400> SEQUENCE: 252
aagugccccc acaguugag ugc                                        23

<210> SEQ ID NO 253
<211> LENGTH: 22
<212> TYPE: RNA
<213> ORGANISM: Homo Sapiens

<400> SEQUENCE: 253
ugcccuuaaa ggugaaccca gu                                        22

<210> SEQ ID NO 254
<211> LENGTH: 22
<212> TYPE: RNA
<213> ORGANISM: Homo Sapiens

<400> SEQUENCE: 254
cacgcucaug cacacaccca ca                                        22

<210> SEQ ID NO 255
<211> LENGTH: 21
<212> TYPE: RNA
<213> ORGANISM: Homo Sapiens

<400> SEQUENCE: 255
ucacagugaa ccggucucuu u                                         21

<210> SEQ ID NO 256
<211> LENGTH: 22
<212> TYPE: RNA
<213> ORGANISM: Homo Sapiens

<400> SEQUENCE: 256
ugugacuggu ugaccagagg gg                                        22

<210> SEQ ID NO 257
<211> LENGTH: 24
<212> TYPE: RNA
<213> ORGANISM: Homo Sapiens

<400> SEQUENCE: 257
agaggacccg uagcugcuag aagg                                      24

<210> SEQ ID NO 258
<211> LENGTH: 22
<212> TYPE: RNA
<213> ORGANISM: Homo Sapiens

<400> SEQUENCE: 258
gauaucagcu caguaggcac cg                                        22

<210> SEQ ID NO 259
<211> LENGTH: 22
<212> TYPE: RNA
```

<213> ORGANISM: Homo Sapiens

<400> SEQUENCE: 259
uccgaacucu ccauuccucu gc                                       22

<210> SEQ ID NO 260
<211> LENGTH: 23
<212> TYPE: RNA
<213> ORGANISM: Homo Sapiens

<400> SEQUENCE: 260
ucucacacag aaaucgcacc cgu                                      23

<210> SEQ ID NO 261
<211> LENGTH: 22
<212> TYPE: RNA
<213> ORGANISM: Homo Sapiens

<400> SEQUENCE: 261
gggguuccug gggaugggau uu                                       22

<210> SEQ ID NO 262
<211> LENGTH: 18
<212> TYPE: RNA
<213> ORGANISM: Homo Sapiens

<400> SEQUENCE: 262
auggucaccu ccgggacu                                            18

<210> SEQ ID NO 263
<211> LENGTH: 22
<212> TYPE: RNA
<213> ORGANISM: Homo Sapiens

<400> SEQUENCE: 263
uuaugguuug ccugggacug ag                                       22

<210> SEQ ID NO 264
<211> LENGTH: 22
<212> TYPE: RNA
<213> ORGANISM: Homo Sapiens

<400> SEQUENCE: 264
cgcgcggccg ugcucggagc ag                                       22

<210> SEQ ID NO 265
<211> LENGTH: 24
<212> TYPE: RNA
<213> ORGANISM: Homo Sapiens

<400> SEQUENCE: 265
agcagaagca gggagguucu ccca                                     24

<210> SEQ ID NO 266
<211> LENGTH: 22
<212> TYPE: RNA
<213> ORGANISM: Homo Sapiens

<400> SEQUENCE: 266
acggauguuu gagcaugugc ua                                       22

<210> SEQ ID NO 267
<211> LENGTH: 20

```
<212> TYPE: RNA
<213> ORGANISM: Homo Sapiens

<400> SEQUENCE: 267
uguuccucug ucucccagac                                               20

<210> SEQ ID NO 268
<211> LENGTH: 22
<212> TYPE: RNA
<213> ORGANISM: Homo Sapiens

<400> SEQUENCE: 268
aggaggcauc uugagaaaug ga                                            22

<210> SEQ ID NO 269
<211> LENGTH: 22
<212> TYPE: RNA
<213> ORGANISM: Homo Sapiens

<400> SEQUENCE: 269
ugagguagua gguugugugg uu                                            22

<210> SEQ ID NO 270
<211> LENGTH: 23
<212> TYPE: RNA
<213> ORGANISM: Homo Sapiens

<400> SEQUENCE: 270
ucggggauca ucaugucacg aga                                           23

<210> SEQ ID NO 271
<211> LENGTH: 20
<212> TYPE: RNA
<213> ORGANISM: Homo Sapiens

<400> SEQUENCE: 271
gugucugggc ggacagcugc                                               20

<210> SEQ ID NO 272
<211> LENGTH: 23
<212> TYPE: RNA
<213> ORGANISM: Homo Sapiens

<400> SEQUENCE: 272
ugugcaaauc caugcaaaac uga                                           23

<210> SEQ ID NO 273
<211> LENGTH: 17
<212> TYPE: RNA
<213> ORGANISM: Homo Sapiens

<400> SEQUENCE: 273
caguguucag agaugga                                                  17

<210> SEQ ID NO 274
<211> LENGTH: 23
<212> TYPE: RNA
<213> ORGANISM: Homo Sapiens

<400> SEQUENCE: 274
uggugcggag agggcccaca gug                                           23

<210> SEQ ID NO 275
```

```
<211> LENGTH: 22
<212> TYPE: RNA
<213> ORGANISM: Homo Sapiens

<400> SEQUENCE: 275
gccugcuggg guggaaccug gu                                              22

<210> SEQ ID NO 276
<211> LENGTH: 23
<212> TYPE: RNA
<213> ORGANISM: Homo Sapiens

<400> SEQUENCE: 276
cccaguguuc agacuaccug uuc                                             23

<210> SEQ ID NO 277
<211> LENGTH: 22
<212> TYPE: RNA
<213> ORGANISM: Homo Sapiens

<400> SEQUENCE: 277
gagaaaugcu ggacuaaucu gc                                              22

<210> SEQ ID NO 278
<211> LENGTH: 17
<212> TYPE: RNA
<213> ORGANISM: Homo Sapiens

<400> SEQUENCE: 278
agggugugug uguuuuu                                                    17

<210> SEQ ID NO 279
<211> LENGTH: 22
<212> TYPE: RNA
<213> ORGANISM: Homo Sapiens

<400> SEQUENCE: 279
uguaaacauc cucgacugga ag                                              22

<210> SEQ ID NO 280
<211> LENGTH: 21
<212> TYPE: RNA
<213> ORGANISM: Homo Sapiens

<400> SEQUENCE: 280
ugaugauaca gguggaggua g                                               21

<210> SEQ ID NO 281
<211> LENGTH: 21
<212> TYPE: RNA
<213> ORGANISM: Homo Sapiens

<400> SEQUENCE: 281
uggcagggag gcugggaggg g                                               21

<210> SEQ ID NO 282
<211> LENGTH: 21
<212> TYPE: RNA
<213> ORGANISM: Homo Sapiens

<400> SEQUENCE: 282
cacaggcuua gaaaagacag u                                               21
```

```
<210> SEQ ID NO 283
<211> LENGTH: 21
<212> TYPE: RNA
<213> ORGANISM: Homo Sapiens

<400> SEQUENCE: 283
cccuuggguc ugaugggua g                                              21

<210> SEQ ID NO 284
<211> LENGTH: 22
<212> TYPE: RNA
<213> ORGANISM: Homo Sapiens

<400> SEQUENCE: 284
acuuuaacau ggaagugcuu uc                                            22

<210> SEQ ID NO 285
<211> LENGTH: 22
<212> TYPE: RNA
<213> ORGANISM: Homo Sapiens

<400> SEQUENCE: 285
ugcuggauca gugguucgag uc                                            22

<210> SEQ ID NO 286
<211> LENGTH: 23
<212> TYPE: RNA
<213> ORGANISM: Homo Sapiens

<400> SEQUENCE: 286
aucccuugca ggggcuguug ggu                                           23

<210> SEQ ID NO 287
<211> LENGTH: 21
<212> TYPE: RNA
<213> ORGANISM: Homo Sapiens

<400> SEQUENCE: 287
ccuggaaaca cugagguugu g                                             21

<210> SEQ ID NO 288
<211> LENGTH: 21
<212> TYPE: RNA
<213> ORGANISM: Homo Sapiens

<400> SEQUENCE: 288
uaguggucag agggcuuaug a                                             21

<210> SEQ ID NO 289
<211> LENGTH: 23
<212> TYPE: RNA
<213> ORGANISM: Homo Sapiens

<400> SEQUENCE: 289
ggcagguucu cacccucucu agg                                           23

<210> SEQ ID NO 290
<211> LENGTH: 22
<212> TYPE: RNA
<213> ORGANISM: Homo Sapiens

<400> SEQUENCE: 290
uugaggagac auggugggg cc                                             22
```

```
<210> SEQ ID NO 291
<211> LENGTH: 21
<212> TYPE: RNA
<213> ORGANISM: Homo Sapiens

<400> SEQUENCE: 291
cccugggccu cugcucccca g                                             21

<210> SEQ ID NO 292
<211> LENGTH: 22
<212> TYPE: RNA
<213> ORGANISM: Homo Sapiens

<400> SEQUENCE: 292
caucaucguc ucaaaugagu cu                                            22

<210> SEQ ID NO 293
<211> LENGTH: 22
<212> TYPE: RNA
<213> ORGANISM: Homo Sapiens

<400> SEQUENCE: 293
aaagugcauc cuuuuagagu gu                                            22

<210> SEQ ID NO 294
<211> LENGTH: 23
<212> TYPE: RNA
<213> ORGANISM: Homo Sapiens

<400> SEQUENCE: 294
ugagcgccuc gacgacagag ccg                                           23

<210> SEQ ID NO 295
<211> LENGTH: 21
<212> TYPE: RNA
<213> ORGANISM: Homo Sapiens

<400> SEQUENCE: 295
uacuuuucua gguuguuggg g                                             21

<210> SEQ ID NO 296
<211> LENGTH: 22
<212> TYPE: RNA
<213> ORGANISM: Homo Sapiens

<400> SEQUENCE: 296
agaaggaaau ugaauucauu ua                                            22

<210> SEQ ID NO 297
<211> LENGTH: 22
<212> TYPE: RNA
<213> ORGANISM: Homo Sapiens

<400> SEQUENCE: 297
uuuaggauaa gcuugacuuu ug                                            22

<210> SEQ ID NO 298
<211> LENGTH: 25
<212> TYPE: RNA
<213> ORGANISM: Homo Sapiens

<400> SEQUENCE: 298
aagggaggag gagcggaggg gcccu                                         25
```

<210> SEQ ID NO 299
<211> LENGTH: 22
<212> TYPE: RNA
<213> ORGANISM: Homo Sapiens

<400> SEQUENCE: 299
aguauucugu accagggaag gu                                              22

<210> SEQ ID NO 300
<211> LENGTH: 22
<212> TYPE: RNA
<213> ORGANISM: Homo Sapiens

<400> SEQUENCE: 300
uugagaauga ugaaucauua gg                                              22

<210> SEQ ID NO 301
<211> LENGTH: 19
<212> TYPE: RNA
<213> ORGANISM: Homo Sapiens

<400> SEQUENCE: 301
aauggauuuu uggagcagg                                                  19

<210> SEQ ID NO 302
<211> LENGTH: 22
<212> TYPE: RNA
<213> ORGANISM: Homo Sapiens

<400> SEQUENCE: 302
ggcuggagcg agugcagugg ug                                              22

<210> SEQ ID NO 303
<211> LENGTH: 23
<212> TYPE: RNA
<213> ORGANISM: Homo Sapiens

<400> SEQUENCE: 303
acuuacagac aagagccuug cuc                                             23

<210> SEQ ID NO 304
<211> LENGTH: 22
<212> TYPE: RNA
<213> ORGANISM: Homo Sapiens

<400> SEQUENCE: 304
auucuaauuu cuccacgucu uu                                              22

<210> SEQ ID NO 305
<211> LENGTH: 23
<212> TYPE: RNA
<213> ORGANISM: Homo Sapiens

<400> SEQUENCE: 305
aagugccgcc aucuuuugag ugu                                             23

<210> SEQ ID NO 306
<211> LENGTH: 22
<212> TYPE: RNA
<213> ORGANISM: Homo Sapiens

<400> SEQUENCE: 306

```
aagcccuuac cccaaaaagu au                                    22

<210> SEQ ID NO 307
<211> LENGTH: 21
<212> TYPE: RNA
<213> ORGANISM: Homo Sapiens

<400> SEQUENCE: 307
ggcuccuccu cucaggaugu g                                     21

<210> SEQ ID NO 308
<211> LENGTH: 22
<212> TYPE: RNA
<213> ORGANISM: Homo Sapiens

<400> SEQUENCE: 308
uaugcauugu auuuuaggu cc                                     22

<210> SEQ ID NO 309
<211> LENGTH: 22
<212> TYPE: RNA
<213> ORGANISM: Homo Sapiens

<400> SEQUENCE: 309
uggauuucuu ugugaaucac ca                                    22

<210> SEQ ID NO 310
<211> LENGTH: 22
<212> TYPE: RNA
<213> ORGANISM: Homo Sapiens

<400> SEQUENCE: 310
aacuccaaac acucaaaacu ca                                    22

<210> SEQ ID NO 311
<211> LENGTH: 21
<212> TYPE: RNA
<213> ORGANISM: Homo Sapiens

<400> SEQUENCE: 311
ggcuagcaac agcgcuuacc u                                     21

<210> SEQ ID NO 312
<211> LENGTH: 22
<212> TYPE: RNA
<213> ORGANISM: Homo Sapiens

<400> SEQUENCE: 312 ugggugccc acuccgcaag uu                                     22

<210> SEQ ID NO 313
<211> LENGTH: 22
<212> TYPE: RNA
<213> ORGANISM: Homo Sapiens

<400> SEQUENCE: 313
cagggcagga agaaguggac aa                                    22

<210> SEQ ID NO 314
<211> LENGTH: 22
<212> TYPE: RNA
<213> ORGANISM: Homo Sapiens

<400> SEQUENCE: 314
```
caaccucgac gaucuccuca gc					22

<210> SEQ ID NO 315
<211> LENGTH: 24
<212> TYPE: RNA
<213> ORGANISM: Homo Sapiens

<400> SEQUENCE: 315
guuccacacu gacacugcag aagu					24

<210> SEQ ID NO 316
<211> LENGTH: 23
<212> TYPE: RNA
<213> ORGANISM: Homo Sapiens

<400> SEQUENCE: 316
uuacaguugu ucaaccaguu acu					23

<210> SEQ ID NO 317
<211> LENGTH: 22
<212> TYPE: RNA
<213> ORGANISM: Homo Sapiens

<400> SEQUENCE: 317
aacaauaucc uggugcugag ug					22

<210> SEQ ID NO 318
<211> LENGTH: 22
<212> TYPE: RNA
<213> ORGANISM: Homo Sapiens

<400> SEQUENCE: 318
uuagggcccu ggcuccaucu cc					22

<210> SEQ ID NO 319
<211> LENGTH: 23
<212> TYPE: RNA
<213> ORGANISM: Homo Sapiens

<400> SEQUENCE: 319
ugagagugga auucacagua uuu					23

<210> SEQ ID NO 320
<211> LENGTH: 21
<212> TYPE: RNA
<213> ORGANISM: Homo Sapiens

<400> SEQUENCE: 320
gcccuccgcc cgugcacccc g						21

<210> SEQ ID NO 321
<211> LENGTH: 22
<212> TYPE: RNA
<213> ORGANISM: Homo Sapiens

<400> SEQUENCE: 321
aaacauucgc ggugcacuuc uu					22

<210> SEQ ID NO 322
<211> LENGTH: 18
<212> TYPE: RNA
<213> ORGANISM: Homo Sapiens

<400> SEQUENCE: 322
gaggcugaag gaagaugg                                                    18

<210> SEQ ID NO 323
<211> LENGTH: 16
<212> TYPE: RNA
<213> ORGANISM: Homo Sapiens

<400> SEQUENCE: 323
uucagcagga acagcu                                                      16

<210> SEQ ID NO 324
<211> LENGTH: 22
<212> TYPE: RNA
<213> ORGANISM: Homo Sapiens

<400> SEQUENCE: 324
aggaggaauu ggugcugguc uu                                               22

<210> SEQ ID NO 325
<211> LENGTH: 18
<212> TYPE: RNA
<213> ORGANISM: Homo Sapiens

<400> SEQUENCE: 325
ucgaggagcu cacagucu                                                    18

<210> SEQ ID NO 326
<211> LENGTH: 21
<212> TYPE: RNA
<213> ORGANISM: Homo Sapiens

<400> SEQUENCE: 326
gcagggacag caaaggggug c                                                21

<210> SEQ ID NO 327
<211> LENGTH: 22
<212> TYPE: RNA
<213> ORGANISM: Homo Sapiens

<400> SEQUENCE: 327
auaagacgag caaaaagcuu gu                                               22

<210> SEQ ID NO 328
<211> LENGTH: 22
<212> TYPE: RNA
<213> ORGANISM: Homo Sapiens

<400> SEQUENCE: 328
agugccugcu augugccagg ca                                               22

<210> SEQ ID NO 329
<211> LENGTH: 21
<212> TYPE: RNA
<213> ORGANISM: Homo Sapiens

<400> SEQUENCE: 329
cacggcaaaa gaaacaaucc a                                                21

<210> SEQ ID NO 330
<211> LENGTH: 23
<212> TYPE: RNA
<213> ORGANISM: Homo Sapiens

```
<400> SEQUENCE: 330
uaauacugcc ggguaaugau gga                                            23

<210> SEQ ID NO 331
<211> LENGTH: 23
<212> TYPE: RNA
<213> ORGANISM: Homo Sapiens

<400> SEQUENCE: 331
cagugcaaug auauugucaa agc                                            23

<210> SEQ ID NO 332
<211> LENGTH: 23
<212> TYPE: RNA
<213> ORGANISM: Homo Sapiens

<400> SEQUENCE: 332
uuuggcacua gcacauuuuu gcu                                            23

<210> SEQ ID NO 333
<211> LENGTH: 21
<212> TYPE: RNA
<213> ORGANISM: Homo Sapiens

<400> SEQUENCE: 333
uaugguacuc cuuaagcuaa c                                              21

<210> SEQ ID NO 334
<211> LENGTH: 25
<212> TYPE: RNA
<213> ORGANISM: Homo Sapiens

<400> SEQUENCE: 334
aggcaccagc caggcauugc ucagc                                          25

<210> SEQ ID NO 335
<211> LENGTH: 22
<212> TYPE: RNA
<213> ORGANISM: Homo Sapiens

<400> SEQUENCE: 335
ugugauauca ugguuccugg ga                                             22

<210> SEQ ID NO 336
<211> LENGTH: 23
<212> TYPE: RNA
<213> ORGANISM: Homo Sapiens

<400> SEQUENCE: 336
aaacucuacu uguccuucug agu                                            23

<210> SEQ ID NO 337
<211> LENGTH: 20
<212> TYPE: RNA
<213> ORGANISM: Homo Sapiens

<400> SEQUENCE: 337
cauuacagca cagccauucu                                                20

<210> SEQ ID NO 338
<211> LENGTH: 18
<212> TYPE: RNA
```

<213> ORGANISM: Homo Sapiens

<400> SEQUENCE: 338
uaaaauuugc auccagga                                                 18

<210> SEQ ID NO 339
<211> LENGTH: 20
<212> TYPE: RNA
<213> ORGANISM: Homo Sapiens

<400> SEQUENCE: 339
ucacaccugc cucgcccccc                                               20

<210> SEQ ID NO 340
<211> LENGTH: 22
<212> TYPE: RNA
<213> ORGANISM: Homo Sapiens

<400> SEQUENCE: 340
cugcaaugua agcacuucuu ac                                            22

<210> SEQ ID NO 341
<211> LENGTH: 22
<212> TYPE: RNA
<213> ORGANISM: Homo Sapiens

<400> SEQUENCE: 341
ugagggcucc aggugacggu gg                                            22

<210> SEQ ID NO 342
<211> LENGTH: 21
<212> TYPE: RNA
<213> ORGANISM: Homo Sapiens

<400> SEQUENCE: 342
ugacaacuau ggaugagcuc u                                             21

<210> SEQ ID NO 343
<211> LENGTH: 22
<212> TYPE: RNA
<213> ORGANISM: Homo Sapiens

<400> SEQUENCE: 343 agugggggaac ccuuccauga gg                                           22

<210> SEQ ID NO 344
<211> LENGTH: 22
<212> TYPE: RNA
<213> ORGANISM: Homo Sapiens

<400> SEQUENCE: 344
ucucccuucc ugcccuggcu ag                                            22

<210> SEQ ID NO 345
<211> LENGTH: 22
<212> TYPE: RNA
<213> ORGANISM: Homo Sapiens

<400> SEQUENCE: 345
aacggcaaug acuuuuguac ca                                            22

<210> SEQ ID NO 346
<211> LENGTH: 23

```
<212> TYPE: RNA
<213> ORGANISM: Homo Sapiens

<400> SEQUENCE: 346
ucuaaagacu agacuucgcu aug                                            23

<210> SEQ ID NO 347
<211> LENGTH: 24
<212> TYPE: RNA
<213> ORGANISM: Homo Sapiens

<400> SEQUENCE: 347
agagcucaca gcuguccuuc ucua                                           24

<210> SEQ ID NO 348
<211> LENGTH: 21
<212> TYPE: RNA
<213> ORGANISM: Homo Sapiens

<400> SEQUENCE: 348
acuccaguuu uaguucucuu g                                              21

<210> SEQ ID NO 349
<211> LENGTH: 17
<212> TYPE: RNA
<213> ORGANISM: Homo Sapiens

<400> SEQUENCE: 349
accccacucc ugguacc                                                   17

<210> SEQ ID NO 350
<211> LENGTH: 22
<212> TYPE: RNA
<213> ORGANISM: Homo Sapiens

<400> SEQUENCE: 350
acugcaguga aggcacuugu ag                                             22

<210> SEQ ID NO 351
<211> LENGTH: 22
<212> TYPE: RNA
<213> ORGANISM: Homo Sapiens

<400> SEQUENCE: 351
ugaaguacca gcuacucgag ag                                             22

<210> SEQ ID NO 352
<211> LENGTH: 22
<212> TYPE: RNA
<213> ORGANISM: Homo Sapiens

<400> SEQUENCE: 352
guucuguuaa cccauccccu ca                                             22

<210> SEQ ID NO 353
<211> LENGTH: 19
<212> TYPE: RNA
<213> ORGANISM: Homo Sapiens

<400> SEQUENCE: 353
aguguggcuu ucuuagagc                                                 19

<210> SEQ ID NO 354
```

```
<211> LENGTH: 22
<212> TYPE: RNA
<213> ORGANISM: Homo Sapiens

<400> SEQUENCE: 354
cguguucaca gcggaccuug au                                              22

<210> SEQ ID NO 355
<211> LENGTH: 22
<212> TYPE: RNA
<213> ORGANISM: Homo Sapiens

<400> SEQUENCE: 355
cgucccgggg cugcgcgagg ca                                              22

<210> SEQ ID NO 356
<211> LENGTH: 21
<212> TYPE: RNA
<213> ORGANISM: Homo Sapiens

<400> SEQUENCE: 356
aauauaacac agauggccug u                                               21

<210> SEQ ID NO 357
<211> LENGTH: 22
<212> TYPE: RNA
<213> ORGANISM: Homo Sapiens

<400> SEQUENCE: 357
ucgacagcac gacacugccu uc                                              22

<210> SEQ ID NO 358
<211> LENGTH: 22
<212> TYPE: RNA
<213> ORGANISM: Homo Sapiens

<400> SEQUENCE: 358
caccuugcgc uacucagguc ug                                              22

<210> SEQ ID NO 359
<211> LENGTH: 22
<212> TYPE: RNA
<213> ORGANISM: Homo Sapiens

<400> SEQUENCE: 359
cggcaacaag aaacugccug ag                                              22

<210> SEQ ID NO 360
<211> LENGTH: 24
<212> TYPE: RNA
<213> ORGANISM: Homo Sapiens

<400> SEQUENCE: 360
aaagacauag gauagaguca ccuc                                            24

<210> SEQ ID NO 361
<211> LENGTH: 18
<212> TYPE: RNA
<213> ORGANISM: Homo Sapiens

<400> SEQUENCE: 361
aaagcugggu ugagaagg                                                   18
```

```
<210> SEQ ID NO 362
<211> LENGTH: 21
<212> TYPE: RNA
<213> ORGANISM: Homo Sapiens

<400> SEQUENCE: 362
ugcuuaaccu ugcccucgaa a                                                    21

<210> SEQ ID NO 363
<211> LENGTH: 22
<212> TYPE: RNA
<213> ORGANISM: Homo Sapiens

<400> SEQUENCE: 363
ucugggcaac aaagugagac cu                                                   22

<210> SEQ ID NO 364
<211> LENGTH: 23
<212> TYPE: RNA
<213> ORGANISM: Homo Sapiens

<400> SEQUENCE: 364
gggaugguag accggugacg ugc                                                  23

<210> SEQ ID NO 365
<211> LENGTH: 22
<212> TYPE: RNA
<213> ORGANISM: Homo Sapiens

<400> SEQUENCE: 365
cugggaggug ugauaucgug gu                                                   22

<210> SEQ ID NO 366
<211> LENGTH: 23
<212> TYPE: RNA
<213> ORGANISM: Homo Sapiens

<400> SEQUENCE: 366
ggggaaagcg aguagggaca uuu                                                  23

<210> SEQ ID NO 367
<211> LENGTH: 22
<212> TYPE: RNA
<213> ORGANISM: Homo Sapiens

<400> SEQUENCE: 367
cuuucagucg gauguuugca gc                                                   22

<210> SEQ ID NO 368
<211> LENGTH: 22
<212> TYPE: RNA
<213> ORGANISM: Homo Sapiens

<400> SEQUENCE: 368
caaaaaccac aguuucuuuu gc                                                   22

<210> SEQ ID NO 369
<211> LENGTH: 19
<212> TYPE: RNA
<213> ORGANISM: Homo Sapiens

<400> SEQUENCE: 369
ggccuuguuc cugucccca                                                       19
```

```
<210> SEQ ID NO 370
<211> LENGTH: 22
<212> TYPE: RNA
<213> ORGANISM: Homo Sapiens

<400> SEQUENCE: 370
uacccagagc augcagugug aa                                              22

<210> SEQ ID NO 371
<211> LENGTH: 17
<212> TYPE: RNA
<213> ORGANISM: Homo Sapiens

<400> SEQUENCE: 371
ggugaggcua gcuggug                                                    17

<210> SEQ ID NO 372
<211> LENGTH: 21
<212> TYPE: RNA
<213> ORGANISM: Homo Sapiens

<400> SEQUENCE: 372
uugccagggc aggaggugga a                                               21

<210> SEQ ID NO 373
<211> LENGTH: 21
<212> TYPE: RNA
<213> ORGANISM: Homo Sapiens

<400> SEQUENCE: 373
cuccagaggg augcacuuuc u                                               21

<210> SEQ ID NO 374
<211> LENGTH: 22
<212> TYPE: RNA
<213> ORGANISM: Homo Sapiens

<400> SEQUENCE: 374
ugaaacauac acgggaaacc uc                                              22

<210> SEQ ID NO 375
<211> LENGTH: 22
<212> TYPE: RNA
<213> ORGANISM: Homo Sapiens

<400> SEQUENCE: 375
uaggccacag ccacccaugu gu                                              22

<210> SEQ ID NO 376
<211> LENGTH: 22
<212> TYPE: RNA
<213> ORGANISM: Homo Sapiens

<400> SEQUENCE: 376
gagcaggcga ggcugggcug aa                                              22

<210> SEQ ID NO 377
<211> LENGTH: 22
<212> TYPE: RNA
<213> ORGANISM: Homo Sapiens

<400> SEQUENCE: 377
cuccuggggc ccgcacucuc gc                                              22
```

```
<210> SEQ ID NO 378
<211> LENGTH: 22
<212> TYPE: RNA
<213> ORGANISM: Homo Sapiens

<400> SEQUENCE: 378
caaaagugau ugugguuuuu gc                                              22

<210> SEQ ID NO 379
<211> LENGTH: 18
<212> TYPE: RNA
<213> ORGANISM: Homo Sapiens

<400> SEQUENCE: 379
cgugucuucu ggcuugau                                                   18

<210> SEQ ID NO 380
<211> LENGTH: 22
<212> TYPE: RNA
<213> ORGANISM: Homo Sapiens

<400> SEQUENCE: 380
cugcagaguu uguacggacc gg                                              22

<210> SEQ ID NO 381
<211> LENGTH: 21
<212> TYPE: RNA
<213> ORGANISM: Homo Sapiens

<400> SEQUENCE: 381
ggccagccac caggagggcu g                                               21

<210> SEQ ID NO 382
<211> LENGTH: 22
<212> TYPE: RNA
<213> ORGANISM: Homo Sapiens

<400> SEQUENCE: 382
aaacaccauu gucacacucc ac                                              22

<210> SEQ ID NO 383
<211> LENGTH: 23
<212> TYPE: RNA
<213> ORGANISM: Homo Sapiens

<400> SEQUENCE: 383
caaagugcuc auagugcagg uag                                             23

<210> SEQ ID NO 384
<211> LENGTH: 22
<212> TYPE: RNA
<213> ORGANISM: Homo Sapiens

<400> SEQUENCE: 384 ugggaaggc gucagugucg gg                                               22

<210> SEQ ID NO 385
<211> LENGTH: 25
<212> TYPE: RNA
<213> ORGANISM: Homo Sapiens

<400> SEQUENCE: 385
```

```
agcggggagg aagugggcgc ugcuu                                          25

<210> SEQ ID NO 386
<211> LENGTH: 18
<212> TYPE: RNA
<213> ORGANISM: Homo Sapiens

<400> SEQUENCE: 386
aucccaccuc ugccacca                                                  18

<210> SEQ ID NO 387
<211> LENGTH: 22
<212> TYPE: RNA
<213> ORGANISM: Homo Sapiens

<400> SEQUENCE: 387
aauaauauca caguaggugu ac                                             22

<210> SEQ ID NO 388
<211> LENGTH: 20
<212> TYPE: RNA
<213> ORGANISM: Homo Sapiens

<400> SEQUENCE: 388
aaagacucug caagaugccu                                                20

<210> SEQ ID NO 389
<211> LENGTH: 23
<212> TYPE: RNA
<213> ORGANISM: Homo Sapiens

<400> SEQUENCE: 389
cugauaagaa cagaggccca gau                                            23

<210> SEQ ID NO 390
<211> LENGTH: 23
<212> TYPE: RNA
<213> ORGANISM: Homo Sapiens

<400> SEQUENCE: 390
uuuaguguga uaauggcguu uga                                            23

<210> SEQ ID NO 391
<211> LENGTH: 23
<212> TYPE: RNA
<213> ORGANISM: Homo Sapiens

<400> SEQUENCE: 391
gggguauugu uuccgcugcc agg                                            23

<210> SEQ ID NO 392
<211> LENGTH: 22
<212> TYPE: RNA
<213> ORGANISM: Homo Sapiens

<400> SEQUENCE: 392
acucggcgug gcgucggucg ug                                             22

<210> SEQ ID NO 393
<211> LENGTH: 21
<212> TYPE: RNA
<213> ORGANISM: Homo Sapiens

<400> SEQUENCE: 393
```
aucauagagg aaaauccacg u                                              21

<210> SEQ ID NO 394
<211> LENGTH: 23
<212> TYPE: RNA
<213> ORGANISM: Homo Sapiens

<400> SEQUENCE: 394
agguugggau cgguugcaau gcu                                            23

<210> SEQ ID NO 395
<211> LENGTH: 22
<212> TYPE: RNA
<213> ORGANISM: Homo Sapiens

<400> SEQUENCE: 395
caguucagaa guguuccuga gu                                             22

<210> SEQ ID NO 396
<211> LENGTH: 23
<212> TYPE: RNA
<213> ORGANISM: Homo Sapiens

<400> SEQUENCE: 396
caaaaaccgc aauuacuuuu gca                                            23

<210> SEQ ID NO 397
<211> LENGTH: 16
<212> TYPE: RNA
<213> ORGANISM: Homo Sapiens

<400> SEQUENCE: 397
ugccuuccug ucugug                                                    16

<210> SEQ ID NO 398
<211> LENGTH: 23
<212> TYPE: RNA
<213> ORGANISM: Homo Sapiens

<400> SEQUENCE: 398
ucaacaaaau cacugaugcu gga                                            23

<210> SEQ ID NO 399
<211> LENGTH: 22
<212> TYPE: RNA
<213> ORGANISM: Homo Sapiens

<400> SEQUENCE: 399
ucacaaggua uugacuggcg ua                                             22

<210> SEQ ID NO 400
<211> LENGTH: 22
<212> TYPE: RNA
<213> ORGANISM: Homo Sapiens

<400> SEQUENCE: 400
uggaauguaa agaaguaugu au                                             22

<210> SEQ ID NO 401
<211> LENGTH: 22
<212> TYPE: RNA
<213> ORGANISM: Homo Sapiens

```
<400> SEQUENCE: 401
ucacaaguca ggcucuuggg ac                                           22

<210> SEQ ID NO 402
<211> LENGTH: 23
<212> TYPE: RNA
<213> ORGANISM: Homo Sapiens

<400> SEQUENCE: 402
uuuugcauga cccugggagu agg                                          23

<210> SEQ ID NO 403
<211> LENGTH: 22
<212> TYPE: RNA
<213> ORGANISM: Homo Sapiens

<400> SEQUENCE: 403
cugcccuggc ccgagggacc ga                                           22

<210> SEQ ID NO 404
<211> LENGTH: 22
<212> TYPE: RNA
<213> ORGANISM: Homo Sapiens

<400> SEQUENCE: 404
aaaaguaauu gcgguuuuug cc                                           22

<210> SEQ ID NO 405
<211> LENGTH: 20
<212> TYPE: RNA
<213> ORGANISM: Homo Sapiens

<400> SEQUENCE: 405
uaggaugggg gugagaggug                                              20

<210> SEQ ID NO 406
<211> LENGTH: 25
<212> TYPE: RNA
<213> ORGANISM: Homo Sapiens

<400> SEQUENCE: 406
aaaaaccaca auuacuuuug cacca                                        25

<210> SEQ ID NO 407
<211> LENGTH: 22
<212> TYPE: RNA
<213> ORGANISM: Homo Sapiens

<400> SEQUENCE: 407
cccaauacac ggucgaccuc uu                                           22

<210> SEQ ID NO 408
<211> LENGTH: 20
<212> TYPE: RNA
<213> ORGANISM: Homo Sapiens

<400> SEQUENCE: 408
ugaggagaug cugggacuga                                              20

<210> SEQ ID NO 409
<211> LENGTH: 22
<212> TYPE: RNA
<213> ORGANISM: Homo Sapiens
```

```
<400> SEQUENCE: 409
cgccucuuca gcgcugucuu cc                                              22

<210> SEQ ID NO 410
<211> LENGTH: 22
<212> TYPE: RNA
<213> ORGANISM: Homo Sapiens

<400> SEQUENCE: 410
ggcgacaaaa cgagacccug uc                                              22

<210> SEQ ID NO 411
<211> LENGTH: 21
<212> TYPE: RNA
<213> ORGANISM: Homo Sapiens

<400> SEQUENCE: 411
ucagcuacua ccucuauuag g                                               21

<210> SEQ ID NO 412
<211> LENGTH: 22
<212> TYPE: RNA
<213> ORGANISM: Homo Sapiens

<400> SEQUENCE: 412
gugcauggcu guauauauaa ca                                              22

<210> SEQ ID NO 413
<211> LENGTH: 21
<212> TYPE: RNA
<213> ORGANISM: Homo Sapiens

<400> SEQUENCE: 413
uggggcuagu gaugcaggac g                                               21

<210> SEQ ID NO 414
<211> LENGTH: 22
<212> TYPE: RNA
<213> ORGANISM: Homo Sapiens

<400> SEQUENCE: 414
gcgacucuga aaacuagaag gu                                              22

<210> SEQ ID NO 415
<211> LENGTH: 18
<212> TYPE: RNA
<213> ORGANISM: Homo Sapiens

<400> SEQUENCE: 415
cacugcagga cucagcag                                                   18

<210> SEQ ID NO 416
<211> LENGTH: 20
<212> TYPE: RNA
<213> ORGANISM: Homo Sapiens

<400> SEQUENCE: 416
acuggacuug gagccagaag                                                 20

<210> SEQ ID NO 417
<211> LENGTH: 22
<212> TYPE: RNA
```

```
<213> ORGANISM: Homo Sapiens

<400> SEQUENCE: 417
gugaauuacc gaagggccau aa                                              22

<210> SEQ ID NO 418
<211> LENGTH: 22
<212> TYPE: RNA
<213> ORGANISM: Homo Sapiens

<400> SEQUENCE: 418 ccagugggc ugcuguuauc ug                                               22

<210> SEQ ID NO 419
<211> LENGTH: 22
<212> TYPE: RNA
<213> ORGANISM: Homo Sapiens

<400> SEQUENCE: 419
ucugcaagug ucagaggcga gg                                              22

<210> SEQ ID NO 420
<211> LENGTH: 19
<212> TYPE: RNA
<213> ORGANISM: Homo Sapiens

<400> SEQUENCE: 420
aaaaacugua auuacuuuu                                                  19

<210> SEQ ID NO 421
<211> LENGTH: 20
<212> TYPE: RNA
<213> ORGANISM: Homo Sapiens

<400> SEQUENCE: 421
uggcuuuuaa cuuugauggc                                                 20

<210> SEQ ID NO 422
<211> LENGTH: 22
<212> TYPE: RNA
<213> ORGANISM: Homo Sapiens

<400> SEQUENCE: 422
cguguauuug acaagcugag uu                                              22

<210> SEQ ID NO 423
<211> LENGTH: 22
<212> TYPE: RNA
<213> ORGANISM: Homo Sapiens

<400> SEQUENCE: 423
cacccccugu uuccuggccc ac                                              22

<210> SEQ ID NO 424
<211> LENGTH: 21
<212> TYPE: RNA
<213> ORGANISM: Homo Sapiens

<400> SEQUENCE: 424
aaaauuucuu ucacuacuua g                                               21

<210> SEQ ID NO 425
<211> LENGTH: 21
```

```
<212> TYPE: RNA
<213> ORGANISM: Homo Sapiens

<400> SEQUENCE: 425
aguuaaugaa uccuggaaag u                                              21

<210> SEQ ID NO 426
<211> LENGTH: 21
<212> TYPE: RNA
<213> ORGANISM: Homo Sapiens

<400> SEQUENCE: 426
uaaagugcug acagugcaga u                                              21

<210> SEQ ID NO 427
<211> LENGTH: 22
<212> TYPE: RNA
<213> ORGANISM: Homo Sapiens

<400> SEQUENCE: 427
uccaguacag gucucucauu uc                                             22

<210> SEQ ID NO 428
<211> LENGTH: 23
<212> TYPE: RNA
<213> ORGANISM: Homo Sapiens

<400> SEQUENCE: 428
agaacucuug cagucuuaga ugu                                            23

<210> SEQ ID NO 429
<211> LENGTH: 22
<212> TYPE: RNA
<213> ORGANISM: Homo Sapiens

<400> SEQUENCE: 429
gugugcggaa augcuucugc ua                                             22

<210> SEQ ID NO 430
<211> LENGTH: 22
<212> TYPE: RNA
<213> ORGANISM: Homo Sapiens

<400> SEQUENCE: 430
gcccgagagg auccgucccu gc                                             22

<210> SEQ ID NO 431
<211> LENGTH: 22
<212> TYPE: RNA
<213> ORGANISM: Homo Sapiens

<400> SEQUENCE: 431
ggaggggucc cgcacuggga gg                                             22

<210> SEQ ID NO 432
<211> LENGTH: 22
<212> TYPE: RNA
<213> ORGANISM: Homo Sapiens

<400> SEQUENCE: 432
caaagcgcuc cccuuuagag gu                                             22

<210> SEQ ID NO 433
```

```
<211> LENGTH: 15
<212> TYPE: RNA
<213> ORGANISM: Homo Sapiens

<400> SEQUENCE: 433
aggagauccu ggguu                                                      15

<210> SEQ ID NO 434
<211> LENGTH: 21
<212> TYPE: RNA
<213> ORGANISM: Homo Sapiens

<400> SEQUENCE: 434
ugguagacua uggaacguag g                                               21

<210> SEQ ID NO 435
<211> LENGTH: 22
<212> TYPE: RNA
<213> ORGANISM: Homo Sapiens

<400> SEQUENCE: 435
aagguauugu ucagacuuau ga                                              22

<210> SEQ ID NO 436
<211> LENGTH: 22
<212> TYPE: RNA
<213> ORGANISM: Homo Sapiens

<400> SEQUENCE: 436
ugagggacag augccagaag ca                                              22

<210> SEQ ID NO 437
<211> LENGTH: 23
<212> TYPE: RNA
<213> ORGANISM: Homo Sapiens

<400> SEQUENCE: 437
gugagugggA gccgguggggG cug                                            23

<210> SEQ ID NO 438
<211> LENGTH: 21
<212> TYPE: RNA
<213> ORGANISM: Homo Sapiens

<400> SEQUENCE: 438
uucaaguaau ucaggauagg u                                               21

<210> SEQ ID NO 439
<211> LENGTH: 21
<212> TYPE: RNA
<213> ORGANISM: Homo Sapiens

<400> SEQUENCE: 439
agggagggac gggggcugug c                                               21

<210> SEQ ID NO 440
<211> LENGTH: 21
<212> TYPE: RNA
<213> ORGANISM: Homo Sapiens

<400> SEQUENCE: 440
gggcuagggc cugcugcccc c                                               21
```

```
<210> SEQ ID NO 441
<211> LENGTH: 22
<212> TYPE: RNA
<213> ORGANISM: Homo Sapiens

<400> SEQUENCE: 441
cggaugagca aagaaagugg uu                                                  22

<210> SEQ ID NO 442
<211> LENGTH: 20
<212> TYPE: RNA
<213> ORGANISM: Homo Sapiens

<400> SEQUENCE: 442
augagcgacu gugccugacc                                                     20

<210> SEQ ID NO 443
<211> LENGTH: 21
<212> TYPE: RNA
<213> ORGANISM: Homo Sapiens

<400> SEQUENCE: 443
ccaaaccagu cgugccugug g                                                   21

<210> SEQ ID NO 444
<211> LENGTH: 22
<212> TYPE: RNA
<213> ORGANISM: Homo Sapiens

<400> SEQUENCE: 444 ccucuuccc  uugucucucc ag                                                  22

<210> SEQ ID NO 445
<211> LENGTH: 24
<212> TYPE: RNA
<213> ORGANISM: Homo Sapiens

<400> SEQUENCE: 445
cugaagugau guguaacuga ucag                                                24

<210> SEQ ID NO 446
<211> LENGTH: 17
<212> TYPE: RNA
<213> ORGANISM: Homo Sapiens

<400> SEQUENCE: 446
cucagugacu caugugc                                                        17

<210> SEQ ID NO 447
<211> LENGTH: 21
<212> TYPE: RNA
<213> ORGANISM: Homo Sapiens

<400> SEQUENCE: 447
ucugaauugu aagaguuguu a                                                   21

<210> SEQ ID NO 448
<211> LENGTH: 21
<212> TYPE: RNA
<213> ORGANISM: Homo Sapiens

<400> SEQUENCE: 448
ggcgcgccca gcucccgggc u                                                   21
```

-continued

```
<210> SEQ ID NO 449
<211> LENGTH: 22
<212> TYPE: RNA
<213> ORGANISM: Homo Sapiens

<400> SEQUENCE: 449
aucuguaaga gaaaguaaau ga                                              22

<210> SEQ ID NO 450
<211> LENGTH: 22
<212> TYPE: RNA
<213> ORGANISM: Homo Sapiens

<400> SEQUENCE: 450
ugagguagua guuuguacag uu                                              22

<210> SEQ ID NO 451
<211> LENGTH: 21
<212> TYPE: RNA
<213> ORGANISM: Homo Sapiens

<400> SEQUENCE: 451
accuccugug ugcauggauu a                                               21

<210> SEQ ID NO 452
<211> LENGTH: 22
<212> TYPE: RNA
<213> ORGANISM: Homo Sapiens

<400> SEQUENCE: 452
caugacguca cagaggcuuc gc                                              22

<210> SEQ ID NO 453
<211> LENGTH: 22
<212> TYPE: RNA
<213> ORGANISM: Homo Sapiens

<400> SEQUENCE: 453
cacacaagug gcccccaaca cu                                              22

<210> SEQ ID NO 454
<211> LENGTH: 19
<212> TYPE: RNA
<213> ORGANISM: Homo Sapiens

<400> SEQUENCE: 454
accaggcaag aaauauugu                                                  19

<210> SEQ ID NO 455
<211> LENGTH: 21
<212> TYPE: RNA
<213> ORGANISM: Homo Sapiens

<400> SEQUENCE: 455
ugcuuaaguu guaccaagua u                                               21

<210> SEQ ID NO 456
<211> LENGTH: 21
<212> TYPE: RNA
<213> ORGANISM: Homo Sapiens

<400> SEQUENCE: 456
gcuugucgcu gcgguguugc u                                               21
```

```
<210> SEQ ID NO 457
<211> LENGTH: 22
<212> TYPE: RNA
<213> ORGANISM: Homo Sapiens

<400> SEQUENCE: 457
ggcuuucuag ucucagcucu cc                                               22

<210> SEQ ID NO 458
<211> LENGTH: 21
<212> TYPE: RNA
<213> ORGANISM: Homo Sapiens

<400> SEQUENCE: 458
gugccagcug cagugggga g                                                 21

<210> SEQ ID NO 459
<211> LENGTH: 21
<212> TYPE: RNA
<213> ORGANISM: Homo Sapiens

<400> SEQUENCE: 459
uggaggagaa ggaaggugau g                                                21

<210> SEQ ID NO 460
<211> LENGTH: 21
<212> TYPE: RNA
<213> ORGANISM: Homo Sapiens

<400> SEQUENCE: 460
ucuaguaaga guggcagucg a                                                21

<210> SEQ ID NO 461
<211> LENGTH: 17
<212> TYPE: RNA
<213> ORGANISM: Homo Sapiens

<400> SEQUENCE: 461
ccggcauguc cagggca                                                     17

<210> SEQ ID NO 462
<211> LENGTH: 24
<212> TYPE: RNA
<213> ORGANISM: Homo Sapiens

<400> SEQUENCE: 462
cccggacagg cguucgugcg acgu                                             24

<210> SEQ ID NO 463
<211> LENGTH: 22
<212> TYPE: RNA
<213> ORGANISM: Homo Sapiens

<400> SEQUENCE: 463
gaagaacugu ugcauuugcc cu                                               22

<210> SEQ ID NO 464
<211> LENGTH: 22
<212> TYPE: RNA
<213> ORGANISM: Homo Sapiens

<400> SEQUENCE: 464
```

```
uuuaagaaaa caccauggag au                                              22

<210> SEQ ID NO 465
<211> LENGTH: 23
<212> TYPE: RNA
<213> ORGANISM: Homo Sapiens

<400> SEQUENCE: 465
ucgaggacug guggaagggc cuu                                             23

<210> SEQ ID NO 466
<211> LENGTH: 22
<212> TYPE: RNA
<213> ORGANISM: Homo Sapiens

<400> SEQUENCE: 466
caugccuuga guguaggacc gu                                              22

<210> SEQ ID NO 467
<211> LENGTH: 21
<212> TYPE: RNA
<213> ORGANISM: Homo Sapiens

<400> SEQUENCE: 467
agggcccccc cucaauccug u                                               21

<210> SEQ ID NO 468
<211> LENGTH: 23
<212> TYPE: RNA
<213> ORGANISM: Homo Sapiens

<400> SEQUENCE: 468
cggguagaga gggcaguggg agg                                             23

<210> SEQ ID NO 469
<211> LENGTH: 22
<212> TYPE: RNA
<213> ORGANISM: Homo Sapiens

<400> SEQUENCE: 469
cuccugacuc cagguccugu gu                                              22

<210> SEQ ID NO 470
<211> LENGTH: 22
<212> TYPE: RNA
<213> ORGANISM: Homo Sapiens

<400> SEQUENCE: 470
caaucacuaa cuccacugcc au                                              22

<210> SEQ ID NO 471
<211> LENGTH: 22
<212> TYPE: RNA
<213> ORGANISM: Homo Sapiens

<400> SEQUENCE: 471
uucuccaaaa gggagcacuu uc                                              22

<210> SEQ ID NO 472
<211> LENGTH: 23
<212> TYPE: RNA
<213> ORGANISM: Homo Sapiens

<400> SEQUENCE: 472
```
ugaguaccgc caugucuguu ggg                                          23

<210> SEQ ID NO 473
<211> LENGTH: 19
<212> TYPE: RNA
<213> ORGANISM: Homo Sapiens

<400> SEQUENCE: 473
acuggaauug gagucaaaa                                               19

<210> SEQ ID NO 474
<211> LENGTH: 23
<212> TYPE: RNA
<213> ORGANISM: Homo Sapiens

<400> SEQUENCE: 474
uaaagugcuu auagugcagg uag                                          23

<210> SEQ ID NO 475
<211> LENGTH: 22
<212> TYPE: RNA
<213> ORGANISM: Homo Sapiens

<400> SEQUENCE: 475
cucaaaccgg cugugccugu gg                                           22

<210> SEQ ID NO 476
<211> LENGTH: 22
<212> TYPE: RNA
<213> ORGANISM: Homo Sapiens

<400> SEQUENCE: 476
uauccagcuu guuacuauau gc                                           22

<210> SEQ ID NO 477
<211> LENGTH: 23
<212> TYPE: RNA
<213> ORGANISM: Homo Sapiens

<400> SEQUENCE: 477
aaaagugcuu acagugcagg uag                                          23

<210> SEQ ID NO 478
<211> LENGTH: 20
<212> TYPE: RNA
<213> ORGANISM: Homo Sapiens

<400> SEQUENCE: 478
aucgcuuuac cauucauguu                                              20

<210> SEQ ID NO 479
<211> LENGTH: 22
<212> TYPE: RNA
<213> ORGANISM: Homo Sapiens

<400> SEQUENCE: 479
aacucugacc ccuuagguug au                                           22

<210> SEQ ID NO 480
<211> LENGTH: 22
<212> TYPE: RNA
<213> ORGANISM: Homo Sapiens

```
<400> SEQUENCE: 480
ugugggaucu ggaggcaucu gg                                              22

<210> SEQ ID NO 481
<211> LENGTH: 21
<212> TYPE: RNA
<213> ORGANISM: Homo Sapiens

<400> SEQUENCE: 481
caacaccagu cgaugggcug u                                               21

<210> SEQ ID NO 482
<211> LENGTH: 21
<212> TYPE: RNA
<213> ORGANISM: Homo Sapiens

<400> SEQUENCE: 482
cucccacaug caggguuugc a                                               21

<210> SEQ ID NO 483
<211> LENGTH: 22
<212> TYPE: RNA
<213> ORGANISM: Homo Sapiens

<400> SEQUENCE: 483
augugccuga gggaguaaga ca                                              22

<210> SEQ ID NO 484
<211> LENGTH: 22
<212> TYPE: RNA
<213> ORGANISM: Homo Sapiens

<400> SEQUENCE: 484
uggucugcaa agagaugacu gu                                              22

<210> SEQ ID NO 485
<211> LENGTH: 22
<212> TYPE: RNA
<213> ORGANISM: Homo Sapiens

<400> SEQUENCE: 485
auuguccuug cuguuuggag au                                              22

<210> SEQ ID NO 486
<211> LENGTH: 21
<212> TYPE: RNA
<213> ORGANISM: Homo Sapiens

<400> SEQUENCE: 486
uguucucuuu gccaaggaca g                                               21

<210> SEQ ID NO 487
<211> LENGTH: 20
<212> TYPE: RNA
<213> ORGANISM: Homo Sapiens

<400> SEQUENCE: 487
guugugucag uuuaucaaac                                                 20

<210> SEQ ID NO 488
<211> LENGTH: 22
<212> TYPE: RNA
<213> ORGANISM: Homo Sapiens
```

```
<400> SEQUENCE: 488
ucagugcauc acagaacuuu gu                                        22

<210> SEQ ID NO 489
<211> LENGTH: 21
<212> TYPE: RNA
<213> ORGANISM: Homo Sapiens

<400> SEQUENCE: 489
uaauuuuaug uauaagcuag u                                         21

<210> SEQ ID NO 490
<211> LENGTH: 21
<212> TYPE: RNA
<213> ORGANISM: Homo Sapiens

<400> SEQUENCE: 490
ggcugggugc ucuugugcag u                                         21

<210> SEQ ID NO 491
<211> LENGTH: 23
<212> TYPE: RNA
<213> ORGANISM: Homo Sapiens

<400> SEQUENCE: 491
caaagacugc aauuacuuuu gcg                                       23

<210> SEQ ID NO 492
<211> LENGTH: 22
<212> TYPE: RNA
<213> ORGANISM: Homo Sapiens

<400> SEQUENCE: 492
aacccguaga uccgaacuug ug                                        22

<210> SEQ ID NO 493
<211> LENGTH: 22
<212> TYPE: RNA
<213> ORGANISM: Homo Sapiens

<400> SEQUENCE: 493
ucaaguaguu ucaugauaaa gg                                        22

<210> SEQ ID NO 494
<211> LENGTH: 23
<212> TYPE: RNA
<213> ORGANISM: Homo Sapiens

<400> SEQUENCE: 494
ucugaguucc uggagccugg ucu                                       23

<210> SEQ ID NO 495
<211> LENGTH: 24
<212> TYPE: RNA
<213> ORGANISM: Homo Sapiens

<400> SEQUENCE: 495
ccugcugguc aggaguggau acug                                      24

<210> SEQ ID NO 496
<211> LENGTH: 18
<212> TYPE: RNA
```

```
<213> ORGANISM: Homo Sapiens

<400> SEQUENCE: 496
cagcagugcg cagggcug                                          18

<210> SEQ ID NO 497
<211> LENGTH: 18
<212> TYPE: RNA
<213> ORGANISM: Homo Sapiens

<400> SEQUENCE: 497
auucuaagug ccuuggcc                                          18

<210> SEQ ID NO 498
<211> LENGTH: 22
<212> TYPE: RNA
<213> ORGANISM: Homo Sapiens

<400> SEQUENCE: 498
agcuacaguu acuuugcac ca                                      22

<210> SEQ ID NO 499
<211> LENGTH: 22
<212> TYPE: RNA
<213> ORGANISM: Homo Sapiens

<400> SEQUENCE: 499
ugaccuggga cucggacagc ug                                     22

<210> SEQ ID NO 500
<211> LENGTH: 18
<212> TYPE: RNA
<213> ORGANISM: Homo Sapiens

<400> SEQUENCE: 500
uggauaugau gacugaaa                                          18

<210> SEQ ID NO 501
<211> LENGTH: 23
<212> TYPE: RNA
<213> ORGANISM: Homo Sapiens

<400> SEQUENCE: 501
ccuggacacc gcucagccgg ccg                                    23

<210> SEQ ID NO 502
<211> LENGTH: 22
<212> TYPE: RNA
<213> ORGANISM: Homo Sapiens

<400> SEQUENCE: 502
ugccugucua cacuugcugu gc                                     22

<210> SEQ ID NO 503
<211> LENGTH: 21
<212> TYPE: RNA
<213> ORGANISM: Homo Sapiens

<400> SEQUENCE: 503
auacauguca gauuguaugc c                                      21

<210> SEQ ID NO 504
<211> LENGTH: 21
```

```
<212> TYPE: RNA
<213> ORGANISM: Homo Sapiens

<400> SEQUENCE: 504
acacuuguug ggaugaccug c                                              21

<210> SEQ ID NO 505
<211> LENGTH: 23
<212> TYPE: RNA
<213> ORGANISM: Homo Sapiens

<400> SEQUENCE: 505
gagggcagcg uggguguggc gga                                            23

<210> SEQ ID NO 506
<211> LENGTH: 23
<212> TYPE: RNA
<213> ORGANISM: Homo Sapiens

<400> SEQUENCE: 506
acuugggcac ugaaacaaug ucc                                            23

<210> SEQ ID NO 507
<211> LENGTH: 23
<212> TYPE: RNA
<213> ORGANISM: Homo Sapiens

<400> SEQUENCE: 507
cagugcaaua guauugucaa agc                                            23

<210> SEQ ID NO 508
<211> LENGTH: 24
<212> TYPE: RNA
<213> ORGANISM: Homo Sapiens

<400> SEQUENCE: 508
uggcccugac ugaagaccag cagu                                           24

<210> SEQ ID NO 509
<211> LENGTH: 21
<212> TYPE: RNA
<213> ORGANISM: Homo Sapiens

<400> SEQUENCE: 509
ugauauguuu gauauugggu u                                              21

<210> SEQ ID NO 510
<211> LENGTH: 22
<212> TYPE: RNA
<213> ORGANISM: Homo Sapiens

<400> SEQUENCE: 510
uccaggcagg agccggacug ga                                             22

<210> SEQ ID NO 511
<211> LENGTH: 22
<212> TYPE: RNA
<213> ORGANISM: Homo Sapiens

<400> SEQUENCE: 511
cuccugagcc auucugagcc uc                                             22

<210> SEQ ID NO 512
```

```
<211> LENGTH: 22
<212> TYPE: RNA
<213> ORGANISM: Homo Sapiens

<400> SEQUENCE: 512
aggcagcggg guguagugga ua                                              22

<210> SEQ ID NO 513
<211> LENGTH: 23
<212> TYPE: RNA
<213> ORGANISM: Homo Sapiens

<400> SEQUENCE: 513
agggacugcc uuaggagaaa guu                                             23

<210> SEQ ID NO 514
<211> LENGTH: 21
<212> TYPE: RNA
<213> ORGANISM: Homo Sapiens

<400> SEQUENCE: 514 acgcccagg cggcauuggu g                                                21

<210> SEQ ID NO 515
<211> LENGTH: 22
<212> TYPE: RNA
<213> ORGANISM: Homo Sapiens

<400> SEQUENCE: 515
gaaguugccc auguuauuuu cg                                              22

<210> SEQ ID NO 516
<211> LENGTH: 21
<212> TYPE: RNA
<213> ORGANISM: Homo Sapiens

<400> SEQUENCE: 516
uaggacuaga uguuggaauu a                                               21

<210> SEQ ID NO 517
<211> LENGTH: 21
<212> TYPE: RNA
<213> ORGANISM: Homo Sapiens

<400> SEQUENCE: 517
uaacgcauaa uauggacaug u                                               21

<210> SEQ ID NO 518
<211> LENGTH: 22
<212> TYPE: RNA
<213> ORGANISM: Homo Sapiens

<400> SEQUENCE: 518
caucuuccag uacaguguug ga                                              22

<210> SEQ ID NO 519
<211> LENGTH: 20
<212> TYPE: RNA
<213> ORGANISM: Homo Sapiens

<400> SEQUENCE: 519
aaaaggcggg agaagcccca                                                 20
```

```
<210> SEQ ID NO 520
<211> LENGTH: 22
<212> TYPE: RNA
<213> ORGANISM: Homo Sapiens

<400> SEQUENCE: 520
acuuguaugc uagcucaggu ag                                                  22

<210> SEQ ID NO 521
<211> LENGTH: 22
<212> TYPE: RNA
<213> ORGANISM: Homo Sapiens

<400> SEQUENCE: 521
cacuguuuca ccacuggcuc uu                                                  22

<210> SEQ ID NO 522
<211> LENGTH: 22
<212> TYPE: RNA
<213> ORGANISM: Homo Sapiens

<400> SEQUENCE: 522
uaggacugug cuuggcacau ag                                                  22

<210> SEQ ID NO 523
<211> LENGTH: 23
<212> TYPE: RNA
<213> ORGANISM: Homo Sapiens

<400> SEQUENCE: 523
uucauuuggu auaaaccgcg auu                                                 23

<210> SEQ ID NO 524
<211> LENGTH: 22
<212> TYPE: RNA
<213> ORGANISM: Homo Sapiens

<400> SEQUENCE: 524
ccuaauuuga acaccuucgg ua                                                  22

<210> SEQ ID NO 525
<211> LENGTH: 22
<212> TYPE: RNA
<213> ORGANISM: Homo Sapiens

<400> SEQUENCE: 525
aagugcuucc uuuuagaggg uu                                                  22

<210> SEQ ID NO 526
<211> LENGTH: 22
<212> TYPE: RNA
<213> ORGANISM: Homo Sapiens

<400> SEQUENCE: 526
uuaucagaau cuccaggggu ac                                                  22

<210> SEQ ID NO 527
<211> LENGTH: 22
<212> TYPE: RNA
<213> ORGANISM: Homo Sapiens

<400> SEQUENCE: 527
ccagagaugg uugccuuccu au                                                  22
```

-continued

<210> SEQ ID NO 528
<211> LENGTH: 21
<212> TYPE: RNA
<213> ORGANISM: Homo Sapiens

<400> SEQUENCE: 528
ugacagcgcc cugccuggcu c                                          21

<210> SEQ ID NO 529
<211> LENGTH: 23
<212> TYPE: RNA
<213> ORGANISM: Homo Sapiens

<400> SEQUENCE: 529
uaaaucccau ggugccuucu ccu                                        23

<210> SEQ ID NO 530
<211> LENGTH: 23
<212> TYPE: RNA
<213> ORGANISM: Homo Sapiens

<400> SEQUENCE: 530
uuagggagua gaagggugggg gag                                       23

<210> SEQ ID NO 531
<211> LENGTH: 21
<212> TYPE: RNA
<213> ORGANISM: Homo Sapiens

<400> SEQUENCE: 531
gcgacccaua cuugguuuca g                                          21

<210> SEQ ID NO 532
<211> LENGTH: 20
<212> TYPE: RNA
<213> ORGANISM: Homo Sapiens

<400> SEQUENCE: 532
gcggagagag aaugggggagc                                           20

<210> SEQ ID NO 533
<211> LENGTH: 23
<212> TYPE: RNA
<213> ORGANISM: Homo Sapiens

<400> SEQUENCE: 533
ugggagggga gaggcagcaa gca                                        23

<210> SEQ ID NO 534
<211> LENGTH: 22
<212> TYPE: RNA
<213> ORGANISM: Homo Sapiens

<400> SEQUENCE: 534
aucacauugc cagugauuac cc                                         22

<210> SEQ ID NO 535
<211> LENGTH: 21
<212> TYPE: RNA
<213> ORGANISM: Homo Sapiens

<400> SEQUENCE: 535
acuggacuag gagucagaag g                                          21

```
<210> SEQ ID NO 536
<211> LENGTH: 22
<212> TYPE: RNA
<213> ORGANISM: Homo Sapiens

<400> SEQUENCE: 536
gcugaacugg gcugagcugg gc                                            22

<210> SEQ ID NO 537
<211> LENGTH: 23
<212> TYPE: RNA
<213> ORGANISM: Homo Sapiens

<400> SEQUENCE: 537
agguuguccg uggugaguuc gca                                           23

<210> SEQ ID NO 538
<211> LENGTH: 21
<212> TYPE: RNA
<213> ORGANISM: Homo Sapiens

<400> SEQUENCE: 538
acacaugggu ggcuguggcc u                                             21

<210> SEQ ID NO 539
<211> LENGTH: 22
<212> TYPE: RNA
<213> ORGANISM: Homo Sapiens

<400> SEQUENCE: 539
aaagugcuuc cuuuuagagg gu                                            22

<210> SEQ ID NO 540
<211> LENGTH: 22
<212> TYPE: RNA
<213> ORGANISM: Homo Sapiens

<400> SEQUENCE: 540
aucgugcauc cuuuuagagu gu                                            22

<210> SEQ ID NO 541
<211> LENGTH: 16
<212> TYPE: RNA
<213> ORGANISM: Homo Sapiens

<400> SEQUENCE: 541
gcagcauuca uguccc                                                   16

<210> SEQ ID NO 542
<211> LENGTH: 20
<212> TYPE: RNA
<213> ORGANISM: Homo Sapiens

<400> SEQUENCE: 542
cugcaaaggg aagcccuuuc                                               20

<210> SEQ ID NO 543
<211> LENGTH: 25
<212> TYPE: RNA
<213> ORGANISM: Homo Sapiens

<400> SEQUENCE: 543
```

```
aggggugguug uugggacagc uccgu                                    25

<210> SEQ ID NO 544
<211> LENGTH: 21
<212> TYPE: RNA
<213> ORGANISM: Homo Sapiens

<400> SEQUENCE: 544
ugggagcuaa gcuaugggua u                                         21

<210> SEQ ID NO 545
<211> LENGTH: 23
<212> TYPE: RNA
<213> ORGANISM: Homo Sapiens

<400> SEQUENCE: 545
uauggagugg acuuucagcu ggc                                       23

<210> SEQ ID NO 546
<211> LENGTH: 21
<212> TYPE: RNA
<213> ORGANISM: Homo Sapiens

<400> SEQUENCE: 546
ucucucggcu ccucgcggcu c                                         21

<210> SEQ ID NO 547
<211> LENGTH: 23
<212> TYPE: RNA
<213> ORGANISM: Homo Sapiens

<400> SEQUENCE: 547
uccaguacca cgugucaggg cca                                       23

<210> SEQ ID NO 548
<211> LENGTH: 21
<212> TYPE: RNA
<213> ORGANISM: Homo Sapiens

<400> SEQUENCE: 548
gcaguucuga gcacaguaca c                                         21

<210> SEQ ID NO 549
<211> LENGTH: 22
<212> TYPE: RNA
<213> ORGANISM: Homo Sapiens

<400> SEQUENCE: 549
ugauuggvac gucugugggu ag                                        22

<210> SEQ ID NO 550
<211> LENGTH: 20
<212> TYPE: RNA
<213> ORGANISM: Homo Sapiens

<400> SEQUENCE: 550
cgcgggucgg ggucugcagg                                           20

<210> SEQ ID NO 551
<211> LENGTH: 22
<212> TYPE: RNA
<213> ORGANISM: Homo Sapiens

<400> SEQUENCE: 551
```
accugccagc accucccugc ag 22

<210> SEQ ID NO 552
<211> LENGTH: 17
<212> TYPE: RNA
<213> ORGANISM: Homo Sapiens

<400> SEQUENCE: 552
gcggggcugg gcgcgcg 17

<210> SEQ ID NO 553
<211> LENGTH: 22
<212> TYPE: RNA
<213> ORGANISM: Homo Sapiens

<400> SEQUENCE: 553
uuaacuccuu ucacacccau gg 22

<210> SEQ ID NO 554
<211> LENGTH: 22
<212> TYPE: RNA
<213> ORGANISM: Homo Sapiens

<400> SEQUENCE: 554
gaggaaacug aagcugagag gg 22

<210> SEQ ID NO 555
<211> LENGTH: 22
<212> TYPE: RNA
<213> ORGANISM: Homo Sapiens

<400> SEQUENCE: 555
uucuggauau gaagacaauc aa 22

<210> SEQ ID NO 556
<211> LENGTH: 23
<212> TYPE: RNA
<213> ORGANISM: Homo Sapiens

<400> SEQUENCE: 556
ucaaaaugua gaggaagacc cca 23

<210> SEQ ID NO 557
<211> LENGTH: 22
<212> TYPE: RNA
<213> ORGANISM: Homo Sapiens

<400> SEQUENCE: 557
ucaaaacuga ggggcauuuu cu 22

<210> SEQ ID NO 558
<211> LENGTH: 22
<212> TYPE: RNA
<213> ORGANISM: Homo Sapiens

<400> SEQUENCE: 558
caacuagacu gugagcuucu ag 22

<210> SEQ ID NO 559
<211> LENGTH: 22
<212> TYPE: RNA
<213> ORGANISM: Homo Sapiens -continued

<400> SEQUENCE: 559
gcuaaggaag uccugugcuc ag                                            22

<210> SEQ ID NO 560
<211> LENGTH: 22
<212> TYPE: RNA
<213> ORGANISM: Homo Sapiens

<400> SEQUENCE: 560
ugagguagua guuugugcug uu                                            22

<210> SEQ ID NO 561
<211> LENGTH: 21
<212> TYPE: RNA
<213> ORGANISM: Homo Sapiens

<400> SEQUENCE: 561
caaaaacugc aauuacuuuc a                                             21

<210> SEQ ID NO 562
<211> LENGTH: 21
<212> TYPE: RNA
<213> ORGANISM: Homo Sapiens

<400> SEQUENCE: 562
gugcauugua guugcauugc a                                             21

<210> SEQ ID NO 563
<211> LENGTH: 18
<212> TYPE: RNA
<213> ORGANISM: Homo Sapiens

<400> SEQUENCE: 563
ccccugggcc ggccuugg                                                 18

<210> SEQ ID NO 564
<211> LENGTH: 20
<212> TYPE: RNA
<213> ORGANISM: Homo Sapiens

<400> SEQUENCE: 564
auuccuagaa auuguucaua                                               20

<210> SEQ ID NO 565
<211> LENGTH: 21
<212> TYPE: RNA
<213> ORGANISM: Homo Sapiens

<400> SEQUENCE: 565
guguugaaac aaucucuacu g                                             21

<210> SEQ ID NO 566
<211> LENGTH: 19
<212> TYPE: RNA
<213> ORGANISM: Homo Sapiens

<400> SEQUENCE: 566
ucaggccucu uucuaccuu                                                19

<210> SEQ ID NO 567
<211> LENGTH: 22
<212> TYPE: RNA
<213> ORGANISM: Homo Sapiens -continued

<400> SEQUENCE: 567
uagguuaucc guguugccuu cg                                          22

<210> SEQ ID NO 568
<211> LENGTH: 21
<212> TYPE: RNA
<213> ORGANISM: Homo Sapiens

<400> SEQUENCE: 568
accacugcac uccagccuga g                                           21

<210> SEQ ID NO 569
<211> LENGTH: 22
<212> TYPE: RNA
<213> ORGANISM: Homo Sapiens

<400> SEQUENCE: 569
cagccacaac uacccugcca cu                                          22

<210> SEQ ID NO 570
<211> LENGTH: 22
<212> TYPE: RNA
<213> ORGANISM: Homo Sapiens

<400> SEQUENCE: 570
aauuuacucu gcaaucuucu cc                                          22

<210> SEQ ID NO 571
<211> LENGTH: 23
<212> TYPE: RNA
<213> ORGANISM: Homo Sapiens

<400> SEQUENCE: 571
caucagcacc cuauguccuu ucu                                         23

<210> SEQ ID NO 572
<211> LENGTH: 22
<212> TYPE: RNA
<213> ORGANISM: Homo Sapiens

<400> SEQUENCE: 572
uauggagguu cuagaccaug uu                                          22

<210> SEQ ID NO 573
<211> LENGTH: 22
<212> TYPE: RNA
<213> ORGANISM: Homo Sapiens

<400> SEQUENCE: 573
agugggaggc cagggcacgg ca                                          22

<210> SEQ ID NO 574
<211> LENGTH: 22
<212> TYPE: RNA
<213> ORGANISM: Homo Sapiens

<400> SEQUENCE: 574
acuaaaggau auagaagguu uu                                          22

<210> SEQ ID NO 575
<211> LENGTH: 18
<212> TYPE: RNA

```
<213> ORGANISM: Homo Sapiens

<400> SEQUENCE: 575
agggcauguc caggggu                                          18

<210> SEQ ID NO 576
<211> LENGTH: 19
<212> TYPE: RNA
<213> ORGANISM: Homo Sapiens

<400> SEQUENCE: 576
ggggagcgag gggcggggc                                        19

<210> SEQ ID NO 577
<211> LENGTH: 22
<212> TYPE: RNA
<213> ORGANISM: Homo Sapiens

<400> SEQUENCE: 577
ucaccagccc uguguucccu ag                                    22

<210> SEQ ID NO 578
<211> LENGTH: 22
<212> TYPE: RNA
<213> ORGANISM: Homo Sapiens

<400> SEQUENCE: 578
ucggauccgu cugagcuugg cu                                    22

<210> SEQ ID NO 579
<211> LENGTH: 22
<212> TYPE: RNA
<213> ORGANISM: Homo Sapiens

<400> SEQUENCE: 579
cuuggauuuu ccugggccuc ag                                    22

<210> SEQ ID NO 580
<211> LENGTH: 22
<212> TYPE: RNA
<213> ORGANISM: Homo Sapiens

<400> SEQUENCE: 580
guuuuaccac cuccaggaga cu                                    22

<210> SEQ ID NO 581
<211> LENGTH: 22
<212> TYPE: RNA
<213> ORGANISM: Homo Sapiens

<400> SEQUENCE: 581
uaugucugcu gaccaucacc uu                                    22

<210> SEQ ID NO 582
<211> LENGTH: 21
<212> TYPE: RNA
<213> ORGANISM: Homo Sapiens

<400> SEQUENCE: 582
aucacauugc cagggauuac c                                     21

<210> SEQ ID NO 583
<211> LENGTH: 22
```

```
<212> TYPE: RNA
<213> ORGANISM: Homo Sapiens

<400> SEQUENCE: 583
uguuguacuu uuuuuuugu uc                                              22

<210> SEQ ID NO 584
<211> LENGTH: 21
<212> TYPE: RNA
<213> ORGANISM: Homo Sapiens

<400> SEQUENCE: 584
guuucaccau guuggucagg c                                              21

<210> SEQ ID NO 585
<211> LENGTH: 22
<212> TYPE: RNA
<213> ORGANISM: Homo Sapiens

<400> SEQUENCE: 585
ucugugauag agauucuuug cu                                             22

<210> SEQ ID NO 586
<211> LENGTH: 22
<212> TYPE: RNA
<213> ORGANISM: Homo Sapiens

<400> SEQUENCE: 586
uaauacuguc ugguaaaacc gu                                             22

<210> SEQ ID NO 587
<211> LENGTH: 23
<212> TYPE: RNA
<213> ORGANISM: Homo Sapiens

<400> SEQUENCE: 587
ccacuuggau cugaaggcug ccc                                            23

<210> SEQ ID NO 588
<211> LENGTH: 22
<212> TYPE: RNA
<213> ORGANISM: Homo Sapiens

<400> SEQUENCE: 588
ucaguuccag gccaaccagg cu                                             22

<210> SEQ ID NO 589
<211> LENGTH: 22
<212> TYPE: RNA
<213> ORGANISM: Homo Sapiens

<400> SEQUENCE: 589
caccggggau ggcagagggu cg                                             22

<210> SEQ ID NO 590
<211> LENGTH: 23
<212> TYPE: RNA
<213> ORGANISM: Homo Sapiens

<400> SEQUENCE: 590
ugauuguagc cuuuuggagu aga                                            23

<210> SEQ ID NO 591
```

```
<211> LENGTH: 21
<212> TYPE: RNA
<213> ORGANISM: Homo Sapiens

<400> SEQUENCE: 591
ccaaaucuug aucagaagcc u                                              21

<210> SEQ ID NO 592
<211> LENGTH: 21
<212> TYPE: RNA
<213> ORGANISM: Homo Sapiens

<400> SEQUENCE: 592
cuuccgcccc gccgggcguc g                                              21

<210> SEQ ID NO 593
<211> LENGTH: 21
<212> TYPE: RNA
<213> ORGANISM: Homo Sapiens

<400> SEQUENCE: 593
agcuguaccu gaaaccaagc a                                              21

<210> SEQ ID NO 594
<211> LENGTH: 22
<212> TYPE: RNA
<213> ORGANISM: Homo Sapiens

<400> SEQUENCE: 594
caucuuacug ggcagcauug ga                                             22

<210> SEQ ID NO 595
<211> LENGTH: 22
<212> TYPE: RNA
<213> ORGANISM: Homo Sapiens

<400> SEQUENCE: 595
cugcccuagu cuagcugaag cu                                             22

<210> SEQ ID NO 596
<211> LENGTH: 22
<212> TYPE: RNA
<213> ORGANISM: Homo Sapiens

<400> SEQUENCE: 596
aaaaguaauu gugguuuuug cc                                             22

<210> SEQ ID NO 597
<211> LENGTH: 22
<212> TYPE: RNA
<213> ORGANISM: Homo Sapiens

<400> SEQUENCE: 597
cuauacaacu uacuacuuuc cc                                             22

<210> SEQ ID NO 598
<211> LENGTH: 18
<212> TYPE: RNA
<213> ORGANISM: Homo Sapiens

<400> SEQUENCE: 598
aauccuugcu accugggu                                                  18
```

<210> SEQ ID NO 599
<211> LENGTH: 23
<212> TYPE: RNA
<213> ORGANISM: Homo Sapiens

<400> SEQUENCE: 599
ccuaguaggu guccaguaag ugu                                              23

<210> SEQ ID NO 600
<211> LENGTH: 23
<212> TYPE: RNA
<213> ORGANISM: Homo Sapiens

<400> SEQUENCE: 600
cgcauccccu agggcauugg ugu                                              23

<210> SEQ ID NO 601
<211> LENGTH: 22
<212> TYPE: RNA
<213> ORGANISM: Homo Sapiens

<400> SEQUENCE: 601
aaccccuaag gcaacuggau gg                                               22

<210> SEQ ID NO 602
<211> LENGTH: 21
<212> TYPE: RNA
<213> ORGANISM: Homo Sapiens

<400> SEQUENCE: 602
gaguguaguu cugagcagag c                                                21

<210> SEQ ID NO 603
<211> LENGTH: 20
<212> TYPE: RNA
<213> ORGANISM: Homo Sapiens

<400> SEQUENCE: 603
gguauccguu uggggauggu                                                  20

<210> SEQ ID NO 604
<211> LENGTH: 22
<212> TYPE: RNA
<213> ORGANISM: Homo Sapiens

<400> SEQUENCE: 604
ccuauucuug guuacuugca cg                                               22

<210> SEQ ID NO 605
<211> LENGTH: 22
<212> TYPE: RNA
<213> ORGANISM: Homo Sapiens

<400> SEQUENCE: 605
ugugagguug gcauuguugu cu                                               22

<210> SEQ ID NO 606
<211> LENGTH: 22
<212> TYPE: RNA
<213> ORGANISM: Homo Sapiens

<400> SEQUENCE: 606
aguugccagg gcugccuuug gu                                               22

<210> SEQ ID NO 607
<211> LENGTH: 22
<212> TYPE: RNA
<213> ORGANISM: Homo Sapiens

<400> SEQUENCE: 607
cucauuuaag uagucugaug cc                                              22

<210> SEQ ID NO 608
<211> LENGTH: 21
<212> TYPE: RNA
<213> ORGANISM: Homo Sapiens

<400> SEQUENCE: 608
cgucccaccc cccacuccug u                                               21

<210> SEQ ID NO 609
<211> LENGTH: 22
<212> TYPE: RNA
<213> ORGANISM: Homo Sapiens

<400> SEQUENCE: 609
uucagccagg cuagugcagu cu                                              22

<210> SEQ ID NO 610
<211> LENGTH: 25
<212> TYPE: RNA
<213> ORGANISM: Homo Sapiens

<400> SEQUENCE: 610
aaaaaccaca auuacuuuug cacca                                           25

<210> SEQ ID NO 611
<211> LENGTH: 21
<212> TYPE: RNA
<213> ORGANISM: Homo Sapiens

<400> SEQUENCE: 611
auugccuaac augugccaga a                                               21

<210> SEQ ID NO 612
<211> LENGTH: 22
<212> TYPE: RNA
<213> ORGANISM: Homo Sapiens

<400> SEQUENCE: 612
aacgccauua ucacacuaaa ua                                              22

<210> SEQ ID NO 613
<211> LENGTH: 22
<212> TYPE: RNA
<213> ORGANISM: Homo Sapiens

<400> SEQUENCE: 613
aaucauacac gguugaccua uu                                              22

<210> SEQ ID NO 614
<211> LENGTH: 22
<212> TYPE: RNA
<213> ORGANISM: Homo Sapiens

<400> SEQUENCE: 614
cugugcgugu gacagcggcu ga                                              22

```
<210> SEQ ID NO 615
<211> LENGTH: 23
<212> TYPE: RNA
<213> ORGANISM: Homo Sapiens

<400> SEQUENCE: 615
cuggagauau ggaagagcug ugu                                         23

<210> SEQ ID NO 616
<211> LENGTH: 17
<212> TYPE: RNA
<213> ORGANISM: Homo Sapiens

<400> SEQUENCE: 616
gaguucuaca gucagac                                                17

<210> SEQ ID NO 617
<211> LENGTH: 23
<212> TYPE: RNA
<213> ORGANISM: Homo Sapiens

<400> SEQUENCE: 617
cugggaucuc cggggucuug guu                                         23

<210> SEQ ID NO 618
<211> LENGTH: 20
<212> TYPE: RNA
<213> ORGANISM: Homo Sapiens

<400> SEQUENCE: 618
ccugcguguu uucuguccaa                                             20

<210> SEQ ID NO 619
<211> LENGTH: 21
<212> TYPE: RNA
<213> ORGANISM: Homo Sapiens

<400> SEQUENCE: 619
ugagaugaag cacuguagcu c                                           21

<210> SEQ ID NO 620
<211> LENGTH: 18
<212> TYPE: RNA
<213> ORGANISM: Homo Sapiens

<400> SEQUENCE: 620
cagccccaca gccucaga                                               18

<210> SEQ ID NO 621
<211> LENGTH: 22
<212> TYPE: RNA
<213> ORGANISM: Homo Sapiens

<400> SEQUENCE: 621
ccugacccac ccccucccgc ag                                          22

<210> SEQ ID NO 622
<211> LENGTH: 23
<212> TYPE: RNA
<213> ORGANISM: Homo Sapiens

<400> SEQUENCE: 622
``` cuggggacg cgugagcgcg agc                                         23

<210> SEQ ID NO 623
<211> LENGTH: 18
<212> TYPE: RNA
<213> ORGANISM: Homo Sapiens

<400> SEQUENCE: 623
ugcuuccuuu cagagggu                                              18

<210> SEQ ID NO 624
<211> LENGTH: 23
<212> TYPE: RNA
<213> ORGANISM: Homo Sapiens

<400> SEQUENCE: 624
uaagugcuuc cauguuuugg uga                                        23

<210> SEQ ID NO 625
<211> LENGTH: 22
<212> TYPE: RNA
<213> ORGANISM: Homo Sapiens

<400> SEQUENCE: 625
uuguucuuug gucuuucagc ca                                         22

<210> SEQ ID NO 626
<211> LENGTH: 23
<212> TYPE: RNA
<213> ORGANISM: Homo Sapiens

<400> SEQUENCE: 626
uacccuguag aaccgaauuu gug                                        23

<210> SEQ ID NO 627
<211> LENGTH: 22
<212> TYPE: RNA
<213> ORGANISM: Homo Sapiens

<400> SEQUENCE: 627
aaguucuguu auacacucag gc                                         22

<210> SEQ ID NO 628
<211> LENGTH: 22
<212> TYPE: RNA
<213> ORGANISM: Homo Sapiens

<400> SEQUENCE: 628
gcaguagugu agagauuggu uu                                         22

<210> SEQ ID NO 629
<211> LENGTH: 18
<212> TYPE: RNA
<213> ORGANISM: Homo Sapiens

<400> SEQUENCE: 629
gcuggugaca ugagaggc                                              18

<210> SEQ ID NO 630
<211> LENGTH: 22
<212> TYPE: RNA
<213> ORGANISM: Homo Sapiens

<400> SEQUENCE: 630
cugccagccc cguccaggg ca                                          22

<210> SEQ ID NO 631
<211> LENGTH: 22
<212> TYPE: RNA
<213> ORGANISM: Homo Sapiens

<400> SEQUENCE: 631
aagugcuguc auagcugagg uc                                         22

<210> SEQ ID NO 632
<211> LENGTH: 20
<212> TYPE: RNA
<213> ORGANISM: Homo Sapiens

<400> SEQUENCE: 632
ggauccgagu cacggcacca                                            20

<210> SEQ ID NO 633
<211> LENGTH: 23
<212> TYPE: RNA
<213> ORGANISM: Homo Sapiens

<400> SEQUENCE: 633
caauggcaca aacucauucu uga                                        23

<210> SEQ ID NO 634
<211> LENGTH: 23
<212> TYPE: RNA
<213> ORGANISM: Homo Sapiens

<400> SEQUENCE: 634
agcucggucu gaggccccuc agu                                        23

<210> SEQ ID NO 635
<211> LENGTH: 21
<212> TYPE: RNA
<213> ORGANISM: Homo Sapiens

<400> SEQUENCE: 635
ccaguccugu gccugccgcc u                                          21

<210> SEQ ID NO 636
<211> LENGTH: 22
<212> TYPE: RNA
<213> ORGANISM: Homo Sapiens

<400> SEQUENCE: 636
cuagguaugg ucccagggau cc                                         22

<210> SEQ ID NO 637
<211> LENGTH: 22
<212> TYPE: RNA
<213> ORGANISM: Homo Sapiens

<400> SEQUENCE: 637
aaucguacag ggucauccac uu                                         22

<210> SEQ ID NO 638
<211> LENGTH: 20
<212> TYPE: RNA
<213> ORGANISM: Homo Sapiens

```
<400> SEQUENCE: 638
ggcggcggcg gaggcggggg                                              20

<210> SEQ ID NO 639
<211> LENGTH: 17
<212> TYPE: RNA
<213> ORGANISM: Homo Sapiens

<400> SEQUENCE: 639
uucugagcug aggacag                                                 17

<210> SEQ ID NO 640
<211> LENGTH: 24
<212> TYPE: RNA
<213> ORGANISM: Homo Sapiens

<400> SEQUENCE: 640
uggguagaga aggagcucag agga                                         24

<210> SEQ ID NO 641
<211> LENGTH: 21
<212> TYPE: RNA
<213> ORGANISM: Homo Sapiens

<400> SEQUENCE: 641
ugagcuaaau gugugcuggg a                                            21

<210> SEQ ID NO 642
<211> LENGTH: 22
<212> TYPE: RNA
<213> ORGANISM: Homo Sapiens

<400> SEQUENCE: 642
caaagugccu cccuuuagag ug                                           22

<210> SEQ ID NO 643
<211> LENGTH: 22
<212> TYPE: RNA
<213> ORGANISM: Homo Sapiens

<400> SEQUENCE: 643
gguccagagg ggagauaggu uc                                           22

<210> SEQ ID NO 644
<211> LENGTH: 22
<212> TYPE: RNA
<213> ORGANISM: Homo Sapiens

<400> SEQUENCE: 644
uuuagauuga acaugaaguu ag                                           22

<210> SEQ ID NO 645
<211> LENGTH: 21
<212> TYPE: RNA
<213> ORGANISM: Homo Sapiens

<400> SEQUENCE: 645
ugugguagau auaugcacga u                                            21

<210> SEQ ID NO 646
<211> LENGTH: 21
<212> TYPE: RNA
<213> ORGANISM: Homo Sapiens
```

-continued

<400> SEQUENCE: 646
aggcaagaug cuggcauagc u                                           21

<210> SEQ ID NO 647
<211> LENGTH: 20
<212> TYPE: RNA
<213> ORGANISM: Homo Sapiens

<400> SEQUENCE: 647
aauaauauca caguaggugu                                             20

<210> SEQ ID NO 648
<211> LENGTH: 22
<212> TYPE: RNA
<213> ORGANISM: Homo Sapiens

<400> SEQUENCE: 648
auauguauau gugacugcua cu                                          22

<210> SEQ ID NO 649
<211> LENGTH: 23
<212> TYPE: RNA
<213> ORGANISM: Homo Sapiens

<400> SEQUENCE: 649
aacauucauu guugucggug ggu                                         23

<210> SEQ ID NO 650
<211> LENGTH: 22
<212> TYPE: RNA
<213> ORGANISM: Homo Sapiens

<400> SEQUENCE: 650
agacccuggu cugcacucua uc                                          22

<210> SEQ ID NO 651
<211> LENGTH: 23
<212> TYPE: RNA
<213> ORGANISM: Homo Sapiens

<400> SEQUENCE: 651
ccaguuaccg cuuccgcuac cgc                                         23

<210> SEQ ID NO 652
<211> LENGTH: 25
<212> TYPE: RNA
<213> ORGANISM: Homo Sapiens

<400> SEQUENCE: 652
gcugggcagg gcuucugagc uccuu                                       25

<210> SEQ ID NO 653
<211> LENGTH: 22
<212> TYPE: RNA
<213> ORGANISM: Homo Sapiens

<400> SEQUENCE: 653
uggugggcac agaaucugga cu                                          22

<210> SEQ ID NO 654
<211> LENGTH: 21
<212> TYPE: RNA

```
<213> ORGANISM: Homo Sapiens

<400> SEQUENCE: 654
gaaagcgcuu cucuuuagag g                                              21

<210> SEQ ID NO 655
<211> LENGTH: 22
<212> TYPE: RNA
<213> ORGANISM: Homo Sapiens

<400> SEQUENCE: 655
uuuaagcagg aaauagaauu ua                                             22

<210> SEQ ID NO 656
<211> LENGTH: 22
<212> TYPE: RNA
<213> ORGANISM: Homo Sapiens

<400> SEQUENCE: 656
ggggcugggg ccggggccga gc                                             22

<210> SEQ ID NO 657
<211> LENGTH: 22
<212> TYPE: RNA
<213> ORGANISM: Homo Sapiens

<400> SEQUENCE: 657
cugguacagg ccuggggac ag                                              22

<210> SEQ ID NO 658
<211> LENGTH: 20
<212> TYPE: RNA
<213> ORGANISM: Homo Sapiens

<400> SEQUENCE: 658
ucacuaccug acaauacagu                                                20

<210> SEQ ID NO 659
<211> LENGTH: 22
<212> TYPE: RNA
<213> ORGANISM: Homo Sapiens

<400> SEQUENCE: 659
gaaaguaauu gcuguuuug cc                                              22

<210> SEQ ID NO 660
<211> LENGTH: 21
<212> TYPE: RNA
<213> ORGANISM: Homo Sapiens

<400> SEQUENCE: 660
uacccagucu ccggugcagc c                                              21

<210> SEQ ID NO 661
<211> LENGTH: 21
<212> TYPE: RNA
<213> ORGANISM: Homo Sapiens

<400> SEQUENCE: 661
cauuauuacu uuggguacgc g                                              21

<210> SEQ ID NO 662
<211> LENGTH: 22
```

```
<212> TYPE: RNA
<213> ORGANISM: Homo Sapiens

<400> SEQUENCE: 662
cugggaggug ugauauugug gu                                    22

<210> SEQ ID NO 663
<211> LENGTH: 22
<212> TYPE: RNA
<213> ORGANISM: Homo Sapiens

<400> SEQUENCE: 663
caaaccacac ugugguguua ga                                    22

<210> SEQ ID NO 664
<211> LENGTH: 22
<212> TYPE: RNA
<213> ORGANISM: Homo Sapiens

<400> SEQUENCE: 664
gucacugaug ucuguagcug ag                                    22

<210> SEQ ID NO 665
<211> LENGTH: 21
<212> TYPE: RNA
<213> ORGANISM: Homo Sapiens

<400> SEQUENCE: 665
aguuaggauu aggucgugga a                                     21

<210> SEQ ID NO 666
<211> LENGTH: 21
<212> TYPE: RNA
<213> ORGANISM: Homo Sapiens

<400> SEQUENCE: 666
cccagauaau ggcacucuca a                                     21

<210> SEQ ID NO 667
<211> LENGTH: 23
<212> TYPE: RNA
<213> ORGANISM: Homo Sapiens

<400> SEQUENCE: 667
acugggaugu cacugaauau ggu                                   23

<210> SEQ ID NO 668
<211> LENGTH: 18
<212> TYPE: RNA
<213> ORGANISM: Homo Sapiens

<400> SEQUENCE: 668
ccgcuuucug agcuggac                                         18

<210> SEQ ID NO 669
<211> LENGTH: 24
<212> TYPE: RNA
<213> ORGANISM: Homo Sapiens

<400> SEQUENCE: 669
uguggacagu gagguagagg gagu                                  24

<210> SEQ ID NO 670
```

```
<211> LENGTH: 22
<212> TYPE: RNA
<213> ORGANISM: Homo Sapiens

<400> SEQUENCE: 670
aaagauggac aauuggcuaa au                                              22

<210> SEQ ID NO 671
<211> LENGTH: 21
<212> TYPE: RNA
<213> ORGANISM: Homo Sapiens

<400> SEQUENCE: 671
cuguccuaag guuguugagu u                                               21

<210> SEQ ID NO 672
<211> LENGTH: 22
<212> TYPE: RNA
<213> ORGANISM: Homo Sapiens

<400> SEQUENCE: 672
aaggccuuuc ugaaccuuca ga                                              22

<210> SEQ ID NO 673
<211> LENGTH: 22
<212> TYPE: RNA
<213> ORGANISM: Homo Sapiens

<400> SEQUENCE: 673
ugggccaugc auuucuagaa cu                                              22

<210> SEQ ID NO 674
<211> LENGTH: 19
<212> TYPE: RNA
<213> ORGANISM: Homo Sapiens

<400> SEQUENCE: 674
aucgggcccu cggcgccgg                                                  19

<210> SEQ ID NO 675
<211> LENGTH: 23
<212> TYPE: RNA
<213> ORGANISM: Homo Sapiens

<400> SEQUENCE: 675
ugggcagggg cuuauuguag gag                                             23

<210> SEQ ID NO 676
<211> LENGTH: 22
<212> TYPE: RNA
<213> ORGANISM: Homo Sapiens

<400> SEQUENCE: 676
cagguagaua uuugauaggc au                                              22

<210> SEQ ID NO 677
<211> LENGTH: 22
<212> TYPE: RNA
<213> ORGANISM: Homo Sapiens

<400> SEQUENCE: 677
uccuccucua ccucauccca gu                                              22
```

```
<210> SEQ ID NO 678
<211> LENGTH: 22
<212> TYPE: RNA
<213> ORGANISM: Homo Sapiens

<400> SEQUENCE: 678
aucauagagg aaaauccaug uu                                              22

<210> SEQ ID NO 679
<211> LENGTH: 22
<212> TYPE: RNA
<213> ORGANISM: Homo Sapiens

<400> SEQUENCE: 679 caguugggic uaggggucag ga                                              22

<210> SEQ ID NO 680
<211> LENGTH: 19
<212> TYPE: RNA
<213> ORGANISM: Homo Sapiens

<400> SEQUENCE: 680
gggcgccugu gaucccaac                                                  19

<210> SEQ ID NO 681
<211> LENGTH: 23
<212> TYPE: RNA
<213> ORGANISM: Homo Sapiens

<400> SEQUENCE: 681
uggagacgcg gcccuguugg agu                                             23

<210> SEQ ID NO 682
<211> LENGTH: 21
<212> TYPE: RNA
<213> ORGANISM: Homo Sapiens

<400> SEQUENCE: 682
gcuaguccug acucagccag u                                               21

<210> SEQ ID NO 683
<211> LENGTH: 20
<212> TYPE: RNA
<213> ORGANISM: Homo Sapiens

<400> SEQUENCE: 683
ccugcguguu uucuguccaa                                                 20

<210> SEQ ID NO 684
<211> LENGTH: 20
<212> TYPE: RNA
<213> ORGANISM: Homo Sapiens

<400> SEQUENCE: 684
acucaaacug uggggggcacu                                                20

<210> SEQ ID NO 685
<211> LENGTH: 22
<212> TYPE: RNA
<213> ORGANISM: Homo Sapiens

<400> SEQUENCE: 685
cuuaugcaag auucccuucu ac                                              22
```

-continued

<210> SEQ ID NO 686
<211> LENGTH: 22
<212> TYPE: RNA
<213> ORGANISM: Homo Sapiens

<400> SEQUENCE: 686
ucuucuuccu uugcagaguu ga                                               22

<210> SEQ ID NO 687
<211> LENGTH: 22
<212> TYPE: RNA
<213> ORGANISM: Homo Sapiens

<400> SEQUENCE: 687
cugccauguc uaagaagaaa ac                                               22

<210> SEQ ID NO 688
<211> LENGTH: 22
<212> TYPE: RNA
<213> ORGANISM: Homo Sapiens

<400> SEQUENCE: 688
auggcaucgu ccccuggugg cu                                               22

<210> SEQ ID NO 689
<211> LENGTH: 22
<212> TYPE: RNA
<213> ORGANISM: Homo Sapiens

<400> SEQUENCE: 689
ucuucucugu uuuggccaug ug                                               22

<210> SEQ ID NO 690
<211> LENGTH: 21
<212> TYPE: RNA
<213> ORGANISM: Homo Sapiens

<400> SEQUENCE: 690
ucagugcaug acagaacuug g                                                21

<210> SEQ ID NO 691
<211> LENGTH: 22
<212> TYPE: RNA
<213> ORGANISM: Homo Sapiens

<400> SEQUENCE: 691
acuggacuua gggucagaag gc                                               22

<210> SEQ ID NO 692
<211> LENGTH: 16
<212> TYPE: RNA
<213> ORGANISM: Homo Sapiens

<400> SEQUENCE: 692
aggaaacagg gaccca                                                      16

<210> SEQ ID NO 693
<211> LENGTH: 21
<212> TYPE: RNA
<213> ORGANISM: Homo Sapiens

<400> SEQUENCE: 693
aacauagagg aaauuccacg u                                                21

<210> SEQ ID NO 694
<211> LENGTH: 21
<212> TYPE: RNA
<213> ORGANISM: Homo Sapiens

<400> SEQUENCE: 694
guaccuucug guucagcuag u                                              21

<210> SEQ ID NO 695
<211> LENGTH: 22
<212> TYPE: RNA
<213> ORGANISM: Homo Sapiens

<400> SEQUENCE: 695
ugagacaggc uuaugcugcu au                                             22

<210> SEQ ID NO 696
<211> LENGTH: 22
<212> TYPE: RNA
<213> ORGANISM: Homo Sapiens

<400> SEQUENCE: 696
ggagacugau gaguucccgg ga                                             22

<210> SEQ ID NO 697
<211> LENGTH: 22
<212> TYPE: RNA
<213> ORGANISM: Homo Sapiens

<400> SEQUENCE: 697
uguaaacauc cuacacucag cu                                             22

<210> SEQ ID NO 698
<211> LENGTH: 22
<212> TYPE: RNA
<213> ORGANISM: Homo Sapiens

<400> SEQUENCE: 698
uuagaacguu uuagggucaa au                                             22

<210> SEQ ID NO 699
<211> LENGTH: 23
<212> TYPE: RNA
<213> ORGANISM: Homo Sapiens

<400> SEQUENCE: 699 ugcccaccu gcugaccacc cuc                                             23

<210> SEQ ID NO 700
<211> LENGTH: 22
<212> TYPE: RNA
<213> ORGANISM: Homo Sapiens

<400> SEQUENCE: 700
auaaagcuag auaaccgaaa gu                                             22

<210> SEQ ID NO 701
<211> LENGTH: 22
<212> TYPE: RNA
<213> ORGANISM: Homo Sapiens

<400> SEQUENCE: 701
aacacaccua uucaaggauu ca                                                22

<210> SEQ ID NO 702
<211> LENGTH: 22
<212> TYPE: RNA
<213> ORGANISM: Homo Sapiens

<400> SEQUENCE: 702
augguacccu ggcauacuga gu                                                22

<210> SEQ ID NO 703
<211> LENGTH: 22
<212> TYPE: RNA
<213> ORGANISM: Homo Sapiens

<400> SEQUENCE: 703 aggggggcgca gucacugacg ug                                               22

<210> SEQ ID NO 704
<211> LENGTH: 22
<212> TYPE: RNA
<213> ORGANISM: Homo Sapiens

<400> SEQUENCE: 704
uaucauggag uugguaaagc ac                                                22

<210> SEQ ID NO 705
<211> LENGTH: 22
<212> TYPE: RNA
<213> ORGANISM: Homo Sapiens

<400> SEQUENCE: 705
uuccagcccu ucuaauggua gg                                                22

<210> SEQ ID NO 706
<211> LENGTH: 20
<212> TYPE: RNA
<213> ORGANISM: Homo Sapiens

<400> SEQUENCE: 706
gguagugagu uaucagcuac                                                   20

<210> SEQ ID NO 707
<211> LENGTH: 20
<212> TYPE: RNA
<213> ORGANISM: Homo Sapiens

<400> SEQUENCE: 707
aaaagcuggg cugagaggcg                                                   20

<210> SEQ ID NO 708
<211> LENGTH: 22
<212> TYPE: RNA
<213> ORGANISM: Homo Sapiens

<400> SEQUENCE: 708
uguguggauc cuggaggagg ca                                                22

<210> SEQ ID NO 709
<211> LENGTH: 21
<212> TYPE: RNA
<213> ORGANISM: Homo Sapiens

<400> SEQUENCE: 709
uuagaccuag uacacguccu u                            21

<210> SEQ ID NO 710
<211> LENGTH: 21
<212> TYPE: RNA
<213> ORGANISM: Homo Sapiens

<400> SEQUENCE: 710
agugaaugau ggguucugac c                            21

<210> SEQ ID NO 711
<211> LENGTH: 23
<212> TYPE: RNA
<213> ORGANISM: Homo Sapiens

<400> SEQUENCE: 711
ugcaucaggc cagaagacau gag                          23

<210> SEQ ID NO 712
<211> LENGTH: 22
<212> TYPE: RNA
<213> ORGANISM: Homo Sapiens

<400> SEQUENCE: 712
aaaaugaaau gagcccagcc ca                           22

<210> SEQ ID NO 713
<211> LENGTH: 19
<212> TYPE: RNA
<213> ORGANISM: Homo Sapiens

<400> SEQUENCE: 713
aaggggcugg gggagcaca                               19

<210> SEQ ID NO 714
<211> LENGTH: 22
<212> TYPE: RNA
<213> ORGANISM: Homo Sapiens

<400> SEQUENCE: 714 acugggagc agaaggagaa cc                            22

<210> SEQ ID NO 715
<211> LENGTH: 22
<212> TYPE: RNA
<213> ORGANISM: Homo Sapiens

<400> SEQUENCE: 715
ccaggaggcg gaggaggugg ag                           22

<210> SEQ ID NO 716
<211> LENGTH: 22
<212> TYPE: RNA
<213> ORGANISM: Homo Sapiens

<400> SEQUENCE: 716
ugagaacuga auuccauagg cu                           22

<210> SEQ ID NO 717
<211> LENGTH: 23
<212> TYPE: RNA
<213> ORGANISM: Homo Sapiens

<400> SEQUENCE: 717
acuucaccug guccacuagc cgu					23

<210> SEQ ID NO 718
<211> LENGTH: 19
<212> TYPE: RNA
<213> ORGANISM: Homo Sapiens

<400> SEQUENCE: 718
aggugugucu guagagucc					19

<210> SEQ ID NO 719
<211> LENGTH: 21
<212> TYPE: RNA
<213> ORGANISM: Homo Sapiens

<400> SEQUENCE: 719
acuggacuug gagucagaag g					21

<210> SEQ ID NO 720
<211> LENGTH: 22
<212> TYPE: RNA
<213> ORGANISM: Homo Sapiens

<400> SEQUENCE: 720
aacucacgaa guauaccgaa gu					22

<210> SEQ ID NO 721
<211> LENGTH: 22
<212> TYPE: RNA
<213> ORGANISM: Homo Sapiens

<400> SEQUENCE: 721
guauacaccu gauaugugua ug					22

<210> SEQ ID NO 722
<211> LENGTH: 22
<212> TYPE: RNA
<213> ORGANISM: Homo Sapiens

<400> SEQUENCE: 722
aaccagcacc ccaacuuugg ac					22

<210> SEQ ID NO 723
<211> LENGTH: 23
<212> TYPE: RNA
<213> ORGANISM: Homo Sapiens

<400> SEQUENCE: 723
uaucugcugg gcuuucuggu guu					23

<210> SEQ ID NO 724
<211> LENGTH: 22
<212> TYPE: RNA
<213> ORGANISM: Homo Sapiens

<400> SEQUENCE: 724 uuugguccccc uucaaccagc ua					22

<210> SEQ ID NO 725
<211> LENGTH: 21
<212> TYPE: RNA
<213> ORGANISM: Homo Sapiens

```
<400> SEQUENCE: 725
gcuggucugc guggugcucg g                                        21

<210> SEQ ID NO 726
<211> LENGTH: 22
<212> TYPE: RNA
<213> ORGANISM: Homo Sapiens

<400> SEQUENCE: 726
caaaaacugc aguuacuuuu gc                                       22

<210> SEQ ID NO 727
<211> LENGTH: 23
<212> TYPE: RNA
<213> ORGANISM: Homo Sapiens

<400> SEQUENCE: 727
aguauguucu uccaggacag aac                                      23

<210> SEQ ID NO 728
<211> LENGTH: 25
<212> TYPE: RNA
<213> ORGANISM: Homo Sapiens

<400> SEQUENCE: 728
caugcugacc ucccuccugc cccag                                    25

<210> SEQ ID NO 729
<211> LENGTH: 23
<212> TYPE: RNA
<213> ORGANISM: Homo Sapiens

<400> SEQUENCE: 729
uggggacgua gcuggccaga cag                                      23

<210> SEQ ID NO 730
<211> LENGTH: 22
<212> TYPE: RNA
<213> ORGANISM: Homo Sapiens

<400> SEQUENCE: 730
cuuccggucu gugagccccg uc                                       22

<210> SEQ ID NO 731
<211> LENGTH: 19
<212> TYPE: RNA
<213> ORGANISM: Homo Sapiens

<400> SEQUENCE: 731
uugccauguc uaagaagaa                                           19

<210> SEQ ID NO 732
<211> LENGTH: 21
<212> TYPE: RNA
<213> ORGANISM: Homo Sapiens

<400> SEQUENCE: 732
auagcagcau aagccugucu c                                        21

<210> SEQ ID NO 733
<211> LENGTH: 20
<212> TYPE: RNA
```

<213> ORGANISM: Homo Sapiens

<400> SEQUENCE: 733
guccgcucgg cgguggccca                    20

<210> SEQ ID NO 734
<211> LENGTH: 22
<212> TYPE: RNA
<213> ORGANISM: Homo Sapiens

<400> SEQUENCE: 734
gcuggugcaa aaguaauggc gg                 22

<210> SEQ ID NO 735
<211> LENGTH: 22
<212> TYPE: RNA
<213> ORGANISM: Homo Sapiens

<400> SEQUENCE: 735
uagcagcaca ucaugguuua ca                 22

<210> SEQ ID NO 736
<211> LENGTH: 17
<212> TYPE: RNA
<213> ORGANISM: Homo Sapiens

<400> SEQUENCE: 736
gaggcugagc ugaggag                       17

<210> SEQ ID NO 737
<211> LENGTH: 20
<212> TYPE: RNA
<213> ORGANISM: Homo Sapiens

<400> SEQUENCE: 737
uguuuugaua acaguaaugu                    20

<210> SEQ ID NO 738
<211> LENGTH: 19
<212> TYPE: RNA
<213> ORGANISM: Homo Sapiens

<400> SEQUENCE: 738
aauguuuuuu ccuguuucc                     19

<210> SEQ ID NO 739
<211> LENGTH: 21
<212> TYPE: RNA
<213> ORGANISM: Homo Sapiens

<400> SEQUENCE: 739
agccgcgggg aucgccgagg g                  21

<210> SEQ ID NO 740
<211> LENGTH: 22
<212> TYPE: RNA
<213> ORGANISM: Homo Sapiens

<400> SEQUENCE: 740
cccugugccc ggcccacuuc ug                 22

<210> SEQ ID NO 741
<211> LENGTH: 22

```
<212> TYPE: RNA
<213> ORGANISM: Homo Sapiens

<400> SEQUENCE: 741
cuggcccucu cugcccuucc gu                                               22

<210> SEQ ID NO 742
<211> LENGTH: 22
<212> TYPE: RNA
<213> ORGANISM: Homo Sapiens

<400> SEQUENCE: 742
ucucugggcc ugugucuuag gc                                               22

<210> SEQ ID NO 743
<211> LENGTH: 23
<212> TYPE: RNA
<213> ORGANISM: Homo Sapiens

<400> SEQUENCE: 743
ggaggcgcag gcucggaaag gcg                                              23

<210> SEQ ID NO 744
<211> LENGTH: 23
<212> TYPE: RNA
<213> ORGANISM: Homo Sapiens

<400> SEQUENCE: 744
ucuacagugc acgugucucc agu                                              23

<210> SEQ ID NO 745
<211> LENGTH: 23
<212> TYPE: RNA
<213> ORGANISM: Homo Sapiens

<400> SEQUENCE: 745
cacccggcug ugugcacaug ugc                                              23

<210> SEQ ID NO 746
<211> LENGTH: 24
<212> TYPE: RNA
<213> ORGANISM: Homo Sapiens

<400> SEQUENCE: 746
aggagcagug ccggccaagg cgcc                                             24

<210> SEQ ID NO 747
<211> LENGTH: 21
<212> TYPE: RNA
<213> ORGANISM: Homo Sapiens

<400> SEQUENCE: 747
agaaguggcu aauaauauug a                                                21

<210> SEQ ID NO 748
<211> LENGTH: 21
<212> TYPE: RNA
<213> ORGANISM: Homo Sapiens

<400> SEQUENCE: 748
cucacugaac aaugaaugca a                                                21

<210> SEQ ID NO 749
```

```
<211> LENGTH: 22
<212> TYPE: RNA
<213> ORGANISM: Homo Sapiens

<400> SEQUENCE: 749
gcucugacuu uauugcacua cu                                            22

<210> SEQ ID NO 750
<211> LENGTH: 21
<212> TYPE: RNA
<213> ORGANISM: Homo Sapiens

<400> SEQUENCE: 750
uuaauaucgg acaaccauug u                                             21

<210> SEQ ID NO 751
<211> LENGTH: 20
<212> TYPE: RNA
<213> ORGANISM: Homo Sapiens

<400> SEQUENCE: 751
gugagucagg gugggggcugg                                              20

<210> SEQ ID NO 752
<211> LENGTH: 21
<212> TYPE: RNA
<213> ORGANISM: Homo Sapiens

<400> SEQUENCE: 752
uugcagcugc gguuguaagg u                                             21

<210> SEQ ID NO 753
<211> LENGTH: 19
<212> TYPE: RNA
<213> ORGANISM: Homo Sapiens

<400> SEQUENCE: 753
aaaaaccaca auuacuuuu                                                19

<210> SEQ ID NO 754
<211> LENGTH: 21
<212> TYPE: RNA
<213> ORGANISM: Homo Sapiens

<400> SEQUENCE: 754
ugaguuggcc aucugaguga g                                             21

<210> SEQ ID NO 755
<211> LENGTH: 23
<212> TYPE: RNA
<213> ORGANISM: Homo Sapiens

<400> SEQUENCE: 755
aggaccugcg ggacaagauu cuu                                           23

<210> SEQ ID NO 756
<211> LENGTH: 23
<212> TYPE: RNA
<213> ORGANISM: Homo Sapiens

<400> SEQUENCE: 756
cagggaggcg cucacucucu gcu                                           23
```

```
<210> SEQ ID NO 757
<211> LENGTH: 22
<212> TYPE: RNA
<213> ORGANISM: Homo Sapiens

<400> SEQUENCE: 757
uccgucucag uuacuuuaua gc                                              22

<210> SEQ ID NO 758
<211> LENGTH: 22
<212> TYPE: RNA
<213> ORGANISM: Homo Sapiens

<400> SEQUENCE: 758
cggggagaga acgcagugac gu                                              22

<210> SEQ ID NO 759
<211> LENGTH: 22
<212> TYPE: RNA
<213> ORGANISM: Homo Sapiens

<400> SEQUENCE: 759
ugugucacuc gaugaccacu gu                                              22

<210> SEQ ID NO 760
<211> LENGTH: 22
<212> TYPE: RNA
<213> ORGANISM: Homo Sapiens

<400> SEQUENCE: 760
agagcugaga cuagaaagcc ca                                              22

<210> SEQ ID NO 761
<211> LENGTH: 21
<212> TYPE: RNA
<213> ORGANISM: Homo Sapiens

<400> SEQUENCE: 761
ccugcagaga ggaagcccuu c                                               21

<210> SEQ ID NO 762
<211> LENGTH: 23
<212> TYPE: RNA
<213> ORGANISM: Homo Sapiens

<400> SEQUENCE: 762
ucaggcaaag ggauauuuac aga                                             23

<210> SEQ ID NO 763
<211> LENGTH: 22
<212> TYPE: RNA
<213> ORGANISM: Homo Sapiens

<400> SEQUENCE: 763
ugccgcccuc ucgcugcucu ag                                              22

<210> SEQ ID NO 764
<211> LENGTH: 22
<212> TYPE: RNA
<213> ORGANISM: Homo Sapiens

<400> SEQUENCE: 764
auuucccugc cauucccuug gc                                              22
```

<210> SEQ ID NO 765
<211> LENGTH: 22
<212> TYPE: RNA
<213> ORGANISM: Homo Sapiens

<400> SEQUENCE: 765
ucguaccgug aguaauaaug cg                                              22

<210> SEQ ID NO 766
<211> LENGTH: 22
<212> TYPE: RNA
<213> ORGANISM: Homo Sapiens

<400> SEQUENCE: 766
aaaccguuac cauuacugag uu                                              22

<210> SEQ ID NO 767
<211> LENGTH: 21
<212> TYPE: RNA
<213> ORGANISM: Homo Sapiens

<400> SEQUENCE: 767
uccuucugcu ccguccccca g                                               21

<210> SEQ ID NO 768
<211> LENGTH: 21
<212> TYPE: RNA
<213> ORGANISM: Homo Sapiens

<400> SEQUENCE: 768
aaagguaauu gugguuucug c                                               21

<210> SEQ ID NO 769
<211> LENGTH: 22
<212> TYPE: RNA
<213> ORGANISM: Homo Sapiens

<400> SEQUENCE: 769
agcucugcug cucacuggca gu                                              22

<210> SEQ ID NO 770
<211> LENGTH: 25
<212> TYPE: RNA
<213> ORGANISM: Homo Sapiens

<400> SEQUENCE: 770
aaauaugaug aaacucacag cugag                                           25

<210> SEQ ID NO 771
<211> LENGTH: 21
<212> TYPE: RNA
<213> ORGANISM: Homo Sapiens

<400> SEQUENCE: 771 ggugggcaa ugggaucagg u                                                21

<210> SEQ ID NO 772
<211> LENGTH: 22
<212> TYPE: RNA
<213> ORGANISM: Homo Sapiens

<400> SEQUENCE: 772
cuccuacaua uuagcauuaa ca                                              22

```
<210> SEQ ID NO 773
<211> LENGTH: 23
<212> TYPE: RNA
<213> ORGANISM: Homo Sapiens

<400> SEQUENCE: 773
ucuggcaagu aaaaaacucu cau                                              23

<210> SEQ ID NO 774
<211> LENGTH: 22
<212> TYPE: RNA
<213> ORGANISM: Homo Sapiens

<400> SEQUENCE: 774
acaacaguga cuugcucucc aa                                               22

<210> SEQ ID NO 775
<211> LENGTH: 22
<212> TYPE: RNA
<213> ORGANISM: Homo Sapiens

<400> SEQUENCE: 775
caggauccac agagcuaguc ca                                               22

<210> SEQ ID NO 776
<211> LENGTH: 24
<212> TYPE: RNA
<213> ORGANISM: Homo Sapiens

<400> SEQUENCE: 776
agcgcgggcu gagcgcugcc aguc                                             24

<210> SEQ ID NO 777
<211> LENGTH: 18
<212> TYPE: RNA
<213> ORGANISM: Homo Sapiens

<400> SEQUENCE: 777
cgggcguggu ggugggg                                                     18

<210> SEQ ID NO 778
<211> LENGTH: 22
<212> TYPE: RNA
<213> ORGANISM: Homo Sapiens

<400> SEQUENCE: 778
cucuagaggg aagcacuuuc ug                                               22

<210> SEQ ID NO 779
<211> LENGTH: 22
<212> TYPE: RNA
<213> ORGANISM: Homo Sapiens

<400> SEQUENCE: 779
caggaaggau uuagggacag gc                                               22

<210> SEQ ID NO 780
<211> LENGTH: 20
<212> TYPE: RNA
<213> ORGANISM: Homo Sapiens

<400> SEQUENCE: 780
```

-continued

| | |
|---|---|
| uagaggaagc uguggagaga | 20 |

<210> SEQ ID NO 781
<211> LENGTH: 22
<212> TYPE: RNA
<213> ORGANISM: Homo Sapiens

<400> SEQUENCE: 781

| | |
|---|---|
| ugggcuggca gggcaagugc ug | 22 |

<210> SEQ ID NO 782
<211> LENGTH: 18
<212> TYPE: RNA
<213> ORGANISM: Homo Sapiens

<400> SEQUENCE: 782

| | |
|---|---|
| cucgaguugg aagaggcg | 18 |

<210> SEQ ID NO 783
<211> LENGTH: 23
<212> TYPE: RNA
<213> ORGANISM: Homo Sapiens

<400> SEQUENCE: 783

| | |
|---|---|
| agcagcauug uacagggcua uga | 23 |

<210> SEQ ID NO 784
<211> LENGTH: 18
<212> TYPE: RNA
<213> ORGANISM: Homo Sapiens

<400> SEQUENCE: 784

| | |
|---|---|
| gguggggggu guuguuuu | 18 |

<210> SEQ ID NO 785
<211> LENGTH: 22
<212> TYPE: RNA
<213> ORGANISM: Homo Sapiens

<400> SEQUENCE: 785

| | |
|---|---|
| cugcgcaagc uacugccuug cu | 22 |

<210> SEQ ID NO 786
<211> LENGTH: 22
<212> TYPE: RNA
<213> ORGANISM: Homo Sapiens

<400> SEQUENCE: 786

| | |
|---|---|
| aauccuuugu cccuggguga ga | 22 |

<210> SEQ ID NO 787
<211> LENGTH: 22
<212> TYPE: RNA
<213> ORGANISM: Homo Sapiens

<400> SEQUENCE: 787

| | |
|---|---|
| ugagucagca acauauccca ug | 22 |

<210> SEQ ID NO 788
<211> LENGTH: 23
<212> TYPE: RNA
<213> ORGANISM: Homo Sapiens

<400> SEQUENCE: 788

-continued cccaguguuu agacuaucug uuc                                          23

<210> SEQ ID NO 789
<211> LENGTH: 21
<212> TYPE: RNA
<213> ORGANISM: Homo Sapiens

<400> SEQUENCE: 789
aggggugcua ucugugauug a                                            21

<210> SEQ ID NO 790
<211> LENGTH: 22
<212> TYPE: RNA
<213> ORGANISM: Homo Sapiens

<400> SEQUENCE: 790
ugcaagacgg auacugucau cu                                           22

<210> SEQ ID NO 791
<211> LENGTH: 21
<212> TYPE: RNA
<213> ORGANISM: Homo Sapiens

<400> SEQUENCE: 791
aaagcgcuuc ccuucagagu g                                            21

<210> SEQ ID NO 792
<211> LENGTH: 23
<212> TYPE: RNA
<213> ORGANISM: Homo Sapiens

<400> SEQUENCE: 792
cucucaccac ugcccuccca cag                                          23

<210> SEQ ID NO 793
<211> LENGTH: 22
<212> TYPE: RNA
<213> ORGANISM: Homo Sapiens

<400> SEQUENCE: 793
ugcuggcuca uuucauaugu gu                                           22

<210> SEQ ID NO 794
<211> LENGTH: 22
<212> TYPE: RNA
<213> ORGANISM: Homo Sapiens

<400> SEQUENCE: 794
ucuauacaga cccuggcuuu uc                                           22

<210> SEQ ID NO 795
<211> LENGTH: 22
<212> TYPE: RNA
<213> ORGANISM: Homo Sapiens

<400> SEQUENCE: 795
agacacauuu ggagagggaa cc                                           22

<210> SEQ ID NO 796
<211> LENGTH: 24
<212> TYPE: RNA
<213> ORGANISM: Homo Sapiens

```
<400> SEQUENCE: 796
guggguaggg uuggggggag agcg                                          24

<210> SEQ ID NO 797
<211> LENGTH: 23
<212> TYPE: RNA
<213> ORGANISM: Homo Sapiens

<400> SEQUENCE: 797
agaagaaggc ggucggucug cgg                                           23

<210> SEQ ID NO 798
<211> LENGTH: 20
<212> TYPE: RNA
<213> ORGANISM: Homo Sapiens

<400> SEQUENCE: 798
cugcaaaggg aagcccuuuc                                               20

<210> SEQ ID NO 799
<211> LENGTH: 20
<212> TYPE: RNA
<213> ORGANISM: Homo Sapiens

<400> SEQUENCE: 799
ucagggaguc aggggagggc                                               20

<210> SEQ ID NO 800
<211> LENGTH: 17
<212> TYPE: RNA
<213> ORGANISM: Homo Sapiens

<400> SEQUENCE: 800
aagacugaga ggaggga                                                  17

<210> SEQ ID NO 801
<211> LENGTH: 21
<212> TYPE: RNA
<213> ORGANISM: Homo Sapiens

<400> SEQUENCE: 801
uagcggggau uccaauauug g                                             21

<210> SEQ ID NO 802
<211> LENGTH: 22
<212> TYPE: RNA
<213> ORGANISM: Homo Sapiens

<400> SEQUENCE: 802
gaugagcuca uuguaauaug ag                                            22

<210> SEQ ID NO 803
<211> LENGTH: 18
<212> TYPE: RNA
<213> ORGANISM: Homo Sapiens

<400> SEQUENCE: 803
cagggaggug aaugugau                                                 18

<210> SEQ ID NO 804
<211> LENGTH: 22
<212> TYPE: RNA
<213> ORGANISM: Homo Sapiens
```

```
<400> SEQUENCE: 804
ucaaucacuu gguaauugcu gu                                              22

<210> SEQ ID NO 805
<211> LENGTH: 18
<212> TYPE: RNA
<213> ORGANISM: Homo Sapiens

<400> SEQUENCE: 805
ccuagacacc uccaguuc                                                   18

<210> SEQ ID NO 806
<211> LENGTH: 22
<212> TYPE: RNA
<213> ORGANISM: Homo Sapiens

<400> SEQUENCE: 806
aaucagugaa ugccuugaac cu                                              22

<210> SEQ ID NO 807
<211> LENGTH: 18
<212> TYPE: RNA
<213> ORGANISM: Homo Sapiens

<400> SEQUENCE: 807
cuaagaaguu gacugaag                                                   18

<210> SEQ ID NO 808
<211> LENGTH: 22
<212> TYPE: RNA
<213> ORGANISM: Homo Sapiens

<400> SEQUENCE: 808
cucuagaggg aagcgcuuuc ug                                              22

<210> SEQ ID NO 809
<211> LENGTH: 22
<212> TYPE: RNA
<213> ORGANISM: Homo Sapiens

<400> SEQUENCE: 809
gcagagugca aacaauuuug ac                                              22

<210> SEQ ID NO 810
<211> LENGTH: 22
<212> TYPE: RNA
<213> ORGANISM: Homo Sapiens

<400> SEQUENCE: 810
ggauuccugg aaauacuguu cu                                              22

<210> SEQ ID NO 811
<211> LENGTH: 21
<212> TYPE: RNA
<213> ORGANISM: Homo Sapiens

<400> SEQUENCE: 811
gguucuuagc auaggagguc u                                               21

<210> SEQ ID NO 812
<211> LENGTH: 23
<212> TYPE: RNA
```

-continued

<213> ORGANISM: Homo Sapiens

<400> SEQUENCE: 812
cgggcugucc ggaggggucg gcu                                    23

<210> SEQ ID NO 813
<211> LENGTH: 22
<212> TYPE: RNA
<213> ORGANISM: Homo Sapiens

<400> SEQUENCE: 813
auaagacgaa caaaagguuu gu                                     22

<210> SEQ ID NO 814
<211> LENGTH: 22
<212> TYPE: RNA
<213> ORGANISM: Homo Sapiens

<400> SEQUENCE: 814
accuugccuu gcugcccggg cc                                     22

<210> SEQ ID NO 815
<211> LENGTH: 21
<212> TYPE: RNA
<213> ORGANISM: Homo Sapiens

<400> SEQUENCE: 815
caagucacua gugguuccgu u                                      21

<210> SEQ ID NO 816
<211> LENGTH: 21
<212> TYPE: RNA
<213> ORGANISM: Homo Sapiens

<400> SEQUENCE: 816
caaaagugau cgugguuuuu g                                      21

<210> SEQ ID NO 817
<211> LENGTH: 22
<212> TYPE: RNA
<213> ORGANISM: Homo Sapiens

<400> SEQUENCE: 817
uagcaccauu ugaaaucggu ua                                     22

<210> SEQ ID NO 818
<211> LENGTH: 22
<212> TYPE: RNA
<213> ORGANISM: Homo Sapiens

<400> SEQUENCE: 818
uccucaucac acugcaccuu ag                                     22

<210> SEQ ID NO 819
<211> LENGTH: 21
<212> TYPE: RNA
<213> ORGANISM: Homo Sapiens

<400> SEQUENCE: 819
uccugcgcgu cccagaugcc c                                      21

<210> SEQ ID NO 820
<211> LENGTH: 22

```
<212> TYPE: RNA
<213> ORGANISM: Homo Sapiens

<400> SEQUENCE: 820
ugagguagua gauuguauag uu                                              22

<210> SEQ ID NO 821
<211> LENGTH: 22
<212> TYPE: RNA
<213> ORGANISM: Homo Sapiens

<400> SEQUENCE: 821
aagacgggag gaaagaaggg ag                                              22

<210> SEQ ID NO 822
<211> LENGTH: 24
<212> TYPE: RNA
<213> ORGANISM: Homo Sapiens

<400> SEQUENCE: 822
uuggaagcuu ggaccaacua gcug                                            24

<210> SEQ ID NO 823
<211> LENGTH: 23
<212> TYPE: RNA
<213> ORGANISM: Homo Sapiens

<400> SEQUENCE: 823 ugagugggc ucccgggacg gcg                                              23

<210> SEQ ID NO 824
<211> LENGTH: 24
<212> TYPE: RNA
<213> ORGANISM: Homo Sapiens

<400> SEQUENCE: 824
cugcaggcag aaguggggcu gaca                                            24

<210> SEQ ID NO 825
<211> LENGTH: 22
<212> TYPE: RNA
<213> ORGANISM: Homo Sapiens

<400> SEQUENCE: 825
agaaguaauu gcgguuuugc ca                                              22

<210> SEQ ID NO 826
<211> LENGTH: 22
<212> TYPE: RNA
<213> ORGANISM: Homo Sapiens

<400> SEQUENCE: 826
caucucuaag gaacuccccc aa                                              22

<210> SEQ ID NO 827
<211> LENGTH: 20
<212> TYPE: RNA
<213> ORGANISM: Homo Sapiens

<400> SEQUENCE: 827
uacaguauag augauguacu                                                 20

<210> SEQ ID NO 828
```

<211> LENGTH: 22
<212> TYPE: RNA
<213> ORGANISM: Homo Sapiens

<400> SEQUENCE: 828
ucuggggaug aggacagugu gu                                              22

<210> SEQ ID NO 829
<211> LENGTH: 22
<212> TYPE: RNA
<213> ORGANISM: Homo Sapiens

<400> SEQUENCE: 829
agagguagua gguugcauag uu                                              22

<210> SEQ ID NO 830
<211> LENGTH: 17
<212> TYPE: RNA
<213> ORGANISM: Homo Sapiens

<400> SEQUENCE: 830
gccggacaag agggagg                                                    17

<210> SEQ ID NO 831
<211> LENGTH: 23
<212> TYPE: RNA
<213> ORGANISM: Homo Sapiens

<400> SEQUENCE: 831
agggcauagg agaggguuga uau                                             23

<210> SEQ ID NO 832
<211> LENGTH: 22
<212> TYPE: RNA
<213> ORGANISM: Homo Sapiens

<400> SEQUENCE: 832
uucucccacu accaggcucc ca                                              22

<210> SEQ ID NO 833
<211> LENGTH: 22
<212> TYPE: RNA
<213> ORGANISM: Homo Sapiens

<400> SEQUENCE: 833
agauguccag ccacaauucu cg                                              22

<210> SEQ ID NO 834
<211> LENGTH: 22
<212> TYPE: RNA
<213> ORGANISM: Homo Sapiens

<400> SEQUENCE: 834
acaaagugcu ucccuuuaga gu                                              22

<210> SEQ ID NO 835
<211> LENGTH: 23
<212> TYPE: RNA
<213> ORGANISM: Homo Sapiens

<400> SEQUENCE: 835
cgagggcauu ucaugaugca ggc                                             23

-continued

<210> SEQ ID NO 836
<211> LENGTH: 21
<212> TYPE: RNA
<213> ORGANISM: Homo Sapiens

<400> SEQUENCE: 836
uuaagacuug cagugauguu u                                             21

<210> SEQ ID NO 837
<211> LENGTH: 17
<212> TYPE: RNA
<213> ORGANISM: Homo Sapiens

<400> SEQUENCE: 837
ccccggggag cccggcg                                                  17

<210> SEQ ID NO 838
<211> LENGTH: 18
<212> TYPE: RNA
<213> ORGANISM: Homo Sapiens

<400> SEQUENCE: 838
gaaagagagc ugagugug                                                 18

<210> SEQ ID NO 839
<211> LENGTH: 22
<212> TYPE: RNA
<213> ORGANISM: Homo Sapiens

<400> SEQUENCE: 839
gcaugugaug aagcaaauca gu                                            22

<210> SEQ ID NO 840
<211> LENGTH: 18
<212> TYPE: RNA
<213> ORGANISM: Homo Sapiens

<400> SEQUENCE: 840
acaggcagga uuggggaa                                                 18

<210> SEQ ID NO 841
<211> LENGTH: 22
<212> TYPE: RNA
<213> ORGANISM: Homo Sapiens

<400> SEQUENCE: 841
uguaaacauc cuugacugga ag                                            22

<210> SEQ ID NO 842
<211> LENGTH: 22
<212> TYPE: RNA
<213> ORGANISM: Homo Sapiens

<400> SEQUENCE: 842
cuuaucagau uguauuguaa uu                                            22

<210> SEQ ID NO 843
<211> LENGTH: 22
<212> TYPE: RNA
<213> ORGANISM: Homo Sapiens

<400> SEQUENCE: 843
cuuggcaccu agcaagcacu ca                                            22

<210> SEQ ID NO 844
<211> LENGTH: 21
<212> TYPE: RNA
<213> ORGANISM: Homo Sapiens

<400> SEQUENCE: 844
aggguaagcu gaaccucuga u                                                 21

<210> SEQ ID NO 845
<211> LENGTH: 22
<212> TYPE: RNA
<213> ORGANISM: Homo Sapiens

<400> SEQUENCE: 845
uaacacuguc ugguaaagau gg                                                22

<210> SEQ ID NO 846
<211> LENGTH: 22
<212> TYPE: RNA
<213> ORGANISM: Homo Sapiens

<400> SEQUENCE: 846
ugagguagua gguuguaugg uu                                                22

<210> SEQ ID NO 847
<211> LENGTH: 22
<212> TYPE: RNA
<213> ORGANISM: Homo Sapiens

<400> SEQUENCE: 847
aaccacuuuc uuugcucauc ca                                                22

<210> SEQ ID NO 848
<211> LENGTH: 22
<212> TYPE: RNA
<213> ORGANISM: Homo Sapiens

<400> SEQUENCE: 848
caaagaauuc uccuuuggg cu                                                 22

<210> SEQ ID NO 849
<211> LENGTH: 23
<212> TYPE: RNA
<213> ORGANISM: Homo Sapiens

<400> SEQUENCE: 849
acugcccuaa gugcuccuuc ugg                                               23

<210> SEQ ID NO 850
<211> LENGTH: 23
<212> TYPE: RNA
<213> ORGANISM: Homo Sapiens

<400> SEQUENCE: 850
ucccuguccu ccaggagcuc acg                                               23

<210> SEQ ID NO 851
<211> LENGTH: 19
<212> TYPE: RNA
<213> ORGANISM: Homo Sapiens

<400> SEQUENCE: 851
acuggacuug gaggcagaa                                                    19

<210> SEQ ID NO 852
<211> LENGTH: 22
<212> TYPE: RNA
<213> ORGANISM: Homo Sapiens

<400> SEQUENCE: 852
uccuguacug agcugccccg ag                                            22

<210> SEQ ID NO 853
<211> LENGTH: 21
<212> TYPE: RNA
<213> ORGANISM: Homo Sapiens

<400> SEQUENCE: 853
gccuaucaca uaucugccug u                                             21

<210> SEQ ID NO 854
<211> LENGTH: 21
<212> TYPE: RNA
<213> ORGANISM: Homo Sapiens

<400> SEQUENCE: 854
aaaaguaauu gugguuuuug c                                             21

<210> SEQ ID NO 855
<211> LENGTH: 22
<212> TYPE: RNA
<213> ORGANISM: Homo Sapiens

<400> SEQUENCE: 855 uaagggugu auggcagaug ca                                             22

<210> SEQ ID NO 856
<211> LENGTH: 22
<212> TYPE: RNA
<213> ORGANISM: Homo Sapiens

<400> SEQUENCE: 856
aucauaugaa ccaaacucua au                                            22

<210> SEQ ID NO 857
<211> LENGTH: 22
<212> TYPE: RNA
<213> ORGANISM: Homo Sapiens

<400> SEQUENCE: 857
uugaggaaaa gauggucuua uu                                            22

<210> SEQ ID NO 858
<211> LENGTH: 18
<212> TYPE: RNA
<213> ORGANISM: Homo Sapiens

<400> SEQUENCE: 858
gggauucugu agcuuccu                                                 18

<210> SEQ ID NO 859
<211> LENGTH: 22
<212> TYPE: RNA
<213> ORGANISM: Homo Sapiens

<400> SEQUENCE: 859
ugauugucuu cauaucuaga ac                                          22

<210> SEQ ID NO 860
<211> LENGTH: 23
<212> TYPE: RNA
<213> ORGANISM: Homo Sapiens

<400> SEQUENCE: 860
ugacacggag gguggcuugg gaa                                         23

<210> SEQ ID NO 861
<211> LENGTH: 20
<212> TYPE: RNA
<213> ORGANISM: Homo Sapiens

<400> SEQUENCE: 861
agacacuaua cgagucauau                                             20

<210> SEQ ID NO 862
<211> LENGTH: 21
<212> TYPE: RNA
<213> ORGANISM: Homo Sapiens

<400> SEQUENCE: 862
uugugcuuga ucuaaccaug u                                           21

<210> SEQ ID NO 863
<211> LENGTH: 22
<212> TYPE: RNA
<213> ORGANISM: Homo Sapiens

<400> SEQUENCE: 863
uuaggccauc aucccauuau gc                                          22

<210> SEQ ID NO 864
<211> LENGTH: 22
<212> TYPE: RNA
<213> ORGANISM: Homo Sapiens

<400> SEQUENCE: 864
ugagccgagc ugagcuuagc ug                                          22

<210> SEQ ID NO 865
<211> LENGTH: 22
<212> TYPE: RNA
<213> ORGANISM: Homo Sapiens

<400> SEQUENCE: 865
gguggcccgg ccgugccuga gg                                          22

<210> SEQ ID NO 866
<211> LENGTH: 22
<212> TYPE: RNA
<213> ORGANISM: Homo Sapiens

<400> SEQUENCE: 866
agaucgaccg uguuauauuc gc                                          22

<210> SEQ ID NO 867
<211> LENGTH: 17
<212> TYPE: RNA
<213> ORGANISM: Homo Sapiens

<400> SEQUENCE: 867
ucauauugcu ucuuucu                                                          17

<210> SEQ ID NO 868
<211> LENGTH: 23
<212> TYPE: RNA
<213> ORGANISM: Homo Sapiens

<400> SEQUENCE: 868
ugggcugagg gcaggaggcc ugu                                                   23

<210> SEQ ID NO 869
<211> LENGTH: 22
<212> TYPE: RNA
<213> ORGANISM: Homo Sapiens

<400> SEQUENCE: 869 ugggauuug gagaaguggu ga                                                     22

<210> SEQ ID NO 870
<211> LENGTH: 21
<212> TYPE: RNA
<213> ORGANISM: Homo Sapiens

<400> SEQUENCE: 870
uuagcggugg accgcccugc g                                                     21

<210> SEQ ID NO 871
<211> LENGTH: 21
<212> TYPE: RNA
<213> ORGANISM: Homo Sapiens

<400> SEQUENCE: 871
aauauuauac agucaaccuc u                                                     21

<210> SEQ ID NO 872
<211> LENGTH: 23
<212> TYPE: RNA
<213> ORGANISM: Homo Sapiens

<400> SEQUENCE: 872
uauggcuuuu uauuccuaug uga                                                   23

<210> SEQ ID NO 873
<211> LENGTH: 23
<212> TYPE: RNA
<213> ORGANISM: Homo Sapiens

<400> SEQUENCE: 873
ucaaggccag aggucccaca gca                                                   23

<210> SEQ ID NO 874
<211> LENGTH: 22
<212> TYPE: RNA
<213> ORGANISM: Homo Sapiens

<400> SEQUENCE: 874
caggcgucug ucuacguggc uu                                                    22

<210> SEQ ID NO 875
<211> LENGTH: 22
<212> TYPE: RNA
<213> ORGANISM: Homo Sapiens

```
<400> SEQUENCE: 875
auaguccgag uaacgucggg gc                                          22

<210> SEQ ID NO 876
<211> LENGTH: 22
<212> TYPE: RNA
<213> ORGANISM: Homo Sapiens

<400> SEQUENCE: 876
acuggcaugc ugcauuuaua ua                                          22

<210> SEQ ID NO 877
<211> LENGTH: 23
<212> TYPE: RNA
<213> ORGANISM: Homo Sapiens

<400> SEQUENCE: 877
uggcccggcg acgucucacg guc                                         23

<210> SEQ ID NO 878
<211> LENGTH: 23
<212> TYPE: RNA
<213> ORGANISM: Homo Sapiens

<400> SEQUENCE: 878
guguuaauua aaccucuauu uac                                         23

<210> SEQ ID NO 879
<211> LENGTH: 20
<212> TYPE: RNA
<213> ORGANISM: Homo Sapiens

<400> SEQUENCE: 879
uugggcuggg cuggguuggg                                             20

<210> SEQ ID NO 880
<211> LENGTH: 23
<212> TYPE: RNA
<213> ORGANISM: Homo Sapiens

<400> SEQUENCE: 880
caaagugcug uucgugcagg uag                                         23

<210> SEQ ID NO 881
<211> LENGTH: 21
<212> TYPE: RNA
<213> ORGANISM: Homo Sapiens

<400> SEQUENCE: 881
gguggauauu ccuucuaugu u                                           21

<210> SEQ ID NO 882
<211> LENGTH: 23
<212> TYPE: RNA
<213> ORGANISM: Homo Sapiens

<400> SEQUENCE: 882
uugaauucuu ggccuuaagu gau                                         23

<210> SEQ ID NO 883
<211> LENGTH: 22
<212> TYPE: RNA
<213> ORGANISM: Homo Sapiens
```

-continued

```
<400> SEQUENCE: 883
aaaaguacuu gcggauuuug cu                                              22

<210> SEQ ID NO 884
<211> LENGTH: 21
<212> TYPE: RNA
<213> ORGANISM: Homo Sapiens

<400> SEQUENCE: 884
agacccugca gccuucccac c                                               21

<210> SEQ ID NO 885
<211> LENGTH: 22
<212> TYPE: RNA
<213> ORGANISM: Homo Sapiens

<400> SEQUENCE: 885
ugagugacag gggaaauggg ga                                              22

<210> SEQ ID NO 886
<211> LENGTH: 22
<212> TYPE: RNA
<213> ORGANISM: Homo Sapiens

<400> SEQUENCE: 886
gcaggugcuc acuguccuc cu                                               22

<210> SEQ ID NO 887
<211> LENGTH: 22
<212> TYPE: RNA
<213> ORGANISM: Homo Sapiens

<400> SEQUENCE: 887
aacccagugg gcuauggaaa ug                                              22

<210> SEQ ID NO 888
<211> LENGTH: 22
<212> TYPE: RNA
<213> ORGANISM: Homo Sapiens

<400> SEQUENCE: 888
uggugggccg cagaacaugu gc                                              22

<210> SEQ ID NO 889
<211> LENGTH: 22
<212> TYPE: RNA
<213> ORGANISM: Homo Sapiens

<400> SEQUENCE: 889
cucuagaggg aagcacuuuc uc                                              22

<210> SEQ ID NO 890
<211> LENGTH: 19
<212> TYPE: RNA
<213> ORGANISM: Homo Sapiens

<400> SEQUENCE: 890
ccucagauca gagccuugc                                                  19

<210> SEQ ID NO 891
<211> LENGTH: 22
<212> TYPE: RNA
```

```
<213> ORGANISM: Homo Sapiens

<400> SEQUENCE: 891
caagcucgcu ucuauggguc ug                                    22

<210> SEQ ID NO 892
<211> LENGTH: 23
<212> TYPE: RNA
<213> ORGANISM: Homo Sapiens

<400> SEQUENCE: 892
ccucaccacc ccuucugccu gca                                   23

<210> SEQ ID NO 893
<211> LENGTH: 19
<212> TYPE: RNA
<213> ORGANISM: Homo Sapiens

<400> SEQUENCE: 893
agcugucuga aaaugucuu                                        19

<210> SEQ ID NO 894
<211> LENGTH: 21
<212> TYPE: RNA
<213> ORGANISM: Homo Sapiens

<400> SEQUENCE: 894
uaugugaccu cggaugaauc a                                     21

<210> SEQ ID NO 895
<211> LENGTH: 21
<212> TYPE: RNA
<213> ORGANISM: Homo Sapiens

<400> SEQUENCE: 895
acucuuuccc uguugcacua c                                     21

<210> SEQ ID NO 896
<211> LENGTH: 21
<212> TYPE: RNA
<213> ORGANISM: Homo Sapiens

<400> SEQUENCE: 896
uaacauaaua guguggauug a                                     21

<210> SEQ ID NO 897
<211> LENGTH: 23
<212> TYPE: RNA
<213> ORGANISM: Homo Sapiens

<400> SEQUENCE: 897
uugccacacu gcaacaccuu aca                                   23

<210> SEQ ID NO 898
<211> LENGTH: 21
<212> TYPE: RNA
<213> ORGANISM: Homo Sapiens

<400> SEQUENCE: 898
acucuagcug ccaaaggcgc u                                     21

<210> SEQ ID NO 899
<211> LENGTH: 22
```

```
<212> TYPE: RNA
<213> ORGANISM: Homo Sapiens

<400> SEQUENCE: 899
uuccacugcc acuaccuaau uu                                    22

<210> SEQ ID NO 900
<211> LENGTH: 20
<212> TYPE: RNA
<213> ORGANISM: Homo Sapiens

<400> SEQUENCE: 900
gucccugagu guauguggug                                       20

<210> SEQ ID NO 901
<211> LENGTH: 21
<212> TYPE: RNA
<213> ORGANISM: Homo Sapiens

<400> SEQUENCE: 901
uggcaguuac uuuugcacca g                                     21

<210> SEQ ID NO 902
<211> LENGTH: 24
<212> TYPE: RNA
<213> ORGANISM: Homo Sapiens

<400> SEQUENCE: 902
uggggagcug aggcucuggg ggug                                  24

<210> SEQ ID NO 903
<211> LENGTH: 22
<212> TYPE: RNA
<213> ORGANISM: Homo Sapiens

<400> SEQUENCE: 903
ccugcaacuu ugccugauca ga                                    22

<210> SEQ ID NO 904
<211> LENGTH: 22
<212> TYPE: RNA
<213> ORGANISM: Homo Sapiens

<400> SEQUENCE: 904
agaggcuggc cgugaugaau uc                                    22

<210> SEQ ID NO 905
<211> LENGTH: 17
<212> TYPE: RNA
<213> ORGANISM: Homo Sapiens

<400> SEQUENCE: 905
ccugagaaaa gggccaa                                          17

<210> SEQ ID NO 906
<211> LENGTH: 23
<212> TYPE: RNA
<213> ORGANISM: Homo Sapiens

<400> SEQUENCE: 906
gaacgccugu ucuugccagg ugg                                   23

<210> SEQ ID NO 907
```

```
<211> LENGTH: 22
<212> TYPE: RNA
<213> ORGANISM: Homo Sapiens

<400> SEQUENCE: 907
uccugcguag gaucugagga gu                                                  22

<210> SEQ ID NO 908
<211> LENGTH: 23
<212> TYPE: RNA
<213> ORGANISM: Homo Sapiens

<400> SEQUENCE: 908
ccccgguguu ggggcgcguc ugc                                                 23

<210> SEQ ID NO 909
<211> LENGTH: 20
<212> TYPE: RNA
<213> ORGANISM: Homo Sapiens

<400> SEQUENCE: 909
aaaugggugg ucugaggcaa                                                     20

<210> SEQ ID NO 910
<211> LENGTH: 22
<212> TYPE: RNA
<213> ORGANISM: Homo Sapiens

<400> SEQUENCE: 910
ggauaucauc auauacugua ag                                                  22

<210> SEQ ID NO 911
<211> LENGTH: 21
<212> TYPE: RNA
<213> ORGANISM: Homo Sapiens

<400> SEQUENCE: 911
cacugugucc uuucugcgua g                                                   21

<210> SEQ ID NO 912
<211> LENGTH: 22
<212> TYPE: RNA
<213> ORGANISM: Homo Sapiens

<400> SEQUENCE: 912
uauguaacau gguccacuaa cu                                                  22

<210> SEQ ID NO 913
<211> LENGTH: 22
<212> TYPE: RNA
<213> ORGANISM: Homo Sapiens

<400> SEQUENCE: 913
ucucacugua gccucgaacc cc                                                  22

<210> SEQ ID NO 914
<211> LENGTH: 22
<212> TYPE: RNA
<213> ORGANISM: Homo Sapiens

<400> SEQUENCE: 914
uggaguguga caaugguguu ug                                                  22
```

```
<210> SEQ ID NO 915
<211> LENGTH: 18
<212> TYPE: RNA
<213> ORGANISM: Homo Sapiens

<400> SEQUENCE: 915
cccagcagga cgggagcg                                                   18

<210> SEQ ID NO 916
<211> LENGTH: 23
<212> TYPE: RNA
<213> ORGANISM: Homo Sapiens

<400> SEQUENCE: 916
gccccggcgc gggcggguuc ugg                                             23

<210> SEQ ID NO 917
<211> LENGTH: 22
<212> TYPE: RNA
<213> ORGANISM: Homo Sapiens

<400> SEQUENCE: 917
uggaauguaa ggaagugugu gg                                              22

<210> SEQ ID NO 918
<211> LENGTH: 21
<212> TYPE: RNA
<213> ORGANISM: Homo Sapiens

<400> SEQUENCE: 918
ccugcgaguc uccggcggug g                                               21

<210> SEQ ID NO 919
<211> LENGTH: 23
<212> TYPE: RNA
<213> ORGANISM: Homo Sapiens

<400> SEQUENCE: 919
acuccauuug uuuugaugau gga                                             23

<210> SEQ ID NO 920
<211> LENGTH: 22
<212> TYPE: RNA
<213> ORGANISM: Homo Sapiens

<400> SEQUENCE: 920
aaguuggcug caguuaaggu gg                                              22

<210> SEQ ID NO 921
<211> LENGTH: 22
<212> TYPE: RNA
<213> ORGANISM: Homo Sapiens

<400> SEQUENCE: 921
ugccuacuga gcugauauca gu                                              22

<210> SEQ ID NO 922
<211> LENGTH: 22
<212> TYPE: RNA
<213> ORGANISM: Homo Sapiens

<400> SEQUENCE: 922
ugugauauca ugguuccugg ga                                              22
```

```
<210> SEQ ID NO 923
<211> LENGTH: 21
<212> TYPE: RNA
<213> ORGANISM: Homo Sapiens

<400> SEQUENCE: 923
auccaguucu cugagggggc u                                              21

<210> SEQ ID NO 924
<211> LENGTH: 18
<212> TYPE: RNA
<213> ORGANISM: Homo Sapiens

<400> SEQUENCE: 924
cagugcaaug uuuuccuu                                                  18

<210> SEQ ID NO 925
<211> LENGTH: 22
<212> TYPE: RNA
<213> ORGANISM: Homo Sapiens

<400> SEQUENCE: 925
uaguucuucc cuuugcccaa uu                                             22

<210> SEQ ID NO 926
<211> LENGTH: 22
<212> TYPE: RNA
<213> ORGANISM: Homo Sapiens

<400> SEQUENCE: 926 aggggggaugg cagagcaaaa uu                                            22

<210> SEQ ID NO 927
<211> LENGTH: 22
<212> TYPE: RNA
<213> ORGANISM: Homo Sapiens

<400> SEQUENCE: 927
ugugauaucg ugcuuccugg ga                                             22

<210> SEQ ID NO 928
<211> LENGTH: 20
<212> TYPE: RNA
<213> ORGANISM: Homo Sapiens

<400> SEQUENCE: 928
gcggaaggcg gagcggcgga                                                20

<210> SEQ ID NO 929
<211> LENGTH: 22
<212> TYPE: RNA
<213> ORGANISM: Homo Sapiens

<400> SEQUENCE: 929
agaguuaacu caaaauggac ua                                             22

<210> SEQ ID NO 930
<211> LENGTH: 25
<212> TYPE: RNA
<213> ORGANISM: Homo Sapiens

<400> SEQUENCE: 930
caacccuagg agagggugcc auuca                                          25
```

<210> SEQ ID NO 931
<211> LENGTH: 22
<212> TYPE: RNA
<213> ORGANISM: Homo Sapiens

<400> SEQUENCE: 931
ucaggccagg cacaguggcu ca                                              22

<210> SEQ ID NO 932
<211> LENGTH: 22
<212> TYPE: RNA
<213> ORGANISM: Homo Sapiens

<400> SEQUENCE: 932
uuauaaagca augagacuga uu                                              22

<210> SEQ ID NO 933
<211> LENGTH: 21
<212> TYPE: RNA
<213> ORGANISM: Homo Sapiens

<400> SEQUENCE: 933
ccugucugug ccugcuguac a                                               21

<210> SEQ ID NO 934
<211> LENGTH: 18
<212> TYPE: RNA
<213> ORGANISM: Homo Sapiens

<400> SEQUENCE: 934
cauucaacua gugauugu                                                   18

<210> SEQ ID NO 935
<211> LENGTH: 22
<212> TYPE: RNA
<213> ORGANISM: Homo Sapiens

<400> SEQUENCE: 935
accaagucug cgucauccuc uc                                              22

<210> SEQ ID NO 936
<211> LENGTH: 22
<212> TYPE: RNA
<213> ORGANISM: Homo Sapiens

<400> SEQUENCE: 936
gccucucucg gagucgcucg ga                                              22

<210> SEQ ID NO 937
<211> LENGTH: 22
<212> TYPE: RNA
<213> ORGANISM: Homo Sapiens

<400> SEQUENCE: 937
gucauacacg gcucuccucu cu                                              22

<210> SEQ ID NO 938
<211> LENGTH: 19
<212> TYPE: RNA
<213> ORGANISM: Homo Sapiens

<400> SEQUENCE: 938

| | |
|---|---|
| gugucugcuu ccugggga | 19 |

<210> SEQ ID NO 939
<211> LENGTH: 21
<212> TYPE: RNA
<213> ORGANISM: Homo Sapiens

<400> SEQUENCE: 939

| | |
|---|---|
| ugauugucca aacgcaauuc u | 21 |

<210> SEQ ID NO 940
<211> LENGTH: 21
<212> TYPE: RNA
<213> ORGANISM: Homo Sapiens

<400> SEQUENCE: 940

| | |
|---|---|
| uuucagauaa caguauuaca u | 21 |

<210> SEQ ID NO 941
<211> LENGTH: 22
<212> TYPE: RNA
<213> ORGANISM: Homo Sapiens

<400> SEQUENCE: 941

| | |
|---|---|
| cauugcacuu gucucggucu ga | 22 |

<210> SEQ ID NO 942
<211> LENGTH: 26
<212> TYPE: RNA
<213> ORGANISM: Homo Sapiens

<400> SEQUENCE: 942

| | |
|---|---|
| aaguaguugg uuuguaugag augguu | 26 |

<210> SEQ ID NO 943
<211> LENGTH: 22
<212> TYPE: RNA
<213> ORGANISM: Homo Sapiens

<400> SEQUENCE: 943

| | |
|---|---|
| uguugcaagu cgguggagac gu | 22 |

<210> SEQ ID NO 944
<211> LENGTH: 22
<212> TYPE: RNA
<213> ORGANISM: Homo Sapiens

<400> SEQUENCE: 944

| | |
|---|---|
| auauuaccau uagcucaucu uu | 22 |

<210> SEQ ID NO 945
<211> LENGTH: 22
<212> TYPE: RNA
<213> ORGANISM: Homo Sapiens

<400> SEQUENCE: 945

| | |
|---|---|
| acucaaaaug ggggcgcuuu cc | 22 |

<210> SEQ ID NO 946
<211> LENGTH: 22
<212> TYPE: RNA
<213> ORGANISM: Homo Sapiens

<400> SEQUENCE: 946
aaaaccgucu aguuacaguu gu                                         22

<210> SEQ ID NO 947
<211> LENGTH: 19
<212> TYPE: RNA
<213> ORGANISM: Homo Sapiens

<400> SEQUENCE: 947
aggcacggug ucagcaggc                                             19

<210> SEQ ID NO 948
<211> LENGTH: 22
<212> TYPE: RNA
<213> ORGANISM: Homo Sapiens

<400> SEQUENCE: 948
aaaaguaauu gcgguuuuug cc                                         22

<210> SEQ ID NO 949
<211> LENGTH: 22
<212> TYPE: RNA
<213> ORGANISM: Homo Sapiens

<400> SEQUENCE: 949
aauugcacuu uagcaauggu ga                                         22

<210> SEQ ID NO 950
<211> LENGTH: 24
<212> TYPE: RNA
<213> ORGANISM: Homo Sapiens

<400> SEQUENCE: 950
ucugggcaca ggcggaugga cagg                                       24

<210> SEQ ID NO 951
<211> LENGTH: 19
<212> TYPE: RNA
<213> ORGANISM: Homo Sapiens

<400> SEQUENCE: 951
gcauugugca gggcuauca                                             19

<210> SEQ ID NO 952
<211> LENGTH: 22
<212> TYPE: RNA
<213> ORGANISM: Homo Sapiens

<400> SEQUENCE: 952
uucauucggc uguccagaug ua                                         22

<210> SEQ ID NO 953
<211> LENGTH: 22
<212> TYPE: RNA
<213> ORGANISM: Homo Sapiens

<400> SEQUENCE: 953
uggucuagga uuguuggagg ag                                         22

<210> SEQ ID NO 954
<211> LENGTH: 22
<212> TYPE: RNA
<213> ORGANISM: Homo Sapiens

```
<400> SEQUENCE: 954 auggggaca uuuugcauuc au                                                    22

<210> SEQ ID NO 955
<211> LENGTH: 19
<212> TYPE: RNA
<213> ORGANISM: Homo Sapiens

<400> SEQUENCE: 955
ggcuugcaug ggggacugg                                                       19

<210> SEQ ID NO 956
<211> LENGTH: 22
<212> TYPE: RNA
<213> ORGANISM: Homo Sapiens

<400> SEQUENCE: 956
uauggaaaga cuuugccacu cu                                                   22

<210> SEQ ID NO 957
<211> LENGTH: 26
<212> TYPE: RNA
<213> ORGANISM: Homo Sapiens

<400> SEQUENCE: 957
cucggccgcg gcgcguagcc cccgcc                                               26

<210> SEQ ID NO 958
<211> LENGTH: 21
<212> TYPE: RNA
<213> ORGANISM: Homo Sapiens

<400> SEQUENCE: 958
ugggcucagg guacaaaggu u                                                    21

<210> SEQ ID NO 959
<211> LENGTH: 22
<212> TYPE: RNA
<213> ORGANISM: Homo Sapiens

<400> SEQUENCE: 959
caaaaacugc aauuacuuuu gc                                                   22

<210> SEQ ID NO 960
<211> LENGTH: 22
<212> TYPE: RNA
<213> ORGANISM: Homo Sapiens

<400> SEQUENCE: 960
aggauaggaa gaaugaagug cu                                                   22

<210> SEQ ID NO 961
<211> LENGTH: 22
<212> TYPE: RNA
<213> ORGANISM: Homo Sapiens

<400> SEQUENCE: 961
ugaaacugga gcgccuggag ga                                                   22

<210> SEQ ID NO 962
<211> LENGTH: 22
<212> TYPE: RNA
<213> ORGANISM: Homo Sapiens
```

-continued

```
<400> SEQUENCE: 962
uggugguuua caaaguaauu ca                                              22

<210> SEQ ID NO 963
<211> LENGTH: 22
<212> TYPE: RNA
<213> ORGANISM: Homo Sapiens

<400> SEQUENCE: 963
ucuggccuug acuugacucu uu                                              22

<210> SEQ ID NO 964
<211> LENGTH: 23
<212> TYPE: RNA
<213> ORGANISM: Homo Sapiens

<400> SEQUENCE: 964
ugaggggcag agagcgagac uuu                                             23

<210> SEQ ID NO 965
<211> LENGTH: 21
<212> TYPE: RNA
<213> ORGANISM: Homo Sapiens

<400> SEQUENCE: 965
gcaguccaug ggcauauaca c                                               21

<210> SEQ ID NO 966
<211> LENGTH: 23
<212> TYPE: RNA
<213> ORGANISM: Homo Sapiens

<400> SEQUENCE: 966
aaugacacga ucacucccgu uga                                             23

<210> SEQ ID NO 967
<211> LENGTH: 22
<212> TYPE: RNA
<213> ORGANISM: Homo Sapiens

<400> SEQUENCE: 967
aacauucaac cugucgguga gu                                              22

<210> SEQ ID NO 968
<211> LENGTH: 22
<212> TYPE: RNA
<213> ORGANISM: Homo Sapiens

<400> SEQUENCE: 968
aggcgaugug gggauguaga ga                                              22

<210> SEQ ID NO 969
<211> LENGTH: 22
<212> TYPE: RNA
<213> ORGANISM: Homo Sapiens

<400> SEQUENCE: 969
acagcccagc aguuaucacg gg                                              22

<210> SEQ ID NO 970
<211> LENGTH: 21
<212> TYPE: RNA
```

<213> ORGANISM: Homo Sapiens

<400> SEQUENCE: 970
aauguagaga uugaucaaaa u                                           21

<210> SEQ ID NO 971
<211> LENGTH: 26
<212> TYPE: RNA
<213> ORGANISM: Homo Sapiens

<400> SEQUENCE: 971
gaugaugaug gcagcaaauu cugaaa                                      26

<210> SEQ ID NO 972
<211> LENGTH: 22
<212> TYPE: RNA
<213> ORGANISM: Homo Sapiens

<400> SEQUENCE: 972
uccagcauca gugauuuugu ug                                          22

<210> SEQ ID NO 973
<211> LENGTH: 21
<212> TYPE: RNA
<213> ORGANISM: Homo Sapiens

<400> SEQUENCE: 973
acagacuugc ugugauguuc a                                           21

<210> SEQ ID NO 974
<211> LENGTH: 18
<212> TYPE: RNA
<213> ORGANISM: Homo Sapiens

<400> SEQUENCE: 974
aggagaagua aaguagaa                                               18

<210> SEQ ID NO 975
<211> LENGTH: 22
<212> TYPE: RNA
<213> ORGANISM: Homo Sapiens

<400> SEQUENCE: 975
uaacacuguc ugguaacgau gu                                          22

<210> SEQ ID NO 976
<211> LENGTH: 21
<212> TYPE: RNA
<213> ORGANISM: Homo Sapiens

<400> SEQUENCE: 976
auggaaugua uauacggaau a                                           21

<210> SEQ ID NO 977
<211> LENGTH: 22
<212> TYPE: RNA
<213> ORGANISM: Homo Sapiens

<400> SEQUENCE: 977
uguaguugua uuguauugcc ac                                          22

<210> SEQ ID NO 978
<211> LENGTH: 22

-continued

<212> TYPE: RNA
<213> ORGANISM: Homo Sapiens

<400> SEQUENCE: 978
uucccuuugu cauccuucgc cu                                    22

<210> SEQ ID NO 979
<211> LENGTH: 21
<212> TYPE: RNA
<213> ORGANISM: Homo Sapiens

<400> SEQUENCE: 979
uacugcagac aguggcaauc a                                     21

<210> SEQ ID NO 980
<211> LENGTH: 20
<212> TYPE: RNA
<213> ORGANISM: Homo Sapiens

<400> SEQUENCE: 980
agcccccugg ccccaaaccc                                       20

<210> SEQ ID NO 981
<211> LENGTH: 23
<212> TYPE: RNA
<213> ORGANISM: Homo Sapiens

<400> SEQUENCE: 981
ugcaccaugg uugucugagc aug                                   23

<210> SEQ ID NO 982
<211> LENGTH: 22
<212> TYPE: RNA
<213> ORGANISM: Homo Sapiens

<400> SEQUENCE: 982
aaauuauugu acaucggaug ag                                    22

<210> SEQ ID NO 983
<211> LENGTH: 23
<212> TYPE: RNA
<213> ORGANISM: Homo Sapiens

<400> SEQUENCE: 983
aaagucucgc ucucugcccc uca                                   23

<210> SEQ ID NO 984
<211> LENGTH: 24
<212> TYPE: RNA
<213> ORGANISM: Homo Sapiens

<400> SEQUENCE: 984
gcugguuuca uauggugguu uaga                                  24

<210> SEQ ID NO 985
<211> LENGTH: 22
<212> TYPE: RNA
<213> ORGANISM: Homo Sapiens

<400> SEQUENCE: 985
guccacuucu gccugcccug cc                                    22

<210> SEQ ID NO 986

```
<211> LENGTH: 22
<212> TYPE: RNA
<213> ORGANISM: Homo Sapiens

<400> SEQUENCE: 986
caggaugugg ucaaguguug uu                                              22

<210> SEQ ID NO 987
<211> LENGTH: 22
<212> TYPE: RNA
<213> ORGANISM: Homo Sapiens

<400> SEQUENCE: 987
caaaaaccgg caauuacuuu ug                                              22

<210> SEQ ID NO 988
<211> LENGTH: 21
<212> TYPE: RNA
<213> ORGANISM: Homo Sapiens

<400> SEQUENCE: 988 guugggugc agggucugc u                                                 21

<210> SEQ ID NO 989
<211> LENGTH: 22
<212> TYPE: RNA
<213> ORGANISM: Homo Sapiens

<400> SEQUENCE: 989
uccuuugccu auucuauuua ag                                              22

<210> SEQ ID NO 990
<211> LENGTH: 21
<212> TYPE: RNA
<213> ORGANISM: Homo Sapiens

<400> SEQUENCE: 990
gaccgagagg gccucggcug u                                               21

<210> SEQ ID NO 991
<211> LENGTH: 22
<212> TYPE: RNA
<213> ORGANISM: Homo Sapiens

<400> SEQUENCE: 991
agaauugugg cuggacaucu gu                                              22

<210> SEQ ID NO 992
<211> LENGTH: 22
<212> TYPE: RNA
<213> ORGANISM: Homo Sapiens

<400> SEQUENCE: 992
gagugccuuc uuuuggagcg uu                                              22

<210> SEQ ID NO 993
<211> LENGTH: 21
<212> TYPE: RNA
<213> ORGANISM: Homo Sapiens

<400> SEQUENCE: 993
cagaucaugg gacugucuca g                                               21
```

```
<210> SEQ ID NO 994
<211> LENGTH: 22
<212> TYPE: RNA
<213> ORGANISM: Homo Sapiens

<400> SEQUENCE: 994 cuuccccca guaaucuuca uc                                          22

<210> SEQ ID NO 995
<211> LENGTH: 21
<212> TYPE: RNA
<213> ORGANISM: Homo Sapiens

<400> SEQUENCE: 995
ugaguguugu cuacgagggc a                                          21

<210> SEQ ID NO 996
<211> LENGTH: 21
<212> TYPE: RNA
<213> ORGANISM: Homo Sapiens

<400> SEQUENCE: 996
uaccacaggg uagaaccacg g                                          21

<210> SEQ ID NO 997
<211> LENGTH: 23
<212> TYPE: RNA
<213> ORGANISM: Homo Sapiens

<400> SEQUENCE: 997
cgcagacaau gccuacuggc cua                                        23

<210> SEQ ID NO 998
<211> LENGTH: 22
<212> TYPE: RNA
<213> ORGANISM: Homo Sapiens

<400> SEQUENCE: 998
gcugacagca gggcuggccg cu                                         22

<210> SEQ ID NO 999
<211> LENGTH: 19
<212> TYPE: RNA
<213> ORGANISM: Homo Sapiens

<400> SEQUENCE: 999
ugagguggua ggauguaga                                             19

<210> SEQ ID NO 1000
<211> LENGTH: 22
<212> TYPE: RNA
<213> ORGANISM: Homo Sapiens

<400> SEQUENCE: 1000
gugaacgggc gccaucccga gg                                         22

<210> SEQ ID NO 1001
<211> LENGTH: 21
<212> TYPE: RNA
<213> ORGANISM: Homo Sapiens

<400> SEQUENCE: 1001 aggggaaag uucuauaguc c                                           21
```

-continued

```
<210> SEQ ID NO 1002
<211> LENGTH: 22
<212> TYPE: RNA
<213> ORGANISM: Homo Sapiens

<400> SEQUENCE: 1002
uagugguccu aaacauuuca ca                                              22

<210> SEQ ID NO 1003
<211> LENGTH: 21
<212> TYPE: RNA
<213> ORGANISM: Homo Sapiens

<400> SEQUENCE: 1003
aauaauacau gguugaucuu u                                               21

<210> SEQ ID NO 1004
<211> LENGTH: 22
<212> TYPE: RNA
<213> ORGANISM: Homo Sapiens

<400> SEQUENCE: 1004
uaacagucua cagccauggu cg                                              22

<210> SEQ ID NO 1005
<211> LENGTH: 17
<212> TYPE: RNA
<213> ORGANISM: Homo Sapiens

<400> SEQUENCE: 1005
acauugccag ggaguuu                                                    17

<210> SEQ ID NO 1006
<211> LENGTH: 22
<212> TYPE: RNA
<213> ORGANISM: Homo Sapiens

<400> SEQUENCE: 1006
ugugacuuua agggaaaugg cg                                              22

<210> SEQ ID NO 1007
<211> LENGTH: 22
<212> TYPE: RNA
<213> ORGANISM: Homo Sapiens

<400> SEQUENCE: 1007
uaaugccccu aaaaauccuu au                                              22

<210> SEQ ID NO 1008
<211> LENGTH: 22
<212> TYPE: RNA
<213> ORGANISM: Homo Sapiens

<400> SEQUENCE: 1008
uaaucucagc uggcaacugu ga                                              22

<210> SEQ ID NO 1009
<211> LENGTH: 23
<212> TYPE: RNA
<213> ORGANISM: Homo Sapiens

<400> SEQUENCE: 1009
uacucuggag agugacaauc aug                                             23
```

<210> SEQ ID NO 1010
<211> LENGTH: 20
<212> TYPE: RNA
<213> ORGANISM: Homo Sapiens

<400> SEQUENCE: 1010
ucuggccagc uacgucccca                                              20

<210> SEQ ID NO 1011
<211> LENGTH: 21
<212> TYPE: RNA
<213> ORGANISM: Homo Sapiens

<400> SEQUENCE: 1011
ugacugccuc acugaccacu u                                            21

<210> SEQ ID NO 1012
<211> LENGTH: 23
<212> TYPE: RNA
<213> ORGANISM: Homo Sapiens

<400> SEQUENCE: 1012
aucgcugcgg uugcgagcgc ugu                                          23

<210> SEQ ID NO 1013
<211> LENGTH: 22
<212> TYPE: RNA
<213> ORGANISM: Homo Sapiens

<400> SEQUENCE: 1013
uggcggcggu aguuaugggc uu                                           22

<210> SEQ ID NO 1014
<211> LENGTH: 23
<212> TYPE: RNA
<213> ORGANISM: Homo Sapiens

<400> SEQUENCE: 1014
uuaaugcuaa ucgugauagg ggu                                          23

<210> SEQ ID NO 1015
<211> LENGTH: 27
<212> TYPE: RNA
<213> ORGANISM: Homo Sapiens

<400> SEQUENCE: 1015
cacuguaggu gauggugaga gugggca                                      27

<210> SEQ ID NO 1016
<211> LENGTH: 20
<212> TYPE: RNA
<213> ORGANISM: Homo Sapiens

<400> SEQUENCE: 1016
uaaaaacugc aauuacuuuc                                              20

<210> SEQ ID NO 1017
<211> LENGTH: 21
<212> TYPE: RNA
<213> ORGANISM: Homo Sapiens

<400> SEQUENCE: 1017

-continued cugccuguuc uuccacucca g                                         21

<210> SEQ ID NO 1018
<211> LENGTH: 21
<212> TYPE: RNA
<213> ORGANISM: Homo Sapiens

<400> SEQUENCE: 1018
caaauggaca ggauaacacc u                                         21

<210> SEQ ID NO 1019
<211> LENGTH: 22
<212> TYPE: RNA
<213> ORGANISM: Homo Sapiens

<400> SEQUENCE: 1019
aggggaccaa agagauauau ag                                        22

<210> SEQ ID NO 1020
<211> LENGTH: 22
<212> TYPE: RNA
<213> ORGANISM: Homo Sapiens

<400> SEQUENCE: 1020
aaaaguaauc gcgguuuuug uc                                        22

<210> SEQ ID NO 1021
<211> LENGTH: 22
<212> TYPE: RNA
<213> ORGANISM: Homo Sapiens

<400> SEQUENCE: 1021
cuauacgacc ugcugccuuu cu                                        22

<210> SEQ ID NO 1022
<211> LENGTH: 21
<212> TYPE: RNA
<213> ORGANISM: Homo Sapiens

<400> SEQUENCE: 1022
gaagugugcc gugguguguc u                                         21

<210> SEQ ID NO 1023
<211> LENGTH: 21
<212> TYPE: RNA
<213> ORGANISM: Homo Sapiens

<400> SEQUENCE: 1023
ucccacguug uggcccagca g                                         21

<210> SEQ ID NO 1024
<211> LENGTH: 22
<212> TYPE: RNA
<213> ORGANISM: Homo Sapiens

<400> SEQUENCE: 1024
cagugcaaug uuaaaagggc au                                        22

<210> SEQ ID NO 1025
<211> LENGTH: 19
<212> TYPE: RNA
<213> ORGANISM: Homo Sapiens

<400> SEQUENCE: 1025
aggcagguua ucugggcug 19

<210> SEQ ID NO 1026
<211> LENGTH: 18
<212> TYPE: RNA
<213> ORGANISM: Homo Sapiens

<400> SEQUENCE: 1026
cggcuggagg ugugagga 18

<210> SEQ ID NO 1027
<211> LENGTH: 22
<212> TYPE: RNA
<213> ORGANISM: Homo Sapiens

<400> SEQUENCE: 1027
ugaggacagg gcaaauucac ga 22

<210> SEQ ID NO 1028
<211> LENGTH: 17
<212> TYPE: RNA
<213> ORGANISM: Homo Sapiens

<400> SEQUENCE: 1028 guggggaga ggcuguc 17

<210> SEQ ID NO 1029
<211> LENGTH: 22
<212> TYPE: RNA
<213> ORGANISM: Homo Sapiens

<400> SEQUENCE: 1029
augcaccugg gcaaggauuc ug 22

<210> SEQ ID NO 1030
<211> LENGTH: 23
<212> TYPE: RNA
<213> ORGANISM: Homo Sapiens

<400> SEQUENCE: 1030
uguaguguuu ccuacuuuau gga 23

<210> SEQ ID NO 1031
<211> LENGTH: 21
<212> TYPE: RNA
<213> ORGANISM: Homo Sapiens

<400> SEQUENCE: 1031
uuagucucau gaucagacac a 21

<210> SEQ ID NO 1032
<211> LENGTH: 20
<212> TYPE: RNA
<213> ORGANISM: Homo Sapiens

<400> SEQUENCE: 1032
cuacaaaggg aagcccuuuc 20

<210> SEQ ID NO 1033
<211> LENGTH: 22
<212> TYPE: RNA
<213> ORGANISM: Homo Sapiens -continued

```
<400> SEQUENCE: 1033
aagcugccag uugaagaacu gu                                    22

<210> SEQ ID NO 1034
<211> LENGTH: 20
<212> TYPE: RNA
<213> ORGANISM: Homo Sapiens

<400> SEQUENCE: 1034
ucugcagggu uugcuuugag                                       20

<210> SEQ ID NO 1035
<211> LENGTH: 22
<212> TYPE: RNA
<213> ORGANISM: Homo Sapiens

<400> SEQUENCE: 1035
aaagguaauu gcaguuuuc cc                                     22

<210> SEQ ID NO 1036
<211> LENGTH: 21
<212> TYPE: RNA
<213> ORGANISM: Homo Sapiens

<400> SEQUENCE: 1036
uaguagaccg uauagcguac g                                     21

<210> SEQ ID NO 1037
<211> LENGTH: 20
<212> TYPE: RNA
<213> ORGANISM: Homo Sapiens

<400> SEQUENCE: 1037
uaacggccgc gguacccuaa                                       20

<210> SEQ ID NO 1038
<211> LENGTH: 22
<212> TYPE: RNA
<213> ORGANISM: Homo Sapiens

<400> SEQUENCE: 1038
ugcaacuuac cugagucauu ga                                    22

<210> SEQ ID NO 1039
<211> LENGTH: 22
<212> TYPE: RNA
<213> ORGANISM: Homo Sapiens

<400> SEQUENCE: 1039
ugggaugagg gauugaagug ga                                    22

<210> SEQ ID NO 1040
<211> LENGTH: 21
<212> TYPE: RNA
<213> ORGANISM: Homo Sapiens

<400> SEQUENCE: 1040
auugucccuc ucccuuccca g                                     21

<210> SEQ ID NO 1041
<211> LENGTH: 22
<212> TYPE: RNA
<213> ORGANISM: Homo Sapiens
```

-continued

<400> SEQUENCE: 1041
caaggagacg ggaacaugga gc                                        22

<210> SEQ ID NO 1042
<211> LENGTH: 21
<212> TYPE: RNA
<213> ORGANISM: Homo Sapiens

<400> SEQUENCE: 1042
uuagugaagg cuauuuuaau u                                         21

<210> SEQ ID NO 1043
<211> LENGTH: 24
<212> TYPE: RNA
<213> ORGANISM: Homo Sapiens

<400> SEQUENCE: 1043
gguugggcag ugaggagggu guga                                      24

<210> SEQ ID NO 1044
<211> LENGTH: 24
<212> TYPE: RNA
<213> ORGANISM: Homo Sapiens

<400> SEQUENCE: 1044
ccccgggaac gucgagacug gagc                                      24

<210> SEQ ID NO 1045
<211> LENGTH: 22
<212> TYPE: RNA
<213> ORGANISM: Homo Sapiens

<400> SEQUENCE: 1045
uaaugcauua aauuauugaa gg                                        22

<210> SEQ ID NO 1046
<211> LENGTH: 23
<212> TYPE: RNA
<213> ORGANISM: Homo Sapiens

<400> SEQUENCE: 1046
uggaguuaag gguugcuugg aga                                       23

<210> SEQ ID NO 1047
<211> LENGTH: 22
<212> TYPE: RNA
<213> ORGANISM: Homo Sapiens

<400> SEQUENCE: 1047
agguagacug ggauuuguug uu                                        22

<210> SEQ ID NO 1048
<211> LENGTH: 23
<212> TYPE: RNA
<213> ORGANISM: Homo Sapiens

<400> SEQUENCE: 1048
ccggggcaga uugguguagg gug                                       23

<210> SEQ ID NO 1049
<211> LENGTH: 22
<212> TYPE: RNA

```
<213> ORGANISM: Homo Sapiens

<400> SEQUENCE: 1049
uucaacgggu auuuauugag ca                                    22

<210> SEQ ID NO 1050
<211> LENGTH: 22
<212> TYPE: RNA
<213> ORGANISM: Homo Sapiens

<400> SEQUENCE: 1050
uaaugccccu aaaaauccuu au                                    22

<210> SEQ ID NO 1051
<211> LENGTH: 21
<212> TYPE: RNA
<213> ORGANISM: Homo Sapiens

<400> SEQUENCE: 1051
uucacagugg cuaaguuccg c                                     21

<210> SEQ ID NO 1052
<211> LENGTH: 22
<212> TYPE: RNA
<213> ORGANISM: Homo Sapiens

<400> SEQUENCE: 1052
agaaggggug aaauuuaaac gu                                    22

<210> SEQ ID NO 1053
<211> LENGTH: 22
<212> TYPE: RNA
<213> ORGANISM: Homo Sapiens

<400> SEQUENCE: 1053
auugccucug uucuaacaca ag                                    22

<210> SEQ ID NO 1054
<211> LENGTH: 22
<212> TYPE: RNA
<213> ORGANISM: Homo Sapiens

<400> SEQUENCE: 1054
cuguugccac uaaccucaac cu                                    22

<210> SEQ ID NO 1055
<211> LENGTH: 23
<212> TYPE: RNA
<213> ORGANISM: Homo Sapiens

<400> SEQUENCE: 1055
aggaagcccu ggaggggcug gag                                   23

<210> SEQ ID NO 1056
<211> LENGTH: 22
<212> TYPE: RNA
<213> ORGANISM: Homo Sapiens

<400> SEQUENCE: 1056
uagagucugg cugauauggu uu                                    22

<210> SEQ ID NO 1057
<211> LENGTH: 21
```

```
<212> TYPE: RNA
<213> ORGANISM: Homo Sapiens

<400> SEQUENCE: 1057
gaucucacuu uguugcccag g                                              21

<210> SEQ ID NO 1058
<211> LENGTH: 21
<212> TYPE: RNA
<213> ORGANISM: Homo Sapiens

<400> SEQUENCE: 1058
gcagagaaca aaggacucag u                                              21

<210> SEQ ID NO 1059
<211> LENGTH: 22
<212> TYPE: RNA
<213> ORGANISM: Homo Sapiens

<400> SEQUENCE: 1059
ggagaaauua uccuuggugu gu                                             22

<210> SEQ ID NO 1060
<211> LENGTH: 22
<212> TYPE: RNA
<213> ORGANISM: Homo Sapiens

<400> SEQUENCE: 1060 acuuccuca cucccgugaa gu                                              22

<210> SEQ ID NO 1061
<211> LENGTH: 22
<212> TYPE: RNA
<213> ORGANISM: Homo Sapiens

<400> SEQUENCE: 1061
gcuauuucac gacaccaggg uu                                             22

<210> SEQ ID NO 1062
<211> LENGTH: 20
<212> TYPE: RNA
<213> ORGANISM: Homo Sapiens

<400> SEQUENCE: 1062
gugcauugcu guugcauugc                                                20

<210> SEQ ID NO 1063
<211> LENGTH: 22
<212> TYPE: RNA
<213> ORGANISM: Homo Sapiens

<400> SEQUENCE: 1063
acguuugaau gcuguacaag gc                                             22

<210> SEQ ID NO 1064
<211> LENGTH: 17
<212> TYPE: RNA
<213> ORGANISM: Homo Sapiens

<400> SEQUENCE: 1064
ccaauuacca cuucuuu                                                   17

<210> SEQ ID NO 1065
```

```
<211> LENGTH: 26
<212> TYPE: RNA
<213> ORGANISM: Homo Sapiens

<400> SEQUENCE: 1065
aagaggaaga aauggcuggu ucucag                                          26

<210> SEQ ID NO 1066
<211> LENGTH: 22
<212> TYPE: RNA
<213> ORGANISM: Homo Sapiens

<400> SEQUENCE: 1066
aaugcaccug ggcaaggauu ca                                              22

<210> SEQ ID NO 1067
<211> LENGTH: 23
<212> TYPE: RNA
<213> ORGANISM: Homo Sapiens

<400> SEQUENCE: 1067
acaggcggcu guagcaaugg ggg                                             23

<210> SEQ ID NO 1068
<211> LENGTH: 19
<212> TYPE: RNA
<213> ORGANISM: Homo Sapiens

<400> SEQUENCE: 1068
agggaccuga gugucuaag                                                  19

<210> SEQ ID NO 1069
<211> LENGTH: 22
<212> TYPE: RNA
<213> ORGANISM: Homo Sapiens

<400> SEQUENCE: 1069 cuggguucu gagacagaca gu                                               22

<210> SEQ ID NO 1070
<211> LENGTH: 23
<212> TYPE: RNA
<213> ORGANISM: Homo Sapiens

<400> SEQUENCE: 1070
augcggaccu ggguuagcgg agu                                             23

<210> SEQ ID NO 1071
<211> LENGTH: 22
<212> TYPE: RNA
<213> ORGANISM: Homo Sapiens

<400> SEQUENCE: 1071
uacucaggag aguggcaauc ac                                              22

<210> SEQ ID NO 1072
<211> LENGTH: 22
<212> TYPE: RNA
<213> ORGANISM: Homo Sapiens

<400> SEQUENCE: 1072
cagagugaca agcugguuaa ag                                              22
```

```
<210> SEQ ID NO 1073
<211> LENGTH: 21
<212> TYPE: RNA
<213> ORGANISM: Homo Sapiens

<400> SEQUENCE: 1073
ucuggcuguu guggugugca a                                              21

<210> SEQ ID NO 1074
<211> LENGTH: 22
<212> TYPE: RNA
<213> ORGANISM: Homo Sapiens

<400> SEQUENCE: 1074
uacugcagac guggcaauca ug                                             22

<210> SEQ ID NO 1075
<211> LENGTH: 20
<212> TYPE: RNA
<213> ORGANISM: Homo Sapiens

<400> SEQUENCE: 1075
ccauggaucu ccaggugggu                                                20

<210> SEQ ID NO 1076
<211> LENGTH: 23
<212> TYPE: RNA
<213> ORGANISM: Homo Sapiens

<400> SEQUENCE: 1076
aggcagugua guuagcugau ugc                                            23

<210> SEQ ID NO 1077
<211> LENGTH: 23
<212> TYPE: RNA
<213> ORGANISM: Homo Sapiens

<400> SEQUENCE: 1077
ccucagggcu guagaacagg gcu                                            23

<210> SEQ ID NO 1078
<211> LENGTH: 22
<212> TYPE: RNA
<213> ORGANISM: Homo Sapiens

<400> SEQUENCE: 1078
aaaaugguuc ccuuuagagu gu                                             22

<210> SEQ ID NO 1079
<211> LENGTH: 23
<212> TYPE: RNA
<213> ORGANISM: Homo Sapiens

<400> SEQUENCE: 1079
acggaauaug uauacggaau aua                                            23

<210> SEQ ID NO 1080
<211> LENGTH: 17
<212> TYPE: RNA
<213> ORGANISM: Homo Sapiens

<400> SEQUENCE: 1080
uggagagaaa ggcagua                                                   17
```

-continued

```
<210> SEQ ID NO 1081
<211> LENGTH: 22
<212> TYPE: RNA
<213> ORGANISM: Homo Sapiens

<400> SEQUENCE: 1081
ugugauauca ugguuccugg ga                                                  22

<210> SEQ ID NO 1082
<211> LENGTH: 22
<212> TYPE: RNA
<213> ORGANISM: Homo Sapiens

<400> SEQUENCE: 1082
aggacuggac ucccggcagc cc                                                  22

<210> SEQ ID NO 1083
<211> LENGTH: 21
<212> TYPE: RNA
<213> ORGANISM: Homo Sapiens

<400> SEQUENCE: 1083
acagggccgc agauggagac u                                                   21

<210> SEQ ID NO 1084
<211> LENGTH: 23
<212> TYPE: RNA
<213> ORGANISM: Homo Sapiens

<400> SEQUENCE: 1084
gaagugcuuc gauuuggggg ugu                                                 23

<210> SEQ ID NO 1085
<211> LENGTH: 24
<212> TYPE: RNA
<213> ORGANISM: Homo Sapiens

<400> SEQUENCE: 1085
agccuggaag cuggagccug cagu                                                24

<210> SEQ ID NO 1086
<211> LENGTH: 23
<212> TYPE: RNA
<213> ORGANISM: Homo Sapiens

<400> SEQUENCE: 1086
uacauggaug gaaaccuuca agc                                                 23

<210> SEQ ID NO 1087
<211> LENGTH: 22
<212> TYPE: RNA
<213> ORGANISM: Homo Sapiens

<400> SEQUENCE: 1087
uuucccuuca gagccuggcu uu                                                  22

<210> SEQ ID NO 1088
<211> LENGTH: 22
<212> TYPE: RNA
<213> ORGANISM: Homo Sapiens

<400> SEQUENCE: 1088
agggacuuuc aggggcagcu gu                                                  22
```

-continued

<210> SEQ ID NO 1089
<211> LENGTH: 22
<212> TYPE: RNA
<213> ORGANISM: Homo Sapiens

<400> SEQUENCE: 1089
gggaccaucc ugccugcugu gg                                    22

<210> SEQ ID NO 1090
<211> LENGTH: 22
<212> TYPE: RNA
<213> ORGANISM: Homo Sapiens

<400> SEQUENCE: 1090
cugccaauuc cauaggucac ag                                    22

<210> SEQ ID NO 1091
<211> LENGTH: 21
<212> TYPE: RNA
<213> ORGANISM: Homo Sapiens

<400> SEQUENCE: 1091
uaaaaacugc aauuacuuuu a                                     21

<210> SEQ ID NO 1092
<211> LENGTH: 23
<212> TYPE: RNA
<213> ORGANISM: Homo Sapiens

<400> SEQUENCE: 1092
aucagggcuu guggaauggg aag                                   23

<210> SEQ ID NO 1093
<211> LENGTH: 22
<212> TYPE: RNA
<213> ORGANISM: Homo Sapiens

<400> SEQUENCE: 1093
uggagagaaa ggcaguuccu ga                                    22

<210> SEQ ID NO 1094
<211> LENGTH: 21
<212> TYPE: RNA
<213> ORGANISM: Homo Sapiens

<400> SEQUENCE: 1094
gggacuagga ugcagaccuc c                                     21

<210> SEQ ID NO 1095
<211> LENGTH: 17
<212> TYPE: RNA
<213> ORGANISM: Homo Sapiens

<400> SEQUENCE: 1095
augugggcuc aggcuca                                          17

<210> SEQ ID NO 1096
<211> LENGTH: 25
<212> TYPE: RNA
<213> ORGANISM: Homo Sapiens

<400> SEQUENCE: 1096

```
cuuccagacg cuccgcccca cgucg                                         25

<210> SEQ ID NO 1097
<211> LENGTH: 22
<212> TYPE: RNA
<213> ORGANISM: Homo Sapiens

<400> SEQUENCE: 1097
aucgugcauc ccuuuagagu gu                                            22

<210> SEQ ID NO 1098
<211> LENGTH: 21
<212> TYPE: RNA
<213> ORGANISM: Homo Sapiens

<400> SEQUENCE: 1098
gcaggaacuu gugagucucc u                                             21

<210> SEQ ID NO 1099
<211> LENGTH: 22
<212> TYPE: RNA
<213> ORGANISM: Homo Sapiens

<400> SEQUENCE: 1099 uggggagug cagugauugu gg                                             22

<210> SEQ ID NO 1100
<211> LENGTH: 22
<212> TYPE: RNA
<213> ORGANISM: Homo Sapiens

<400> SEQUENCE: 1100
auuaaggaca uuugugauug au                                            22

<210> SEQ ID NO 1101
<211> LENGTH: 22
<212> TYPE: RNA
<213> ORGANISM: Homo Sapiens

<400> SEQUENCE: 1101
uagucccuuc cuugaagcgg uc                                            22

<210> SEQ ID NO 1102
<211> LENGTH: 20
<212> TYPE: RNA
<213> ORGANISM: Homo Sapiens

<400> SEQUENCE: 1102
aaaagugauu gcaguguuug                                               20

<210> SEQ ID NO 1103
<211> LENGTH: 21
<212> TYPE: RNA
<213> ORGANISM: Homo Sapiens

<400> SEQUENCE: 1103
uacucaaaaa gcugucaguc a                                             21

<210> SEQ ID NO 1104
<211> LENGTH: 22
<212> TYPE: RNA
<213> ORGANISM: Homo Sapiens

<400> SEQUENCE: 1104
```
caacaaaucc cagucuaccu aa                                          22

<210> SEQ ID NO 1105
<211> LENGTH: 22
<212> TYPE: RNA
<213> ORGANISM: Homo Sapiens

<400> SEQUENCE: 1105
uuuccggcuc gcugggugu gu                                           22

<210> SEQ ID NO 1106
<211> LENGTH: 22
<212> TYPE: RNA
<213> ORGANISM: Homo Sapiens

<400> SEQUENCE: 1106
cucaguagcc aguguagauc cu                                          22

<210> SEQ ID NO 1107
<211> LENGTH: 22
<212> TYPE: RNA
<213> ORGANISM: Homo Sapiens

<400> SEQUENCE: 1107
ugugacagau ugauaacuga aa                                          22

<210> SEQ ID NO 1108
<211> LENGTH: 21
<212> TYPE: RNA
<213> ORGANISM: Homo Sapiens

<400> SEQUENCE: 1108
cuccguuugc cuguuucgcu g                                           21

<210> SEQ ID NO 1109
<211> LENGTH: 21
<212> TYPE: RNA
<213> ORGANISM: Homo Sapiens

<400> SEQUENCE: 1109
gggaagagcu guacggccuu c                                           21

<210> SEQ ID NO 1110
<211> LENGTH: 23
<212> TYPE: RNA
<213> ORGANISM: Homo Sapiens

<400> SEQUENCE: 1110
auacugugaa uuucacuguc aca                                         23

<210> SEQ ID NO 1111
<211> LENGTH: 17
<212> TYPE: RNA
<213> ORGANISM: Homo Sapiens

<400> SEQUENCE: 1111
cagagaauug uuuaauc                                                17

<210> SEQ ID NO 1112
<211> LENGTH: 22
<212> TYPE: RNA
<213> ORGANISM: Homo Sapiens

```
<400> SEQUENCE: 1112
auucucucug gaucccaugg au                                          22

<210> SEQ ID NO 1113
<211> LENGTH: 17
<212> TYPE: RNA
<213> ORGANISM: Homo Sapiens

<400> SEQUENCE: 1113 ugggggcucag cgaguuu                                               17

<210> SEQ ID NO 1114
<211> LENGTH: 22
<212> TYPE: RNA
<213> ORGANISM: Homo Sapiens

<400> SEQUENCE: 1114
ugagaaccac gucugcucug ag                                          22

<210> SEQ ID NO 1115
<211> LENGTH: 22
<212> TYPE: RNA
<213> ORGANISM: Homo Sapiens

<400> SEQUENCE: 1115
ccaguauuaa cugugcugcu ga                                          22

<210> SEQ ID NO 1116
<211> LENGTH: 23
<212> TYPE: RNA
<213> ORGANISM: Homo Sapiens

<400> SEQUENCE: 1116
gcagcagaga auaggacuac guc                                         23

<210> SEQ ID NO 1117
<211> LENGTH: 22
<212> TYPE: RNA
<213> ORGANISM: Homo Sapiens

<400> SEQUENCE: 1117
aaccaucgac cguugagugg ac                                          22

<210> SEQ ID NO 1118
<211> LENGTH: 22
<212> TYPE: RNA
<213> ORGANISM: Homo Sapiens

<400> SEQUENCE: 1118
aucgugcauc ccuuuagagu gu                                          22

<210> SEQ ID NO 1119
<211> LENGTH: 22
<212> TYPE: RNA
<213> ORGANISM: Homo Sapiens

<400> SEQUENCE: 1119
ccaaaacugc aguuacuuuu gc                                          22

<210> SEQ ID NO 1120
<211> LENGTH: 21
<212> TYPE: RNA
<213> ORGANISM: Homo Sapiens
```

-continued

```
<400> SEQUENCE: 1120
cacaagguau ugguauuacc u                                              21

<210> SEQ ID NO 1121
<211> LENGTH: 22
<212> TYPE: RNA
<213> ORGANISM: Homo Sapiens

<400> SEQUENCE: 1121
auaccucauc uagaaugcug ua                                             22

<210> SEQ ID NO 1122
<211> LENGTH: 22
<212> TYPE: RNA
<213> ORGANISM: Homo Sapiens

<400> SEQUENCE: 1122
accacugacc guugacugua cc                                             22

<210> SEQ ID NO 1123
<211> LENGTH: 21
<212> TYPE: RNA
<213> ORGANISM: Homo Sapiens

<400> SEQUENCE: 1123
gcccugaccu guccuguucu g                                              21

<210> SEQ ID NO 1124
<211> LENGTH: 22
<212> TYPE: RNA
<213> ORGANISM: Homo Sapiens

<400> SEQUENCE: 1124
uuuuucauua uugcuccuga cc                                             22

<210> SEQ ID NO 1125
<211> LENGTH: 21
<212> TYPE: RNA
<213> ORGANISM: Homo Sapiens

<400> SEQUENCE: 1125
cacacauagc agguguauau a                                              21

<210> SEQ ID NO 1126
<211> LENGTH: 18
<212> TYPE: RNA
<213> ORGANISM: Homo Sapiens

<400> SEQUENCE: 1126
gggcucacau caccccau                                                  18

<210> SEQ ID NO 1127
<211> LENGTH: 22
<212> TYPE: RNA
<213> ORGANISM: Homo Sapiens

<400> SEQUENCE: 1127
gaaaacgaca augacuuuug ca                                             22

<210> SEQ ID NO 1128
<211> LENGTH: 22
<212> TYPE: RNA
```

```
<213> ORGANISM: Homo Sapiens

<400> SEQUENCE: 1128
agaguugagu cuggacgucc cg                                    22

<210> SEQ ID NO 1129
<211> LENGTH: 22
<212> TYPE: RNA
<213> ORGANISM: Homo Sapiens

<400> SEQUENCE: 1129
agccuuccag gagaaaugga ga                                    22

<210> SEQ ID NO 1130
<211> LENGTH: 22
<212> TYPE: RNA
<213> ORGANISM: Homo Sapiens

<400> SEQUENCE: 1130
agggcuuagc ugcuugugag ca                                    22

<210> SEQ ID NO 1131
<211> LENGTH: 18
<212> TYPE: RNA
<213> ORGANISM: Homo Sapiens

<400> SEQUENCE: 1131
uucacaggga ggugucau                                         18

<210> SEQ ID NO 1132
<211> LENGTH: 22
<212> TYPE: RNA
<213> ORGANISM: Homo Sapiens

<400> SEQUENCE: 1132
uauaccucag uuuuaucagg ug                                    22

<210> SEQ ID NO 1133
<211> LENGTH: 21
<212> TYPE: RNA
<213> ORGANISM: Homo Sapiens

<400> SEQUENCE: 1133
gcaggcacag acagcccugg c                                     21

<210> SEQ ID NO 1134
<211> LENGTH: 21
<212> TYPE: RNA
<213> ORGANISM: Homo Sapiens

<400> SEQUENCE: 1134
gguagauuuu ccuucuaugg u                                     21

<210> SEQ ID NO 1135
<211> LENGTH: 21
<212> TYPE: RNA
<213> ORGANISM: Homo Sapiens

<400> SEQUENCE: 1135
aggaggcagc gcucucagga c                                     21

<210> SEQ ID NO 1136
<211> LENGTH: 21
```

-continued

<212> TYPE: RNA
<213> ORGANISM: Homo Sapiens

<400> SEQUENCE: 1136
aagugaucua aaggccuaca u                                              21

<210> SEQ ID NO 1137
<211> LENGTH: 22
<212> TYPE: RNA
<213> ORGANISM: Homo Sapiens

<400> SEQUENCE: 1137
aaagacccau ugaggagaag gu                                             22

<210> SEQ ID NO 1138
<211> LENGTH: 23
<212> TYPE: RNA
<213> ORGANISM: Homo Sapiens

<400> SEQUENCE: 1138
ccugcagcga cuugauggcu ucc                                            23

<210> SEQ ID NO 1139
<211> LENGTH: 18
<212> TYPE: RNA
<213> ORGANISM: Homo Sapiens

<400> SEQUENCE: 1139
aucugaccug augaaggu                                                  18

<210> SEQ ID NO 1140
<211> LENGTH: 22
<212> TYPE: RNA
<213> ORGANISM: Homo Sapiens

<400> SEQUENCE: 1140 uuugguccccc uucaaccagc ug                                            22

<210> SEQ ID NO 1141
<211> LENGTH: 22
<212> TYPE: RNA
<213> ORGANISM: Homo Sapiens

<400> SEQUENCE: 1141
ccucuagaug gaagcacugu cu                                             22

<210> SEQ ID NO 1142
<211> LENGTH: 22
<212> TYPE: RNA
<213> ORGANISM: Homo Sapiens

<400> SEQUENCE: 1142
uuuugcgaug uguuccuaau au                                             22

<210> SEQ ID NO 1143
<211> LENGTH: 21
<212> TYPE: RNA
<213> ORGANISM: Homo Sapiens

<400> SEQUENCE: 1143
agccaagugg aaguuacuuu a                                              21

<210> SEQ ID NO 1144

-continued

```
<211> LENGTH: 23
<212> TYPE: RNA
<213> ORGANISM: Homo Sapiens

<400> SEQUENCE: 1144
ugugacugca uuaugaaaau ucu                                            23

<210> SEQ ID NO 1145
<211> LENGTH: 21
<212> TYPE: RNA
<213> ORGANISM: Homo Sapiens

<400> SEQUENCE: 1145
agcaugacag aggagaggug g                                              21

<210> SEQ ID NO 1146
<211> LENGTH: 21
<212> TYPE: RNA
<213> ORGANISM: Homo Sapiens

<400> SEQUENCE: 1146
ucuugaaguc agaacccgca a                                              21

<210> SEQ ID NO 1147
<211> LENGTH: 17
<212> TYPE: RNA
<213> ORGANISM: Homo Sapiens

<400> SEQUENCE: 1147
auggagaagg cuucuga                                                   17

<210> SEQ ID NO 1148
<211> LENGTH: 22
<212> TYPE: RNA
<213> ORGANISM: Homo Sapiens

<400> SEQUENCE: 1148
uauaaaauga gggcaguaag ac                                             22

<210> SEQ ID NO 1149
<211> LENGTH: 19
<212> TYPE: RNA
<213> ORGANISM: Homo Sapiens

<400> SEQUENCE: 1149
uggauuuuug gaucaggga                                                 19

<210> SEQ ID NO 1150
<211> LENGTH: 21
<212> TYPE: RNA
<213> ORGANISM: Homo Sapiens

<400> SEQUENCE: 1150
gacagagugc cacuuacuga a                                              21

<210> SEQ ID NO 1151
<211> LENGTH: 23
<212> TYPE: RNA
<213> ORGANISM: Homo Sapiens

<400> SEQUENCE: 1151
uaaggugcau cuagugcagu uag                                            23
```

```
<210> SEQ ID NO 1152
<211> LENGTH: 22
<212> TYPE: RNA
<213> ORGANISM: Homo Sapiens

<400> SEQUENCE: 1152 aggcgggcg ccgcgggacc gc                                          22

<210> SEQ ID NO 1153
<211> LENGTH: 23
<212> TYPE: RNA
<213> ORGANISM: Homo Sapiens

<400> SEQUENCE: 1153
uaaggugcau cuagugcaga uag                                        23

<210> SEQ ID NO 1154
<211> LENGTH: 24
<212> TYPE: RNA
<213> ORGANISM: Homo Sapiens

<400> SEQUENCE: 1154
uugcagcugc cugggaguga cuuc                                       24

<210> SEQ ID NO 1155
<211> LENGTH: 23
<212> TYPE: RNA
<213> ORGANISM: Homo Sapiens

<400> SEQUENCE: 1155
ucuuugguua ucuagcugua uga                                        23

<210> SEQ ID NO 1156
<211> LENGTH: 22
<212> TYPE: RNA
<213> ORGANISM: Homo Sapiens

<400> SEQUENCE: 1156
aauucuguaa aggaagaaga gg                                         22

<210> SEQ ID NO 1157
<211> LENGTH: 23
<212> TYPE: RNA
<213> ORGANISM: Homo Sapiens

<400> SEQUENCE: 1157
uagcccccag gcuucacuug gcg                                        23

<210> SEQ ID NO 1158
<211> LENGTH: 25
<212> TYPE: RNA
<213> ORGANISM: Homo Sapiens

<400> SEQUENCE: 1158
acuggacuug gagucagaag agugg                                      25

<210> SEQ ID NO 1159
<211> LENGTH: 22
<212> TYPE: RNA
<213> ORGANISM: Homo Sapiens

<400> SEQUENCE: 1159
ucacaguggu cucugggauu au                                         22
```

```
<210> SEQ ID NO 1160
<211> LENGTH: 22
<212> TYPE: RNA
<213> ORGANISM: Homo Sapiens

<400> SEQUENCE: 1160 caaagccuu ccuauuuuc cc                                              22

<210> SEQ ID NO 1161
<211> LENGTH: 22
<212> TYPE: RNA
<213> ORGANISM: Homo Sapiens

<400> SEQUENCE: 1161
caacaaauca cagucugcca ua                                            22

<210> SEQ ID NO 1162
<211> LENGTH: 19
<212> TYPE: RNA
<213> ORGANISM: Homo Sapiens

<400> SEQUENCE: 1162
acuggauuug gagccagaa                                                19

<210> SEQ ID NO 1163
<211> LENGTH: 22
<212> TYPE: RNA
<213> ORGANISM: Homo Sapiens

<400> SEQUENCE: 1163
cacuguuucc uuucugagug ga                                            22

<210> SEQ ID NO 1164
<211> LENGTH: 24
<212> TYPE: RNA
<213> ORGANISM: Homo Sapiens

<400> SEQUENCE: 1164
ucccugagac ccuuuaaccu guga                                          24

<210> SEQ ID NO 1165
<211> LENGTH: 21
<212> TYPE: RNA
<213> ORGANISM: Homo Sapiens

<400> SEQUENCE: 1165
gaacggcuuc auacaggagu u                                             21

<210> SEQ ID NO 1166
<211> LENGTH: 19
<212> TYPE: RNA
<213> ORGANISM: Homo Sapiens

<400> SEQUENCE: 1166
acuggacuug gagucagga                                                19

<210> SEQ ID NO 1167
<211> LENGTH: 19
<212> TYPE: RNA
<213> ORGANISM: Homo Sapiens

<400> SEQUENCE: 1167
cauccguccg ucuguccac                                                19
```

-continued

```
<210> SEQ ID NO 1168
<211> LENGTH: 22
<212> TYPE: RNA
<213> ORGANISM: Homo Sapiens

<400> SEQUENCE: 1168
aaagacauag uugcaagaug gg                                              22

<210> SEQ ID NO 1169
<211> LENGTH: 22
<212> TYPE: RNA
<213> ORGANISM: Homo Sapiens

<400> SEQUENCE: 1169
uuauaauaca accugauaag ug                                              22

<210> SEQ ID NO 1170
<211> LENGTH: 21
<212> TYPE: RNA
<213> ORGANISM: Homo Sapiens

<400> SEQUENCE: 1170
ucaaguguca ucugucccua g                                               21

<210> SEQ ID NO 1171
<211> LENGTH: 24
<212> TYPE: RNA
<213> ORGANISM: Homo Sapiens

<400> SEQUENCE: 1171
gaaaaugaug aguagugacu gaug                                            24

<210> SEQ ID NO 1172
<211> LENGTH: 22
<212> TYPE: RNA
<213> ORGANISM: Homo Sapiens

<400> SEQUENCE: 1172
auagcagcau gaaccugucu ca                                              22

<210> SEQ ID NO 1173
<211> LENGTH: 18
<212> TYPE: RNA
<213> ORGANISM: Homo Sapiens

<400> SEQUENCE: 1173
cuaggggguu ugcccuug                                                   18

<210> SEQ ID NO 1174
<211> LENGTH: 19
<212> TYPE: RNA
<213> ORGANISM: Homo Sapiens

<400> SEQUENCE: 1174
aggcugcgga auucaggac                                                  19

<210> SEQ ID NO 1175
<211> LENGTH: 22
<212> TYPE: RNA
<213> ORGANISM: Homo Sapiens

<400> SEQUENCE: 1175
```
cacuagauug ugagcuccug ga                                                22

<210> SEQ ID NO 1176
<211> LENGTH: 23
<212> TYPE: RNA
<213> ORGANISM: Homo Sapiens

<400> SEQUENCE: 1176
ugucacucgg cucggcccac uac                                               23

<210> SEQ ID NO 1177
<211> LENGTH: 23
<212> TYPE: RNA
<213> ORGANISM: Homo Sapiens

<400> SEQUENCE: 1177
ugggccaggg agcagcuggu ggg                                               23

<210> SEQ ID NO 1178
<211> LENGTH: 22
<212> TYPE: RNA
<213> ORGANISM: Homo Sapiens

<400> SEQUENCE: 1178
agcuuuuggg aauucaggua gu                                                22

<210> SEQ ID NO 1179
<211> LENGTH: 21
<212> TYPE: RNA
<213> ORGANISM: Homo Sapiens

<400> SEQUENCE: 1179
uugugaagaa agaaauucuu a                                                 21

<210> SEQ ID NO 1180
<211> LENGTH: 21
<212> TYPE: RNA
<213> ORGANISM: Homo Sapiens

<400> SEQUENCE: 1180
uuaguccugc cuguagguuu a                                                 21

<210> SEQ ID NO 1181
<211> LENGTH: 23
<212> TYPE: RNA
<213> ORGANISM: Homo Sapiens

<400> SEQUENCE: 1181
uacccuguag auccgaauuu gug                                               23

<210> SEQ ID NO 1182
<211> LENGTH: 19
<212> TYPE: RNA
<213> ORGANISM: Homo Sapiens

<400> SEQUENCE: 1182
ugagggagug gauuguaug                                                    19

<210> SEQ ID NO 1183
<211> LENGTH: 22
<212> TYPE: RNA
<213> ORGANISM: Homo Sapiens

<400> SEQUENCE: 1183

-continued aggugcucca ggcuggcuca ca                                         22

<210> SEQ ID NO 1184
<211> LENGTH: 22
<212> TYPE: RNA
<213> ORGANISM: Homo Sapiens

<400> SEQUENCE: 1184
cugguuucac augguggcuu ag                                         22

<210> SEQ ID NO 1185
<211> LENGTH: 22
<212> TYPE: RNA
<213> ORGANISM: Homo Sapiens

<400> SEQUENCE: 1185
ugaaggucua cugugugcca gg                                         22

<210> SEQ ID NO 1186
<211> LENGTH: 22
<212> TYPE: RNA
<213> ORGANISM: Homo Sapiens

<400> SEQUENCE: 1186
uccuaaaucu gaaaguccaa aa                                         22

<210> SEQ ID NO 1187
<211> LENGTH: 17
<212> TYPE: RNA
<213> ORGANISM: Homo Sapiens

<400> SEQUENCE: 1187
ccugguggcu uccuuuu                                               17

<210> SEQ ID NO 1188
<211> LENGTH: 22
<212> TYPE: RNA
<213> ORGANISM: Homo Sapiens

<400> SEQUENCE: 1188
aacccguaga uccgaucuug ug                                         22

<210> SEQ ID NO 1189
<211> LENGTH: 23
<212> TYPE: RNA
<213> ORGANISM: Homo Sapiens

<400> SEQUENCE: 1189
uggccggaug ggacaggagg cau                                        23

<210> SEQ ID NO 1190
<211> LENGTH: 22
<212> TYPE: RNA
<213> ORGANISM: Homo Sapiens

<400> SEQUENCE: 1190 auaguggga gcuggcagau uc                                          22

<210> SEQ ID NO 1191
<211> LENGTH: 22
<212> TYPE: RNA
<213> ORGANISM: Homo Sapiens

```
<400> SEQUENCE: 1191
uagguaguuu cauguuguug gg                                              22

<210> SEQ ID NO 1192
<211> LENGTH: 22
<212> TYPE: RNA
<213> ORGANISM: Homo Sapiens

<400> SEQUENCE: 1192
caaaguuuaa gauccuugaa gu                                              22

<210> SEQ ID NO 1193
<211> LENGTH: 22
<212> TYPE: RNA
<213> ORGANISM: Homo Sapiens

<400> SEQUENCE: 1193
cccucucugg cuccucccca aa                                              22

<210> SEQ ID NO 1194
<211> LENGTH: 22
<212> TYPE: RNA
<213> ORGANISM: Homo Sapiens

<400> SEQUENCE: 1194
uucucaagag ggaggcaauc au                                              22

<210> SEQ ID NO 1195
<211> LENGTH: 22
<212> TYPE: RNA
<213> ORGANISM: Homo Sapiens

<400> SEQUENCE: 1195
ggaggaaccu uggagcuucg gc                                              22

<210> SEQ ID NO 1196
<211> LENGTH: 25
<212> TYPE: RNA
<213> ORGANISM: Homo Sapiens

<400> SEQUENCE: 1196
agggaucgcg ggcggguggc ggccu                                           25

<210> SEQ ID NO 1197
<211> LENGTH: 20
<212> TYPE: RNA
<213> ORGANISM: Homo Sapiens

<400> SEQUENCE: 1197
acuguaaacg cuuucugaug                                                 20

<210> SEQ ID NO 1198
<211> LENGTH: 22
<212> TYPE: RNA
<213> ORGANISM: Homo Sapiens

<400> SEQUENCE: 1198
caugcuagga uagaaagaau gg                                              22

<210> SEQ ID NO 1199
<211> LENGTH: 22
<212> TYPE: RNA
<213> ORGANISM: Homo Sapiens
```

-continued

```
<400> SEQUENCE: 1199
agcccgcccc agccgagguu cu                                    22

<210> SEQ ID NO 1200
<211> LENGTH: 16
<212> TYPE: RNA
<213> ORGANISM: Homo Sapiens

<400> SEQUENCE: 1200
uccagcucgg uggcac                                           16

<210> SEQ ID NO 1201
<211> LENGTH: 21
<212> TYPE: RNA
<213> ORGANISM: Homo Sapiens

<400> SEQUENCE: 1201
ucccuccuuc uguccccaca g                                     21

<210> SEQ ID NO 1202
<211> LENGTH: 21
<212> TYPE: RNA
<213> ORGANISM: Homo Sapiens

<400> SEQUENCE: 1202
uacuuggaaa ggcaucaguu g                                     21

<210> SEQ ID NO 1203
<211> LENGTH: 22
<212> TYPE: RNA
<213> ORGANISM: Homo Sapiens

<400> SEQUENCE: 1203
acccgucccg uucguccccg ga                                    22

<210> SEQ ID NO 1204
<211> LENGTH: 22
<212> TYPE: RNA
<213> ORGANISM: Homo Sapiens

<400> SEQUENCE: 1204
uaccauuaga agagcuggaa ga                                    22

<210> SEQ ID NO 1205
<211> LENGTH: 18
<212> TYPE: RNA
<213> ORGANISM: Homo Sapiens

<400> SEQUENCE: 1205
uugcacuugu cucaguga                                         18

<210> SEQ ID NO 1206
<211> LENGTH: 24
<212> TYPE: RNA
<213> ORGANISM: Homo Sapiens

<400> SEQUENCE: 1206
acaaaaaaaa aagcccaacc cuuc                                  24

<210> SEQ ID NO 1207
<211> LENGTH: 21
<212> TYPE: RNA
```

```
<213> ORGANISM: Homo Sapiens

<400> SEQUENCE: 1207
gccccgggca gugugaucau c                                              21

<210> SEQ ID NO 1208
<211> LENGTH: 22
<212> TYPE: RNA
<213> ORGANISM: Homo Sapiens

<400> SEQUENCE: 1208
aaaaguaauu gcgaguuuua cc                                             22

<210> SEQ ID NO 1209
<211> LENGTH: 22
<212> TYPE: RNA
<213> ORGANISM: Homo Sapiens

<400> SEQUENCE: 1209
gaaagugcuu ccuuuuagag gc                                             22

<210> SEQ ID NO 1210
<211> LENGTH: 23
<212> TYPE: RNA
<213> ORGANISM: Homo Sapiens

<400> SEQUENCE: 1210
agggccagag gagccuggag ugg                                            23

<210> SEQ ID NO 1211
<211> LENGTH: 22
<212> TYPE: RNA
<213> ORGANISM: Homo Sapiens

<400> SEQUENCE: 1211
uguguccggg aaguggagga gg                                             22

<210> SEQ ID NO 1212
<211> LENGTH: 22
<212> TYPE: RNA
<213> ORGANISM: Homo Sapiens

<400> SEQUENCE: 1212
caaccuggag gacuccaugc ug                                             22

<210> SEQ ID NO 1213
<211> LENGTH: 21
<212> TYPE: RNA
<213> ORGANISM: Homo Sapiens

<400> SEQUENCE: 1213
guggcugcac ucacuuccuu c                                              21

<210> SEQ ID NO 1214
<211> LENGTH: 22
<212> TYPE: RNA
<213> ORGANISM: Homo Sapiens

<400> SEQUENCE: 1214
acccagguuc ccucuggccg ca                                             22

<210> SEQ ID NO 1215
<211> LENGTH: 21
```

-continued

<212> TYPE: RNA
<213> ORGANISM: Homo Sapiens

<400> SEQUENCE: 1215
cagcagcaca cuggguuug u                                        21

<210> SEQ ID NO 1216
<211> LENGTH: 21
<212> TYPE: RNA
<213> ORGANISM: Homo Sapiens

<400> SEQUENCE: 1216
uaaaguaaau augcaccaaa a                                       21

<210> SEQ ID NO 1217
<211> LENGTH: 21
<212> TYPE: RNA
<213> ORGANISM: Homo Sapiens

<400> SEQUENCE: 1217
uacaguacug ugauaacuga a                                       21

<210> SEQ ID NO 1218
<211> LENGTH: 17
<212> TYPE: RNA
<213> ORGANISM: Homo Sapiens

<400> SEQUENCE: 1218
gaagauggac guacuuu                                            17

<210> SEQ ID NO 1219
<211> LENGTH: 24
<212> TYPE: RNA
<213> ORGANISM: Homo Sapiens

<400> SEQUENCE: 1219
uauagagagc aggaagauua augu                                    24

<210> SEQ ID NO 1220
<211> LENGTH: 23
<212> TYPE: RNA
<213> ORGANISM: Homo Sapiens

<400> SEQUENCE: 1220
uggagagaga aaagagacag aag                                     23

<210> SEQ ID NO 1221
<211> LENGTH: 18
<212> TYPE: RNA
<213> ORGANISM: Homo Sapiens

<400> SEQUENCE: 1221
cggggcggca ggggccuc                                           18

<210> SEQ ID NO 1222
<211> LENGTH: 22
<212> TYPE: RNA
<213> ORGANISM: Homo Sapiens

<400> SEQUENCE: 1222
ggugguugag gcugcaguaa gu                                      22

<210> SEQ ID NO 1223

```
<211> LENGTH: 20
<212> TYPE: RNA
<213> ORGANISM: Homo Sapiens

<400> SEQUENCE: 1223
ugggaauggg gguaagggcc                                                    20

<210> SEQ ID NO 1224
<211> LENGTH: 23
<212> TYPE: RNA
<213> ORGANISM: Homo Sapiens

<400> SEQUENCE: 1224
ugauggauaa aagacuacau auu                                                23

<210> SEQ ID NO 1225
<211> LENGTH: 22
<212> TYPE: RNA
<213> ORGANISM: Homo Sapiens

<400> SEQUENCE: 1225
cugaagcuca gagggcucug au                                                 22

<210> SEQ ID NO 1226
<211> LENGTH: 24
<212> TYPE: RNA
<213> ORGANISM: Homo Sapiens

<400> SEQUENCE: 1226
agcugagcuc cauggacgug cagu                                               24

<210> SEQ ID NO 1227
<211> LENGTH: 22
<212> TYPE: RNA
<213> ORGANISM: Homo Sapiens

<400> SEQUENCE: 1227
agacacauuu ggagagggac cc                                                 22

<210> SEQ ID NO 1228
<211> LENGTH: 22
<212> TYPE: RNA
<213> ORGANISM: Homo Sapiens

<400> SEQUENCE: 1228
aacuggcccu caaagucccg cu                                                 22

<210> SEQ ID NO 1229
<211> LENGTH: 22
<212> TYPE: RNA
<213> ORGANISM: Homo Sapiens

<400> SEQUENCE: 1229
aauugcacgg uauccaucug ua                                                 22

<210> SEQ ID NO 1230
<211> LENGTH: 22
<212> TYPE: RNA
<213> ORGANISM: Homo Sapiens

<400> SEQUENCE: 1230
ucacccugca ucccgcaccc ag                                                 22
```

```
<210> SEQ ID NO 1231
<211> LENGTH: 19
<212> TYPE: RNA
<213> ORGANISM: Homo Sapiens

<400> SEQUENCE: 1231
cugugggcuc agcucuggg                                                   19

<210> SEQ ID NO 1232
<211> LENGTH: 24
<212> TYPE: RNA
<213> ORGANISM: Homo Sapiens

<400> SEQUENCE: 1232
ucagaacaaa ugccgguucc caga                                             24

<210> SEQ ID NO 1233
<211> LENGTH: 17
<212> TYPE: RNA
<213> ORGANISM: Homo Sapiens

<400> SEQUENCE: 1233
ugagggagga gacugca                                                     17

<210> SEQ ID NO 1234
<211> LENGTH: 20
<212> TYPE: RNA
<213> ORGANISM: Homo Sapiens

<400> SEQUENCE: 1234
aggcgcaccc gaccacaugc                                                  20

<210> SEQ ID NO 1235
<211> LENGTH: 22
<212> TYPE: RNA
<213> ORGANISM: Homo Sapiens

<400> SEQUENCE: 1235 ugaggguuu ggaaugggau gg                                                22

<210> SEQ ID NO 1236
<211> LENGTH: 22
<212> TYPE: RNA
<213> ORGANISM: Homo Sapiens

<400> SEQUENCE: 1236
aaagugcuuc ccuuuggacu gu                                               22

<210> SEQ ID NO 1237
<211> LENGTH: 22
<212> TYPE: RNA
<213> ORGANISM: Homo Sapiens

<400> SEQUENCE: 1237
cagaagggga guugggagca ga                                               22

<210> SEQ ID NO 1238
<211> LENGTH: 23
<212> TYPE: RNA
<213> ORGANISM: Homo Sapiens

<400> SEQUENCE: 1238
ugcaaaagua auugcaguuu uug                                              23
```

<210> SEQ ID NO 1239
<211> LENGTH: 26
<212> TYPE: RNA
<213> ORGANISM: Homo Sapiens

<400> SEQUENCE: 1239
cccagggcuu ggagugggggc aagguu                                        26

<210> SEQ ID NO 1240
<211> LENGTH: 19
<212> TYPE: RNA
<213> ORGANISM: Homo Sapiens

<400> SEQUENCE: 1240
ugggcguauc uguaugcua                                                 19

<210> SEQ ID NO 1241
<211> LENGTH: 24
<212> TYPE: RNA
<213> ORGANISM: Homo Sapiens

<400> SEQUENCE: 1241
guggaaagca ugcauccagg gugu                                           24

<210> SEQ ID NO 1242
<211> LENGTH: 24
<212> TYPE: RNA
<213> ORGANISM: Homo Sapiens

<400> SEQUENCE: 1242
uacagaugca gauucucuga cuuc                                           24

<210> SEQ ID NO 1243
<211> LENGTH: 22
<212> TYPE: RNA
<213> ORGANISM: Homo Sapiens

<400> SEQUENCE: 1243
uuguacaugg uaggcuuuca uu                                             22

<210> SEQ ID NO 1244
<211> LENGTH: 22
<212> TYPE: RNA
<213> ORGANISM: Homo Sapiens

<400> SEQUENCE: 1244
gcccgcgugu ggagccaggu gu                                             22

<210> SEQ ID NO 1245
<211> LENGTH: 22
<212> TYPE: RNA
<213> ORGANISM: Homo Sapiens

<400> SEQUENCE: 1245
ggggcuguga uugaccagca gg                                             22

<210> SEQ ID NO 1246
<211> LENGTH: 21
<212> TYPE: RNA
<213> ORGANISM: Homo Sapiens

<400> SEQUENCE: 1246
uggguuuacg uugggagaac u                                              21

<210> SEQ ID NO 1247
<211> LENGTH: 21
<212> TYPE: RNA
<213> ORGANISM: Homo Sapiens

<400> SEQUENCE: 1247
aauaaaguuc auguauggca a                                              21

<210> SEQ ID NO 1248
<211> LENGTH: 22
<212> TYPE: RNA
<213> ORGANISM: Homo Sapiens

<400> SEQUENCE: 1248
aguugccuuu uuguucccau gc                                             22

<210> SEQ ID NO 1249
<211> LENGTH: 24
<212> TYPE: RNA
<213> ORGANISM: Homo Sapiens

<400> SEQUENCE: 1249
uuggacuuuu ucagauuugg ggau                                           24

<210> SEQ ID NO 1250
<211> LENGTH: 22
<212> TYPE: RNA
<213> ORGANISM: Homo Sapiens

<400> SEQUENCE: 1250
uggcucaguu cagcaggaac ag                                             22

<210> SEQ ID NO 1251
<211> LENGTH: 22
<212> TYPE: RNA
<213> ORGANISM: Homo Sapiens

<400> SEQUENCE: 1251
ucaggugugg aaacugaggc ag                                             22

<210> SEQ ID NO 1252
<211> LENGTH: 21
<212> TYPE: RNA
<213> ORGANISM: Homo Sapiens

<400> SEQUENCE: 1252
ucuagaaaug caugacccac c                                              21

<210> SEQ ID NO 1253
<211> LENGTH: 22
<212> TYPE: RNA
<213> ORGANISM: Homo Sapiens

<400> SEQUENCE: 1253
ucauuauaug uaugaucugg ac                                             22

<210> SEQ ID NO 1254
<211> LENGTH: 17
<212> TYPE: RNA
<213> ORGANISM: Homo Sapiens

<400> SEQUENCE: 1254

-continued uuggaggcgu ggguuuu   17

<210> SEQ ID NO 1255
<211> LENGTH: 20
<212> TYPE: RNA
<213> ORGANISM: Homo Sapiens

<400> SEQUENCE: 1255
cuuccucguc ugucugcccc   20

<210> SEQ ID NO 1256
<211> LENGTH: 21
<212> TYPE: RNA
<213> ORGANISM: Homo Sapiens

<400> SEQUENCE: 1256
ccucccaugc caagaacucc c   21

<210> SEQ ID NO 1257
<211> LENGTH: 20
<212> TYPE: RNA
<213> ORGANISM: Homo Sapiens

<400> SEQUENCE: 1257
aaaaggcauu gugguuuuug   20

<210> SEQ ID NO 1258
<211> LENGTH: 22
<212> TYPE: RNA
<213> ORGANISM: Homo Sapiens

<400> SEQUENCE: 1258
aguucuucag uggcaagcuu ua   22

<210> SEQ ID NO 1259
<211> LENGTH: 23
<212> TYPE: RNA
<213> ORGANISM: Homo Sapiens

<400> SEQUENCE: 1259
uguggaaggu agacggccag aga   23

<210> SEQ ID NO 1260
<211> LENGTH: 21
<212> TYPE: RNA
<213> ORGANISM: Homo Sapiens

<400> SEQUENCE: 1260
caaagguauu guggguuuuu g   21

<210> SEQ ID NO 1261
<211> LENGTH: 22
<212> TYPE: RNA
<213> ORGANISM: Homo Sapiens

<400> SEQUENCE: 1261
cagggccuca cuguaucgcc ca   22

<210> SEQ ID NO 1262
<211> LENGTH: 22
<212> TYPE: RNA
<213> ORGANISM: Homo Sapiens

<400> SEQUENCE: 1262

| | |
|---|---|
| ugcccuaaau gccccuucug gc | 22 |

<210> SEQ ID NO 1263
<211> LENGTH: 22
<212> TYPE: RNA
<213> ORGANISM: Homo Sapiens

<400> SEQUENCE: 1263

| | |
|---|---|
| aaggagcuca cagucuauug ag | 22 |

<210> SEQ ID NO 1264
<211> LENGTH: 21
<212> TYPE: RNA
<213> ORGANISM: Homo Sapiens

<400> SEQUENCE: 1264

| | |
|---|---|
| ugguucuaga cuugccaacu a | 21 |

<210> SEQ ID NO 1265
<211> LENGTH: 19
<212> TYPE: RNA
<213> ORGANISM: Homo Sapiens

<400> SEQUENCE: 1265

| | |
|---|---|
| ccgguuccag ucccuggag | 19 |

<210> SEQ ID NO 1266
<211> LENGTH: 22
<212> TYPE: RNA
<213> ORGANISM: Homo Sapiens

<400> SEQUENCE: 1266

| | |
|---|---|
| gacuauagaa cuuucccccu ca | 22 |

<210> SEQ ID NO 1267
<211> LENGTH: 21
<212> TYPE: RNA
<213> ORGANISM: Homo Sapiens

<400> SEQUENCE: 1267

| | |
|---|---|
| cacauuacac ggucgaccuc u | 21 |

<210> SEQ ID NO 1268
<211> LENGTH: 22
<212> TYPE: RNA
<213> ORGANISM: Homo Sapiens

<400> SEQUENCE: 1268

| | |
|---|---|
| acucaaaacc cuucagugac uu | 22 |

<210> SEQ ID NO 1269
<211> LENGTH: 22
<212> TYPE: RNA
<213> ORGANISM: Homo Sapiens

<400> SEQUENCE: 1269

| | |
|---|---|
| aaaggaggaa auaggcaggc ca | 22 |

<210> SEQ ID NO 1270
<211> LENGTH: 23
<212> TYPE: RNA
<213> ORGANISM: Homo Sapiens

<400> SEQUENCE: 1270
agcugguguu gugaaucagg ccg    23

<210> SEQ ID NO 1271
<211> LENGTH: 20
<212> TYPE: RNA
<213> ORGANISM: Homo Sapiens

<400> SEQUENCE: 1271
ggcuccuugg ucuaggggua    20

<210> SEQ ID NO 1272
<211> LENGTH: 18
<212> TYPE: RNA
<213> ORGANISM: Homo Sapiens

<400> SEQUENCE: 1272
aggcuggagu gagcggag    18

<210> SEQ ID NO 1273
<211> LENGTH: 21
<212> TYPE: RNA
<213> ORGANISM: Homo Sapiens

<400> SEQUENCE: 1273
auaggacuca uauagugcca g    21

<210> SEQ ID NO 1274
<211> LENGTH: 23
<212> TYPE: RNA
<213> ORGANISM: Homo Sapiens

<400> SEQUENCE: 1274
ucagcaccag gauauuguug gag    23

<210> SEQ ID NO 1275
<211> LENGTH: 22
<212> TYPE: RNA
<213> ORGANISM: Homo Sapiens

<400> SEQUENCE: 1275
aaagugcauc uuuuuagagg au    22

<210> SEQ ID NO 1276
<211> LENGTH: 22
<212> TYPE: RNA
<213> ORGANISM: Homo Sapiens

<400> SEQUENCE: 1276
uuggaauagg ggauaucuca gc    22

<210> SEQ ID NO 1277
<211> LENGTH: 23
<212> TYPE: RNA
<213> ORGANISM: Homo Sapiens

<400> SEQUENCE: 1277
agggacuuuu gggggcagau gug    23

<210> SEQ ID NO 1278
<211> LENGTH: 21
<212> TYPE: RNA
<213> ORGANISM: Homo Sapiens

```
<400> SEQUENCE: 1278
cuuuuugcgg ucugggcuug c                                          21

<210> SEQ ID NO 1279
<211> LENGTH: 22
<212> TYPE: RNA
<213> ORGANISM: Homo Sapiens

<400> SEQUENCE: 1279
uauguaauau gguccacauc uu                                         22

<210> SEQ ID NO 1280
<211> LENGTH: 22
<212> TYPE: RNA
<213> ORGANISM: Homo Sapiens

<400> SEQUENCE: 1280
aucauacaag gacaauuucu uu                                         22

<210> SEQ ID NO 1281
<211> LENGTH: 19
<212> TYPE: RNA
<213> ORGANISM: Homo Sapiens

<400> SEQUENCE: 1281
agagcuggcu gaagggcag                                             19

<210> SEQ ID NO 1282
<211> LENGTH: 22
<212> TYPE: RNA
<213> ORGANISM: Homo Sapiens

<400> SEQUENCE: 1282
aauaggccac ggaucugggc aa                                         22

<210> SEQ ID NO 1283
<211> LENGTH: 22
<212> TYPE: RNA
<213> ORGANISM: Homo Sapiens

<400> SEQUENCE: 1283
caaaaguaau uguggauuuu gu                                         22

<210> SEQ ID NO 1284
<211> LENGTH: 22
<212> TYPE: RNA
<213> ORGANISM: Homo Sapiens

<400> SEQUENCE: 1284
aaucccaaug cuagacccgg ug                                         22

<210> SEQ ID NO 1285
<211> LENGTH: 23
<212> TYPE: RNA
<213> ORGANISM: Homo Sapiens

<400> SEQUENCE: 1285
uacugcauca ggaacugauu gga                                        23

<210> SEQ ID NO 1286
<211> LENGTH: 22
<212> TYPE: RNA
```

```
<213> ORGANISM: Homo Sapiens

<400> SEQUENCE: 1286
cacuggcucc uuucugggua ga                                              22

<210> SEQ ID NO 1287
<211> LENGTH: 22
<212> TYPE: RNA
<213> ORGANISM: Homo Sapiens

<400> SEQUENCE: 1287
uggcccaacc uauucaguua gu                                              22

<210> SEQ ID NO 1288
<211> LENGTH: 21
<212> TYPE: RNA
<213> ORGANISM: Homo Sapiens

<400> SEQUENCE: 1288
uggacugccc ugaucuggag a                                               21

<210> SEQ ID NO 1289
<211> LENGTH: 22
<212> TYPE: RNA
<213> ORGANISM: Homo Sapiens

<400> SEQUENCE: 1289
aagcaauacu guuaccugaa au                                              22

<210> SEQ ID NO 1290
<211> LENGTH: 25
<212> TYPE: RNA
<213> ORGANISM: Homo Sapiens

<400> SEQUENCE: 1290
ggcggaggga aguagguccg uuggu                                           25

<210> SEQ ID NO 1291
<211> LENGTH: 24
<212> TYPE: RNA
<213> ORGANISM: Homo Sapiens

<400> SEQUENCE: 1291
uuuggcaaug guagaacuca cacu                                            24

<210> SEQ ID NO 1292
<211> LENGTH: 21
<212> TYPE: RNA
<213> ORGANISM: Homo Sapiens

<400> SEQUENCE: 1292
uaggccuuua gaucacuuaa a                                               21

<210> SEQ ID NO 1293
<211> LENGTH: 22
<212> TYPE: RNA
<213> ORGANISM: Homo Sapiens

<400> SEQUENCE: 1293
cuauacggcc uccuagcuuu cc                                              22

<210> SEQ ID NO 1294
<211> LENGTH: 22
```

```
<212> TYPE: RNA
<213> ORGANISM: Homo Sapiens

<400> SEQUENCE: 1294
aggaccuucc cugaaccaag ga                                              22

<210> SEQ ID NO 1295
<211> LENGTH: 21
<212> TYPE: RNA
<213> ORGANISM: Homo Sapiens

<400> SEQUENCE: 1295
acuggcauua gugggacuuu u                                               21

<210> SEQ ID NO 1296
<211> LENGTH: 22
<212> TYPE: RNA
<213> ORGANISM: Homo Sapiens

<400> SEQUENCE: 1296
cucucuggcc gucuaccuuc ca                                              22

<210> SEQ ID NO 1297
<211> LENGTH: 21
<212> TYPE: RNA
<213> ORGANISM: Homo Sapiens

<400> SEQUENCE: 1297
aaaaguaacu gcgguuuuug a                                               21

<210> SEQ ID NO 1298
<211> LENGTH: 22
<212> TYPE: RNA
<213> ORGANISM: Homo Sapiens

<400> SEQUENCE: 1298
uggggcggag cuuccggagg cc                                              22

<210> SEQ ID NO 1299
<211> LENGTH: 25
<212> TYPE: RNA
<213> ORGANISM: Homo Sapiens

<400> SEQUENCE: 1299
auaacauugu aaagcgcuuc uuucg                                           25

<210> SEQ ID NO 1300
<211> LENGTH: 23
<212> TYPE: RNA
<213> ORGANISM: Homo Sapiens

<400> SEQUENCE: 1300
ugaggcucug uuagccuugg cuc                                             23

<210> SEQ ID NO 1301
<211> LENGTH: 22
<212> TYPE: RNA
<213> ORGANISM: Homo Sapiens

<400> SEQUENCE: 1301
uaacaaacac cuguaaaaca gc                                              22

<210> SEQ ID NO 1302
```

```
<211> LENGTH: 23
<212> TYPE: RNA
<213> ORGANISM: Homo Sapiens

<400> SEQUENCE: 1302
ugaggauaug gcagggaagg gga                                              23

<210> SEQ ID NO 1303
<211> LENGTH: 22
<212> TYPE: RNA
<213> ORGANISM: Homo Sapiens

<400> SEQUENCE: 1303
ccagacugug gcugaccaga gg                                               22

<210> SEQ ID NO 1304
<211> LENGTH: 22
<212> TYPE: RNA
<213> ORGANISM: Homo Sapiens

<400> SEQUENCE: 1304
gugacugaua ccuuggaggc au                                               22

<210> SEQ ID NO 1305
<211> LENGTH: 22
<212> TYPE: RNA
<213> ORGANISM: Homo Sapiens

<400> SEQUENCE: 1305
uauguaacac gguccacuaa cc                                               22

<210> SEQ ID NO 1306
<211> LENGTH: 22
<212> TYPE: RNA
<213> ORGANISM: Homo Sapiens

<400> SEQUENCE: 1306
aaaaguaauu gcgguuuuug cc                                               22

<210> SEQ ID NO 1307
<211> LENGTH: 21
<212> TYPE: RNA
<213> ORGANISM: Homo Sapiens

<400> SEQUENCE: 1307
auugacacuu cugugaguag a                                                21

<210> SEQ ID NO 1308
<211> LENGTH: 22
<212> TYPE: RNA
<213> ORGANISM: Homo Sapiens

<400> SEQUENCE: 1308
ccaaccuagg uggucagagu ug                                               22

<210> SEQ ID NO 1309
<211> LENGTH: 21
<212> TYPE: RNA
<213> ORGANISM: Homo Sapiens

<400> SEQUENCE: 1309
uuacacagcu ggacagaggc a                                                21
```

```
<210> SEQ ID NO 1310
<211> LENGTH: 22
<212> TYPE: RNA
<213> ORGANISM: Homo Sapiens

<400> SEQUENCE: 1310
uucucuuucu uuagccuugu gu                                           22

<210> SEQ ID NO 1311
<211> LENGTH: 22
<212> TYPE: RNA
<213> ORGANISM: Homo Sapiens

<400> SEQUENCE: 1311
cgaaucauua uuugcugcuc ua                                           22

<210> SEQ ID NO 1312
<211> LENGTH: 22
<212> TYPE: RNA
<213> ORGANISM: Homo Sapiens

<400> SEQUENCE: 1312
uucauuugcc ucccagccua ca                                           22

<210> SEQ ID NO 1313
<211> LENGTH: 22
<212> TYPE: RNA
<213> ORGANISM: Homo Sapiens

<400> SEQUENCE: 1313
aagagaacug aaaguggagc cu                                           22

<210> SEQ ID NO 1314
<211> LENGTH: 18
<212> TYPE: RNA
<213> ORGANISM: Homo Sapiens

<400> SEQUENCE: 1314
uccagugccc uccucucc                                                18

<210> SEQ ID NO 1315
<211> LENGTH: 24
<212> TYPE: RNA
<213> ORGANISM: Homo Sapiens

<400> SEQUENCE: 1315
ugucagugac uccugccccu uggu                                         24

<210> SEQ ID NO 1316
<211> LENGTH: 22
<212> TYPE: RNA
<213> ORGANISM: Homo Sapiens

<400> SEQUENCE: 1316
agacaguagu ucuugccugg uu                                           22

<210> SEQ ID NO 1317
<211> LENGTH: 19
<212> TYPE: RNA
<213> ORGANISM: Homo Sapiens

<400> SEQUENCE: 1317
agagguaggu guggaagaa                                               19
```

<210> SEQ ID NO 1318
<211> LENGTH: 22
<212> TYPE: RNA
<213> ORGANISM: Homo Sapiens

<400> SEQUENCE: 1318
uagguaguuu ccuguuguug gg                                            22

<210> SEQ ID NO 1319
<211> LENGTH: 23
<212> TYPE: RNA
<213> ORGANISM: Homo Sapiens

<400> SEQUENCE: 1319
aacauucauu gcugucggug ggu                                           23

<210> SEQ ID NO 1320
<211> LENGTH: 22
<212> TYPE: RNA
<213> ORGANISM: Homo Sapiens

<400> SEQUENCE: 1320
accguggcuu ucgauuguua cu                                            22

<210> SEQ ID NO 1321
<211> LENGTH: 22
<212> TYPE: RNA
<213> ORGANISM: Homo Sapiens

<400> SEQUENCE: 1321
ugcucagguu gcacagcugg ga                                            22

<210> SEQ ID NO 1322
<211> LENGTH: 21
<212> TYPE: RNA
<213> ORGANISM: Homo Sapiens

<400> SEQUENCE: 1322
auuagguagu ggcaguggaa c                                             21

<210> SEQ ID NO 1323
<211> LENGTH: 21
<212> TYPE: RNA
<213> ORGANISM: Homo Sapiens

<400> SEQUENCE: 1323
agcggugcuc cugcgggccg a                                             21

<210> SEQ ID NO 1324
<211> LENGTH: 22
<212> TYPE: RNA
<213> ORGANISM: Homo Sapiens

<400> SEQUENCE: 1324
agaagauugc agaguaaguu cc                                            22

<210> SEQ ID NO 1325
<211> LENGTH: 23
<212> TYPE: RNA
<213> ORGANISM: Homo Sapiens

<400> SEQUENCE: 1325
agguuacccg agcaacuuug cau                                           23

<210> SEQ ID NO 1326
<211> LENGTH: 20
<212> TYPE: RNA
<213> ORGANISM: Homo Sapiens

<400> SEQUENCE: 1326
gggcuggggc gcgggaggu                                             20

<210> SEQ ID NO 1327
<211> LENGTH: 23
<212> TYPE: RNA
<213> ORGANISM: Homo Sapiens

<400> SEQUENCE: 1327
uacuccagag ggcgucacuc aug                                        23

<210> SEQ ID NO 1328
<211> LENGTH: 22
<212> TYPE: RNA
<213> ORGANISM: Homo Sapiens

<400> SEQUENCE: 1328
cgcaggggcc gggugcucac cg                                         22

<210> SEQ ID NO 1329
<211> LENGTH: 22
<212> TYPE: RNA
<213> ORGANISM: Homo Sapiens

<400> SEQUENCE: 1329
uguccucuag ggccugcagu cu                                         22

<210> SEQ ID NO 1330
<211> LENGTH: 23
<212> TYPE: RNA
<213> ORGANISM: Homo Sapiens

<400> SEQUENCE: 1330
uguaaacauc cuacacucuc agc                                        23

<210> SEQ ID NO 1331
<211> LENGTH: 22
<212> TYPE: RNA
<213> ORGANISM: Homo Sapiens

<400> SEQUENCE: 1331
ugugacaaua gagaugaaca ug                                         22

<210> SEQ ID NO 1332
<211> LENGTH: 22
<212> TYPE: RNA
<213> ORGANISM: Homo Sapiens

<400> SEQUENCE: 1332
uaugugccuu uggacuacau cg                                         22

<210> SEQ ID NO 1333
<211> LENGTH: 21
<212> TYPE: RNA
<213> ORGANISM: Homo Sapiens

<400> SEQUENCE: 1333
gagggcaugc gcacuuuguc c          21

<210> SEQ ID NO 1334
<211> LENGTH: 22
<212> TYPE: RNA
<213> ORGANISM: Homo Sapiens

<400> SEQUENCE: 1334
cugaauagcu gggacuacag gu          22

<210> SEQ ID NO 1335
<211> LENGTH: 22
<212> TYPE: RNA
<213> ORGANISM: Homo Sapiens

<400> SEQUENCE: 1335
aaauucaugu ucaaucuaaa cc          22

<210> SEQ ID NO 1336
<211> LENGTH: 22
<212> TYPE: RNA
<213> ORGANISM: Homo Sapiens

<400> SEQUENCE: 1336
ugcgacauug gaaguaguau ca          22

<210> SEQ ID NO 1337
<211> LENGTH: 22
<212> TYPE: RNA
<213> ORGANISM: Homo Sapiens

<400> SEQUENCE: 1337
gugaaauguu uaggaccacu ag          22

<210> SEQ ID NO 1338
<211> LENGTH: 24
<212> TYPE: RNA
<213> ORGANISM: Homo Sapiens

<400> SEQUENCE: 1338
gaccuggaca uguuugugcc cagu          24

<210> SEQ ID NO 1339
<211> LENGTH: 20
<212> TYPE: RNA
<213> ORGANISM: Homo Sapiens

<400> SEQUENCE: 1339
caccaggcau uguggucucc          20

<210> SEQ ID NO 1340
<211> LENGTH: 22
<212> TYPE: RNA
<213> ORGANISM: Homo Sapiens

<400> SEQUENCE: 1340
ccaauauugg cugugcugcu cc          22

<210> SEQ ID NO 1341
<211> LENGTH: 21
<212> TYPE: RNA
<213> ORGANISM: Homo Sapiens

<400> SEQUENCE: 1341
uuuccauagg ugaugaguca c 21

<210> SEQ ID NO 1342
<211> LENGTH: 22
<212> TYPE: RNA
<213> ORGANISM: Homo Sapiens

<400> SEQUENCE: 1342
uuuagagacg ggucuugcu cu 22

<210> SEQ ID NO 1343
<211> LENGTH: 23
<212> TYPE: RNA
<213> ORGANISM: Homo Sapiens

<400> SEQUENCE: 1343
ugcacauggc aaccuagcuc cca 23

<210> SEQ ID NO 1344
<211> LENGTH: 18
<212> TYPE: RNA
<213> ORGANISM: Homo Sapiens

<400> SEQUENCE: 1344 gguggggcuuc ccggaggg 18

<210> SEQ ID NO 1345
<211> LENGTH: 21
<212> TYPE: RNA
<213> ORGANISM: Homo Sapiens

<400> SEQUENCE: 1345
ucugaggccu gccucucccc a 21

<210> SEQ ID NO 1346
<211> LENGTH: 22
<212> TYPE: RNA
<213> ORGANISM: Homo Sapiens

<400> SEQUENCE: 1346
gcucccucua gggucgcucg ga 22

<210> SEQ ID NO 1347
<211> LENGTH: 23
<212> TYPE: RNA
<213> ORGANISM: Homo Sapiens

<400> SEQUENCE: 1347
ugcaaaagua auugcaguuu uug 23

<210> SEQ ID NO 1348
<211> LENGTH: 22
<212> TYPE: RNA
<213> ORGANISM: Homo Sapiens

<400> SEQUENCE: 1348
uaguaccagu accuuguguu ca 22

<210> SEQ ID NO 1349
<211> LENGTH: 22
<212> TYPE: RNA
<213> ORGANISM: Homo Sapiens

```
<400> SEQUENCE: 1349
aaggcccggg cuuccuccc ag                                           22

<210> SEQ ID NO 1350
<211> LENGTH: 19
<212> TYPE: RNA
<213> ORGANISM: Homo Sapiens

<400> SEQUENCE: 1350
aaaaguaauu gcggucuuu                                              19

<210> SEQ ID NO 1351
<211> LENGTH: 22
<212> TYPE: RNA
<213> ORGANISM: Homo Sapiens

<400> SEQUENCE: 1351
cgggguuuug agggcgagau ga                                          22

<210> SEQ ID NO 1352
<211> LENGTH: 22
<212> TYPE: RNA
<213> ORGANISM: Homo Sapiens

<400> SEQUENCE: 1352
uuugaggcua cagugagaug ug                                          22

<210> SEQ ID NO 1353
<211> LENGTH: 20
<212> TYPE: RNA
<213> ORGANISM: Homo Sapiens

<400> SEQUENCE: 1353
gauauucaga ggcuaggugg                                             20

<210> SEQ ID NO 1354
<211> LENGTH: 22
<212> TYPE: RNA
<213> ORGANISM: Homo Sapiens

<400> SEQUENCE: 1354
aaaucucugc aggcaaaugu ga                                          22

<210> SEQ ID NO 1355
<211> LENGTH: 23
<212> TYPE: RNA
<213> ORGANISM: Homo Sapiens

<400> SEQUENCE: 1355
agugccugag ggaguaagag ccc                                         23

<210> SEQ ID NO 1356
<211> LENGTH: 21
<212> TYPE: RNA
<213> ORGANISM: Homo Sapiens

<400> SEQUENCE: 1356
uuaggccgca gaucugggug a                                           21

<210> SEQ ID NO 1357
<211> LENGTH: 22
<212> TYPE: RNA
<213> ORGANISM: Homo Sapiens
```

```
<400> SEQUENCE: 1357
cagcagggga gagagaggag uc                                          22

<210> SEQ ID NO 1358
<211> LENGTH: 23
<212> TYPE: RNA
<213> ORGANISM: Homo Sapiens

<400> SEQUENCE: 1358
ugaggaugga uagcaaggaa gcc                                         23

<210> SEQ ID NO 1359
<211> LENGTH: 20
<212> TYPE: RNA
<213> ORGANISM: Homo Sapiens

<400> SEQUENCE: 1359
cgggcguggu gguggggggug                                            20

<210> SEQ ID NO 1360
<211> LENGTH: 22
<212> TYPE: RNA
<213> ORGANISM: Homo Sapiens

<400> SEQUENCE: 1360
uacuaacugc agauucaagu ga                                          22

<210> SEQ ID NO 1361
<211> LENGTH: 22
<212> TYPE: RNA
<213> ORGANISM: Homo Sapiens

<400> SEQUENCE: 1361
cguggauauu ccuucuaugu uu                                          22

<210> SEQ ID NO 1362
<211> LENGTH: 22
<212> TYPE: RNA
<213> ORGANISM: Homo Sapiens

<400> SEQUENCE: 1362
uauucaggaa gguguuacuu aa                                          22

<210> SEQ ID NO 1363
<211> LENGTH: 19
<212> TYPE: RNA
<213> ORGANISM: Homo Sapiens

<400> SEQUENCE: 1363
ugagggaguu ggguguaua                                              19

<210> SEQ ID NO 1364
<211> LENGTH: 23
<212> TYPE: RNA
<213> ORGANISM: Homo Sapiens

<400> SEQUENCE: 1364
gagggucuug ggagggaugu gac                                         23

<210> SEQ ID NO 1365
<211> LENGTH: 22
<212> TYPE: RNA
```

```
<213> ORGANISM: Homo Sapiens

<400> SEQUENCE: 1365
ugguuuaccg ucccacauac au                                              22

<210> SEQ ID NO 1366
<211> LENGTH: 22
<212> TYPE: RNA
<213> ORGANISM: Homo Sapiens

<400> SEQUENCE: 1366
uagcaaaaac ugcaguuacu uu                                              22

<210> SEQ ID NO 1367
<211> LENGTH: 21
<212> TYPE: RNA
<213> ORGANISM: Homo Sapiens

<400> SEQUENCE: 1367
uggcaaacgu ggaagccgag a                                               21

<210> SEQ ID NO 1368
<211> LENGTH: 22
<212> TYPE: RNA
<213> ORGANISM: Homo Sapiens

<400> SEQUENCE: 1368
cugggaggug gauguuuacu uc                                              22

<210> SEQ ID NO 1369
<211> LENGTH: 21
<212> TYPE: RNA
<213> ORGANISM: Homo Sapiens

<400> SEQUENCE: 1369
uggcuguugg aggggggcagg c                                              21

<210> SEQ ID NO 1370
<211> LENGTH: 21
<212> TYPE: RNA
<213> ORGANISM: Homo Sapiens

<400> SEQUENCE: 1370
cccggagcca ggaugcagcu c                                               21

<210> SEQ ID NO 1371
<211> LENGTH: 24
<212> TYPE: RNA
<213> ORGANISM: Homo Sapiens

<400> SEQUENCE: 1371
ucuguagccu gggagcaaug gggu                                            24

<210> SEQ ID NO 1372
<211> LENGTH: 22
<212> TYPE: RNA
<213> ORGANISM: Homo Sapiens

<400> SEQUENCE: 1372
uccgagccug ggucucccuc uu                                              22

<210> SEQ ID NO 1373
<211> LENGTH: 22
```

```
<212> TYPE: RNA
<213> ORGANISM: Homo Sapiens

<400> SEQUENCE: 1373
uugcucugag cuccgagaaa gc                                          22

<210> SEQ ID NO 1374
<211> LENGTH: 22
<212> TYPE: RNA
<213> ORGANISM: Homo Sapiens

<400> SEQUENCE: 1374
auauacaggg ggagacucuc au                                          22

<210> SEQ ID NO 1375
<211> LENGTH: 22
<212> TYPE: RNA
<213> ORGANISM: Homo Sapiens

<400> SEQUENCE: 1375
cuacaaaggg aagcacuuuc uc                                          22

<210> SEQ ID NO 1376
<211> LENGTH: 22
<212> TYPE: RNA
<213> ORGANISM: Homo Sapiens

<400> SEQUENCE: 1376
ucuggcuauc ucacgagacu gu                                          22

<210> SEQ ID NO 1377
<211> LENGTH: 22
<212> TYPE: RNA
<213> ORGANISM: Homo Sapiens

<400> SEQUENCE: 1377
uuuccuaccc uaccugaaga cu                                          22

<210> SEQ ID NO 1378
<211> LENGTH: 22
<212> TYPE: RNA
<213> ORGANISM: Homo Sapiens

<400> SEQUENCE: 1378 gcggggugg cggcggcauc cc                                           22

<210> SEQ ID NO 1379
<211> LENGTH: 23
<212> TYPE: RNA
<213> ORGANISM: Homo Sapiens

<400> SEQUENCE: 1379
uugcuaguug cacuccucuc ugu                                         23

<210> SEQ ID NO 1380
<211> LENGTH: 22
<212> TYPE: RNA
<213> ORGANISM: Homo Sapiens

<400> SEQUENCE: 1380
uuccaugccu ccuagaaguu cc                                          22

<210> SEQ ID NO 1381
```

```
<211> LENGTH: 23
<212> TYPE: RNA
<213> ORGANISM: Homo Sapiens

<400> SEQUENCE: 1381
uucucgagga aagaagcacu uuc                                              23

<210> SEQ ID NO 1382
<211> LENGTH: 22
<212> TYPE: RNA
<213> ORGANISM: Homo Sapiens

<400> SEQUENCE: 1382
acagauucga uucuagggga au                                               22

<210> SEQ ID NO 1383
<211> LENGTH: 23
<212> TYPE: RNA
<213> ORGANISM: Homo Sapiens

<400> SEQUENCE: 1383
uagcaccauu ugaaaucagu guu                                              23

<210> SEQ ID NO 1384
<211> LENGTH: 22
<212> TYPE: RNA
<213> ORGANISM: Homo Sapiens

<400> SEQUENCE: 1384
ugggauccag acagugggag aa                                               22

<210> SEQ ID NO 1385
<211> LENGTH: 22
<212> TYPE: RNA
<213> ORGANISM: Homo Sapiens

<400> SEQUENCE: 1385
acccuaucaa uauugucucu gc                                               22

<210> SEQ ID NO 1386
<211> LENGTH: 22
<212> TYPE: RNA
<213> ORGANISM: Homo Sapiens

<400> SEQUENCE: 1386
uuucuucuua gacauggcag cu                                               22

<210> SEQ ID NO 1387
<211> LENGTH: 23
<212> TYPE: RNA
<213> ORGANISM: Homo Sapiens

<400> SEQUENCE: 1387
uuugggauug acgccacaug ucu                                              23

<210> SEQ ID NO 1388
<211> LENGTH: 22
<212> TYPE: RNA
<213> ORGANISM: Homo Sapiens

<400> SEQUENCE: 1388
caaaaccgcg auuacucuug ca                                               22
```

```
<210> SEQ ID NO 1389
<211> LENGTH: 22
<212> TYPE: RNA
<213> ORGANISM: Homo Sapiens

<400> SEQUENCE: 1389
uuagcuuaag gaguaccaga uc                                              22

<210> SEQ ID NO 1390
<211> LENGTH: 22
<212> TYPE: RNA
<213> ORGANISM: Homo Sapiens

<400> SEQUENCE: 1390
uucagauccc agcggugccu cu                                              22

<210> SEQ ID NO 1391
<211> LENGTH: 21
<212> TYPE: RNA
<213> ORGANISM: Homo Sapiens

<400> SEQUENCE: 1391
uauauauaca gccaugcacu c                                               21

<210> SEQ ID NO 1392
<211> LENGTH: 17
<212> TYPE: RNA
<213> ORGANISM: Homo Sapiens

<400> SEQUENCE: 1392
ugguagagcu gaggaca                                                    17

<210> SEQ ID NO 1393
<211> LENGTH: 21
<212> TYPE: RNA
<213> ORGANISM: Homo Sapiens

<400> SEQUENCE: 1393
ugucuugcag gccgucaugc a                                               21

<210> SEQ ID NO 1394
<211> LENGTH: 22
<212> TYPE: RNA
<213> ORGANISM: Homo Sapiens

<400> SEQUENCE: 1394
uaauacugcc ugguaaugau ga                                              22

<210> SEQ ID NO 1395
<211> LENGTH: 21
<212> TYPE: RNA
<213> ORGANISM: Homo Sapiens

<400> SEQUENCE: 1395
aaaaguaauu gcaguuuuug c                                               21

<210> SEQ ID NO 1396
<211> LENGTH: 17
<212> TYPE: RNA
<213> ORGANISM: Homo Sapiens

<400> SEQUENCE: 1396
gggauaugaa gaaaaau                                                    17
```

```
<210> SEQ ID NO 1397
<211> LENGTH: 22
<212> TYPE: RNA
<213> ORGANISM: Homo Sapiens

<400> SEQUENCE: 1397
uugcuugaac ccaggaagug ga                                          22

<210> SEQ ID NO 1398
<211> LENGTH: 22
<212> TYPE: RNA
<213> ORGANISM: Homo Sapiens

<400> SEQUENCE: 1398
ucgggcgcaa gagcacugca gu                                          22

<210> SEQ ID NO 1399
<211> LENGTH: 22
<212> TYPE: RNA
<213> ORGANISM: Homo Sapiens

<400> SEQUENCE: 1399
uauugcacuu gucccggccu gu                                          22

<210> SEQ ID NO 1400
<211> LENGTH: 22
<212> TYPE: RNA
<213> ORGANISM: Homo Sapiens

<400> SEQUENCE: 1400
cuccuauaug augccuuucu uc                                          22

<210> SEQ ID NO 1401
<211> LENGTH: 22
<212> TYPE: RNA
<213> ORGANISM: Homo Sapiens

<400> SEQUENCE: 1401
uuuucaacuc uaaugggaga ga                                          22

<210> SEQ ID NO 1402
<211> LENGTH: 22
<212> TYPE: RNA
<213> ORGANISM: Homo Sapiens

<400> SEQUENCE: 1402
uacgucaucg uugucaucgu ca                                          22

<210> SEQ ID NO 1403
<211> LENGTH: 24
<212> TYPE: RNA
<213> ORGANISM: Homo Sapiens

<400> SEQUENCE: 1403
aggcaggggc uggugcuggg cggg                                        24

<210> SEQ ID NO 1404
<211> LENGTH: 22
<212> TYPE: RNA
<213> ORGANISM: Homo Sapiens

<400> SEQUENCE: 1404
auccgcgcuc ugacucucug cc                                          22
```

```
<210> SEQ ID NO 1405
<211> LENGTH: 17
<212> TYPE: RNA
<213> ORGANISM: Homo Sapiens

<400> SEQUENCE: 1405
uaauugcuuc cauguuu                                                    17

<210> SEQ ID NO 1406
<211> LENGTH: 21
<212> TYPE: RNA
<213> ORGANISM: Homo Sapiens

<400> SEQUENCE: 1406
cuggauggcu ccuccauguc u                                               21

<210> SEQ ID NO 1407
<211> LENGTH: 21
<212> TYPE: RNA
<213> ORGANISM: Homo Sapiens

<400> SEQUENCE: 1407
caccgacucu gucuccugca g                                               21

<210> SEQ ID NO 1408
<211> LENGTH: 22
<212> TYPE: RNA
<213> ORGANISM: Homo Sapiens

<400> SEQUENCE: 1408
aaaaguaauu gcggauuuug cc                                              22

<210> SEQ ID NO 1409
<211> LENGTH: 22
<212> TYPE: RNA
<213> ORGANISM: Homo Sapiens

<400> SEQUENCE: 1409
uacccauugc auaucggagu ug                                              22

<210> SEQ ID NO 1410
<211> LENGTH: 21
<212> TYPE: RNA
<213> ORGANISM: Homo Sapiens

<400> SEQUENCE: 1410
acugacagga gagcauuuug a                                               21

<210> SEQ ID NO 1411
<211> LENGTH: 24
<212> TYPE: RNA
<213> ORGANISM: Homo Sapiens

<400> SEQUENCE: 1411
ggaggccggg gugggcggg gcgg                                             24

<210> SEQ ID NO 1412
<211> LENGTH: 20
<212> TYPE: RNA
<213> ORGANISM: Homo Sapiens

<400> SEQUENCE: 1412
```

| | |
|---|---|
| ucuuacuccc ucaggcacug | 20 |

<210> SEQ ID NO 1413
<211> LENGTH: 21
<212> TYPE: RNA
<213> ORGANISM: Homo Sapiens

<400> SEQUENCE: 1413

| | |
|---|---|
| cuccagaggg aaguacuuuc u | 21 |

<210> SEQ ID NO 1414
<211> LENGTH: 21
<212> TYPE: RNA
<213> ORGANISM: Homo Sapiens

<400> SEQUENCE: 1414

| | |
|---|---|
| aaacuacuga aaaucaaaga u | 21 |

<210> SEQ ID NO 1415
<211> LENGTH: 19
<212> TYPE: RNA
<213> ORGANISM: Homo Sapiens

<400> SEQUENCE: 1415

| | |
|---|---|
| ugggcggag cuuccggag | 19 |

<210> SEQ ID NO 1416
<211> LENGTH: 23
<212> TYPE: RNA
<213> ORGANISM: Homo Sapiens

<400> SEQUENCE: 1416

| | |
|---|---|
| aucaacagac auuaauuggg cgc | 23 |

<210> SEQ ID NO 1417
<211> LENGTH: 22
<212> TYPE: RNA
<213> ORGANISM: Homo Sapiens

<400> SEQUENCE: 1417

| | |
|---|---|
| aagugccucc uuuuagagug uu | 22 |

<210> SEQ ID NO 1418
<211> LENGTH: 21
<212> TYPE: RNA
<213> ORGANISM: Homo Sapiens

<400> SEQUENCE: 1418

| | |
|---|---|
| ucgaggagcu cacagucuag u | 21 |

<210> SEQ ID NO 1419
<211> LENGTH: 20
<212> TYPE: RNA
<213> ORGANISM: Homo Sapiens

<400> SEQUENCE: 1419

| | |
|---|---|
| acugggcuug gagucagaag | 20 |

<210> SEQ ID NO 1420
<211> LENGTH: 22
<212> TYPE: RNA
<213> ORGANISM: Homo Sapiens

<400> SEQUENCE: 1420
uggaaggagg uugccggacg cu                                      22

<210> SEQ ID NO 1421
<211> LENGTH: 22
<212> TYPE: RNA
<213> ORGANISM: Homo Sapiens

<400> SEQUENCE: 1421
acugauuucu uuggguguuc ag                                      22

<210> SEQ ID NO 1422
<211> LENGTH: 22
<212> TYPE: RNA
<213> ORGANISM: Homo Sapiens

<400> SEQUENCE: 1422
aacgcacuuc ccuuuagagu gu                                      22

<210> SEQ ID NO 1423
<211> LENGTH: 22
<212> TYPE: RNA
<213> ORGANISM: Homo Sapiens

<400> SEQUENCE: 1423
uuacacacaa cugaggauca ua                                      22

<210> SEQ ID NO 1424
<211> LENGTH: 18
<212> TYPE: RNA
<213> ORGANISM: Homo Sapiens

<400> SEQUENCE: 1424
ccaggcucug caguggga                                           18

<210> SEQ ID NO 1425
<211> LENGTH: 21
<212> TYPE: RNA
<213> ORGANISM: Homo Sapiens

<400> SEQUENCE: 1425
cuagacugaa gcuccuugag g                                       21

<210> SEQ ID NO 1426
<211> LENGTH: 22
<212> TYPE: RNA
<213> ORGANISM: Homo Sapiens

<400> SEQUENCE: 1426
cgucuuaccc agcaguguuu gg                                      22

<210> SEQ ID NO 1427
<211> LENGTH: 18
<212> TYPE: RNA
<213> ORGANISM: Homo Sapiens

<400> SEQUENCE: 1427
cagggucagc ugagcaug                                           18

<210> SEQ ID NO 1428
<211> LENGTH: 22
<212> TYPE: RNA
<213> ORGANISM: Homo Sapiens

```
<400> SEQUENCE: 1428
aacacaccug guuaaccucu uu                                        22

<210> SEQ ID NO 1429
<211> LENGTH: 23
<212> TYPE: RNA
<213> ORGANISM: Homo Sapiens

<400> SEQUENCE: 1429
ucucuggagg gaagcacuuu cug                                       23

<210> SEQ ID NO 1430
<211> LENGTH: 19
<212> TYPE: RNA
<213> ORGANISM: Homo Sapiens

<400> SEQUENCE: 1430
aagcagcugc cucugaggc                                            19

<210> SEQ ID NO 1431
<211> LENGTH: 22
<212> TYPE: RNA
<213> ORGANISM: Homo Sapiens

<400> SEQUENCE: 1431
uuacggacca gcuaagggag gc                                        22

<210> SEQ ID NO 1432
<211> LENGTH: 22
<212> TYPE: RNA
<213> ORGANISM: Homo Sapiens

<400> SEQUENCE: 1432
uugcauaguc acaaaaguga uc                                        22

<210> SEQ ID NO 1433
<211> LENGTH: 22
<212> TYPE: RNA
<213> ORGANISM: Homo Sapiens

<400> SEQUENCE: 1433
ccuguucucc auuacuuggc uc                                        22

<210> SEQ ID NO 1434
<211> LENGTH: 22
<212> TYPE: RNA
<213> ORGANISM: Homo Sapiens

<400> SEQUENCE: 1434
gagcuuauuc auaaaagugc ag                                        22

<210> SEQ ID NO 1435
<211> LENGTH: 21
<212> TYPE: RNA
<213> ORGANISM: Homo Sapiens

<400> SEQUENCE: 1435
acaggcacga cugguuuggc a                                         21

<210> SEQ ID NO 1436
<211> LENGTH: 22
<212> TYPE: RNA
<213> ORGANISM: Homo Sapiens
```

<400> SEQUENCE: 1436
cucuagaggg aagcgcuuuc ug                                              22

<210> SEQ ID NO 1437
<211> LENGTH: 17
<212> TYPE: RNA
<213> ORGANISM: Homo Sapiens

<400> SEQUENCE: 1437
gggguggucu guuguug                                                    17

<210> SEQ ID NO 1438
<211> LENGTH: 17
<212> TYPE: RNA
<213> ORGANISM: Homo Sapiens

<400> SEQUENCE: 1438
ucgccuccuc cucuccc                                                    17

<210> SEQ ID NO 1439
<211> LENGTH: 22
<212> TYPE: RNA
<213> ORGANISM: Homo Sapiens

<400> SEQUENCE: 1439
aggagagugg auuccaggug gu                                              22

<210> SEQ ID NO 1440
<211> LENGTH: 22
<212> TYPE: RNA
<213> ORGANISM: Homo Sapiens

<400> SEQUENCE: 1440
uaaaguggca gaguauagac ac                                              22

<210> SEQ ID NO 1441
<211> LENGTH: 17
<212> TYPE: RNA
<213> ORGANISM: Homo Sapiens

<400> SEQUENCE: 1441
gacauucaga cuaccug                                                    17

<210> SEQ ID NO 1442
<211> LENGTH: 21
<212> TYPE: RNA
<213> ORGANISM: Homo Sapiens

<400> SEQUENCE: 1442 uguguccau uauuggugau u                                                21

<210> SEQ ID NO 1443
<211> LENGTH: 22
<212> TYPE: RNA
<213> ORGANISM: Homo Sapiens

<400> SEQUENCE: 1443
uaacugguug aacaacugaa cc                                              22

<210> SEQ ID NO 1444
<211> LENGTH: 22
<212> TYPE: RNA

-continued

```
<213> ORGANISM: Homo Sapiens

<400> SEQUENCE: 1444
ucagugcacu acagaacuuu gu                                            22

<210> SEQ ID NO 1445
<211> LENGTH: 23
<212> TYPE: RNA
<213> ORGANISM: Homo Sapiens

<400> SEQUENCE: 1445
guccuccagg ccaugagcug cgg                                           23

<210> SEQ ID NO 1446
<211> LENGTH: 22
<212> TYPE: RNA
<213> ORGANISM: Homo Sapiens

<400> SEQUENCE: 1446
ccgcacugug gguacuugcu gc                                            22

<210> SEQ ID NO 1447
<211> LENGTH: 22
<212> TYPE: RNA
<213> ORGANISM: Homo Sapiens

<400> SEQUENCE: 1447
uuucuauuuc ucagugggc uc                                             22

<210> SEQ ID NO 1448
<211> LENGTH: 21
<212> TYPE: RNA
<213> ORGANISM: Homo Sapiens

<400> SEQUENCE: 1448
caauucucaa aggagccucc c                                             21

<210> SEQ ID NO 1449
<211> LENGTH: 22
<212> TYPE: RNA
<213> ORGANISM: Homo Sapiens

<400> SEQUENCE: 1449
gugacaucac auauacggca gc                                            22

<210> SEQ ID NO 1450
<211> LENGTH: 22
<212> TYPE: RNA
<213> ORGANISM: Homo Sapiens

<400> SEQUENCE: 1450
agcucuagaa agauuguuga cc                                            22

<210> SEQ ID NO 1451
<211> LENGTH: 22
<212> TYPE: RNA
<213> ORGANISM: Homo Sapiens

<400> SEQUENCE: 1451
uggaaaaaac uggugugugc uu                                            22

<210> SEQ ID NO 1452
<211> LENGTH: 21
```

```
<212> TYPE: RNA
<213> ORGANISM: Homo Sapiens

<400> SEQUENCE: 1452
auuugugcuu ggcucuguca c                                          21

<210> SEQ ID NO 1453
<211> LENGTH: 22
<212> TYPE: RNA
<213> ORGANISM: Homo Sapiens

<400> SEQUENCE: 1453
cgaaaacagc aauuaccuuu gc                                         22

<210> SEQ ID NO 1454
<211> LENGTH: 22
<212> TYPE: RNA
<213> ORGANISM: Homo Sapiens

<400> SEQUENCE: 1454
cuucugauca agauuugugg ug                                         22

<210> SEQ ID NO 1455
<211> LENGTH: 22
<212> TYPE: RNA
<213> ORGANISM: Homo Sapiens

<400> SEQUENCE: 1455
cuggacugag ccaugcuacu gg                                         22

<210> SEQ ID NO 1456
<211> LENGTH: 20
<212> TYPE: RNA
<213> ORGANISM: Homo Sapiens

<400> SEQUENCE: 1456
cccugagacc cuaaccuuaa                                            20

<210> SEQ ID NO 1457
<211> LENGTH: 23
<212> TYPE: RNA
<213> ORGANISM: Homo Sapiens

<400> SEQUENCE: 1457
aggccucugu gacgucacgg ugu                                        23

<210> SEQ ID NO 1458
<211> LENGTH: 22
<212> TYPE: RNA
<213> ORGANISM: Homo Sapiens

<400> SEQUENCE: 1458
ugccuaggcu gagacugcag ug                                         22

<210> SEQ ID NO 1459
<211> LENGTH: 22
<212> TYPE: RNA
<213> ORGANISM: Homo Sapiens

<400> SEQUENCE: 1459
aagcccuuac cccaaaaagc au                                         22

<210> SEQ ID NO 1460
```

```
<211> LENGTH: 20
<212> TYPE: RNA
<213> ORGANISM: Homo Sapiens

<400> SEQUENCE: 1460
acugccccag gugcugcugg                                               20

<210> SEQ ID NO 1461
<211> LENGTH: 21
<212> TYPE: RNA
<213> ORGANISM: Homo Sapiens

<400> SEQUENCE: 1461
acagucugcu gagguuggag c                                             21

<210> SEQ ID NO 1462
<211> LENGTH: 19
<212> TYPE: RNA
<213> ORGANISM: Homo Sapiens

<400> SEQUENCE: 1462
guccuaggag gcuccucug                                                19

<210> SEQ ID NO 1463
<211> LENGTH: 23
<212> TYPE: RNA
<213> ORGANISM: Homo Sapiens

<400> SEQUENCE: 1463
uguguacaca cgugccaggc gcu                                           23

<210> SEQ ID NO 1464
<211> LENGTH: 22
<212> TYPE: RNA
<213> ORGANISM: Homo Sapiens

<400> SEQUENCE: 1464
uaggagggaa uaguaaaagc ag                                            22

<210> SEQ ID NO 1465
<211> LENGTH: 17
<212> TYPE: RNA
<213> ORGANISM: Homo Sapiens

<400> SEQUENCE: 1465
ggggcugggc gcgcgcc                                                  17

<210> SEQ ID NO 1466
<211> LENGTH: 21
<212> TYPE: RNA
<213> ORGANISM: Homo Sapiens

<400> SEQUENCE: 1466
ucuuguguuc ucuagaucag u                                             21

<210> SEQ ID NO 1467
<211> LENGTH: 18
<212> TYPE: RNA
<213> ORGANISM: Homo Sapiens

<400> SEQUENCE: 1467
ucagcuggcc cucauuuc                                                 18
```

<210> SEQ ID NO 1468
<211> LENGTH: 22
<212> TYPE: RNA
<213> ORGANISM: Homo Sapiens

<400> SEQUENCE: 1468
caucuggcau ccgucacaca ga                                          22

<210> SEQ ID NO 1469
<211> LENGTH: 22
<212> TYPE: RNA
<213> ORGANISM: Homo Sapiens

<400> SEQUENCE: 1469
uucugccucu guccaggucc uu                                          22

<210> SEQ ID NO 1470
<211> LENGTH: 24
<212> TYPE: RNA
<213> ORGANISM: Homo Sapiens

<400> SEQUENCE: 1470
agauauuuug aguguuugga auug                                        24

<210> SEQ ID NO 1471
<211> LENGTH: 21
<212> TYPE: RNA
<213> ORGANISM: Homo Sapiens

<400> SEQUENCE: 1471
uaaggcaccc uucugaguag a                                           21

<210> SEQ ID NO 1472
<211> LENGTH: 21
<212> TYPE: RNA
<213> ORGANISM: Homo Sapiens

<400> SEQUENCE: 1472
aacaggugac ugguuagaca a                                           21

<210> SEQ ID NO 1473
<211> LENGTH: 22
<212> TYPE: RNA
<213> ORGANISM: Homo Sapiens

<400> SEQUENCE: 1473
aagcgaccau gauguaacuu ca                                          22

<210> SEQ ID NO 1474
<211> LENGTH: 22
<212> TYPE: RNA
<213> ORGANISM: Homo Sapiens

<400> SEQUENCE: 1474
ugcuaugcca acauauugcc au                                          22

<210> SEQ ID NO 1475
<211> LENGTH: 22
<212> TYPE: RNA
<213> ORGANISM: Homo Sapiens

<400> SEQUENCE: 1475
ugagguagua aguuguauug uu                                          22

```
<210> SEQ ID NO 1476
<211> LENGTH: 21
<212> TYPE: RNA
<213> ORGANISM: Homo Sapiens

<400> SEQUENCE: 1476
ucuucaaccu caggacuugc a                                              21

<210> SEQ ID NO 1477
<211> LENGTH: 22
<212> TYPE: RNA
<213> ORGANISM: Homo Sapiens

<400> SEQUENCE: 1477
caucagaauu cauggaggcu ag                                             22

<210> SEQ ID NO 1478
<211> LENGTH: 22
<212> TYPE: RNA
<213> ORGANISM: Homo Sapiens

<400> SEQUENCE: 1478
uagcaccauc ugaaaucggu ua                                             22

<210> SEQ ID NO 1479
<211> LENGTH: 24
<212> TYPE: RNA
<213> ORGANISM: Homo Sapiens

<400> SEQUENCE: 1479
aauccuugga accuaggugu gagu                                           24

<210> SEQ ID NO 1480
<211> LENGTH: 22
<212> TYPE: RNA
<213> ORGANISM: Homo Sapiens

<400> SEQUENCE: 1480 auaggguug ugaauuuacc uu                                              22

<210> SEQ ID NO 1481
<211> LENGTH: 21
<212> TYPE: RNA
<213> ORGANISM: Homo Sapiens

<400> SEQUENCE: 1481
ugcaggacca agaugagccc u                                              21

<210> SEQ ID NO 1482
<211> LENGTH: 22
<212> TYPE: RNA
<213> ORGANISM: Homo Sapiens

<400> SEQUENCE: 1482
agaaagggug gcaauaccuc uu                                             22

<210> SEQ ID NO 1483
<211> LENGTH: 23
<212> TYPE: RNA
<213> ORGANISM: Homo Sapiens

<400> SEQUENCE: 1483
aaaggucauu guaagguuaa ugc                                            23
```

<210> SEQ ID NO 1484
<211> LENGTH: 20
<212> TYPE: RNA
<213> ORGANISM: Homo Sapiens

<400> SEQUENCE: 1484
cuuauaucag aggcuguggg                                               20

<210> SEQ ID NO 1485
<211> LENGTH: 22
<212> TYPE: RNA
<213> ORGANISM: Homo Sapiens

<400> SEQUENCE: 1485
cgucaacacu ugcugguuuc cu                                            22

<210> SEQ ID NO 1486
<211> LENGTH: 23
<212> TYPE: RNA
<213> ORGANISM: Homo Sapiens

<400> SEQUENCE: 1486 uaugggcuu cuguagagau uuc                                            23

<210> SEQ ID NO 1487
<211> LENGTH: 22
<212> TYPE: RNA
<213> ORGANISM: Homo Sapiens

<400> SEQUENCE: 1487
uagcagcaca uaaugguuug ug                                            22

<210> SEQ ID NO 1488
<211> LENGTH: 22
<212> TYPE: RNA
<213> ORGANISM: Homo Sapiens

<400> SEQUENCE: 1488
ucaggcucag uccccucccg au                                            22

<210> SEQ ID NO 1489
<211> LENGTH: 22
<212> TYPE: RNA
<213> ORGANISM: Homo Sapiens

<400> SEQUENCE: 1489
aaaaguaauu gcggguuuug cc                                            22

<210> SEQ ID NO 1490
<211> LENGTH: 21
<212> TYPE: RNA
<213> ORGANISM: Homo Sapiens

<400> SEQUENCE: 1490
aaucauucac ggacaacacu u                                             21

<210> SEQ ID NO 1491
<211> LENGTH: 22
<212> TYPE: RNA
<213> ORGANISM: Homo Sapiens

<400> SEQUENCE: 1491

```
gguucccucu ccaaaugugu cu                                    22

<210> SEQ ID NO 1492
<211> LENGTH: 20
<212> TYPE: RNA
<213> ORGANISM: Homo Sapiens

<400> SEQUENCE: 1492
agugccugag ggaguaagag                                       20

<210> SEQ ID NO 1493
<211> LENGTH: 22
<212> TYPE: RNA
<213> ORGANISM: Homo Sapiens

<400> SEQUENCE: 1493
uuguggaucu caaggaugug cu                                    22

<210> SEQ ID NO 1494
<211> LENGTH: 22
<212> TYPE: RNA
<213> ORGANISM: Homo Sapiens

<400> SEQUENCE: 1494
uuggccacca caccuacccc uu                                    22

<210> SEQ ID NO 1495
<211> LENGTH: 20
<212> TYPE: RNA
<213> ORGANISM: Homo Sapiens

<400> SEQUENCE: 1495
aggcauggga ggucagguga                                       20

<210> SEQ ID NO 1496
<211> LENGTH: 20
<212> TYPE: RNA
<213> ORGANISM: Homo Sapiens

<400> SEQUENCE: 1496 gugugugaa augcuucugc                                        20

<210> SEQ ID NO 1497
<211> LENGTH: 22
<212> TYPE: RNA
<213> ORGANISM: Homo Sapiens

<400> SEQUENCE: 1497
acuuuaacau ggaggcacuu gc                                    22

<210> SEQ ID NO 1498
<211> LENGTH: 25
<212> TYPE: RNA
<213> ORGANISM: Homo Sapiens

<400> SEQUENCE: 1498
gggcgacaaa gcaagacucu uucuu                                 25

<210> SEQ ID NO 1499
<211> LENGTH: 23
<212> TYPE: RNA
<213> ORGANISM: Homo Sapiens

<400> SEQUENCE: 1499
```
ucuuggagua ggucauuggg ugg                                        23

<210> SEQ ID NO 1500
<211> LENGTH: 21
<212> TYPE: RNA
<213> ORGANISM: Homo Sapiens

<400> SEQUENCE: 1500
gcugggaagg caaagggacg u                                          21

<210> SEQ ID NO 1501
<211> LENGTH: 23
<212> TYPE: RNA
<213> ORGANISM: Homo Sapiens

<400> SEQUENCE: 1501
cugggcccgc ggcgggcgug ggg                                        23

<210> SEQ ID NO 1502
<211> LENGTH: 23
<212> TYPE: RNA
<213> ORGANISM: Homo Sapiens

<400> SEQUENCE: 1502
ugagcaccac acaggccggg cgc                                        23

<210> SEQ ID NO 1503
<211> LENGTH: 20
<212> TYPE: RNA
<213> ORGANISM: Homo Sapiens

<400> SEQUENCE: 1503
uaaggcacgc ggugaaugcc                                            20

<210> SEQ ID NO 1504
<211> LENGTH: 22
<212> TYPE: RNA
<213> ORGANISM: Homo Sapiens

<400> SEQUENCE: 1504
aacuaguaau guuggauuag gg                                         22

<210> SEQ ID NO 1505
<211> LENGTH: 23
<212> TYPE: RNA
<213> ORGANISM: Homo Sapiens

<400> SEQUENCE: 1505
aggaaaugag gcuggcuagg agc                                        23

<210> SEQ ID NO 1506
<211> LENGTH: 21
<212> TYPE: RNA
<213> ORGANISM: Homo Sapiens

<400> SEQUENCE: 1506
aaaagcauca ggaaguaccc a                                          21

<210> SEQ ID NO 1507
<211> LENGTH: 22
<212> TYPE: RNA
<213> ORGANISM: Homo Sapiens -continued

```
<400> SEQUENCE: 1507
aaucaugugc agugccaaua ug                                              22

<210> SEQ ID NO 1508
<211> LENGTH: 17
<212> TYPE: RNA
<213> ORGANISM: Homo Sapiens

<400> SEQUENCE: 1508
acagggagga gauugua                                                    17

<210> SEQ ID NO 1509
<211> LENGTH: 22
<212> TYPE: RNA
<213> ORGANISM: Homo Sapiens

<400> SEQUENCE: 1509 ucugccccu ccgcugcugc ca                                               22

<210> SEQ ID NO 1510
<211> LENGTH: 23
<212> TYPE: RNA
<213> ORGANISM: Homo Sapiens

<400> SEQUENCE: 1510
uugcauguca gauuguaauu ccc                                             23

<210> SEQ ID NO 1511
<211> LENGTH: 22
<212> TYPE: RNA
<213> ORGANISM: Homo Sapiens

<400> SEQUENCE: 1511
aggccaucag caguccaaug aa                                              22

<210> SEQ ID NO 1512
<211> LENGTH: 17
<212> TYPE: RNA
<213> ORGANISM: Homo Sapiens

<400> SEQUENCE: 1512
guggaccugg cugggac                                                    17

<210> SEQ ID NO 1513
<211> LENGTH: 18
<212> TYPE: RNA
<213> ORGANISM: Homo Sapiens

<400> SEQUENCE: 1513
cuggagucua ggauucca                                                   18

<210> SEQ ID NO 1514
<211> LENGTH: 24
<212> TYPE: RNA
<213> ORGANISM: Homo Sapiens

<400> SEQUENCE: 1514
ugaggggccu cagaccgagc uuuu                                            24

<210> SEQ ID NO 1515
<211> LENGTH: 20
<212> TYPE: RNA
<213> ORGANISM: Homo Sapiens
```

<400> SEQUENCE: 1515
auaugccugg cuagcccuc                                          20

<210> SEQ ID NO 1516
<211> LENGTH: 21
<212> TYPE: RNA
<213> ORGANISM: Homo Sapiens

<400> SEQUENCE: 1516
gagccagugg ugagacagug a                                       21

<210> SEQ ID NO 1517
<211> LENGTH: 19
<212> TYPE: RNA
<213> ORGANISM: Homo Sapiens

<400> SEQUENCE: 1517
aaaagcuggg uugagagga                                          19

<210> SEQ ID NO 1518
<211> LENGTH: 24
<212> TYPE: RNA
<213> ORGANISM: Homo Sapiens

<400> SEQUENCE: 1518
ccagacagaa uucuaugcac uuuc                                    24

<210> SEQ ID NO 1519
<211> LENGTH: 19
<212> TYPE: RNA
<213> ORGANISM: Homo Sapiens

<400> SEQUENCE: 1519
ugcccuccuu ucuucccuc                                          19

<210> SEQ ID NO 1520
<211> LENGTH: 23
<212> TYPE: RNA
<213> ORGANISM: Homo Sapiens

<400> SEQUENCE: 1520
cucuugaggg aagcacuuuc ugu                                     23

<210> SEQ ID NO 1521
<211> LENGTH: 22
<212> TYPE: RNA
<213> ORGANISM: Homo Sapiens

<400> SEQUENCE: 1521
gugggcuggg cugggcuggg cc                                      22

<210> SEQ ID NO 1522
<211> LENGTH: 21
<212> TYPE: RNA
<213> ORGANISM: Homo Sapiens

<400> SEQUENCE: 1522
uggccaaaaa gcaggcagag a                                       21

<210> SEQ ID NO 1523
<211> LENGTH: 22
<212> TYPE: RNA

<213> ORGANISM: Homo Sapiens

<400> SEQUENCE: 1523
uaggggcagc agaggaccug gg                                              22

<210> SEQ ID NO 1524
<211> LENGTH: 21
<212> TYPE: RNA
<213> ORGANISM: Homo Sapiens

<400> SEQUENCE: 1524
agcuacaucu ggcuacuggg u                                               21

<210> SEQ ID NO 1525
<211> LENGTH: 22
<212> TYPE: RNA
<213> ORGANISM: Homo Sapiens

<400> SEQUENCE: 1525
gcccugaacg aggggucugg ag                                              22

<210> SEQ ID NO 1526
<211> LENGTH: 22
<212> TYPE: RNA
<213> ORGANISM: Homo Sapiens

<400> SEQUENCE: 1526
agacuuccca uuugaaggug gc                                              22

<210> SEQ ID NO 1527
<211> LENGTH: 18
<212> TYPE: RNA
<213> ORGANISM: Homo Sapiens

<400> SEQUENCE: 1527
gcggcgaguc cgacucau                                                   18

<210> SEQ ID NO 1528
<211> LENGTH: 19
<212> TYPE: RNA
<213> ORGANISM: Homo Sapiens

<400> SEQUENCE: 1528
acuggccugg gacuaccgg                                                  19

<210> SEQ ID NO 1529
<211> LENGTH: 21
<212> TYPE: RNA
<213> ORGANISM: Homo Sapiens

<400> SEQUENCE: 1529
uugcucacug uucuucccua g                                               21

<210> SEQ ID NO 1530
<211> LENGTH: 22
<212> TYPE: RNA
<213> ORGANISM: Homo Sapiens

<400> SEQUENCE: 1530
ugucuauacu cugucacuuu ac                                              22

<210> SEQ ID NO 1531
<211> LENGTH: 21

```
<212> TYPE: RNA
<213> ORGANISM: Homo Sapiens

<400> SEQUENCE: 1531
auccuugcua ucugggugcu a                                              21

<210> SEQ ID NO 1532
<211> LENGTH: 21
<212> TYPE: RNA
<213> ORGANISM: Homo Sapiens

<400> SEQUENCE: 1532
acugaauccu cuuuccuca g                                               21

<210> SEQ ID NO 1533
<211> LENGTH: 21
<212> TYPE: RNA
<213> ORGANISM: Homo Sapiens

<400> SEQUENCE: 1533
aagguuugga uagaugcaau a                                              21

<210> SEQ ID NO 1534
<211> LENGTH: 17
<212> TYPE: RNA
<213> ORGANISM: Homo Sapiens

<400> SEQUENCE: 1534
uucaaguaau ucaggug                                                   17

<210> SEQ ID NO 1535
<211> LENGTH: 21
<212> TYPE: RNA
<213> ORGANISM: Homo Sapiens

<400> SEQUENCE: 1535
ugugcagcag gccaaccgag a                                              21

<210> SEQ ID NO 1536
<211> LENGTH: 22
<212> TYPE: RNA
<213> ORGANISM: Homo Sapiens

<400> SEQUENCE: 1536
aaaaguuauu gcgguuuugg cu                                             22

<210> SEQ ID NO 1537
<211> LENGTH: 23
<212> TYPE: RNA
<213> ORGANISM: Homo Sapiens

<400> SEQUENCE: 1537
uauucauuua uccccagccu aca                                            23

<210> SEQ ID NO 1538
<211> LENGTH: 22
<212> TYPE: RNA
<213> ORGANISM: Homo Sapiens

<400> SEQUENCE: 1538
ggugcagugc ugcaucucug gu                                             22

<210> SEQ ID NO 1539
```

```
<211> LENGTH: 20
<212> TYPE: RNA
<213> ORGANISM: Homo Sapiens

<400> SEQUENCE: 1539
agaccauggg uucucauugu                                              20

<210> SEQ ID NO 1540
<211> LENGTH: 20
<212> TYPE: RNA
<213> ORGANISM: Homo Sapiens

<400> SEQUENCE: 1540
ucacuguuca gacaggcgga                                              20

<210> SEQ ID NO 1541
<211> LENGTH: 21
<212> TYPE: RNA
<213> ORGANISM: Homo Sapiens

<400> SEQUENCE: 1541
augaccuaug aauugacaga c                                            21

<210> SEQ ID NO 1542
<211> LENGTH: 22
<212> TYPE: RNA
<213> ORGANISM: Homo Sapiens

<400> SEQUENCE: 1542
caaggccaaa ggaagagaac ag                                           22

<210> SEQ ID NO 1543
<211> LENGTH: 21
<212> TYPE: RNA
<213> ORGANISM: Homo Sapiens

<400> SEQUENCE: 1543
ugacucugcc uguaggccgg u                                            21

<210> SEQ ID NO 1544
<211> LENGTH: 22
<212> TYPE: RNA
<213> ORGANISM: Homo Sapiens

<400> SEQUENCE: 1544
aaucacuaac cacacggcca gg                                           22

<210> SEQ ID NO 1545
<211> LENGTH: 23
<212> TYPE: RNA
<213> ORGANISM: Homo Sapiens

<400> SEQUENCE: 1545
uagcagcggg aacaguucug cag                                          23

<210> SEQ ID NO 1546
<211> LENGTH: 23
<212> TYPE: RNA
<213> ORGANISM: Homo Sapiens

<400> SEQUENCE: 1546
ucugcucaua ccccaugguu ucu                                          23
```

-continued

```
<210> SEQ ID NO 1547
<211> LENGTH: 22
<212> TYPE: RNA
<213> ORGANISM: Homo Sapiens

<400> SEQUENCE: 1547
ucggccugac cacccacccc ac                                              22

<210> SEQ ID NO 1548
<211> LENGTH: 22
<212> TYPE: RNA
<213> ORGANISM: Homo Sapiens

<400> SEQUENCE: 1548
aguuuugcau aguugcacua ca                                              22

<210> SEQ ID NO 1549
<211> LENGTH: 21
<212> TYPE: RNA
<213> ORGANISM: Homo Sapiens

<400> SEQUENCE: 1549
agagaagaag aucagccugc a                                               21

<210> SEQ ID NO 1550
<211> LENGTH: 21
<212> TYPE: RNA
<213> ORGANISM: Homo Sapiens

<400> SEQUENCE: 1550
uggaugugga aggaguuauc u                                               21

<210> SEQ ID NO 1551
<211> LENGTH: 22
<212> TYPE: RNA
<213> ORGANISM: Homo Sapiens

<400> SEQUENCE: 1551
acaguagagg gaggaaucgc ag                                              22

<210> SEQ ID NO 1552
<211> LENGTH: 25
<212> TYPE: RNA
<213> ORGANISM: Homo Sapiens

<400> SEQUENCE: 1552
cuagugaggg acagaaccag gauuc                                           25

<210> SEQ ID NO 1553
<211> LENGTH: 20
<212> TYPE: RNA
<213> ORGANISM: Homo Sapiens

<400> SEQUENCE: 1553
ugagcccugu ccucccgcag                                                 20

<210> SEQ ID NO 1554
<211> LENGTH: 22
<212> TYPE: RNA
<213> ORGANISM: Homo Sapiens

<400> SEQUENCE: 1554
aacuggccua caaaguccca gu                                              22
```

<210> SEQ ID NO 1555
<211> LENGTH: 21
<212> TYPE: RNA
<213> ORGANISM: Homo Sapiens

<400> SEQUENCE: 1555
agaggauacc cuuuguaugu u                                    21

<210> SEQ ID NO 1556
<211> LENGTH: 19
<212> TYPE: RNA
<213> ORGANISM: Homo Sapiens

<400> SEQUENCE: 1556
ggggccuggc ggugggcgg                                       19

<210> SEQ ID NO 1557
<211> LENGTH: 23
<212> TYPE: RNA
<213> ORGANISM: Homo Sapiens

<400> SEQUENCE: 1557
ccagagcagc cugcgguaac agu                                  23

<210> SEQ ID NO 1558
<211> LENGTH: 19
<212> TYPE: RNA
<213> ORGANISM: Homo Sapiens

<400> SEQUENCE: 1558
aucccaccac ugccaccau                                       19

<210> SEQ ID NO 1559
<211> LENGTH: 21
<212> TYPE: RNA
<213> ORGANISM: Homo Sapiens

<400> SEQUENCE: 1559
acccucguca gguccccggg g                                    21

<210> SEQ ID NO 1560
<211> LENGTH: 21
<212> TYPE: RNA
<213> ORGANISM: Homo Sapiens

<400> SEQUENCE: 1560
ucgugcauau aucuaccaca u                                    21

<210> SEQ ID NO 1561
<211> LENGTH: 22
<212> TYPE: RNA
<213> ORGANISM: Homo Sapiens

<400> SEQUENCE: 1561
aggggcuggc uuuccucugg uc                                   22

<210> SEQ ID NO 1562
<211> LENGTH: 21
<212> TYPE: RNA
<213> ORGANISM: Homo Sapiens

<400> SEQUENCE: 1562
auuggacugc ugauggcccg u                                    21

```
<210> SEQ ID NO 1563
<211> LENGTH: 25
<212> TYPE: RNA
<213> ORGANISM: Homo Sapiens

<400> SEQUENCE: 1563
gaacccauga gguugaggcu gcagu                                          25

<210> SEQ ID NO 1564
<211> LENGTH: 22
<212> TYPE: RNA
<213> ORGANISM: Homo Sapiens

<400> SEQUENCE: 1564
uacguagaua uauauguauu uu                                             22

<210> SEQ ID NO 1565
<211> LENGTH: 23
<212> TYPE: RNA
<213> ORGANISM: Homo Sapiens

<400> SEQUENCE: 1565
cuugccaucc ugguccacug cau                                            23

<210> SEQ ID NO 1566
<211> LENGTH: 23
<212> TYPE: RNA
<213> ORGANISM: Homo Sapiens

<400> SEQUENCE: 1566
cggcccgggc ugcugcuguu ccu                                            23

<210> SEQ ID NO 1567
<211> LENGTH: 22
<212> TYPE: RNA
<213> ORGANISM: Homo Sapiens

<400> SEQUENCE: 1567
ugccuggaac auaguaggga cu                                             22

<210> SEQ ID NO 1568
<211> LENGTH: 22
<212> TYPE: RNA
<213> ORGANISM: Homo Sapiens

<400> SEQUENCE: 1568
cugggagaag gcuguuuacu cu                                             22

<210> SEQ ID NO 1569
<211> LENGTH: 22
<212> TYPE: RNA
<213> ORGANISM: Homo Sapiens

<400> SEQUENCE: 1569
aacuggauca auuauaggag ug                                             22

<210> SEQ ID NO 1570
<211> LENGTH: 22
<212> TYPE: RNA
<213> ORGANISM: Homo Sapiens

<400> SEQUENCE: 1570
```

```
accagcgcgu uucaguuuc au                                                  22

<210> SEQ ID NO 1571
<211> LENGTH: 22
<212> TYPE: RNA
<213> ORGANISM: Homo Sapiens

<400> SEQUENCE: 1571
cuuucagucg gauguuuaca gc                                                 22

<210> SEQ ID NO 1572
<211> LENGTH: 22
<212> TYPE: RNA
<213> ORGANISM: Homo Sapiens

<400> SEQUENCE: 1572
gcagcagggu gaaacugaca ca                                                 22

<210> SEQ ID NO 1573
<211> LENGTH: 23
<212> TYPE: RNA
<213> ORGANISM: Homo Sapiens

<400> SEQUENCE: 1573
ucuggcuccg ugucuucacu ccc                                                23

<210> SEQ ID NO 1574
<211> LENGTH: 22
<212> TYPE: RNA
<213> ORGANISM: Homo Sapiens

<400> SEQUENCE: 1574
acugggaaga ggagcugagg ga                                                 22

<210> SEQ ID NO 1575
<211> LENGTH: 22
<212> TYPE: RNA
<213> ORGANISM: Homo Sapiens

<400> SEQUENCE: 1575
guggaguccu ggggaaugga ga                                                 22

<210> SEQ ID NO 1576
<211> LENGTH: 21
<212> TYPE: RNA
<213> ORGANISM: Homo Sapiens

<400> SEQUENCE: 1576
ccagugacug agcuggagcc a                                                  21

<210> SEQ ID NO 1577
<211> LENGTH: 23
<212> TYPE: RNA
<213> ORGANISM: Homo Sapiens

<400> SEQUENCE: 1577
agcuacauug ucugcugggu uuc                                                23

<210> SEQ ID NO 1578
<211> LENGTH: 21
<212> TYPE: RNA
<213> ORGANISM: Homo Sapiens

<400> SEQUENCE: 1578
```
aaugagagac cuguacugua u                                              21

<210> SEQ ID NO 1579
<211> LENGTH: 23
<212> TYPE: RNA
<213> ORGANISM: Homo Sapiens

<400> SEQUENCE: 1579
uaggagcuca acagaugccu guu                                            23

<210> SEQ ID NO 1580
<211> LENGTH: 21
<212> TYPE: RNA
<213> ORGANISM: Homo Sapiens

<400> SEQUENCE: 1580
ugcuguauug ucagguagug a                                              21

<210> SEQ ID NO 1581
<211> LENGTH: 17
<212> TYPE: RNA
<213> ORGANISM: Homo Sapiens

<400> SEQUENCE: 1581
ggagugggcu ggugguu                                                   17

<210> SEQ ID NO 1582
<211> LENGTH: 22
<212> TYPE: RNA
<213> ORGANISM: Homo Sapiens

<400> SEQUENCE: 1582
acuguaguau gggcacuucc ag                                             22

<210> SEQ ID NO 1583
<211> LENGTH: 22
<212> TYPE: RNA
<213> ORGANISM: Homo Sapiens

<400> SEQUENCE: 1583
aacucguguu caaagccuuu ag                                             22

<210> SEQ ID NO 1584
<211> LENGTH: 22
<212> TYPE: RNA
<213> ORGANISM: Homo Sapiens

<400> SEQUENCE: 1584
aggcagugua uuguuagcug gc                                             22

<210> SEQ ID NO 1585
<211> LENGTH: 22
<212> TYPE: RNA
<213> ORGANISM: Homo Sapiens

<400> SEQUENCE: 1585
ucugacauca gugauucucc ug                                             22

<210> SEQ ID NO 1586
<211> LENGTH: 23
<212> TYPE: RNA
<213> ORGANISM: Homo Sapiens

```
<400> SEQUENCE: 1586
aaucggaccc auuuaaaccg gag                                           23

<210> SEQ ID NO 1587
<211> LENGTH: 22
<212> TYPE: RNA
<213> ORGANISM: Homo Sapiens

<400> SEQUENCE: 1587
aggggacugg uuaauagaac ua                                            22

<210> SEQ ID NO 1588
<211> LENGTH: 21
<212> TYPE: RNA
<213> ORGANISM: Homo Sapiens

<400> SEQUENCE: 1588
aauggcgcca cuagguugu g                                              21

<210> SEQ ID NO 1589
<211> LENGTH: 20
<212> TYPE: RNA
<213> ORGANISM: Homo Sapiens

<400> SEQUENCE: 1589
augcgaggau gcugacagug                                               20

<210> SEQ ID NO 1590
<211> LENGTH: 17
<212> TYPE: RNA
<213> ORGANISM: Homo Sapiens

<400> SEQUENCE: 1590
ggcgggugcg gggugg                                                   17

<210> SEQ ID NO 1591
<211> LENGTH: 23
<212> TYPE: RNA
<213> ORGANISM: Homo Sapiens

<400> SEQUENCE: 1591
uuucaagcca gggggcguuu uuc                                           23

<210> SEQ ID NO 1592
<211> LENGTH: 22
<212> TYPE: RNA
<213> ORGANISM: Homo Sapiens

<400> SEQUENCE: 1592
gcugcgggcu gcggucaggg cg                                            22

<210> SEQ ID NO 1593
<211> LENGTH: 17
<212> TYPE: RNA
<213> ORGANISM: Homo Sapiens

<400> SEQUENCE: 1593
cacugugggu acaugcu                                                  17

<210> SEQ ID NO 1594
<211> LENGTH: 22
<212> TYPE: RNA
<213> ORGANISM: Homo Sapiens
```

```
<400> SEQUENCE: 1594
cucggcgcgg ggcgcgggcu cc                                        22

<210> SEQ ID NO 1595
<211> LENGTH: 22
<212> TYPE: RNA
<213> ORGANISM: Homo Sapiens

<400> SEQUENCE: 1595
ucugguaaga gauuugggca ua                                        22

<210> SEQ ID NO 1596
<211> LENGTH: 19
<212> TYPE: RNA
<213> ORGANISM: Homo Sapiens

<400> SEQUENCE: 1596
cuuggggcau ggaguccca                                            19

<210> SEQ ID NO 1597
<211> LENGTH: 22
<212> TYPE: RNA
<213> ORGANISM: Homo Sapiens

<400> SEQUENCE: 1597
augggugaau uuguagaagg au                                        22

<210> SEQ ID NO 1598
<211> LENGTH: 22
<212> TYPE: RNA
<213> ORGANISM: Homo Sapiens

<400> SEQUENCE: 1598
agcuuccaug acuccugaug ga                                        22

<210> SEQ ID NO 1599
<211> LENGTH: 22
<212> TYPE: RNA
<213> ORGANISM: Homo Sapiens

<400> SEQUENCE: 1599
agguauugcc acccuuucua gu                                        22

<210> SEQ ID NO 1600
<211> LENGTH: 22
<212> TYPE: RNA
<213> ORGANISM: Homo Sapiens

<400> SEQUENCE: 1600
auauuauuag ccacuucugg au                                        22

<210> SEQ ID NO 1601
<211> LENGTH: 22
<212> TYPE: RNA
<213> ORGANISM: Homo Sapiens

<400> SEQUENCE: 1601
uuagccaauu guccaucuuu ag                                        22

<210> SEQ ID NO 1602
<211> LENGTH: 23
<212> TYPE: RNA
```

```
<213> ORGANISM: Homo Sapiens

<400> SEQUENCE: 1602
cuaauaguau cuaccacaau aaa                                          23

<210> SEQ ID NO 1603
<211> LENGTH: 20
<212> TYPE: RNA
<213> ORGANISM: Homo Sapiens

<400> SEQUENCE: 1603
uuccgccagu cgguggccgg                                              20

<210> SEQ ID NO 1604
<211> LENGTH: 20
<212> TYPE: RNA
<213> ORGANISM: Homo Sapiens

<400> SEQUENCE: 1604
ccguguuucc cccacgcuuu                                              20

<210> SEQ ID NO 1605
<211> LENGTH: 22
<212> TYPE: RNA
<213> ORGANISM: Homo Sapiens

<400> SEQUENCE: 1605
auauaauaca accugcuaag ug                                           22

<210> SEQ ID NO 1606
<211> LENGTH: 22
<212> TYPE: RNA
<213> ORGANISM: Homo Sapiens

<400> SEQUENCE: 1606
ugaccgauuu cuccuggugu uc                                           22

<210> SEQ ID NO 1607
<211> LENGTH: 22
<212> TYPE: RNA
<213> ORGANISM: Homo Sapiens

<400> SEQUENCE: 1607
ugggaacuua guagagguuu aa                                           22

<210> SEQ ID NO 1608
<211> LENGTH: 22
<212> TYPE: RNA
<213> ORGANISM: Homo Sapiens

<400> SEQUENCE: 1608
cugggagagg guuguuuacu cc                                           22

<210> SEQ ID NO 1609
<211> LENGTH: 23
<212> TYPE: RNA
<213> ORGANISM: Homo Sapiens

<400> SEQUENCE: 1609
aaaaguaacu gcgguuuuug ccu                                          23

<210> SEQ ID NO 1610
<211> LENGTH: 22
```

<212> TYPE: RNA
<213> ORGANISM: Homo Sapiens

<400> SEQUENCE: 1610
agucauugga ggguuugagc ag                                              22

<210> SEQ ID NO 1611
<211> LENGTH: 21
<212> TYPE: RNA
<213> ORGANISM: Homo Sapiens

<400> SEQUENCE: 1611
uaacagucuc cagucacggc c                                               21

<210> SEQ ID NO 1612
<211> LENGTH: 22
<212> TYPE: RNA
<213> ORGANISM: Homo Sapiens

<400> SEQUENCE: 1612
agauuguuuc uuuugccgug ca                                              22

<210> SEQ ID NO 1613
<211> LENGTH: 22
<212> TYPE: RNA
<213> ORGANISM: Homo Sapiens

<400> SEQUENCE: 1613
aucaaggauc uuaaacuuug cc                                              22

<210> SEQ ID NO 1614
<211> LENGTH: 19
<212> TYPE: RNA
<213> ORGANISM: Homo Sapiens

<400> SEQUENCE: 1614
gugaggacuc gggaggugg                                                  19

<210> SEQ ID NO 1615
<211> LENGTH: 21
<212> TYPE: RNA
<213> ORGANISM: Homo Sapiens

<400> SEQUENCE: 1615
uaucguaucg uauuguauug u                                               21

<210> SEQ ID NO 1616
<211> LENGTH: 22
<212> TYPE: RNA
<213> ORGANISM: Homo Sapiens

<400> SEQUENCE: 1616
ugaucaggca aaauugcaga cu                                              22

<210> SEQ ID NO 1617
<211> LENGTH: 22
<212> TYPE: RNA
<213> ORGANISM: Homo Sapiens

<400> SEQUENCE: 1617
ugaagccagc ucuggucugg gc                                              22

<210> SEQ ID NO 1618

-continued

```
<211> LENGTH: 22
<212> TYPE: RNA
<213> ORGANISM: Homo Sapiens

<400> SEQUENCE: 1618
aagggcuucc ucucugcagg ac                                                  22

<210> SEQ ID NO 1619
<211> LENGTH: 21
<212> TYPE: RNA
<213> ORGANISM: Homo Sapiens

<400> SEQUENCE: 1619
ucugaauaga gucugaagag u                                                   21

<210> SEQ ID NO 1620
<211> LENGTH: 22
<212> TYPE: RNA
<213> ORGANISM: Homo Sapiens

<400> SEQUENCE: 1620
uggguuccug gcaugcugau uu                                                  22

<210> SEQ ID NO 1621
<211> LENGTH: 22
<212> TYPE: RNA
<213> ORGANISM: Homo Sapiens

<400> SEQUENCE: 1621
uuugggacug aucuugaugu cu                                                  22

<210> SEQ ID NO 1622
<211> LENGTH: 21
<212> TYPE: RNA
<213> ORGANISM: Homo Sapiens

<400> SEQUENCE: 1622
aaaacgguga gauuuuguuu u                                                   21

<210> SEQ ID NO 1623
<211> LENGTH: 20
<212> TYPE: RNA
<213> ORGANISM: Homo Sapiens

<400> SEQUENCE: 1623
auguauaaau guauacacac                                                     20

<210> SEQ ID NO 1624
<211> LENGTH: 23
<212> TYPE: RNA
<213> ORGANISM: Homo Sapiens

<400> SEQUENCE: 1624
caguaacaaa gauucauccu ugu                                                 23

<210> SEQ ID NO 1625
<211> LENGTH: 22
<212> TYPE: RNA
<213> ORGANISM: Homo Sapiens

<400> SEQUENCE: 1625
gaaggcagca gugcucccu gu                                                   22
```

-continued

```
<210> SEQ ID NO 1626
<211> LENGTH: 22
<212> TYPE: RNA
<213> ORGANISM: Homo Sapiens

<400> SEQUENCE: 1626
ucccugagac ccuaacuugu ga                                                  22

<210> SEQ ID NO 1627
<211> LENGTH: 22
<212> TYPE: RNA
<213> ORGANISM: Homo Sapiens

<400> SEQUENCE: 1627
uugugucaau augcgaugau gu                                                  22

<210> SEQ ID NO 1628
<211> LENGTH: 21
<212> TYPE: RNA
<213> ORGANISM: Homo Sapiens

<400> SEQUENCE: 1628
aagccugccc ggcuccucgg g                                                   21

<210> SEQ ID NO 1629
<211> LENGTH: 25
<212> TYPE: RNA
<213> ORGANISM: Homo Sapiens

<400> SEQUENCE: 1629
ugccccaucu gugcccuggg uagga                                               25

<210> SEQ ID NO 1630
<211> LENGTH: 24
<212> TYPE: RNA
<213> ORGANISM: Homo Sapiens

<400> SEQUENCE: 1630
cauagcccgg ucgcugguac auga                                                24

<210> SEQ ID NO 1631
<211> LENGTH: 22
<212> TYPE: RNA
<213> ORGANISM: Homo Sapiens

<400> SEQUENCE: 1631
augaagugca cucaugauau gu                                                  22

<210> SEQ ID NO 1632
<211> LENGTH: 23
<212> TYPE: RNA
<213> ORGANISM: Homo Sapiens

<400> SEQUENCE: 1632
cagggcucag ggauuggaug gag                                                 23

<210> SEQ ID NO 1633
<211> LENGTH: 22
<212> TYPE: RNA
<213> ORGANISM: Homo Sapiens

<400> SEQUENCE: 1633
ucaguaaaug uuuauuagau ga                                                  22
```

```
<210> SEQ ID NO 1634
<211> LENGTH: 22
<212> TYPE: RNA
<213> ORGANISM: Homo Sapiens

<400> SEQUENCE: 1634
cagaacagga gcauagaaag gc                                              22

<210> SEQ ID NO 1635
<211> LENGTH: 22
<212> TYPE: RNA
<213> ORGANISM: Homo Sapiens

<400> SEQUENCE: 1635
acucaaaaga uggcggcacu uu                                              22

<210> SEQ ID NO 1636
<211> LENGTH: 18
<212> TYPE: RNA
<213> ORGANISM: Homo Sapiens

<400> SEQUENCE: 1636
agagcagaag gaugagau                                                   18

<210> SEQ ID NO 1637
<211> LENGTH: 21
<212> TYPE: RNA
<213> ORGANISM: Homo Sapiens

<400> SEQUENCE: 1637
aaggcagggc ccccgcuccc c                                               21

<210> SEQ ID NO 1638
<211> LENGTH: 22
<212> TYPE: RNA
<213> ORGANISM: Homo Sapiens

<400> SEQUENCE: 1638
cagugccucg gcagugcagc cc                                              22

<210> SEQ ID NO 1639
<211> LENGTH: 22
<212> TYPE: RNA
<213> ORGANISM: Homo Sapiens

<400> SEQUENCE: 1639
ucucugagca aggcuuaaca cc                                              22

<210> SEQ ID NO 1640
<211> LENGTH: 23
<212> TYPE: RNA
<213> ORGANISM: Homo Sapiens

<400> SEQUENCE: 1640
gaaaauccuu uuuguuuuc cag                                              23

<210> SEQ ID NO 1641
<211> LENGTH: 21
<212> TYPE: RNA
<213> ORGANISM: Homo Sapiens

<400> SEQUENCE: 1641
uuggccacaa ugggguuagaa c                                              21
```

```
<210> SEQ ID NO 1642
<211> LENGTH: 23
<212> TYPE: RNA
<213> ORGANISM: Homo Sapiens

<400> SEQUENCE: 1642
uaagugcuuc cauguuucag ugg                                              23

<210> SEQ ID NO 1643
<211> LENGTH: 22
<212> TYPE: RNA
<213> ORGANISM: Homo Sapiens

<400> SEQUENCE: 1643
aucuggaggu aagaagcacu uu                                               22

<210> SEQ ID NO 1644
<211> LENGTH: 21
<212> TYPE: RNA
<213> ORGANISM: Homo Sapiens

<400> SEQUENCE: 1644
uccgguucuc agggcuccac c                                                21

<210> SEQ ID NO 1645
<211> LENGTH: 22
<212> TYPE: RNA
<213> ORGANISM: Homo Sapiens

<400> SEQUENCE: 1645
ucagcaaaca uuuauugugu gc                                               22

<210> SEQ ID NO 1646
<211> LENGTH: 19
<212> TYPE: RNA
<213> ORGANISM: Homo Sapiens

<400> SEQUENCE: 1646
auggauaagg cuuuggcuu                                                   19

<210> SEQ ID NO 1647
<211> LENGTH: 18
<212> TYPE: RNA
<213> ORGANISM: Homo Sapiens

<400> SEQUENCE: 1647
aggagaaguc gggaaggu                                                    18

<210> SEQ ID NO 1648
<211> LENGTH: 22
<212> TYPE: RNA
<213> ORGANISM: Homo Sapiens

<400> SEQUENCE: 1648
uggacggaga acugauaagg gu                                               22

<210> SEQ ID NO 1649
<211> LENGTH: 22
<212> TYPE: RNA
<213> ORGANISM: Homo Sapiens

<400> SEQUENCE: 1649
```

```
ccucugaaau ucaguucuuc ag                                            22

<210> SEQ ID NO 1650
<211> LENGTH: 25
<212> TYPE: RNA
<213> ORGANISM: Homo Sapiens

<400> SEQUENCE: 1650
uaggcagugu auugcuagcg gcugu                                         25

<210> SEQ ID NO 1651
<211> LENGTH: 23
<212> TYPE: RNA
<213> ORGANISM: Homo Sapiens

<400> SEQUENCE: 1651
ggguuuguag cuuugcuggc aug                                           23

<210> SEQ ID NO 1652
<211> LENGTH: 22
<212> TYPE: RNA
<213> ORGANISM: Homo Sapiens

<400> SEQUENCE: 1652
acugcugagc uagcacuucc cg                                            22

<210> SEQ ID NO 1653
<211> LENGTH: 23
<212> TYPE: RNA
<213> ORGANISM: Homo Sapiens

<400> SEQUENCE: 1653
uauggcuuuu cauuccuaug uga                                           23

<210> SEQ ID NO 1654
<211> LENGTH: 22
<212> TYPE: RNA
<213> ORGANISM: Homo Sapiens

<400> SEQUENCE: 1654
agacaucaag aucaguccca aa                                            22

<210> SEQ ID NO 1655
<211> LENGTH: 21
<212> TYPE: RNA
<213> ORGANISM: Homo Sapiens

<400> SEQUENCE: 1655
uagcagcaca gaaauauugg c                                             21

<210> SEQ ID NO 1656
<211> LENGTH: 20
<212> TYPE: RNA
<213> ORGANISM: Homo Sapiens

<400> SEQUENCE: 1656
ucgcgccccg gcucccguuc                                               20

<210> SEQ ID NO 1657
<211> LENGTH: 22
<212> TYPE: RNA
<213> ORGANISM: Homo Sapiens

<400> SEQUENCE: 1657
```
acaggugagg uucuugggag cc                                                22

<210> SEQ ID NO 1658
<211> LENGTH: 20
<212> TYPE: RNA
<213> ORGANISM: Homo Sapiens

<400> SEQUENCE: 1658
aaaacugcag uuacuuuugc                                                   20

<210> SEQ ID NO 1659
<211> LENGTH: 19
<212> TYPE: RNA
<213> ORGANISM: Homo Sapiens

<400> SEQUENCE: 1659
uuauugucac guucugauu                                                    19

<210> SEQ ID NO 1660
<211> LENGTH: 22
<212> TYPE: RNA
<213> ORGANISM: Homo Sapiens

<400> SEQUENCE: 1660
uugggaucau uuugcaucca ua                                                22

<210> SEQ ID NO 1661
<211> LENGTH: 17
<212> TYPE: RNA
<213> ORGANISM: Homo Sapiens

<400> SEQUENCE: 1661
cuccgggacg gcugggc                                                      17

<210> SEQ ID NO 1662
<211> LENGTH: 17
<212> TYPE: RNA
<213> ORGANISM: Homo Sapiens

<400> SEQUENCE: 1662
ccccgccacc gccuugg                                                      17

<210> SEQ ID NO 1663
<211> LENGTH: 23
<212> TYPE: RNA
<213> ORGANISM: Homo Sapiens

<400> SEQUENCE: 1663
ccugggcagc guguggcuga agg                                               23

<210> SEQ ID NO 1664
<211> LENGTH: 22
<212> TYPE: RNA
<213> ORGANISM: Homo Sapiens

<400> SEQUENCE: 1664
cuguacagcc uccuagcuuu cc                                                22

<210> SEQ ID NO 1665
<211> LENGTH: 21
<212> TYPE: RNA
<213> ORGANISM: Homo Sapiens

<400> SEQUENCE: 1665
ccgucgccgc cacccgagcc g                                    21

<210> SEQ ID NO 1666
<211> LENGTH: 23
<212> TYPE: RNA
<213> ORGANISM: Homo Sapiens

<400> SEQUENCE: 1666
aaaauggugc ccuagugacu aca                                  23

<210> SEQ ID NO 1667
<211> LENGTH: 22
<212> TYPE: RNA
<213> ORGANISM: Homo Sapiens

<400> SEQUENCE: 1667
uaaauagagu aggcaaagga ca                                   22

<210> SEQ ID NO 1668
<211> LENGTH: 22
<212> TYPE: RNA
<213> ORGANISM: Homo Sapiens

<400> SEQUENCE: 1668
aaagugcuuc ucuuuggugg gu                                   22

<210> SEQ ID NO 1669
<211> LENGTH: 17
<212> TYPE: RNA
<213> ORGANISM: Homo Sapiens

<400> SEQUENCE: 1669
ggugggggcu guuguuu                                         17

<210> SEQ ID NO 1670
<211> LENGTH: 22
<212> TYPE: RNA
<213> ORGANISM: Homo Sapiens

<400> SEQUENCE: 1670
gacacuaggc augugaguga uu                                   22

<210> SEQ ID NO 1671
<211> LENGTH: 17
<212> TYPE: RNA
<213> ORGANISM: Homo Sapiens

<400> SEQUENCE: 1671
gcuucuguag uguaguc                                         17

<210> SEQ ID NO 1672
<211> LENGTH: 22
<212> TYPE: RNA
<213> ORGANISM: Homo Sapiens

<400> SEQUENCE: 1672
uuuugcaaua uguuccugaa ua                                   22

<210> SEQ ID NO 1673
<211> LENGTH: 18
<212> TYPE: RNA
<213> ORGANISM: Homo Sapiens

```
<400> SEQUENCE: 1673
cggugagcgc ucgcuggc                                                    18

<210> SEQ ID NO 1674
<211> LENGTH: 19
<212> TYPE: RNA
<213> ORGANISM: Homo Sapiens

<400> SEQUENCE: 1674
gggggaagaa aaggugggg                                                   19

<210> SEQ ID NO 1675
<211> LENGTH: 23
<212> TYPE: RNA
<213> ORGANISM: Homo Sapiens

<400> SEQUENCE: 1675
uggagaucca gugcucgccc gau                                              23

<210> SEQ ID NO 1676
<211> LENGTH: 22
<212> TYPE: RNA
<213> ORGANISM: Homo Sapiens

<400> SEQUENCE: 1676
ugaaugguaa agcgauguca ca                                               22

<210> SEQ ID NO 1677
<211> LENGTH: 22
<212> TYPE: RNA
<213> ORGANISM: Homo Sapiens

<400> SEQUENCE: 1677
aacuguuugc agaggaaacu ga                                               22

<210> SEQ ID NO 1678
<211> LENGTH: 19
<212> TYPE: RNA
<213> ORGANISM: Homo Sapiens

<400> SEQUENCE: 1678
gaauacgucu gguugaucc                                                   19

<210> SEQ ID NO 1679
<211> LENGTH: 23
<212> TYPE: RNA
<213> ORGANISM: Homo Sapiens

<400> SEQUENCE: 1679
ccagccacgg acugagagug cau                                              23

<210> SEQ ID NO 1680
<211> LENGTH: 19
<212> TYPE: RNA
<213> ORGANISM: Homo Sapiens

<400> SEQUENCE: 1680
gacuggacaa gcugaggaa                                                   19

<210> SEQ ID NO 1681
<211> LENGTH: 21
<212> TYPE: RNA
```

<213> ORGANISM: Homo Sapiens

<400> SEQUENCE: 1681
gugggcgggg gcaggugugu g                                              21

<210> SEQ ID NO 1682
<211> LENGTH: 22
<212> TYPE: RNA
<213> ORGANISM: Homo Sapiens

<400> SEQUENCE: 1682
gucccucucc aaaugugucu ug                                             22

<210> SEQ ID NO 1683
<211> LENGTH: 21
<212> TYPE: RNA
<213> ORGANISM: Homo Sapiens

<400> SEQUENCE: 1683
ucguggccug gucuccauua u                                              21

<210> SEQ ID NO 1684
<211> LENGTH: 22
<212> TYPE: RNA
<213> ORGANISM: Homo Sapiens

<400> SEQUENCE: 1684
aaagaucugg aagugggaga ca                                             22

<210> SEQ ID NO 1685
<211> LENGTH: 22
<212> TYPE: RNA
<213> ORGANISM: Homo Sapiens

<400> SEQUENCE: 1685
uaugugggau gguaaaccgc uu                                             22

<210> SEQ ID NO 1686
<211> LENGTH: 22
<212> TYPE: RNA
<213> ORGANISM: Homo Sapiens

<400> SEQUENCE: 1686
cggguggauc acgaugcaau uu                                             22

<210> SEQ ID NO 1687
<211> LENGTH: 23
<212> TYPE: RNA
<213> ORGANISM: Homo Sapiens

<400> SEQUENCE: 1687
ugugcuugcu cgucccgccc gca                                            23

<210> SEQ ID NO 1688
<211> LENGTH: 22
<212> TYPE: RNA
<213> ORGANISM: Homo Sapiens

<400> SEQUENCE: 1688
aaaaguaauu gcggucuuug gu                                             22

<210> SEQ ID NO 1689
<211> LENGTH: 23

<212> TYPE: RNA
<213> ORGANISM: Homo Sapiens

<400> SEQUENCE: 1689
gccuggagcu acuccaccau cuc                                    23

<210> SEQ ID NO 1690
<211> LENGTH: 22
<212> TYPE: RNA
<213> ORGANISM: Homo Sapiens

<400> SEQUENCE: 1690
uguguuagaa uagggcaau aa                                      22

<210> SEQ ID NO 1691
<211> LENGTH: 21
<212> TYPE: RNA
<213> ORGANISM: Homo Sapiens

<400> SEQUENCE: 1691
aaagugcuuc cuuuuugagg g                                      21

<210> SEQ ID NO 1692
<211> LENGTH: 21
<212> TYPE: RNA
<213> ORGANISM: Homo Sapiens

<400> SEQUENCE: 1692
guucaaaucc agaucuauaa c                                      21

<210> SEQ ID NO 1693
<211> LENGTH: 22
<212> TYPE: RNA
<213> ORGANISM: Homo Sapiens

<400> SEQUENCE: 1693
cucuagaggg aagcacuuuc ug                                     22

<210> SEQ ID NO 1694
<211> LENGTH: 21
<212> TYPE: RNA
<213> ORGANISM: Homo Sapiens

<400> SEQUENCE: 1694
cuucuugugc ucuaggauug u                                      21

<210> SEQ ID NO 1695
<211> LENGTH: 21
<212> TYPE: RNA
<213> ORGANISM: Homo Sapiens

<400> SEQUENCE: 1695
ucugaaagag caguuggugu u                                      21

<210> SEQ ID NO 1696
<211> LENGTH: 22
<212> TYPE: RNA
<213> ORGANISM: Homo Sapiens

<400> SEQUENCE: 1696
caaccucgag gaucucccca gc                                     22

<210> SEQ ID NO 1697

```
<211> LENGTH: 22
<212> TYPE: RNA
<213> ORGANISM: Homo Sapiens

<400> SEQUENCE: 1697
agaucagaag gugauugugg cu                                              22

<210> SEQ ID NO 1698
<211> LENGTH: 22
<212> TYPE: RNA
<213> ORGANISM: Homo Sapiens

<400> SEQUENCE: 1698 aaggggaag gaaacaugga ga                                               22

<210> SEQ ID NO 1699
<211> LENGTH: 23
<212> TYPE: RNA
<213> ORGANISM: Homo Sapiens

<400> SEQUENCE: 1699
uagugaguua gagaugcaga gcc                                             23

<210> SEQ ID NO 1700
<211> LENGTH: 21
<212> TYPE: RNA
<213> ORGANISM: Homo Sapiens

<400> SEQUENCE: 1700
aggcggagac uugggcaauu g                                               21

<210> SEQ ID NO 1701
<211> LENGTH: 21
<212> TYPE: RNA
<213> ORGANISM: Homo Sapiens

<400> SEQUENCE: 1701
uguucaugua gauguuuaag c                                               21

<210> SEQ ID NO 1702
<211> LENGTH: 22
<212> TYPE: RNA
<213> ORGANISM: Homo Sapiens

<400> SEQUENCE: 1702 ugcuacuac uggagacacu gg                                               22

<210> SEQ ID NO 1703
<211> LENGTH: 22
<212> TYPE: RNA
<213> ORGANISM: Homo Sapiens

<400> SEQUENCE: 1703
uacgcgcaga ccacaggaug uc                                              22

<210> SEQ ID NO 1704
<211> LENGTH: 22
<212> TYPE: RNA
<213> ORGANISM: Homo Sapiens

<400> SEQUENCE: 1704
caaaaacugc aguuacuuuu gu                                              22
```

-continued

```
<210> SEQ ID NO 1705
<211> LENGTH: 22
<212> TYPE: RNA
<213> ORGANISM: Homo Sapiens

<400> SEQUENCE: 1705
cagcagcaau ucauguuuug aa                                              22

<210> SEQ ID NO 1706
<211> LENGTH: 21
<212> TYPE: RNA
<213> ORGANISM: Homo Sapiens

<400> SEQUENCE: 1706
uagaccaucu uucuagagua u                                               21

<210> SEQ ID NO 1707
<211> LENGTH: 17
<212> TYPE: RNA
<213> ORGANISM: Homo Sapiens

<400> SEQUENCE: 1707
ggggcgcggc cggaucg                                                    17

<210> SEQ ID NO 1708
<211> LENGTH: 22
<212> TYPE: RNA
<213> ORGANISM: Homo Sapiens

<400> SEQUENCE: 1708
uguaacagca acuccaugug ga                                              22

<210> SEQ ID NO 1709
<211> LENGTH: 22
<212> TYPE: RNA
<213> ORGANISM: Homo Sapiens

<400> SEQUENCE: 1709
caagaaccuc aguugcuuuu gu                                              22

<210> SEQ ID NO 1710
<211> LENGTH: 22
<212> TYPE: RNA
<213> ORGANISM: Homo Sapiens

<400> SEQUENCE: 1710
accuuccucu ccaugggucu uu                                              22

<210> SEQ ID NO 1711
<211> LENGTH: 20
<212> TYPE: RNA
<213> ORGANISM: Homo Sapiens

<400> SEQUENCE: 1711
cggggugggu gaggucgggc                                                 20

<210> SEQ ID NO 1712
<211> LENGTH: 19
<212> TYPE: RNA
<213> ORGANISM: Homo Sapiens

<400> SEQUENCE: 1712
gaugaugcug cugaugcug                                                  19
```

```
<210> SEQ ID NO 1713
<211> LENGTH: 22
<212> TYPE: RNA
<213> ORGANISM: Homo Sapiens

<400> SEQUENCE: 1713
uucgguauac uuugugaauu gg                                          22

<210> SEQ ID NO 1714
<211> LENGTH: 23
<212> TYPE: RNA
<213> ORGANISM: Homo Sapiens

<400> SEQUENCE: 1714
ucuguauucu ccuuugccug cag                                         23

<210> SEQ ID NO 1715
<211> LENGTH: 22
<212> TYPE: RNA
<213> ORGANISM: Homo Sapiens

<400> SEQUENCE: 1715
aaaguucuga gacacuccga cu                                          22

<210> SEQ ID NO 1716
<211> LENGTH: 22
<212> TYPE: RNA
<213> ORGANISM: Homo Sapiens

<400> SEQUENCE: 1716
aauguuggaa uccucgcuag ag                                          22

<210> SEQ ID NO 1717
<211> LENGTH: 21
<212> TYPE: RNA
<213> ORGANISM: Homo Sapiens

<400> SEQUENCE: 1717
aauguaaaca ggcuuuuugc u                                           21

<210> SEQ ID NO 1718
<211> LENGTH: 22
<212> TYPE: RNA
<213> ORGANISM: Homo Sapiens

<400> SEQUENCE: 1718
gagcuuggau gagcugggcu ga                                          22

<210> SEQ ID NO 1719
<211> LENGTH: 26
<212> TYPE: RNA
<213> ORGANISM: Homo Sapiens

<400> SEQUENCE: 1719
gcucagggau gauaacugug cugaga                                      26

<210> SEQ ID NO 1720
<211> LENGTH: 23
<212> TYPE: RNA
<213> ORGANISM: Homo Sapiens

<400> SEQUENCE: 1720
uucgggcugg ccugcugcuc cgg                                         23
```

```
<210> SEQ ID NO 1721
<211> LENGTH: 24
<212> TYPE: RNA
<213> ORGANISM: Homo Sapiens

<400> SEQUENCE: 1721
caaagugaug aguaauacug gcug                                              24

<210> SEQ ID NO 1722
<211> LENGTH: 20
<212> TYPE: RNA
<213> ORGANISM: Homo Sapiens

<400> SEQUENCE: 1722
gugcaaaagu caucacgguu                                                   20

<210> SEQ ID NO 1723
<211> LENGTH: 20
<212> TYPE: RNA
<213> ORGANISM: Homo Sapiens

<400> SEQUENCE: 1723
aggguguuuc ucucaucucu                                                   20

<210> SEQ ID NO 1724
<211> LENGTH: 22
<212> TYPE: RNA
<213> ORGANISM: Homo Sapiens

<400> SEQUENCE: 1724
ugcagggguc ggugggcca gg                                                 22

<210> SEQ ID NO 1725
<211> LENGTH: 22
<212> TYPE: RNA
<213> ORGANISM: Homo Sapiens

<400> SEQUENCE: 1725
uccauguuuc cuucccccuu cu                                                22

<210> SEQ ID NO 1726
<211> LENGTH: 22
<212> TYPE: RNA
<213> ORGANISM: Homo Sapiens

<400> SEQUENCE: 1726
caaaacuggc aauuacuuuu gc                                                22

<210> SEQ ID NO 1727
<211> LENGTH: 18
<212> TYPE: RNA
<213> ORGANISM: Homo Sapiens

<400> SEQUENCE: 1727
gugaaggccc ggcggaga                                                     18

<210> SEQ ID NO 1728
<211> LENGTH: 22
<212> TYPE: RNA
<213> ORGANISM: Homo Sapiens

<400> SEQUENCE: 1728
```
ugucgugggg cuugcuggcu ug                                                22

<210> SEQ ID NO 1729
<211> LENGTH: 21
<212> TYPE: RNA
<213> ORGANISM: Homo Sapiens

<400> SEQUENCE: 1729
acuggacuug gugucagaug g                                                 21

<210> SEQ ID NO 1730
<211> LENGTH: 23
<212> TYPE: RNA
<213> ORGANISM: Homo Sapiens

<400> SEQUENCE: 1730
aggaugagca aagaaaguag auu                                               23

<210> SEQ ID NO 1731
<211> LENGTH: 23
<212> TYPE: RNA
<213> ORGANISM: Homo Sapiens

<400> SEQUENCE: 1731
acaaaguaca gcauuagccu uag                                               23

<210> SEQ ID NO 1732
<211> LENGTH: 22
<212> TYPE: RNA
<213> ORGANISM: Homo Sapiens

<400> SEQUENCE: 1732
cacccguaga accgaccuug cg                                                22

<210> SEQ ID NO 1733
<211> LENGTH: 21
<212> TYPE: RNA
<213> ORGANISM: Homo Sapiens

<400> SEQUENCE: 1733
aaaaguaauu gcgguuuuug c                                                 21

<210> SEQ ID NO 1734
<211> LENGTH: 22
<212> TYPE: RNA
<213> ORGANISM: Homo Sapiens

<400> SEQUENCE: 1734
cucaucugca aagaaguaag ug                                                22

<210> SEQ ID NO 1735
<211> LENGTH: 22
<212> TYPE: RNA
<213> ORGANISM: Homo Sapiens

<400> SEQUENCE: 1735
ucacaaaucu auaauaugca gg                                                22

<210> SEQ ID NO 1736
<211> LENGTH: 22
<212> TYPE: RNA
<213> ORGANISM: Homo Sapiens

<400> SEQUENCE: 1736
aguuuugcag guuugcauuu ca                                                    22

<210> SEQ ID NO 1737
<211> LENGTH: 21
<212> TYPE: RNA
<213> ORGANISM: Homo Sapiens

<400> SEQUENCE: 1737
aucugccagc uuccacagug g                                                     21

<210> SEQ ID NO 1738
<211> LENGTH: 22
<212> TYPE: RNA
<213> ORGANISM: Homo Sapiens

<400> SEQUENCE: 1738
accuggcaua caauguagau uu                                                    22

<210> SEQ ID NO 1739
<211> LENGTH: 21
<212> TYPE: RNA
<213> ORGANISM: Homo Sapiens

<400> SEQUENCE: 1739
cugugggcuc agcgcguggg g                                                     21

<210> SEQ ID NO 1740
<211> LENGTH: 20
<212> TYPE: RNA
<213> ORGANISM: Homo Sapiens

<400> SEQUENCE: 1740
auggagauag auauagaaau                                                       20

<210> SEQ ID NO 1741
<211> LENGTH: 19
<212> TYPE: RNA
<213> ORGANISM: Homo Sapiens

<400> SEQUENCE: 1741
ccugagaccc uaguuccac                                                        19

<210> SEQ ID NO 1742
<211> LENGTH: 21
<212> TYPE: RNA
<213> ORGANISM: Homo Sapiens

<400> SEQUENCE: 1742
caaaaccgca guaacuuuug u                                                     21

<210> SEQ ID NO 1743
<211> LENGTH: 22
<212> TYPE: RNA
<213> ORGANISM: Homo Sapiens

<400> SEQUENCE: 1743
ucagucacau aucuaguguc ua                                                    22

<210> SEQ ID NO 1744
<211> LENGTH: 22
<212> TYPE: RNA
<213> ORGANISM: Homo Sapiens -continued

```
<400> SEQUENCE: 1744
ucucaggagu aaagacagag uu                                              22

<210> SEQ ID NO 1745
<211> LENGTH: 22
<212> TYPE: RNA
<213> ORGANISM: Homo Sapiens

<400> SEQUENCE: 1745
uagcaagaga accauuacca uu                                              22

<210> SEQ ID NO 1746
<211> LENGTH: 20
<212> TYPE: RNA
<213> ORGANISM: Homo Sapiens

<400> SEQUENCE: 1746 uguggacug caaaugggag                                                  20

<210> SEQ ID NO 1747
<211> LENGTH: 22
<212> TYPE: RNA
<213> ORGANISM: Homo Sapiens

<400> SEQUENCE: 1747
cuauacaguc uacugucuuu cc                                              22

<210> SEQ ID NO 1748
<211> LENGTH: 21
<212> TYPE: RNA
<213> ORGANISM: Homo Sapiens

<400> SEQUENCE: 1748
gcgacccacu cuugguuucc a                                               21

<210> SEQ ID NO 1749
<211> LENGTH: 22
<212> TYPE: RNA
<213> ORGANISM: Homo Sapiens

<400> SEQUENCE: 1749
ugcggggaca ggccagggca uc                                              22

<210> SEQ ID NO 1750
<211> LENGTH: 22
<212> TYPE: RNA
<213> ORGANISM: Homo Sapiens

<400> SEQUENCE: 1750
aggauuucag aaauacuggu gu                                              22

<210> SEQ ID NO 1751
<211> LENGTH: 21
<212> TYPE: RNA
<213> ORGANISM: Homo Sapiens

<400> SEQUENCE: 1751
cacccagauc ugcggccuaa u                                               21

<210> SEQ ID NO 1752
<211> LENGTH: 23
<212> TYPE: RNA
<213> ORGANISM: Homo Sapiens
```

```
<400> SEQUENCE: 1752
ugcagcucug guggaaaaug gag                                          23

<210> SEQ ID NO 1753
<211> LENGTH: 23
<212> TYPE: RNA
<213> ORGANISM: Homo Sapiens

<400> SEQUENCE: 1753
agaauugcgu uuggacaauc agu                                          23

<210> SEQ ID NO 1754
<211> LENGTH: 19
<212> TYPE: RNA
<213> ORGANISM: Homo Sapiens

<400> SEQUENCE: 1754
ugagggagug ggugggagg                                               19

<210> SEQ ID NO 1755
<211> LENGTH: 25
<212> TYPE: RNA
<213> ORGANISM: Homo Sapiens

<400> SEQUENCE: 1755
ugggaacggg uuccggcaga cgcug                                        25

<210> SEQ ID NO 1756
<211> LENGTH: 22
<212> TYPE: RNA
<213> ORGANISM: Homo Sapiens

<400> SEQUENCE: 1756
ugaaguuaca ucauggucgc uu                                           22

<210> SEQ ID NO 1757
<211> LENGTH: 22
<212> TYPE: RNA
<213> ORGANISM: Homo Sapiens

<400> SEQUENCE: 1757
ugucuuacuc ccucaggcac au                                           22

<210> SEQ ID NO 1758
<211> LENGTH: 22
<212> TYPE: RNA
<213> ORGANISM: Homo Sapiens

<400> SEQUENCE: 1758
ccuggcauau uugguauaac uu                                           22

<210> SEQ ID NO 1759
<211> LENGTH: 22
<212> TYPE: RNA
<213> ORGANISM: Homo Sapiens

<400> SEQUENCE: 1759
auauaccugu ucggucucuu ua                                           22

<210> SEQ ID NO 1760
<211> LENGTH: 20
<212> TYPE: RNA
```

```
<213> ORGANISM: Homo Sapiens

<400> SEQUENCE: 1760
aacucuagcc ugagcaacag                                              20

<210> SEQ ID NO 1761
<211> LENGTH: 22
<212> TYPE: RNA
<213> ORGANISM: Homo Sapiens

<400> SEQUENCE: 1761
ucucccaacc cuuguaccag ug                                           22

<210> SEQ ID NO 1762
<211> LENGTH: 23
<212> TYPE: RNA
<213> ORGANISM: Homo Sapiens

<400> SEQUENCE: 1762 uccccaggu gugauucuga uuu                                           23

<210> SEQ ID NO 1763
<211> LENGTH: 19
<212> TYPE: RNA
<213> ORGANISM: Homo Sapiens

<400> SEQUENCE: 1763
ugagggagga gguugggua                                               19

<210> SEQ ID NO 1764
<211> LENGTH: 22
<212> TYPE: RNA
<213> ORGANISM: Homo Sapiens

<400> SEQUENCE: 1764
cagggcuggc agugacaugg gu                                           22

<210> SEQ ID NO 1765
<211> LENGTH: 18
<212> TYPE: RNA
<213> ORGANISM: Homo Sapiens

<400> SEQUENCE: 1765
ggaucccggg gaggggggg                                               18

<210> SEQ ID NO 1766
<211> LENGTH: 22
<212> TYPE: RNA
<213> ORGANISM: Homo Sapiens

<400> SEQUENCE: 1766
uccccuucug caggccugcu gg                                           22

<210> SEQ ID NO 1767
<211> LENGTH: 22
<212> TYPE: RNA
<213> ORGANISM: Homo Sapiens

<400> SEQUENCE: 1767
ugagguagga gguuguauag uu                                           22

<210> SEQ ID NO 1768
<211> LENGTH: 22
```

```
<212> TYPE: RNA
<213> ORGANISM: Homo Sapiens

<400> SEQUENCE: 1768
ugagggagua ggauguaugg uu                                        22

<210> SEQ ID NO 1769
<211> LENGTH: 22
<212> TYPE: RNA
<213> ORGANISM: Homo Sapiens

<400> SEQUENCE: 1769
augcugacau auuuacuaga gg                                        22

<210> SEQ ID NO 1770
<211> LENGTH: 21
<212> TYPE: RNA
<213> ORGANISM: Homo Sapiens

<400> SEQUENCE: 1770
agagaugccg ccuugcuccu u                                         21

<210> SEQ ID NO 1771
<211> LENGTH: 20
<212> TYPE: RNA
<213> ORGANISM: Homo Sapiens

<400> SEQUENCE: 1771
ucccacuacu ucacuuguga                                           20

<210> SEQ ID NO 1772
<211> LENGTH: 23
<212> TYPE: RNA
<213> ORGANISM: Homo Sapiens

<400> SEQUENCE: 1772
ucugggaggu uguagcagug gaa                                       23

<210> SEQ ID NO 1773
<211> LENGTH: 17
<212> TYPE: RNA
<213> ORGANISM: Homo Sapiens

<400> SEQUENCE: 1773 gugggggccag gcggugg                                             17

<210> SEQ ID NO 1774
<211> LENGTH: 22
<212> TYPE: RNA
<213> ORGANISM: Homo Sapiens

<400> SEQUENCE: 1774
cuauacaauc uauugccuuc cc                                        22

<210> SEQ ID NO 1775
<211> LENGTH: 22
<212> TYPE: RNA
<213> ORGANISM: Homo Sapiens

<400> SEQUENCE: 1775
caagcuugua ucuauaggua ug                                        22

<210> SEQ ID NO 1776
```

```
<211> LENGTH: 22
<212> TYPE: RNA
<213> ORGANISM: Homo Sapiens

<400> SEQUENCE: 1776
uaaagaacuc uuaaaaccca au                                              22

<210> SEQ ID NO 1777
<211> LENGTH: 21
<212> TYPE: RNA
<213> ORGANISM: Homo Sapiens

<400> SEQUENCE: 1777
caaagaggaa ggucccauua c                                               21

<210> SEQ ID NO 1778
<211> LENGTH: 20
<212> TYPE: RNA
<213> ORGANISM: Homo Sapiens

<400> SEQUENCE: 1778
cggcucuggg ucugugggga                                                 20

<210> SEQ ID NO 1779
<211> LENGTH: 22
<212> TYPE: RNA
<213> ORGANISM: Homo Sapiens

<400> SEQUENCE: 1779
cugggacagg aggaggaggc ag                                              22

<210> SEQ ID NO 1780
<211> LENGTH: 22
<212> TYPE: RNA
<213> ORGANISM: Homo Sapiens

<400> SEQUENCE: 1780
aggugguccg uggcgcguuc gc                                              22

<210> SEQ ID NO 1781
<211> LENGTH: 23
<212> TYPE: RNA
<213> ORGANISM: Homo Sapiens

<400> SEQUENCE: 1781
uugaacuguu aagaaccacu gga                                             23

<210> SEQ ID NO 1782
<211> LENGTH: 23
<212> TYPE: RNA
<213> ORGANISM: Homo Sapiens

<400> SEQUENCE: 1782
gcgaggaccc cucgggucu gac                                              23

<210> SEQ ID NO 1783
<211> LENGTH: 22
<212> TYPE: RNA
<213> ORGANISM: Homo Sapiens

<400> SEQUENCE: 1783
gcugacuccu aguccagggc uc                                              22
```

-continued

```
<210> SEQ ID NO 1784
<211> LENGTH: 20
<212> TYPE: RNA
<213> ORGANISM: Homo Sapiens

<400> SEQUENCE: 1784
guagaggaga uggcgcaggg                                                      20

<210> SEQ ID NO 1785
<211> LENGTH: 23
<212> TYPE: RNA
<213> ORGANISM: Homo Sapiens

<400> SEQUENCE: 1785
aacugaacca ggagugagcu ucg                                                  23

<210> SEQ ID NO 1786
<211> LENGTH: 23
<212> TYPE: RNA
<213> ORGANISM: Homo Sapiens

<400> SEQUENCE: 1786
uagcaauaca guacaaauau agu                                                  23

<210> SEQ ID NO 1787
<211> LENGTH: 22
<212> TYPE: RNA
<213> ORGANISM: Homo Sapiens

<400> SEQUENCE: 1787
ugaggcccuu ggggcacagu gg                                                   22

<210> SEQ ID NO 1788
<211> LENGTH: 26
<212> TYPE: RNA
<213> ORGANISM: Homo Sapiens

<400> SEQUENCE: 1788
cacaggacug acuccucacc ccagug                                               26

<210> SEQ ID NO 1789
<211> LENGTH: 22
<212> TYPE: RNA
<213> ORGANISM: Homo Sapiens

<400> SEQUENCE: 1789
agagcuuagc ugauugguga ac                                                   22

<210> SEQ ID NO 1790
<211> LENGTH: 22
<212> TYPE: RNA
<213> ORGANISM: Homo Sapiens

<400> SEQUENCE: 1790
ucaggacacu ucugaacuug ga                                                   22

<210> SEQ ID NO 1791
<211> LENGTH: 19
<212> TYPE: RNA
<213> ORGANISM: Homo Sapiens

<400> SEQUENCE: 1791
ucucccuuga gggcacuuu                                                       19
```

```
<210> SEQ ID NO 1792
<211> LENGTH: 22
<212> TYPE: RNA
<213> ORGANISM: Homo Sapiens

<400> SEQUENCE: 1792
guggaccagg auggcaaggg cu                                                    22

<210> SEQ ID NO 1793
<211> LENGTH: 20
<212> TYPE: RNA
<213> ORGANISM: Homo Sapiens

<400> SEQUENCE: 1793
cgugccaccc uuuuccccag                                                       20

<210> SEQ ID NO 1794
<211> LENGTH: 22
<212> TYPE: RNA
<213> ORGANISM: Homo Sapiens

<400> SEQUENCE: 1794
cuugguucag ggaggguccc ca                                                    22

<210> SEQ ID NO 1795
<211> LENGTH: 22
<212> TYPE: RNA
<213> ORGANISM: Homo Sapiens

<400> SEQUENCE: 1795 gggugggau uuguugcauu ac                                                     22

<210> SEQ ID NO 1796
<211> LENGTH: 23
<212> TYPE: RNA
<213> ORGANISM: Homo Sapiens

<400> SEQUENCE: 1796
gaggcugaug ugaguagacc acu                                                   23

<210> SEQ ID NO 1797
<211> LENGTH: 22
<212> TYPE: RNA
<213> ORGANISM: Homo Sapiens

<400> SEQUENCE: 1797
aggcauugac uucucacuag cu                                                    22

<210> SEQ ID NO 1798
<211> LENGTH: 23
<212> TYPE: RNA
<213> ORGANISM: Homo Sapiens

<400> SEQUENCE: 1798
ucaaaugcuc agacccugu ggu                                                    23

<210> SEQ ID NO 1799
<211> LENGTH: 22
<212> TYPE: RNA
<213> ORGANISM: Homo Sapiens

<400> SEQUENCE: 1799
agccaggcuc ugaagggaaa gu                                                    22
```

```
<210> SEQ ID NO 1800
<211> LENGTH: 21
<212> TYPE: RNA
<213> ORGANISM: Homo Sapiens

<400> SEQUENCE: 1800
augauccagg aaccugccuc u                                          21

<210> SEQ ID NO 1801
<211> LENGTH: 21
<212> TYPE: RNA
<213> ORGANISM: Homo Sapiens

<400> SEQUENCE: 1801
agaccuggcc cagaccucag c                                          21

<210> SEQ ID NO 1802
<211> LENGTH: 22
<212> TYPE: RNA
<213> ORGANISM: Homo Sapiens

<400> SEQUENCE: 1802
acaguagucu gcacauuggu ua                                         22

<210> SEQ ID NO 1803
<211> LENGTH: 21
<212> TYPE: RNA
<213> ORGANISM: Homo Sapiens

<400> SEQUENCE: 1803
ccccaccucc ucucuccuca g                                          21

<210> SEQ ID NO 1804
<211> LENGTH: 23
<212> TYPE: RNA
<213> ORGANISM: Homo Sapiens

<400> SEQUENCE: 1804
ucucugagua ccauaugccu ugu                                        23

<210> SEQ ID NO 1805
<211> LENGTH: 22
<212> TYPE: RNA
<213> ORGANISM: Homo Sapiens

<400> SEQUENCE: 1805
ucugguaugu aguagguaau aa                                         22

<210> SEQ ID NO 1806
<211> LENGTH: 22
<212> TYPE: RNA
<213> ORGANISM: Homo Sapiens

<400> SEQUENCE: 1806
cuuucaguca gauguuugcu gc                                         22

<210> SEQ ID NO 1807
<211> LENGTH: 22
<212> TYPE: RNA
<213> ORGANISM: Homo Sapiens

<400> SEQUENCE: 1807
```

```
acggguuagg cucuugggag cu                                              22

<210> SEQ ID NO 1808
<211> LENGTH: 22
<212> TYPE: RNA
<213> ORGANISM: Homo Sapiens

<400> SEQUENCE: 1808
ugauauguuu gauauauuag gu                                              22

<210> SEQ ID NO 1809
<211> LENGTH: 22
<212> TYPE: RNA
<213> ORGANISM: Homo Sapiens

<400> SEQUENCE: 1809
caauuuagug ugugugauau uu                                              22

<210> SEQ ID NO 1810
<211> LENGTH: 21
<212> TYPE: RNA
<213> ORGANISM: Homo Sapiens

<400> SEQUENCE: 1810
ucgaccggac cucgaccggc u                                               21

<210> SEQ ID NO 1811
<211> LENGTH: 17
<212> TYPE: RNA
<213> ORGANISM: Homo Sapiens

<400> SEQUENCE: 1811
ugagguagua guuucuu                                                    17

<210> SEQ ID NO 1812
<211> LENGTH: 22
<212> TYPE: RNA
<213> ORGANISM: Homo Sapiens

<400> SEQUENCE: 1812
auggccagag cucacacaga gg                                              22

<210> SEQ ID NO 1813
<211> LENGTH: 16
<212> TYPE: RNA
<213> ORGANISM: Homo Sapiens

<400> SEQUENCE: 1813
cuaggaggcc uuggcc                                                     16

<210> SEQ ID NO 1814
<211> LENGTH: 18
<212> TYPE: RNA
<213> ORGANISM: Homo Sapiens

<400> SEQUENCE: 1814
guguucucug auggacag                                                   18

<210> SEQ ID NO 1815
<211> LENGTH: 22
<212> TYPE: RNA
<213> ORGANISM: Homo Sapiens

<400> SEQUENCE: 1815
```

| | |
|---|---|
| gaaggcgcuu cccuuuagag cg | 22 |

<210> SEQ ID NO 1816
<211> LENGTH: 23
<212> TYPE: RNA
<213> ORGANISM: Homo Sapiens

<400> SEQUENCE: 1816

| | |
|---|---|
| aaggagcuua caaucuagcu ggg | 23 |

<210> SEQ ID NO 1817
<211> LENGTH: 21
<212> TYPE: RNA
<213> ORGANISM: Homo Sapiens

<400> SEQUENCE: 1817

| | |
|---|---|
| uugaaaggcu auuucuuggu c | 21 |

<210> SEQ ID NO 1818
<211> LENGTH: 18
<212> TYPE: RNA
<213> ORGANISM: Homo Sapiens

<400> SEQUENCE: 1818

| | |
|---|---|
| gggugcgggc cggcgggg | 18 |

<210> SEQ ID NO 1819
<211> LENGTH: 22
<212> TYPE: RNA
<213> ORGANISM: Homo Sapiens

<400> SEQUENCE: 1819

| | |
|---|---|
| agcagaggca gagaggcuca gg | 22 |

<210> SEQ ID NO 1820
<211> LENGTH: 22
<212> TYPE: RNA
<213> ORGANISM: Homo Sapiens

<400> SEQUENCE: 1820

| | |
|---|---|
| ucugccaucc ucccuccccu ac | 22 |

<210> SEQ ID NO 1821
<211> LENGTH: 22
<212> TYPE: RNA
<213> ORGANISM: Homo Sapiens

<400> SEQUENCE: 1821

| | |
|---|---|
| aaaaguaauu guggauuuug cu | 22 |

<210> SEQ ID NO 1822
<211> LENGTH: 22
<212> TYPE: RNA
<213> ORGANISM: Homo Sapiens

<400> SEQUENCE: 1822

| | |
|---|---|
| aaaaguaauc acuguuuuug cc | 22 |

<210> SEQ ID NO 1823
<211> LENGTH: 22
<212> TYPE: RNA
<213> ORGANISM: Homo Sapiens

```
<400> SEQUENCE: 1823
aaggaaccag aaaugagaa gu                                              22

<210> SEQ ID NO 1824
<211> LENGTH: 22
<212> TYPE: RNA
<213> ORGANISM: Homo Sapiens

<400> SEQUENCE: 1824
accaucgacc guugauugua cc                                             22

<210> SEQ ID NO 1825
<211> LENGTH: 24
<212> TYPE: RNA
<213> ORGANISM: Homo Sapiens

<400> SEQUENCE: 1825
acuggcuagg gaaaaugauu ggau                                           24

<210> SEQ ID NO 1826
<211> LENGTH: 22
<212> TYPE: RNA
<213> ORGANISM: Homo Sapiens

<400> SEQUENCE: 1826
uggcaguguc uuagcugguu gu                                             22

<210> SEQ ID NO 1827
<211> LENGTH: 16
<212> TYPE: RNA
<213> ORGANISM: Homo Sapiens

<400> SEQUENCE: 1827
cucuccuccc ggcuuc                                                    16

<210> SEQ ID NO 1828
<211> LENGTH: 23
<212> TYPE: RNA
<213> ORGANISM: Homo Sapiens

<400> SEQUENCE: 1828
auacacauac acgcaacaca cau                                            23

<210> SEQ ID NO 1829
<211> LENGTH: 23
<212> TYPE: RNA
<213> ORGANISM: Homo Sapiens

<400> SEQUENCE: 1829
ucaagagcaa uaacgaaaaa ugu                                            23

<210> SEQ ID NO 1830
<211> LENGTH: 22
<212> TYPE: RNA
<213> ORGANISM: Homo Sapiens

<400> SEQUENCE: 1830
gggacccagg gagagacgua ag                                             22

<210> SEQ ID NO 1831
<211> LENGTH: 19
<212> TYPE: RNA
<213> ORGANISM: Homo Sapiens
```

<210> SEQ ID NO 1831
<211> LENGTH: 19
<212> TYPE: RNA
<213> ORGANISM: Homo Sapiens

<400> SEQUENCE: 1831
aagucccacu aaugccagc                                                19

<210> SEQ ID NO 1832
<211> LENGTH: 22
<212> TYPE: RNA
<213> ORGANISM: Homo Sapiens

<400> SEQUENCE: 1832
uguugggauu cagcaggacc au                                            22

<210> SEQ ID NO 1833
<211> LENGTH: 23
<212> TYPE: RNA
<213> ORGANISM: Homo Sapiens

<400> SEQUENCE: 1833
acggagacga caagacugug cug                                           23

<210> SEQ ID NO 1834
<211> LENGTH: 22
<212> TYPE: RNA
<213> ORGANISM: Homo Sapiens

<400> SEQUENCE: 1834
uucaaguaau ccaggauagg cu                                            22

<210> SEQ ID NO 1835
<211> LENGTH: 22
<212> TYPE: RNA
<213> ORGANISM: Homo Sapiens

<400> SEQUENCE: 1835
caagcucgug ucuguggguc cg                                            22

<210> SEQ ID NO 1836
<211> LENGTH: 24
<212> TYPE: RNA
<213> ORGANISM: Homo Sapiens

<400> SEQUENCE: 1836
acauccugcu ccacagggca gagg                                          24

<210> SEQ ID NO 1837
<211> LENGTH: 22
<212> TYPE: RNA
<213> ORGANISM: Homo Sapiens

<400> SEQUENCE: 1837
aaaagcuggg uugagagggc ga                                            22

<210> SEQ ID NO 1838
<211> LENGTH: 22
<212> TYPE: RNA
<213> ORGANISM: Homo Sapiens

<400> SEQUENCE: 1838
ccaauauuac ugugcugcuu ua                                            22

<210> SEQ ID NO 1839
<211> LENGTH: 22
<212> TYPE: RNA

<213> ORGANISM: Homo Sapiens

<400> SEQUENCE: 1839
guggguacgg cccagugggg gg 22

<210> SEQ ID NO 1840
<211> LENGTH: 17
<212> TYPE: RNA
<213> ORGANISM: Homo Sapiens

<400> SEQUENCE: 1840
uugucugcug aguuucc 17

<210> SEQ ID NO 1841
<211> LENGTH: 23
<212> TYPE: RNA
<213> ORGANISM: Homo Sapiens

<400> SEQUENCE: 1841
aacauucaac gcugucggug agu 23

<210> SEQ ID NO 1842
<211> LENGTH: 22
<212> TYPE: RNA
<213> ORGANISM: Homo Sapiens

<400> SEQUENCE: 1842
aaagauagac aauuggcuaa au 22

<210> SEQ ID NO 1843
<211> LENGTH: 21
<212> TYPE: RNA
<213> ORGANISM: Homo Sapiens

<400> SEQUENCE: 1843
auagcaauug cucuuuugga a 21

<210> SEQ ID NO 1844
<211> LENGTH: 22
<212> TYPE: RNA
<213> ORGANISM: Homo Sapiens

<400> SEQUENCE: 1844
ucagaugauc uaaaggccua ua 22

<210> SEQ ID NO 1845
<211> LENGTH: 22
<212> TYPE: RNA
<213> ORGANISM: Homo Sapiens

<400> SEQUENCE: 1845
acgcccuucc cccccuucuu ca 22

<210> SEQ ID NO 1846
<211> LENGTH: 23
<212> TYPE: RNA
<213> ORGANISM: Homo Sapiens

<400> SEQUENCE: 1846
gaagauggug cugugcugag gaa 23

<210> SEQ ID NO 1847
<211> LENGTH: 22

```
<212> TYPE: RNA
<213> ORGANISM: Homo Sapiens

<400> SEQUENCE: 1847
auuguagaac cuaagauugg cc                                              22

<210> SEQ ID NO 1848
<211> LENGTH: 22
<212> TYPE: RNA
<213> ORGANISM: Homo Sapiens

<400> SEQUENCE: 1848
acuccaagaa gaaucuagac ag                                              22

<210> SEQ ID NO 1849
<211> LENGTH: 22
<212> TYPE: RNA
<213> ORGANISM: Homo Sapiens

<400> SEQUENCE: 1849
agguggaugc aaugugaccu ca                                              22

<210> SEQ ID NO 1850
<211> LENGTH: 18
<212> TYPE: RNA
<213> ORGANISM: Homo Sapiens

<400> SEQUENCE: 1850
ugaggcagua gauugaau                                                   18

<210> SEQ ID NO 1851
<211> LENGTH: 22
<212> TYPE: RNA
<213> ORGANISM: Homo Sapiens

<400> SEQUENCE: 1851
caaaaaucuc aauuacuuuu gc                                              22

<210> SEQ ID NO 1852
<211> LENGTH: 22
<212> TYPE: RNA
<213> ORGANISM: Homo Sapiens

<400> SEQUENCE: 1852
uucuggaauu cugugugagg ga                                              22

<210> SEQ ID NO 1853
<211> LENGTH: 18
<212> TYPE: RNA
<213> ORGANISM: Homo Sapiens

<400> SEQUENCE: 1853
ucccuggagu uucuucuu                                                   18

<210> SEQ ID NO 1854
<211> LENGTH: 20
<212> TYPE: RNA
<213> ORGANISM: Homo Sapiens

<400> SEQUENCE: 1854
augggugaug ggugguggugu                                                20

<210> SEQ ID NO 1855
```

-continued

```
<211> LENGTH: 22
<212> TYPE: RNA
<213> ORGANISM: Homo Sapiens

<400> SEQUENCE: 1855
cacuuagcag guuguauuau au                                                22

<210> SEQ ID NO 1856
<211> LENGTH: 19
<212> TYPE: RNA
<213> ORGANISM: Homo Sapiens

<400> SEQUENCE: 1856
ggcuggucag augggagug                                                    19

<210> SEQ ID NO 1857
<211> LENGTH: 21
<212> TYPE: RNA
<213> ORGANISM: Homo Sapiens

<400> SEQUENCE: 1857
gcugcaccgg agacugggua a                                                 21

<210> SEQ ID NO 1858
<211> LENGTH: 21
<212> TYPE: RNA
<213> ORGANISM: Homo Sapiens

<400> SEQUENCE: 1858
cagugcaagu guagaugccg a                                                 21

<210> SEQ ID NO 1859
<211> LENGTH: 22
<212> TYPE: RNA
<213> ORGANISM: Homo Sapiens

<400> SEQUENCE: 1859
aaaagcuggg uugagagggc aa                                                22

<210> SEQ ID NO 1860
<211> LENGTH: 22
<212> TYPE: RNA
<213> ORGANISM: Homo Sapiens

<400> SEQUENCE: 1860
gggagccagg aaguauugau gu                                                22

<210> SEQ ID NO 1861
<211> LENGTH: 22
<212> TYPE: RNA
<213> ORGANISM: Homo Sapiens

<400> SEQUENCE: 1861
uugcuaagua ggcugagauu ga                                                22

<210> SEQ ID NO 1862
<211> LENGTH: 21
<212> TYPE: RNA
<213> ORGANISM: Homo Sapiens

<400> SEQUENCE: 1862
auguaugugu gcaugugcau g                                                 21
```

```
<210> SEQ ID NO 1863
<211> LENGTH: 23
<212> TYPE: RNA
<213> ORGANISM: Homo Sapiens

<400> SEQUENCE: 1863
caagucuuau uugagcaccu guu                                                 23

<210> SEQ ID NO 1864
<211> LENGTH: 22
<212> TYPE: RNA
<213> ORGANISM: Homo Sapiens

<400> SEQUENCE: 1864
ucauuuaucu guugggaagc ua                                                  22

<210> SEQ ID NO 1865
<211> LENGTH: 22
<212> TYPE: RNA
<213> ORGANISM: Homo Sapiens

<400> SEQUENCE: 1865
gaauaugggu auauuaguuu gg                                                  22

<210> SEQ ID NO 1866
<211> LENGTH: 23
<212> TYPE: RNA
<213> ORGANISM: Homo Sapiens

<400> SEQUENCE: 1866
agaggcuuug ugcggauacg ggg                                                 23

<210> SEQ ID NO 1867
<211> LENGTH: 22
<212> TYPE: RNA
<213> ORGANISM: Homo Sapiens

<400> SEQUENCE: 1867
aacucugucu ucacucauga gu                                                  22

<210> SEQ ID NO 1868
<211> LENGTH: 22
<212> TYPE: RNA
<213> ORGANISM: Homo Sapiens

<400> SEQUENCE: 1868
ugagguagua gguuguauag uu                                                  22

<210> SEQ ID NO 1869
<211> LENGTH: 21
<212> TYPE: RNA
<213> ORGANISM: Homo Sapiens

<400> SEQUENCE: 1869
cugaccuaug aauugacagc c                                                   21

<210> SEQ ID NO 1870
<211> LENGTH: 19
<212> TYPE: RNA
<213> ORGANISM: Homo Sapiens

<400> SEQUENCE: 1870
ucuagugcgg gcguucccg                                                      19
```

```
<210> SEQ ID NO 1871
<211> LENGTH: 23
<212> TYPE: RNA
<213> ORGANISM: Homo Sapiens

<400> SEQUENCE: 1871
uggaagacua gugauuuugu ugu                                             23

<210> SEQ ID NO 1872
<211> LENGTH: 22
<212> TYPE: RNA
<213> ORGANISM: Homo Sapiens

<400> SEQUENCE: 1872
aaaaguauuu gcggguuuug uc                                              22

<210> SEQ ID NO 1873
<211> LENGTH: 21
<212> TYPE: RNA
<213> ORGANISM: Homo Sapiens

<400> SEQUENCE: 1873
acaggagugg ggugggaca u                                                21

<210> SEQ ID NO 1874
<211> LENGTH: 23
<212> TYPE: RNA
<213> ORGANISM: Homo Sapiens

<400> SEQUENCE: 1874
cugacugaau agguaggguc auu                                             23

<210> SEQ ID NO 1875
<211> LENGTH: 22
<212> TYPE: RNA
<213> ORGANISM: Homo Sapiens

<400> SEQUENCE: 1875
ucuacaaagg aaagcgcuuu cu                                              22

<210> SEQ ID NO 1876
<211> LENGTH: 22
<212> TYPE: RNA
<213> ORGANISM: Homo Sapiens

<400> SEQUENCE: 1876
aacaucacag caagucugug cu                                              22

<210> SEQ ID NO 1877
<211> LENGTH: 22
<212> TYPE: RNA
<213> ORGANISM: Homo Sapiens

<400> SEQUENCE: 1877
aaaaacugag acuacuuuug ca                                              22

<210> SEQ ID NO 1878
<211> LENGTH: 22
<212> TYPE: RNA
<213> ORGANISM: Homo Sapiens

<400> SEQUENCE: 1878
guucucccaa cguaagccca gc                                              22
```

```
<210> SEQ ID NO 1879
<211> LENGTH: 22
<212> TYPE: RNA
<213> ORGANISM: Homo Sapiens

<400> SEQUENCE: 1879
agcauacacc uguaguccua ga                                          22

<210> SEQ ID NO 1880
<211> LENGTH: 21
<212> TYPE: RNA
<213> ORGANISM: Homo Sapiens

<400> SEQUENCE: 1880
uuucccuuuc cauccuggca g                                           21

<210> SEQ ID NO 1881
<211> LENGTH: 21
<212> TYPE: RNA
<213> ORGANISM: Homo Sapiens

<400> SEQUENCE: 1881
agcagacuug accuacaauu a                                           21

<210> SEQ ID NO 1882
<211> LENGTH: 22
<212> TYPE: RNA
<213> ORGANISM: Homo Sapiens

<400> SEQUENCE: 1882
cagugcaaug augaaagggc au                                          22

<210> SEQ ID NO 1883
<211> LENGTH: 23
<212> TYPE: RNA
<213> ORGANISM: Homo Sapiens

<400> SEQUENCE: 1883
caaaaaccgc aauuacuuuu gca                                         23

<210> SEQ ID NO 1884
<211> LENGTH: 22
<212> TYPE: RNA
<213> ORGANISM: Homo Sapiens

<400> SEQUENCE: 1884
auaauacaug guuaaccucu uu                                          22

<210> SEQ ID NO 1885
<211> LENGTH: 21
<212> TYPE: RNA
<213> ORGANISM: Homo Sapiens

<400> SEQUENCE: 1885
caaagcgcuu cccuuuggag c                                           21

<210> SEQ ID NO 1886
<211> LENGTH: 22
<212> TYPE: RNA
<213> ORGANISM: Homo Sapiens

<400> SEQUENCE: 1886
```
aucacacaaa ggcaacuuuu gu                                          22

<210> SEQ ID NO 1887
<211> LENGTH: 17
<212> TYPE: RNA
<213> ORGANISM: Homo Sapiens

<400> SEQUENCE: 1887
ucccugagca aagccac                                                17

<210> SEQ ID NO 1888
<211> LENGTH: 22
<212> TYPE: RNA
<213> ORGANISM: Homo Sapiens

<400> SEQUENCE: 1888
ugcaacgaac cugagccacu ga                                          22

<210> SEQ ID NO 1889
<211> LENGTH: 22
<212> TYPE: RNA
<213> ORGANISM: Homo Sapiens

<400> SEQUENCE: 1889
auaauacaac cugcuaagug cu                                          22

<210> SEQ ID NO 1890
<211> LENGTH: 22
<212> TYPE: RNA
<213> ORGANISM: Homo Sapiens

<400> SEQUENCE: 1890
uucacauugu gcuacugucu gc                                          22

<210> SEQ ID NO 1891
<211> LENGTH: 23
<212> TYPE: RNA
<213> ORGANISM: Homo Sapiens

<400> SEQUENCE: 1891
uuauugcuua agaauacgcg uag                                         23

<210> SEQ ID NO 1892
<211> LENGTH: 22
<212> TYPE: RNA
<213> ORGANISM: Homo Sapiens

<400> SEQUENCE: 1892
acaguagucu gcacauuggu ua                                          22

<210> SEQ ID NO 1893
<211> LENGTH: 19
<212> TYPE: RNA
<213> ORGANISM: Homo Sapiens

<400> SEQUENCE: 1893
cagcaggagg ugaggggag                                              19

<210> SEQ ID NO 1894
<211> LENGTH: 20
<212> TYPE: RNA
<213> ORGANISM: Homo Sapiens

<400> SEQUENCE: 1894
ucacucucac cuugcuuugc                                              20

<210> SEQ ID NO 1895
<211> LENGTH: 23
<212> TYPE: RNA
<213> ORGANISM: Homo Sapiens

<400> SEQUENCE: 1895
uagugcaaua uugcuuauag ggu                                          23

<210> SEQ ID NO 1896
<211> LENGTH: 21
<212> TYPE: RNA
<213> ORGANISM: Homo Sapiens

<400> SEQUENCE: 1896
gccccugggc cuauccuaga a                                            21

<210> SEQ ID NO 1897
<211> LENGTH: 22
<212> TYPE: RNA
<213> ORGANISM: Homo Sapiens

<400> SEQUENCE: 1897
uaguacugug cauaucaucu au                                           22

<210> SEQ ID NO 1898
<211> LENGTH: 22
<212> TYPE: RNA
<213> ORGANISM: Homo Sapiens

<400> SEQUENCE: 1898
ucgugucuug uguugcagcc gg                                           22

<210> SEQ ID NO 1899
<211> LENGTH: 22
<212> TYPE: RNA
<213> ORGANISM: Homo Sapiens

<400> SEQUENCE: 1899
cuggggagau ccucgagguu gg                                           22

<210> SEQ ID NO 1900
<211> LENGTH: 22
<212> TYPE: RNA
<213> ORGANISM: Homo Sapiens

<400> SEQUENCE: 1900
cgcgccugca ggaacuggua ga                                           22

<210> SEQ ID NO 1901
<211> LENGTH: 20
<212> TYPE: RNA
<213> ORGANISM: Homo Sapiens

<400> SEQUENCE: 1901
agagucuugu gaugucuugc                                              20

<210> SEQ ID NO 1902
<211> LENGTH: 23
<212> TYPE: RNA
<213> ORGANISM: Homo Sapiens

```
<400> SEQUENCE: 1902
gaacgcgcuu cccuauagag ggu                                            23

<210> SEQ ID NO 1903
<211> LENGTH: 21
<212> TYPE: RNA
<213> ORGANISM: Homo Sapiens

<400> SEQUENCE: 1903
ugacuucuac cucuuccaaa g                                              21

<210> SEQ ID NO 1904
<211> LENGTH: 21
<212> TYPE: RNA
<213> ORGANISM: Homo Sapiens

<400> SEQUENCE: 1904
uagauaaaau auugguaccu g                                              21

<210> SEQ ID NO 1905
<211> LENGTH: 22
<212> TYPE: RNA
<213> ORGANISM: Homo Sapiens

<400> SEQUENCE: 1905
gaaguuguuc gugguggauu cg                                             22

<210> SEQ ID NO 1906
<211> LENGTH: 18
<212> TYPE: RNA
<213> ORGANISM: Homo Sapiens

<400> SEQUENCE: 1906
ugagaugaca cuguagcu                                                  18

<210> SEQ ID NO 1907
<211> LENGTH: 22
<212> TYPE: RNA
<213> ORGANISM: Homo Sapiens

<400> SEQUENCE: 1907
cuagugcucu ccguuacaag ua                                             22

<210> SEQ ID NO 1908
<211> LENGTH: 19
<212> TYPE: RNA
<213> ORGANISM: Homo Sapiens

<400> SEQUENCE: 1908
accgugcaaa gguagcaua                                                 19

<210> SEQ ID NO 1909
<211> LENGTH: 21
<212> TYPE: RNA
<213> ORGANISM: Homo Sapiens

<400> SEQUENCE: 1909
gggggggggg gggggggcc g                                               21

<210> SEQ ID NO 1910
<211> LENGTH: 22
<212> TYPE: RNA
<213> ORGANISM: Homo Sapiens
```

```
<400> SEQUENCE: 1910
augguuccgu caagcaccau gg                                          22

<210> SEQ ID NO 1911
<211> LENGTH: 22
<212> TYPE: RNA
<213> ORGANISM: Homo Sapiens

<400> SEQUENCE: 1911
aaacuaaucu cuacacugcu gc                                          22

<210> SEQ ID NO 1912
<211> LENGTH: 22
<212> TYPE: RNA
<213> ORGANISM: Homo Sapiens

<400> SEQUENCE: 1912
gacugacacc ucuuugggug aa                                          22

<210> SEQ ID NO 1913
<211> LENGTH: 20
<212> TYPE: RNA
<213> ORGANISM: Homo Sapiens

<400> SEQUENCE: 1913 auaugggu uu acuaguuggu                                            20

<210> SEQ ID NO 1914
<211> LENGTH: 23
<212> TYPE: RNA
<213> ORGANISM: Homo Sapiens

<400> SEQUENCE: 1914 ccgucccag gagaaccugc aga                                          23

<210> SEQ ID NO 1915
<211> LENGTH: 23
<212> TYPE: RNA
<213> ORGANISM: Homo Sapiens

<400> SEQUENCE: 1915
agcagcauug uacagggcua uca                                         23

<210> SEQ ID NO 1916
<211> LENGTH: 22
<212> TYPE: RNA
<213> ORGANISM: Homo Sapiens

<400> SEQUENCE: 1916
uuuugugucu cccauucccc ag                                          22

<210> SEQ ID NO 1917
<211> LENGTH: 23
<212> TYPE: RNA
<213> ORGANISM: Homo Sapiens

<400> SEQUENCE: 1917
ucacaacaac cuugcagggu aga                                         23

<210> SEQ ID NO 1918
<211> LENGTH: 21
<212> TYPE: RNA
```

<213> ORGANISM: Homo Sapiens

<400> SEQUENCE: 1918
uuggacggua agguuaagca a                                    21

<210> SEQ ID NO 1919
<211> LENGTH: 22
<212> TYPE: RNA
<213> ORGANISM: Homo Sapiens

<400> SEQUENCE: 1919
guagauucuc cuucuaugag ua                                   22

<210> SEQ ID NO 1920
<211> LENGTH: 22
<212> TYPE: RNA
<213> ORGANISM: Homo Sapiens

<400> SEQUENCE: 1920
uauacaaggg cagacucucu cu                                   22

<210> SEQ ID NO 1921
<211> LENGTH: 21
<212> TYPE: RNA
<213> ORGANISM: Homo Sapiens

<400> SEQUENCE: 1921
caucccuugc augguggagg g                                    21

<210> SEQ ID NO 1922
<211> LENGTH: 21
<212> TYPE: RNA
<213> ORGANISM: Homo Sapiens

<400> SEQUENCE: 1922 gaagauagg agggacuuug u                                     21

<210> SEQ ID NO 1923
<211> LENGTH: 20
<212> TYPE: RNA
<213> ORGANISM: Homo Sapiens

<400> SEQUENCE: 1923
uccguacaaa cucugcugug                                      20

<210> SEQ ID NO 1924
<211> LENGTH: 22
<212> TYPE: RNA
<213> ORGANISM: Homo Sapiens

<400> SEQUENCE: 1924
ccaccagguc uagcauuggg au                                   22

<210> SEQ ID NO 1925
<211> LENGTH: 22
<212> TYPE: RNA
<213> ORGANISM: Homo Sapiens

<400> SEQUENCE: 1925
uuaauuuuuu guuucgguca cu                                   22

<210> SEQ ID NO 1926
<211> LENGTH: 20

```
<212> TYPE: RNA
<213> ORGANISM: Homo Sapiens

<400> SEQUENCE: 1926
cuggguuggg cugggcuggg                                              20

<210> SEQ ID NO 1927
<211> LENGTH: 21
<212> TYPE: RNA
<213> ORGANISM: Homo Sapiens

<400> SEQUENCE: 1927
cucccacuuc cagaucuuuc u                                            21

<210> SEQ ID NO 1928
<211> LENGTH: 22
<212> TYPE: RNA
<213> ORGANISM: Homo Sapiens

<400> SEQUENCE: 1928
aaacaaacau ggugcacuuc uu                                           22

<210> SEQ ID NO 1929
<211> LENGTH: 21
<212> TYPE: RNA
<213> ORGANISM: Homo Sapiens

<400> SEQUENCE: 1929
uuagugcaua gucuuugguc u                                            21

<210> SEQ ID NO 1930
<211> LENGTH: 23
<212> TYPE: RNA
<213> ORGANISM: Homo Sapiens

<400> SEQUENCE: 1930
gugagugugg auccuggagg aau                                          23

<210> SEQ ID NO 1931
<211> LENGTH: 22
<212> TYPE: RNA
<213> ORGANISM: Homo Sapiens

<400> SEQUENCE: 1931
ugugcgcagg gagaccucuc cc                                           22

<210> SEQ ID NO 1932
<211> LENGTH: 17
<212> TYPE: RNA
<213> ORGANISM: Homo Sapiens

<400> SEQUENCE: 1932
cagccugaca ggaacag                                                 17

<210> SEQ ID NO 1933
<211> LENGTH: 17
<212> TYPE: RNA
<213> ORGANISM: Homo Sapiens

<400> SEQUENCE: 1933
gggagaaggg ucggggc                                                 17

<210> SEQ ID NO 1934
```

```
<211> LENGTH: 22
<212> TYPE: RNA
<213> ORGANISM: Homo Sapiens

<400> SEQUENCE: 1934
caagggacca agcauucauu au                                            22

<210> SEQ ID NO 1935
<211> LENGTH: 23
<212> TYPE: RNA
<213> ORGANISM: Homo Sapiens

<400> SEQUENCE: 1935
caaagcgcuu cucuuuagag ugu                                           23

<210> SEQ ID NO 1936
<211> LENGTH: 22
<212> TYPE: RNA
<213> ORGANISM: Homo Sapiens

<400> SEQUENCE: 1936
aacgggaaug caggcuguau cu                                            22

<210> SEQ ID NO 1937
<211> LENGTH: 22
<212> TYPE: RNA
<213> ORGANISM: Homo Sapiens

<400> SEQUENCE: 1937
gaauguugcu cggugaaccc cu                                            22

<210> SEQ ID NO 1938
<211> LENGTH: 22
<212> TYPE: RNA
<213> ORGANISM: Homo Sapiens

<400> SEQUENCE: 1938
uucccuuugu cauccuaugc cu                                            22

<210> SEQ ID NO 1939
<211> LENGTH: 22
<212> TYPE: RNA
<213> ORGANISM: Homo Sapiens

<400> SEQUENCE: 1939
gugagucucu aagaaaagag ga                                            22

<210> SEQ ID NO 1940
<211> LENGTH: 21
<212> TYPE: RNA
<213> ORGANISM: Homo Sapiens

<400> SEQUENCE: 1940
cauacaaucu gacauguauu u                                             21

<210> SEQ ID NO 1941
<211> LENGTH: 22
<212> TYPE: RNA
<213> ORGANISM: Homo Sapiens

<400> SEQUENCE: 1941
cagcccggau cccagcccac uu                                            22
```

<210> SEQ ID NO 1942
<211> LENGTH: 24
<212> TYPE: RNA
<213> ORGANISM: Homo Sapiens

<400> SEQUENCE: 1942
gaugcgccgc ccacugcccc gcgc                                          24

<210> SEQ ID NO 1943
<211> LENGTH: 19
<212> TYPE: RNA
<213> ORGANISM: Homo Sapiens

<400> SEQUENCE: 1943
uucugcugcc ggccaaggc                                                19

<210> SEQ ID NO 1944
<211> LENGTH: 22
<212> TYPE: RNA
<213> ORGANISM: Homo Sapiens

<400> SEQUENCE: 1944 cauguucug ucaagcaccg cg                                             22

<210> SEQ ID NO 1945
<211> LENGTH: 22
<212> TYPE: RNA
<213> ORGANISM: Homo Sapiens

<400> SEQUENCE: 1945
acugauuauc uuaacucucu ga                                            22

<210> SEQ ID NO 1946
<211> LENGTH: 23
<212> TYPE: RNA
<213> ORGANISM: Homo Sapiens

<400> SEQUENCE: 1946
uaaauuucac cuuucugaga aga                                           23

<210> SEQ ID NO 1947
<211> LENGTH: 23
<212> TYPE: RNA
<213> ORGANISM: Homo Sapiens

<400> SEQUENCE: 1947
accuuggcuc uagacugcuu acu                                           23

<210> SEQ ID NO 1948
<211> LENGTH: 22
<212> TYPE: RNA
<213> ORGANISM: Homo Sapiens

<400> SEQUENCE: 1948
cucuagaggg aagcgcuuuc ug                                            22

<210> SEQ ID NO 1949
<211> LENGTH: 21
<212> TYPE: RNA
<213> ORGANISM: Homo Sapiens

<400> SEQUENCE: 1949
aaaaacugca aucacuuuug c                                             21

```
<210> SEQ ID NO 1950
<211> LENGTH: 23
<212> TYPE: RNA
<213> ORGANISM: Homo Sapiens

<400> SEQUENCE: 1950
cuguaauaua aauuuaauuu auu                                              23

<210> SEQ ID NO 1951
<211> LENGTH: 22
<212> TYPE: RNA
<213> ORGANISM: Homo Sapiens

<400> SEQUENCE: 1951
uauggcacug guagaauuca cu                                               22

<210> SEQ ID NO 1952
<211> LENGTH: 22
<212> TYPE: RNA
<213> ORGANISM: Homo Sapiens

<400> SEQUENCE: 1952
auucugcauu uuuagcaagu uc                                               22

<210> SEQ ID NO 1953
<211> LENGTH: 22
<212> TYPE: RNA
<213> ORGANISM: Homo Sapiens

<400> SEQUENCE: 1953
caggccauau ugugcugccu ca                                               22

<210> SEQ ID NO 1954
<211> LENGTH: 22
<212> TYPE: RNA
<213> ORGANISM: Homo Sapiens

<400> SEQUENCE: 1954
auguagggcu aaaagccaug gg                                               22

<210> SEQ ID NO 1955
<211> LENGTH: 23
<212> TYPE: RNA
<213> ORGANISM: Homo Sapiens

<400> SEQUENCE: 1955
uagccuucag aucuuggugu uuu                                              23

<210> SEQ ID NO 1956
<211> LENGTH: 22
<212> TYPE: RNA
<213> ORGANISM: Homo Sapiens

<400> SEQUENCE: 1956
aaagguaauu gcaguuuuuc cc                                               22

<210> SEQ ID NO 1957
<211> LENGTH: 22
<212> TYPE: RNA
<213> ORGANISM: Homo Sapiens

<400> SEQUENCE: 1957
uuggacagaa aacacgcagg aa                                               22
```

```
<210> SEQ ID NO 1958
<211> LENGTH: 22
<212> TYPE: RNA
<213> ORGANISM: Homo Sapiens

<400> SEQUENCE: 1958
aaugcacccg ggcaaggauu cu                                              22

<210> SEQ ID NO 1959
<211> LENGTH: 23
<212> TYPE: RNA
<213> ORGANISM: Homo Sapiens

<400> SEQUENCE: 1959
ugagugugug ugugagug ugu                                               23

<210> SEQ ID NO 1960
<211> LENGTH: 22
<212> TYPE: RNA
<213> ORGANISM: Homo Sapiens

<400> SEQUENCE: 1960
caggaggcag ugggcgagca gg                                              22

<210> SEQ ID NO 1961
<211> LENGTH: 22
<212> TYPE: RNA
<213> ORGANISM: Homo Sapiens

<400> SEQUENCE: 1961
caauguuucc acagugcauc ac                                              22

<210> SEQ ID NO 1962
<211> LENGTH: 21
<212> TYPE: RNA
<213> ORGANISM: Homo Sapiens

<400> SEQUENCE: 1962
ugagugccgg ugccugcccu g                                               21

<210> SEQ ID NO 1963
<211> LENGTH: 22
<212> TYPE: RNA
<213> ORGANISM: Homo Sapiens

<400> SEQUENCE: 1963
aaaacuguaa uuacuuuugu ac                                              22

<210> SEQ ID NO 1964
<211> LENGTH: 22
<212> TYPE: RNA
<213> ORGANISM: Homo Sapiens

<400> SEQUENCE: 1964
cacauaugaa gugagccagc ac                                              22

<210> SEQ ID NO 1965
<211> LENGTH: 22
<212> TYPE: RNA
<213> ORGANISM: Homo Sapiens

<400> SEQUENCE: 1965
```

-continued ucaggcagug uggguaucag au                                              22

<210> SEQ ID NO 1966
<211> LENGTH: 23
<212> TYPE: RNA
<213> ORGANISM: Homo Sapiens

<400> SEQUENCE: 1966
gauugagacu aguagggcua ggc                                             23

<210> SEQ ID NO 1967
<211> LENGTH: 23
<212> TYPE: RNA
<213> ORGANISM: Homo Sapiens

<400> SEQUENCE: 1967
ucauagcccu guacaaugcu gcu                                             23

<210> SEQ ID NO 1968
<211> LENGTH: 22
<212> TYPE: RNA
<213> ORGANISM: Homo Sapiens

<400> SEQUENCE: 1968
agaaguaacu acgguuuuug ca                                              22

<210> SEQ ID NO 1969
<211> LENGTH: 26
<212> TYPE: RNA
<213> ORGANISM: Homo Sapiens

<400> SEQUENCE: 1969
gugagggcau gcaggccugg augggg                                          26

<210> SEQ ID NO 1970
<211> LENGTH: 23
<212> TYPE: RNA
<213> ORGANISM: Homo Sapiens

<400> SEQUENCE: 1970
aauguggaag uggucugagg cau                                             23

<210> SEQ ID NO 1971
<211> LENGTH: 18
<212> TYPE: RNA
<213> ORGANISM: Homo Sapiens

<400> SEQUENCE: 1971
agcaggugcg gggcggcg                                                   18

<210> SEQ ID NO 1972
<211> LENGTH: 20
<212> TYPE: RNA
<213> ORGANISM: Homo Sapiens

<400> SEQUENCE: 1972
gaaucggaaa ggaggcgccg                                                 20

<210> SEQ ID NO 1973
<211> LENGTH: 21
<212> TYPE: RNA
<213> ORGANISM: Homo Sapiens

<400> SEQUENCE: 1973
uuacaggcgu gaaccaccgc g  21

<210> SEQ ID NO 1974
<211> LENGTH: 23
<212> TYPE: RNA
<213> ORGANISM: Homo Sapiens

<400> SEQUENCE: 1974
cgcgggcgcu ccuggccgcc gcc  23

<210> SEQ ID NO 1975
<211> LENGTH: 22
<212> TYPE: RNA
<213> ORGANISM: Homo Sapiens

<400> SEQUENCE: 1975
gaggguuggg uggaggcucu cc  22

<210> SEQ ID NO 1976
<211> LENGTH: 21
<212> TYPE: RNA
<213> ORGANISM: Homo Sapiens

<400> SEQUENCE: 1976
gaaggcgcuu cccuuuggag u  21

<210> SEQ ID NO 1977
<211> LENGTH: 21
<212> TYPE: RNA
<213> ORGANISM: Homo Sapiens

<400> SEQUENCE: 1977
auaggcacca aaaagcaaca a  21

<210> SEQ ID NO 1978
<211> LENGTH: 22
<212> TYPE: RNA
<213> ORGANISM: Homo Sapiens

<400> SEQUENCE: 1978
acagcaggca cagacaggca gu  22

<210> SEQ ID NO 1979
<211> LENGTH: 22
<212> TYPE: RNA
<213> ORGANISM: Homo Sapiens

<400> SEQUENCE: 1979
cucuagaggg aagcgcuuuc ug  22

<210> SEQ ID NO 1980
<211> LENGTH: 21
<212> TYPE: RNA
<213> ORGANISM: Homo Sapiens

<400> SEQUENCE: 1980
uccucuucuc ccuccuccca g  21

<210> SEQ ID NO 1981
<211> LENGTH: 21
<212> TYPE: RNA
<213> ORGANISM: Homo Sapiens

```
<400> SEQUENCE: 1981
uaggacacau ggucuacuuc u                                      21

<210> SEQ ID NO 1982
<211> LENGTH: 18
<212> TYPE: RNA
<213> ORGANISM: Homo Sapiens

<400> SEQUENCE: 1982
ugaggcgggg gggcgagc                                          18

<210> SEQ ID NO 1983
<211> LENGTH: 21
<212> TYPE: RNA
<213> ORGANISM: Homo Sapiens

<400> SEQUENCE: 1983
ccugugcucc cagggccucg c                                      21

<210> SEQ ID NO 1984
<211> LENGTH: 19
<212> TYPE: RNA
<213> ORGANISM: Homo Sapiens

<400> SEQUENCE: 1984
gagggcgggu ggaggagga                                         19

<210> SEQ ID NO 1985
<211> LENGTH: 23
<212> TYPE: RNA
<213> ORGANISM: Homo Sapiens

<400> SEQUENCE: 1985
ugucugcccg caugccugcc ucu                                    23

<210> SEQ ID NO 1986
<211> LENGTH: 21
<212> TYPE: RNA
<213> ORGANISM: Homo Sapiens

<400> SEQUENCE: 1986
uucacagugg cuaaguucug c                                      21

<210> SEQ ID NO 1987
<211> LENGTH: 22
<212> TYPE: RNA
<213> ORGANISM: Homo Sapiens

<400> SEQUENCE: 1987
uagcuuauca gacugauguu ga                                     22

<210> SEQ ID NO 1988
<211> LENGTH: 22
<212> TYPE: RNA
<213> ORGANISM: Homo Sapiens

<400> SEQUENCE: 1988
uucaccaccu ucuccaccca gc                                     22

<210> SEQ ID NO 1989
<211> LENGTH: 23
<212> TYPE: RNA
<213> ORGANISM: Homo Sapiens
```

<400> SEQUENCE: 1989
aaagugcugc gacauuugag cgu                                              23

<210> SEQ ID NO 1990
<211> LENGTH: 22
<212> TYPE: RNA
<213> ORGANISM: Homo Sapiens

<400> SEQUENCE: 1990
aaaccugugu uguucaagag uc                                               22

<210> SEQ ID NO 1991
<211> LENGTH: 20
<212> TYPE: RNA
<213> ORGANISM: Homo Sapiens

<400> SEQUENCE: 1991
ccucugggcc cuuccuccag                                                  20

<210> SEQ ID NO 1992
<211> LENGTH: 22
<212> TYPE: RNA
<213> ORGANISM: Homo Sapiens

<400> SEQUENCE: 1992
uaaaacuuua agugugccua gg                                               22

<210> SEQ ID NO 1993
<211> LENGTH: 22
<212> TYPE: RNA
<213> ORGANISM: Homo Sapiens

<400> SEQUENCE: 1993
ugagaccagg acuggaugca cc                                               22

<210> SEQ ID NO 1994
<211> LENGTH: 21
<212> TYPE: RNA
<213> ORGANISM: Homo Sapiens

<400> SEQUENCE: 1994
gauuucagug gagugaaguu c                                                21

<210> SEQ ID NO 1995
<211> LENGTH: 22
<212> TYPE: RNA
<213> ORGANISM: Homo Sapiens

<400> SEQUENCE: 1995
ugccuacuga gcugaaacac ag                                               22

<210> SEQ ID NO 1996
<211> LENGTH: 23
<212> TYPE: RNA
<213> ORGANISM: Homo Sapiens

<400> SEQUENCE: 1996
ugcaaaagua auugcaguuu uug                                              23

<210> SEQ ID NO 1997
<211> LENGTH: 22
<212> TYPE: RNA

```
<213> ORGANISM: Homo Sapiens

<400> SEQUENCE: 1997
auauacaggg ggagacucuu au                                          22

<210> SEQ ID NO 1998
<211> LENGTH: 22
<212> TYPE: RNA
<213> ORGANISM: Homo Sapiens

<400> SEQUENCE: 1998
uucucaagga ggugucguuu au                                          22

<210> SEQ ID NO 1999
<211> LENGTH: 22
<212> TYPE: RNA
<213> ORGANISM: Homo Sapiens

<400> SEQUENCE: 1999
aucaugaugg gcuccucggu gu                                          22

<210> SEQ ID NO 2000
<211> LENGTH: 20
<212> TYPE: RNA
<213> ORGANISM: Homo Sapiens

<400> SEQUENCE: 2000
ggagguuggg aagggcagag                                             20

<210> SEQ ID NO 2001
<211> LENGTH: 21
<212> TYPE: RNA
<213> ORGANISM: Homo Sapiens

<400> SEQUENCE: 2001
aguggaccga ggaaggaagg a                                           21

<210> SEQ ID NO 2002
<211> LENGTH: 23
<212> TYPE: RNA
<213> ORGANISM: Homo Sapiens

<400> SEQUENCE: 2002
guccaguuuu cccaggaauc ccu                                         23

<210> SEQ ID NO 2003
<211> LENGTH: 22
<212> TYPE: RNA
<213> ORGANISM: Homo Sapiens

<400> SEQUENCE: 2003
gcaguggcuc ugaaaugaac uc                                          22

<210> SEQ ID NO 2004
<211> LENGTH: 22
<212> TYPE: RNA
<213> ORGANISM: Homo Sapiens

<400> SEQUENCE: 2004
uacacaagaa aaccaaggcu ca                                          22

<210> SEQ ID NO 2005
<211> LENGTH: 22
```

```
<212> TYPE: RNA
<213> ORGANISM: Homo Sapiens

<400> SEQUENCE: 2005
acccuugagc cugaucccua gc                                              22

<210> SEQ ID NO 2006
<211> LENGTH: 22
<212> TYPE: RNA
<213> ORGANISM: Homo Sapiens

<400> SEQUENCE: 2006
uguagauacg agcaccagcc ac                                              22

<210> SEQ ID NO 2007
<211> LENGTH: 23
<212> TYPE: RNA
<213> ORGANISM: Homo Sapiens

<400> SEQUENCE: 2007
gacacgggcg acagcugcgg ccc                                             23

<210> SEQ ID NO 2008
<211> LENGTH: 24
<212> TYPE: RNA
<213> ORGANISM: Homo Sapiens

<400> SEQUENCE: 2008
aacaacaaaa ucacuagucu ucca                                            24

<210> SEQ ID NO 2009
<211> LENGTH: 22
<212> TYPE: RNA
<213> ORGANISM: Homo Sapiens

<400> SEQUENCE: 2009
aacuagcucu guggauccug ac                                              22

<210> SEQ ID NO 2010
<211> LENGTH: 21
<212> TYPE: RNA
<213> ORGANISM: Homo Sapiens

<400> SEQUENCE: 2010
auccccagau acaauggaca a                                               21

<210> SEQ ID NO 2011
<211> LENGTH: 22
<212> TYPE: RNA
<213> ORGANISM: Homo Sapiens

<400> SEQUENCE: 2011
uaaaacccac aauuauguuu gu                                              22

<210> SEQ ID NO 2012
<211> LENGTH: 19
<212> TYPE: RNA
<213> ORGANISM: Homo Sapiens

<400> SEQUENCE: 2012
ggccacugag ucagcacca                                                  19

<210> SEQ ID NO 2013
```

```
<211> LENGTH: 24
<212> TYPE: RNA
<213> ORGANISM: Homo Sapiens

<400> SEQUENCE: 2013
aggagcuauc cacuccaggu gucc                                            24

<210> SEQ ID NO 2014
<211> LENGTH: 20
<212> TYPE: RNA
<213> ORGANISM: Homo Sapiens

<400> SEQUENCE: 2014
ccaggagauc cagagagaau                                                 20

<210> SEQ ID NO 2015
<211> LENGTH: 21
<212> TYPE: RNA
<213> ORGANISM: Homo Sapiens

<400> SEQUENCE: 2015
acggugcugg auguggccuu u                                               21

<210> SEQ ID NO 2016
<211> LENGTH: 21
<212> TYPE: RNA
<213> ORGANISM: Homo Sapiens

<400> SEQUENCE: 2016
auacccauag cuuagcuccc a                                               21

<210> SEQ ID NO 2017
<211> LENGTH: 22
<212> TYPE: RNA
<213> ORGANISM: Homo Sapiens

<400> SEQUENCE: 2017
uaggcacacu uaaaguuaua gc                                              22

<210> SEQ ID NO 2018
<211> LENGTH: 22
<212> TYPE: RNA
<213> ORGANISM: Homo Sapiens

<400> SEQUENCE: 2018
uagcagcacg uaaauauugg cg                                              22

<210> SEQ ID NO 2019
<211> LENGTH: 20
<212> TYPE: RNA
<213> ORGANISM: Homo Sapiens

<400> SEQUENCE: 2019
gggaaaagga aggggagga                                                  20

<210> SEQ ID NO 2020
<211> LENGTH: 20
<212> TYPE: RNA
<213> ORGANISM: Homo Sapiens

<400> SEQUENCE: 2020
gagcuugguc uguagcgguu                                                 20
```

```
<210> SEQ ID NO 2021
<211> LENGTH: 22
<212> TYPE: RNA
<213> ORGANISM: Homo Sapiens

<400> SEQUENCE: 2021
cugggaggug ugauauugug gu                                             22

<210> SEQ ID NO 2022
<211> LENGTH: 22
<212> TYPE: RNA
<213> ORGANISM: Homo Sapiens

<400> SEQUENCE: 2022
uaggauuaca agugucggcc ac                                             22

<210> SEQ ID NO 2023
<211> LENGTH: 21
<212> TYPE: RNA
<213> ORGANISM: Homo Sapiens

<400> SEQUENCE: 2023
uugggacaua cuuaugcuaa a                                              21

<210> SEQ ID NO 2024
<211> LENGTH: 22
<212> TYPE: RNA
<213> ORGANISM: Homo Sapiens

<400> SEQUENCE: 2024
ggcuacaaca caggacccgg gc                                             22

<210> SEQ ID NO 2025
<211> LENGTH: 19
<212> TYPE: RNA
<213> ORGANISM: Homo Sapiens

<400> SEQUENCE: 2025
ugagcugcug uaccaaaau                                                 19

<210> SEQ ID NO 2026
<211> LENGTH: 21
<212> TYPE: RNA
<213> ORGANISM: Homo Sapiens

<400> SEQUENCE: 2026
auugacaccu cugugagugg a                                              21

<210> SEQ ID NO 2027
<211> LENGTH: 20
<212> TYPE: RNA
<213> ORGANISM: Homo Sapiens

<400> SEQUENCE: 2027
aggaauguuc cuucuuugcc                                                20

<210> SEQ ID NO 2028
<211> LENGTH: 22
<212> TYPE: RNA
<213> ORGANISM: Homo Sapiens

<400> SEQUENCE: 2028 ugggugguticu ggagauuugu gc                                           22
```

```
<210> SEQ ID NO 2029
<211> LENGTH: 21
<212> TYPE: RNA
<213> ORGANISM: Homo Sapiens

<400> SEQUENCE: 2029
agagucggcg acgccgccag c                                              21

<210> SEQ ID NO 2030
<211> LENGTH: 24
<212> TYPE: RNA
<213> ORGANISM: Homo Sapiens

<400> SEQUENCE: 2030 uggggagcc augagauaag agca                                            24

<210> SEQ ID NO 2031
<211> LENGTH: 22
<212> TYPE: RNA
<213> ORGANISM: Homo Sapiens

<400> SEQUENCE: 2031
aucaaauaag gacuagucug ca                                             22

<210> SEQ ID NO 2032
<211> LENGTH: 20
<212> TYPE: RNA
<213> ORGANISM: Homo Sapiens

<400> SEQUENCE: 2032
cgccccuccu gcccccacag                                                20

<210> SEQ ID NO 2033
<211> LENGTH: 22
<212> TYPE: RNA
<213> ORGANISM: Homo Sapiens

<400> SEQUENCE: 2033 ugagcccug ugccgccccc ag                                              22

<210> SEQ ID NO 2034
<211> LENGTH: 22
<212> TYPE: RNA
<213> ORGANISM: Homo Sapiens

<400> SEQUENCE: 2034
gcugaugaug auggugcuga ag                                             22

<210> SEQ ID NO 2035
<211> LENGTH: 17
<212> TYPE: RNA
<213> ORGANISM: Homo Sapiens

<400> SEQUENCE: 2035
gggagucuac agcaggg                                                   17

<210> SEQ ID NO 2036
<211> LENGTH: 23
<212> TYPE: RNA
<213> ORGANISM: Homo Sapiens

<400> SEQUENCE: 2036
cacucagccu ugagggcacu uuc                                            23
```

```
<210> SEQ ID NO 2037
<211> LENGTH: 22
<212> TYPE: RNA
<213> ORGANISM: Homo Sapiens

<400> SEQUENCE: 2037
gacacaugac cauaaaugcu aa                                              22

<210> SEQ ID NO 2038
<211> LENGTH: 23
<212> TYPE: RNA
<213> ORGANISM: Homo Sapiens

<400> SEQUENCE: 2038
uaagugcuuc cauguuugag ugu                                             23

<210> SEQ ID NO 2039
<211> LENGTH: 21
<212> TYPE: RNA
<213> ORGANISM: Homo Sapiens

<400> SEQUENCE: 2039
ugcacggcac uggggacacg u                                               21

<210> SEQ ID NO 2040
<211> LENGTH: 20
<212> TYPE: RNA
<213> ORGANISM: Homo Sapiens

<400> SEQUENCE: 2040
ccuccugccc uccuugcugu                                                 20

<210> SEQ ID NO 2041
<211> LENGTH: 23
<212> TYPE: RNA
<213> ORGANISM: Homo Sapiens

<400> SEQUENCE: 2041
caacggaauc ccaaaagcag cug                                             23

<210> SEQ ID NO 2042
<211> LENGTH: 22
<212> TYPE: RNA
<213> ORGANISM: Homo Sapiens

<400> SEQUENCE: 2042
cagcccuccu cccgcaccca aa                                              22
```

US 9,725,721 B2

OLIGOMERS WITH IMPROVED OFF-TARGET PROFILE

This application is a National Stage Application of PCT/DK2013/050308, filed 26 Sep. 2013, which claims benefit of Serial No. PA 2012 00587, filed 26 Sep. 2012 in Denmark, and also claims benefit of Ser. No. 61/705,668, filed 26 Sep. 2012 in the United States and which applications are incorporated herein by reference. To the extent appropriate, a claim of priority is made to each of the above disclosed applications.

BACKGROUND OF THE INVENTION

The present invention relate to oligomers and oligonucleotides that can bind to complementary RNA. Oligonucleotides are useful as reagents in science, research and development e.g. for detection and analysis of cellular RNA or for modulation of the activity of cellular RNA.

Oligonucleotides are also being developed as therapeutics, where they are typically also intended to bind to and modulate the activity of cellular RNA. Oligonucleotides that bind cellular RNA are herein also termed antisense oligonucleotides.

Some antisense oligonucleotides act by inducing destabilization of their target RNA e.g. by activating RNase H degradation of the target RNA or by activating the RISC pathway. Such oligonucleotides are typically described as gapmers and siRNAs respectively. Another class of oligonucleotides act as steric blocker and hence prevents the target RNA from interacting with another macromolecule. One example is splice switching oligonucleotides that modulate splicing of pre-mRNA. Another example is microRNA inhibitors that bind to microRNA and prevent the microRNA from binding to its mRNA targets. A thorough description of the design, preparation and use of antisense oligonucleotides can be found in "Antisense Drug Technology, Principles, Strategies and Applications, 2nd Edition, Edited by Stanley Crooke".

It is easy to design an antisense oligonucleotide that is complementary to a given target RNA and hence is capable of binding to the target RNA. However, when attempting to develop antisense oligonucleotides as therapeutics, complementarity to the target is not enough. The antisense oligonucleotide need to be modified to give it more drug-like properties, e.g. better potency, bioavailability and biostability. Moreover, it has turned out that a problem of many antisense oligonucleotides is off-target binding, i.e. binding to non-intended RNAs, which may lead to undesirable effects. To minimize off-target binding, it is typically attempted to target unique sequences in the RNA transcriptome. Even so, off-target binding of antisense oligonucleotides is still a problem. One object of the present invention is to provide antisense oligonucleotides, in particular steric block oligonucleotides that have new and desirable characteristics in terms of off-target binding.

SUMMARY OF THE INVENTION

The present invention provides oligomers that can bind RNA consisting of
  a lower affinity region,
  a higher affinity region,
  wherein the monomers in the higher affinity region increases the melting temperature (i.e. affinity) of the oligomer base paired to RNA more than the monomers used in the lower affinity region, wherein said increase in melting temperature is relatively to the alternative use of DNA monomers of the same (base) sequence.

The oligomers of the invention are useful for binding to target RNA such as mRNA and non-coding RNA and have the advantage that they will be less prone to off-target binding via the lower affinity region than via the higher affinity region.

In theory, all 3 oligomers have a similar affinity toward complementary RNA and would therefore be expected to have a similar potency, e.g. when used in cells or organisms. However, they have a different off-target profile (binds to a different set of off-targets).

Figure 1:
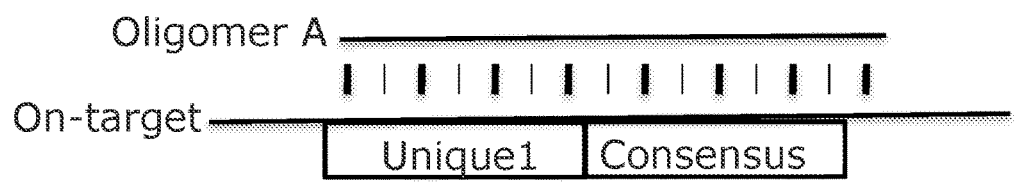
FIG. 1A show a typical steric block oligomer bound to its intended target (the on-target). The consensus sequence is a sequence that is shared with other RNAs and is preferably part of a binding site for at cellular molecule, e.g. a microRNA. The sequence adjacent to the consensus sequence is denoted unique 1 and is sequence that differs (also herein termed "specificity sequence") among RNAs sharing the consensus sequence. Base pairs are indicated by lines between the oligomer and the target. The oligomer is uniformly modified with monomer analogues that enhance affinity toward complementary RNA and the position of these modifications is shown by a bold (base pair) line to the target. The oligomer may e.g. be a BNA/2'O-methyl RNA oligomer and the affinity enhancing analogues is then BNA (bicyclic nucleic acids). The illustrated design could just as well have been affinity enhancing analogues in every third position or even in all positions or any other repeating pattern, which gives a relatively uniform affinity over the length of the oligomer. It is clear that G:C base pairs are stronger than A:U base pairs. However, for the sake of simplicity such sequence specific affinity variations are not considered in the present example.
FIG. 1B shows a steric block oligonucleotide of same sequence as oligomer A of FIG. 1A, but with a non-uniform distribution of affinity increasing modifications bound to its intended target. The affinity of this oligomer toward complementary RNA will not differ dramatically from the oligomer of 1A. Depending on the monomers chosen, the overall affinity may be higher or lower.
FIG. 1C shows a yet another steric block oligonucleotide of same sequence as oligomer A of FIG. 1A, but with a non-uniform distribution of affinity increasing modifications bound to its intended target. The affinity of this oligomer toward complementary RNA will not differ dramatically from the oligomer of 1A or 1B. Depending on the monomers chosen, the overall affinity may be higher or lower.
Figure 1:
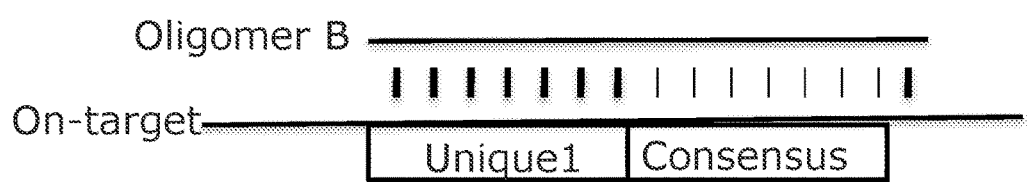
Figure 1:
Figure 2:
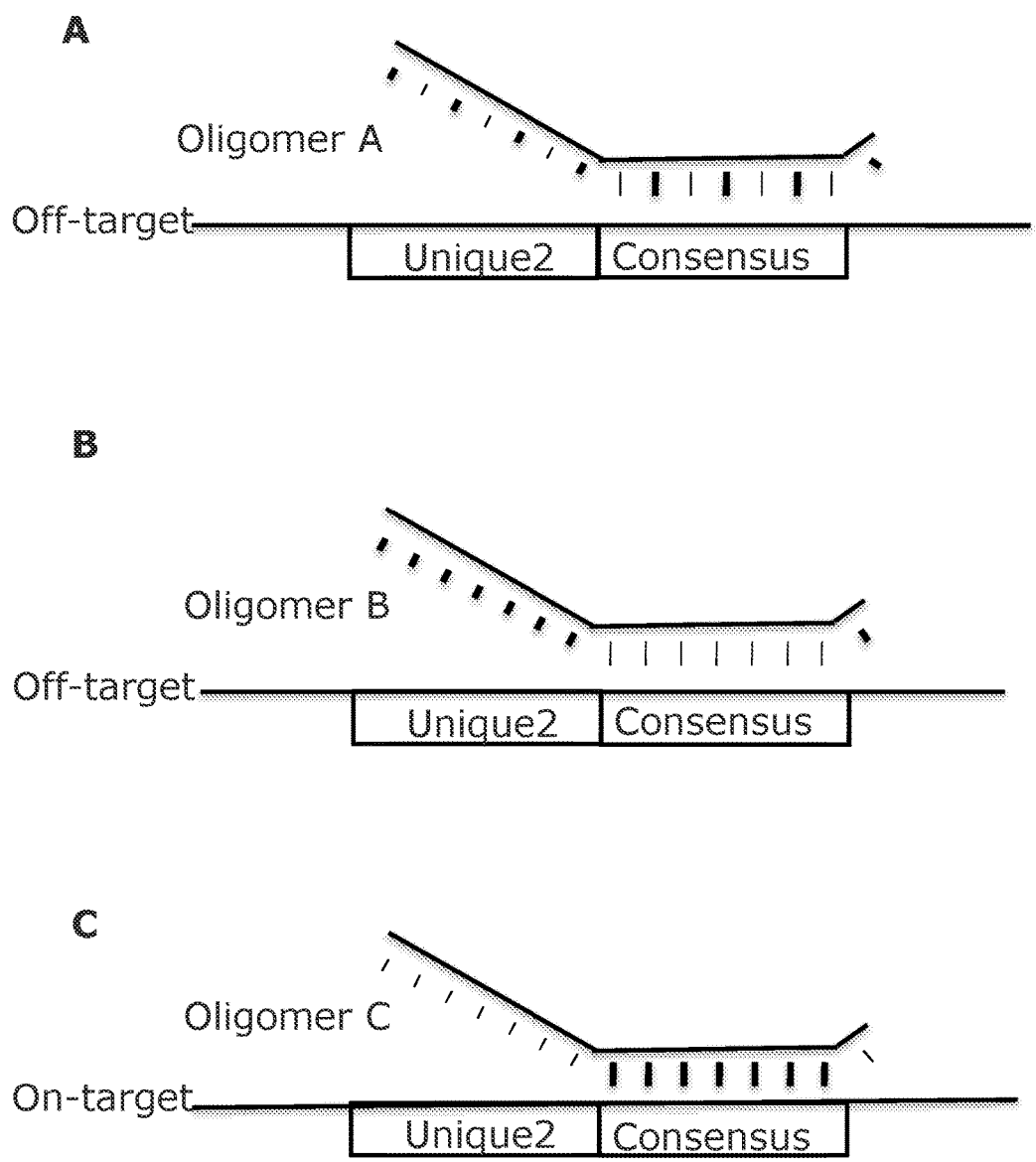

FIG. 2 shows the same oligomers as illustrated in FIG. 1, however, bound to an off-target that shares the consensus sequence with the intended target.

The oligomer in 2A will have an intermediate affinity toward the off-target, whereas the oligomer in 2B will have a lowered affinity toward the off-target because the region complementary to the consensus sequence is a "lower affinity region", as seen by the lower density of affinity increasing modifications, such as BNA. I.e. the B oligomer will be less likely bind to off-targets comprising the consensus sequence.

On the other hand, the C oligomer in 2C will however be more likely to bind to off-targets comprising the consensus sequence, because it does so via its "higher affinity region".

Figure 3:
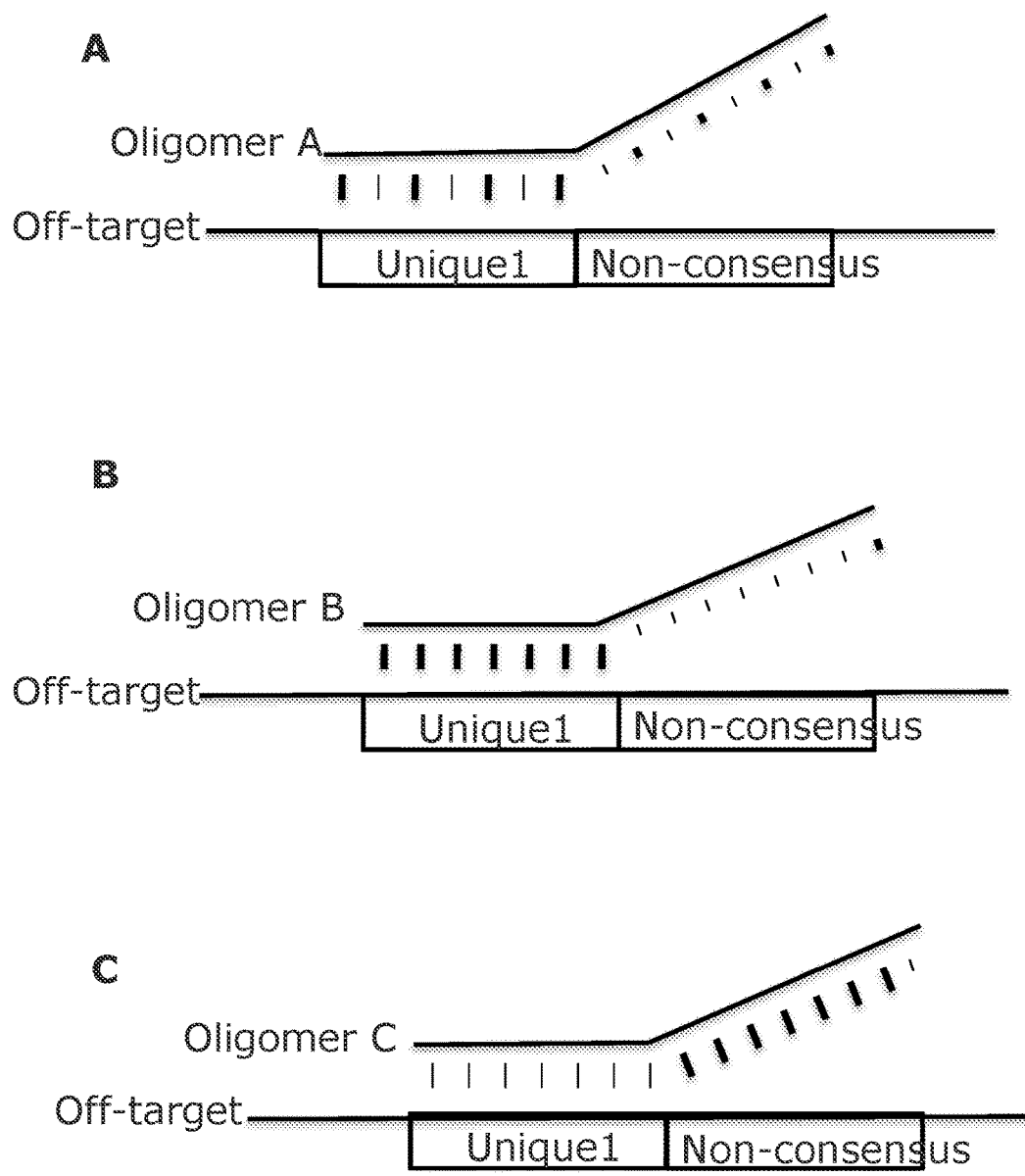

FIG. 3 shows the same oligomers as illustrated in FIGS. 1 and 2, however, bound to an off-target that does not share the consensus sequence. It is seen that oligomer B in 3B will do so most potently, because it binds via its higher affinity region, whereas oligomer C in 3C will do so least potently because it does so via its lower affinity region. I.e. the increased specificity of oligomer B toward RNA targets that share the consensus sequence is achieved at the expense of decreased specificity toward RNA targets comprising the specificity region. Oligomer A in FIG. 3A will bind with intermediate affinity.

DISCLOSURE OF THE INVENTION

The present invention provides oligomers for targeting RNA, e.g. mRNA and non-coding RNA.

A first aspect of the invention is an oligomer of 10-40 monomers that binds RNA comprising (or more preferably consisting of)

a lower affinity region,
a higher affinity region,
wherein the monomers in the higher affinity region (altogether) increases the melting temperature (i.e. affinity) of the oligomer base paired to complementary RNA more than the monomers used in the lower affinity region (altogether), wherein said increase in melting temperature is relatively to the alternative use of DNA monomers of the same (base) sequence,
and wherein the lower affinity region or higher affinity region is of 5-12 contiguous monomers, such as 5-10, 5-9, 5-8, 6-10, 7-10, 8-10, 6-9 or 6-8 contiguous monomers and wherein the other region is either contiguous or consists of two sub regions flanking the region of 5-12 monomers.

It should be understood that when referring to "the monomers in the higher affinity region . . . " and "the monomers used in the lower affinity region" in the above, reference is to the monomers altogether in the region and not to the monomers individually. Thus, not every monomer in the higher affinity region does necessarily increase the melting temperature more than individual monomers used in the lower affinity region.

Preferably, the monomers in the higher affinity region (altogether) increases the melting temperature (i.e. affinity) of the oligomer base paired to RNA at least 5 degrees Celsius more than the monomers used in the lower affinity region, such as at least 5 degrees, 10 degrees, 15 degrees, 20 degrees, 25 degrees, 30 degrees, 35 degrees, 40 degrees Celsius more than the monomers used in the lower affinity region, wherein said increase in melting temperature is relatively to the alternative use of DNA monomers of the same sequence.

When referring to the melting temperature (also herein termed tm or tm value) of the oligomer base paired to RNA, the temperature is preferably measured in 100 mM NaCl, 0.1 mM EDTA, 10 mM NaH$_2$PO$_4$, 5 mM Na$_2$HPO$_4$, pH 7.0), using 1.0 µM concentrations of both oligomer and complementary RNA.

In a preferred embodiment, the monomers in the higher affinity region on average (per monomer) increase the melting temperature more than the monomers in the lower affinity region. I.e. the increase in tm of the lower and higher affinity region is divided by the number of monomers in the lower and higher affinity region, respectively. It should be noted that the increase in tm of the lower affinity region may be negative, which is the case when the tm is decreased relatively to the alternative use of DNA monomers of the same sequence.

Preferably, the monomers in the higher affinity region on average (per monomer) increase the melting temperature at least 2 degrees Celsius, such as 3, 4, 5, 6, 7 or 8 degrees Celsius more than the monomers in the lower affinity region.

The oligomer is typically an oligonucleotide and preferably comprise at least two different types of monomers, e.g. selected from the group consisting of DNA, RNA, BNA (in particular 2',4'-bicyclic nucleic acids (2'4'-BNA) such as ENA and LNA (2'-O,4'-C-methylene-beta-D-ribofuranosyl and analogues thereof e.g., amino-LNA, thio-LNA, alfa-L-ribo-LNA, beta-D-xylo-LNA, S-cMOE (2',4'-constrained MOE), R-cMOE, cEt (2',4'-constrained ethyl), morpholino, phosphoramidate, FANA, PNA, CENA, 2'MOE, 2'F, 2'O-methyl.

It is particular preferred that the higher affinity region comprises 2',4'-bicyclic nucleic acids (2'4'-BNA).

In another embodiment, the lower affinity region comprises only two types of monomers, preferably selected from the group consisting of DNA, RNA, morpholino, phosphoramidate, FANA, PNA, UNA, 2'MOE, 2'F and 2'O-methyl.

In another embodiment, the lower affinity region comprises only one type of monomer, preferably selected from the group consisting of morpholino, phosphoramidate, FANA, PNA, UNA, 2'MOE, 2'F, and 2'O-methyl.

As is known to the skilled man, different monomers generally have different effects on tm. E.g. BNAs have a strong effect on tm and 2'-modifications have a moderate effect. Some modifications like e.g. UNA even decrease tm, i.e. have a negative effect.

As used in the present context, 2',4'-bicyclic nucleic acids are herein classified as monomers that have a strong effect on tm. Morpholino, phosphoramidate-, FANA, PNA, CENA, 2'MOE, 2'F, 2'O-methyl monomers are herein classified as monomers that have a moderate effect on tm. Monomers that decrease tm are e.g. UNA (unlocked nucleic acid). DNA and RNA monomers are herein classified as neutral monomers with regard to tm (DNA monomers are reference monomers).

In a preferred embodiment, the lower affinity region has a lower density (number of affinity increasing monomers/total number of monomers in the given region) of monomers that have a strong and/or moderate effect on tm than does the higher affinity region. This feature can usually be used to easily identify oligomers of the invention, e.g. by identifying the lower affinity region within the oligomer.

It follows that oligomers with a uniform distribution of high affinity/and or moderate monomers are not part of the scope of this invention, because they do not comprise a lower affinity region. Also oligomers with slight deviations from a uniform distribution are not part of the scope of this invention, as slight deviations are not enough to create a region of lower affinity that differ substantially in affinity (as expressed in the melting temperature of the oligonucleotide) from the rest of the oligomer.

In many embodiments, the oligomer comprises one or more phosphorothioate linkages. The oligomer may e.g. be fully modified with phosphorothioate linkages or e.g. one, two or three phosphorothioate linkages at each end. Phosphorothioate linkages generally decrease melting temperature. However, this may be counteracted e.g. by the use of 2'4' BNA monomers. I.e. the higher affinity region may very well comprise phosphorothioate linkages.

Length and Affinity of the Oligomer

The overall affinity (as expressed by the melting temperature) of the oligomer toward complementary RNA depends on the length of the oligomer as well as the content of affinity increasing (and sometimes decreasing) monomers. It is an object of the invention to design the oligomer such that it has sufficient affinity toward its intended target, while displaying improved selectivity and/or potency toward its intended target over other targets sharing an identical sequence (which is hence a shared sequence).

The length of the oligomer is preferably between 10 and 40 monomers. In other embodiments, the length is between 10 and 35 monomers, between 10 and 30 monomers, between 10 and 25 monomers. Even more preferably, the length of the oligomer is between 10 and 20 monomers, such as between 11 and 19 monomers or between 12 and 18 monomers.

When using shorter lengths, it is necessary to use a higher density of monomers that increase the affinity of the oligomer. Particular preferred are 2',4'-bicyclic nucleic acids (2'4'-BNA) that have a strong effect on affinity. Hence, in a preferred embodiment, at least 30% of the monomers are 2'4'-BNA monomers, e.g. selected from the group consisting of: LNA (2'-O,4'-C-methylene-beta-D-ribofuranosyl and analogues thereof e.g., amino-LNA, thio-LNA, alfa-L-ribo-LNA, beta-D-xylo-LNA, S-cMOE (2',4'-constrained MOE), R-cMOE, cEt (2',4'-constrained ethyl). More preferably, at least 35%, such as least 40%, 45%, 50%, 55% or 60% are 2'4'-BNA monomers.

The melting temperature of the oligomer base paired to RNA should preferably be at least 60 degrees Celsius. In other embodiments, it is preferred that the tm of the oligomer is at least 65 degrees Celsius, at least 70 degrees Celsius, at least 75 degrees Celsius, at least 80 degrees Celsius, at least 85 degrees Celsius, at least 90 degrees Celsius or at least 95 degrees Celsius.

It is even more preferred that the tm is at least 75 degrees Celsius, such as 80, 85, 90 or 95 degrees Celsius.

In one embodiment, the lower affinity region is shorter than the higher affinity region. In another region, the lower affinity region is longer than the higher affinity region.

The Lower and Higher Affinity Regions

As mentioned above, it is preferred that the lower affinity region has a lower density of monomers that have a strong and/or moderate effect on tm than does the higher affinity region.

When the oligomer comprise 2'4'-BNA monomers, the density of these may e.g. 100% in the higher affinity region (full modification), 50% (mixmer with 1 BNA per 1 other monomer, e.g. 1 BNA monomer in every second position), 33% (1 BNA per 2 other monomers, e.g. in every third position), 25% etc. The BNAs need not necessarily be evenly dispersed the high affinity region. At any rate, the lower affinity region is easily identified by the lower density of 2'4'-BNA monomers. When the higher affinity region comprises 2'4' BNA monomers, it typically contains at least 1 BNA per 4 non-BNA monomers and also typically does not contain 4 or 5 contiguous non-BNA monomers.

The amount of 2'4'-BNA monomers in the higher affinity region is preferably at least 2 fold, or even more preferably 3, 4 or 5 fold higher than in the lower affinity region of the oligomer.

In a preferred embodiment, the lower affinity region does not comprise any affinity enhancing monomers selected from the group consisting of 2'4'-BNA, PNA, 2'MOE and 2'F.

More preferably, the lower affinity region does not comprise any 2'4'-BNA monomers.

In another embodiment, the lower affinity region comprise at least 5 contiguous monomers, such as 6 or 7 contiguous monomers which are not 2'4'BNA monomers.

In yet another embodiment, the lower affinity region comprise at least 5 contiguous monomers, such as 6 or 7 contiguous monomers which are not DNA monomers.

In yet another embodiment, neither the 5'end of the lower affinity region nor the 3'end of the lower affinity region is a BNA monomer. Even more preferably, neither the two monomers at the 5'end of the lower affinity region nor the two monomers at the 5'end of the monomer are BNA monomers. This feature further helps define the lower affinity region within an oligomer of the invention.

Preferably, the melting temperature of the lower affinity region toward complementary RNA is less than 70 degrees Celsius, such as less than 65, 60, 55, 50, 45, 40 and 35 degrees Celsius. The melting temperature in this embodiment may be determined by measuring the tm against a truncated RNA with a length corresponding to the lower affinity region, i.e. where the truncated RNA cannot base pair to the higher affinity region of the oligomer. It is even more preferred that the melting temperature of the lower affinity region toward complementary RNA is less than 60 degrees Celsius, such as less than 55, 50, 45, 40 and 35 degrees Celsius.

Preferably, the lower affinity region is contiguous and of 5-12 monomers, such as 5-10, 5-9, 5-8, 6-10, 7-10, 8-10, 6-9 or 6-8 contiguous monomers. Even more preferred is a lower affinity region of 6-10 contiguous monomers. I.e. in a preferred embodiment, the lower affinity region of the oligomer can be identified as a region with none or just 1 BNA monomers over a region of 6-10 monomers, wherein the density of BNA monomers in the remaining part of the oligomer has a higher density of BNA monomers, and hence the remaining part of the oligomer is the higher affinity region.

Uses and Advantages—Selectivity

The oligomers of the invention are useful for binding to target RNA such as mRNA and non-coding RNA and have the advantage that they will be less prone to off-target binding via the lower affinity region than via the higher affinity region.

Consider e.g. two RNA sequences of 10-40 monomers (within RNA targets such as mRNA or non-coding RNA) that have identical sequences in one region and differ e.g. by 1, 2 or 3 nucleotides over a length of between 5 and 10 nucleotides in sequence in an adjacent region. The region that differs may be termed the "specificity region", whereas the identical region may be referred to as the "shared region". There could just as well be multiple target RNAs that share the shared sequence and differ in the adjacent specificity region.

When the goal is to design an oligomer that preferentially bind one RNA sequence (the intended target, herein also termed the on-target) over the other target (the off-target), it is obvious that the oligomer should be complementary to the intended target. However, before the present invention, it was not obvious to design and use an oligomer comprising a higher affinity region and a lower affinity such that the higher affinity region of the oligomer should be complementary to the specificity region of the (intended) on-target and the lower affinity region should be complementary to the shared region (shared between the off-targets and the on-target). In this way, off-target binding via the shared region will be minimized because of a lower affinity as expressed in tm, while still maintaining high affinity to the intended target.

On the other hand, if a certain degree of off-target binding is acceptable or even desirable, the higher affinity region of the oligomer should be complementary to the shared region and the lower affinity region should be complementary to the specificity sequence. In this way, off-target binding via the shared region will be increased.

It is to be understood that oligomers of the invention do not necessarily overall have less or more binding to off-targets in the transcriptome of a cell when compared to a uniformly modified oligomer of the same sequence. However, they will have decreased binding to off-targets sharing the same shared sequence (because the lower affinity region is complementary to the shared sequence). Potentially, this may be achieved at the expense of more off-target binding via the higher affinity region. At any rate, the oligomers of the invention have a different off-target profile as compared to uniformly modified oligomers of the same sequence.

Hence, the oligomers of the invention can be designed to have less off-target binding among off-targets of interest or more off-target binding among off-targets of interest compared to a uniformly modified oligomer of the same sequence and similar tm value.

It should be understood that the oligomer will preferably have perfect complementarity to its intended target.

The non-obvious characteristics and uses of the oligomer of the invention will be further described below.

Activity/Mechanism of Action of the Oligomer of the Invention—Steric Block

The oligomers of the invention are typically steric blockers, i.e. they bind to target RNA without mediating degradation of the target RNA. Steric block oligonucleotides are well described in the art and are e.g. used as splice switching oligonucleotides and microRNA inhibitors. As is known by the skilled man, many monomers can be used in the design of steric block oligonucleotides, since most artificial nucleotide monomers do not allow recruitment of RNase H. See e.g. Antisense Drug Technology, Principles, Strategies and Applications, 2$^{nd}$ Edition, Edited by Stanley Crooke, page 93, which mentions 2-O-Me, 2-O-methoxyethyl (MOE), and 2-O-aminopropyl, phosphoramidate, and methylphosphonate derivatives, as well as locked nucleic acid (LNA/2'4'-BNA), peptide nucleic acid (PNA), and morpholino based oligomers. Also mixtures of these monomers do not allow RNase H recruitment. RNase H recruitment generally requires at least 5 contiguous DNA monomers and most often 6, 7 or 8 contiguous monomers are used. Therefore, in a preferred embodiment, the oligomer of the invention does not comprise contiguous DNA monomers, such as 5, 6, 7 or 8 contiguous DNA monomers.

In one embodiment, the oligomer does not comprise a Morpholino monomer

In another embodiment, the oligomer does not comprise a FANA monomer.

In another embodiment, the oligomer does not comprise a PNA monomer.

In another embodiment, the oligomer does not comprise a CENA monomer.

In another embodiment, the oligomer does not comprise a 2'MOE monomer.

In another embodiment, the oligomer does not comprise a 2'F monomer.

In another embodiment, the oligomer does not comprise a 2'O-methyl monomer.

In yet another embodiment, the oligomer does not comprise a phosphoramidate monomer.

Preferred Target RNAs and Sequences

Binding sites for cellular macromolecules such as RNA binding proteins and RNA (e.g. mRNA or microRNA) often comprise a sequence which is shared among other binding sites of the same cellular macromolecule. Such sequences are herein referred to as consensus sequences. As described above, it is one objective of the present invention to provide oligomers that have improved (or reduced) selectivity in terms of targeting an intended target (RNA) over other RNAs that share a sequence with the intended target. In a preferred embodiment, the shared sequence is a binding site for an RNA binding protein or RNA or and the shared sequence may be represented by a consensus sequence.

One way to avoid or reduce off-target binding to other RNAs sharing the same (consensus) sequence could be to avoid the consensus sequence as target, i.e. not included a sequence complementary to the consensus region in the oligomer. However, when the oligomer is intended to block a binding site, this may reduce the activity of the oligomer, since the binding site is then not completely blocked. Most often it will be desirable to indeed target the consensus sequence as well as adjacent sequence(s).

Oligomers with increased selectivity are most preferred. In these embodiments, the lower affinity region is preferably complementary to a consensus sequence. The length of the lower affinity region is preferably the same as the length of the consensus sequence or 1, 2, 3 or 4 monomers longer. The additional monomers may be added to the 5'end of the lower affinity region, the 3'end of the lower affinity region or both.

Preferred consensus sequences are microRNA binding sites in mRNA of a given microRNA, which typically share complementarity to position 2-7 (the so-called seed sequence) of the microRNA, but differ in sequence outside of this region. I.e. in this instance the consensus sequence of the binding site is a sequence that is complementary to the seed sequence of the microRNA.

Another preferred consensus sequence is the seed sequence shared among microRNA families that typically differ outside of the seed sequence.

Hence, in a preferred embodiment, the oligomer of the invention comprise a lower affinity region that can bind to a RNA sequence that is complementary to position 1-7, 2-7, 1-8 or 2-8 of any of SEQ ID NOs: 1-2042 or a lower affinity region that can bind to a RNA sequence that comprise position 1-7, 2-7, 1-8 or 2-8 of any SEQ ID NOs: 1-2042, wherein the positions are counted from the 5' end. The region capable of binding to the consensus sequence may be referred to as the anti-consensus sequence, which is hence comprised within the lower affinity region of the oligomer or is identical to the lower affinity region of the oligomer. In this embodiment, the oligomer improves selectivity, when targeting one microRNA over other microRNA in the same family or when targeting one microRNA binding site over other binding sites of the same microRNA.

Likewise, the oligomers may also be used for decreasing selectivity. In this embodiment, the oligomer of the invention comprise a higher affinity region can bind to a RNA sequence that is complementary to position 1-7, 2-7, 1-8 or 2-8 of any of SEQ ID NOs: 1-2042 or a lower affinity region that can bind to a RNA sequence that comprise position 1-7, 2-7, 1-8 or 2-8 of any SEQ ID NOs: 1-2042, wherein the positions are counted from the 5' end.

Oligomers with increased selectivity are most preferred.

TABLE 1

| Human microRNA sequences | | |
|---|---|---|
| NO | Sequence (5' to 3') | ID and accession |
| 1 | AAGAUGUGGAAAAAUUGGAAUC | >hsa-miR-576-3p MIMAT0004796 |
| 2 | CAGUGGUUUUACCCUAUGGUAG | >hsa-miR-140-5p MIMAT0000431 |

TABLE 1-continued

Human microRNA sequences

| NO | Sequence(5' to 3') | ID and accession |
|---|---|---|
| 3 | CAGGCAGUGACUGUUCAGACGUC | >hsa-miR-2682-5p MIMAT0013517 |
| 4 | AAGAAGAGACUGAGUCAUCGAAU | >hsa-miR-5197-3p MIMAT0021131 |
| 5 | CUCUAGAGGGAAGCGCUUUCUG | >hsa-miR-522-5p MIMAT0005451 |
| 6 | UUUCUGUCUUUUCUGGUCCAG | >hsa-miR-4743-3p MIMAT0022978 |
| 7 | GUUUGCACGGGUGGGCCUUGUCU | >hsa-miR-557 MIMAT0003221 |
| 8 | AAAGACCGUGACUACUUUUGCA | >hsa-miR-548ao-3p MIMAT0021030 |
| 9 | AAAAGUACUUGCGGAUUU | >hsa-miR-548av-5p MIMAT0022303 |
| 10 | UGUAAACAUCCCCGACUGGAAG | >hsa-miR-30d-5p MIMAT0000245 |
| 11 | UGGGCGAGGGGUGGGCUCUCAGAG | >hsa-miR-4649-5p MIMAT0019711 |
| 12 | ACCAGGAGGCUGAGGCCCCU | >hsa-miR-665 MIMAT0004952 |
| 13 | CUCUAGAGGGAAGCACUUUCUG | >hsa-miR-518d-5p MIMAT0005456 |
| 14 | AGGACUGAUCCUCUCGGGCAGG | >hsa-miR-4740-5p MIMAT0019869 |
| 15 | UCACCUGAGCUCCCGUGCCUG | >hsa-miR-3622b-3p MIMAT0018006 |
| 16 | ACUGGGGCUUUCGGGCUCUGCGU | >hsa-miR-637 MIMAT0003307 |
| 17 | AGAAGGCCUUUCCAUCUCUGU | >hsa-miR-4493 MIMAT0019028 |
| 18 | CAGGCACGGGAGCUCAGGUGAG | >hsa-miR-3622a-5p MIMAT0018003 |
| 19 | AAAGUGCUUCCUUUUAGAGGG | >hsa-miR-520b MIMAT0002843 |
| 20 | ACCUGGACCCAGCGUAGACAAAG | >hsa-miR-3690 MIMAT0018119 |
| 21 | UAGGCAGUGUCAUUAGCUGAUUG | >hsa-miR-34b-5p MIMAT0000685 |
| 22 | UAUACAAGGGCAAGCUCUCUGU | >hsa-miR-381-3p MIMAT0000736 |
| 23 | UUGAAGAGGAGGUGCUCUGUAGC | >hsa-miR-4709-3p MIMAT0019812 |
| 24 | GAAAGCGCUUCCCUUUGCUGGA | >hsa-miR-518a-3p MIMAT0002863 |
| 25 | UGAGGCUAAUGCACUACUUCAC | >hsa-miR-3975 MIMAT0019360 |
| 26 | UCUAGGCUGGUACUGCUGA | >hsa-miR-645 MIMAT0003315 |
| 27 | CUUAGCAGGUUGUAUUAUCAUU | >hsa-miR-374b-3p MIMAT0004956 |
| 28 | GAGACAGGUUCAUGCUGCUA | >hsa-miR-4524b-3p MIMAT0022256 |
| 29 | CAAAGUGCUUACAGUGCAGGUAG | >hsa-miR-17-5p MIMAT0000070 |
| 30 | CUGGGCUCGGGACGCGCGGCU | >hsa-miR-4674 MIMAT0019756 |
| 31 | AAUCUGAGAAGGCGCACAAGGU | >hsa-miR-3200-5p MIMAT0017392 |
| 32 | UUGCAUAUGUAGGAUGUCCCAU | >hsa-miR-448 MIMAT0001532 |
| 33 | CUGGCGGAGCCCAUUCCAUGCCA | >hsa-miR-4730 MIMAT0019852 |
| 34 | GUUAGGGCCAACAUCUCUUGG | >hsa-miR-2909 MIMAT0013863 |
| 35 | UAGUGGAUGAUGCACUCUGUGC | >hsa-miR-3681-5p MIMAT0018108 |
| 36 | AUGGCCAAAACUGCAGUUAUUUU | >hsa-miR-548s MIMAT0014987 |
| 37 | UAAGUGCUUCCAUGUUUUAGUAG | >hsa-miR-302b-3p MIMAT0000715 |
| 38 | UUCUCCAAAAGAAAGCACUUUCUG | >hsa-miR-515-5p MIMAT0002826 |
| 39 | UAUUGCACUCGUCCCGGCCUCC | >hsa-miR-92b-3p MIMAT0003218 |
| 40 | GUGGGUUGGGGCGGGCUCUG | >hsa-miR-3940-5p MIMAT0019229 |

TABLE 1-continued

Human microRNA sequences

| NO | Sequence(5' to 3') | ID and accession |
|---|---|---|
| 41 | ACCUGAAUUACCAAAAGCUUU | >hsa-miR-3140-5p MIMAT0019204 |
| 42 | GACUCACUCACAGGAUUGUGCA | >hsa-miR-3680-5p MIMAT0018106 |
| 43 | CAGGUCGUCUUGCAGGGCUUCU | >hsa-miR-431-3p MIMAT0004757 |
| 44 | AGCUUCUUUACAGUGCUGCCUUG | >hsa-miR-103a-2-5p MIMAT0009196 |
| 45 | UCGUAUCAGAGAUUCCAGACAC | >hsa-miR-6506-3p MIMAT0025469 |
| 46 | UUGGCCAUGGGGCUGCGCGG | >hsa-miR-3187-3p MIMAT0015069 |
| 47 | AUGCUACUCGGAAAUCCCACUGA | >hsa-miR-5089-3p MIMAT0022984 |
| 48 | CUACUUCUACCUGUGUUAUCAU | >hsa-miR-3682-5p MIMAT0019222 |
| 49 | CCAGGCUCUGCAGUGGGAACU | >hsa-miR-3155a MIMAT0015029 |
| 50 | GAUGGUUGACCAGAGAGCACAC | >hsa-miR-758-5p MIMAT0022929 |
| 51 | GUGGGAUUUCUGAGUAGCAUC | >hsa-miR-5089-5p MIMAT0021081 |
| 52 | GUGCUUCAUCGUAAUUAACCUUA | >hsa-miR-3977 MIMAT0019362 |
| 53 | GUAGCACCUUGCAGGAUAAGGU | >hsa-miR-5682 MIMAT0022470 |
| 54 | AAGUGUGCAGGGCACUGGU | >hsa-miR-648 MIMAT0003318 |
| 55 | ACUGUUGCUAAUAUGCAACUCU | >hsa-miR-367-5p MIMAT0004686 |
| 56 | UGAUCUCACCGCUGCCUCCUUC | >hsa-miR-4695-3p MIMAT0019789 |
| 57 | AGAGGUUGCCCUUGGUGAAUUC | >hsa-miR-377-5p MIMAT0004689 |
| 58 | AAAGUAGCUGUACCAUUUGC | >hsa-miR-562 MIMAT0003226 |
| 59 | CCAGUUUUCCCAGGAUU | >hsa-miR-4328 MIMAT0016926 |
| 60 | UCAUCCUCGUCUCCCUCCCAG | >hsa-miR-5196-3p MIMAT0021129 |
| 61 | UCACCUGACCUCCCAUGCCUGU | >hsa-miR-3622a-3p MIMAT0018004 |
| 62 | AAAGGAUUCUGCUGUCGGUCCCACU | >hsa-miR-541-5p MIMAT0004919 |
| 63 | AGAGGUAUAGGGCAUGGGAA | >hsa-miR-202-3p MIMAT0002811 |
| 64 | UCUCUUCAUCUACCCCCCAG | >hsa-miR-6515-3p MIMAT0025487 |
| 65 | CUCUGGGAAAUGGGACAG | >hsa-miR-4314 MIMAT0016868 |
| 66 | UAAAGAGCCCUGUGGAGACA | >hsa-miR-1276 MIMAT0005930 |
| 67 | ACACAGUGCUUCAUCCACUACU | >hsa-miR-3681-3p MIMAT0018109 |
| 68 | CGAGCCUCAAGCAAGGGACUU | >hsa-miR-2114-3p MIMAT0011157 |
| 69 | ACAAAGUGCUUCCCUUUAGAGUGU | >hsa-miR-520g MIMAT0002858 |
| 70 | AGCAGUGUUUGUUUUGCCCACA | >hsa-miR-6499-3p MIMAT0025451 |
| 71 | CAAAUAAUACCACAGUGGGUGU | >hsa-miR-5692a MIMAT0022484 |
| 72 | GGGGGUCCCCGGUGCUCGGAUC | >hsa-miR-615-5p MIMAT0004804 |
| 73 | CACAGCAAGUGUAGACAGGCA | >hsa-miR-3120-3p MIMAT0014982 |
| 74 | GGUGGGAUGGAGAGAAGGUAUGAG | >hsa-miR-4769-5p MIMAT0019922 |
| 75 | CCACCUCCCCUGCAAACGUCCA | >hsa-miR-1306-5p MIMAT0022726 |
| 76 | CUCGUGGGCUCUGGCCACGGCC | >hsa-miR-3677-3p MIMAT0018101 |
| 77 | AAAGUGCAUCCUUUUAGAGGUU | >hsa-miR-519b-3p MIMAT0002837 |
| 78 | GCUACUUCACAACACCAGGGCC | >hsa-miR-138-1-3p MIMAT0004607 |

TABLE 1-continued

Human microRNA sequences

| NO | Sequence(5' to 3') | ID and accession |
|---|---|---|
| 79 | UGCCCAUGCCAUACUUUUGCCUCA | >hsa-miR-4641 MIMAT0019701 |
| 80 | UUCACAAGGAGGUGUCAUUUAU | >hsa-miR-513b MIMAT0005788 |
| 81 | AUCACAUUGCCAGGGAUUUCC | >hsa-miR-23a-3p MIMAT0000078 |
| 82 | UUUGGACAGAAAACACGCAGGU | >hsa-miR-4520b-3p MIMAT0020300 |
| 83 | UGUAGAGCAGGGAGCAGGAAGCU | >hsa-miR-4732-5p MIMAT0019855 |
| 84 | CUGUAUGCCCUCACCGCUCA | >hsa-miR-675-3p MIMAT0006790 |
| 85 | UUGGGGAAACGGCCGCUGAGUG | >hsa-miR-2110 MIMAT0010133 |
| 86 | CUGGACUGAGCCGUGCUACUGG | >hsa-miR-1269a MIMAT0005923 |
| 87 | CGGGGGCGGGGCCGAAGCGCG | >hsa-miR-1237-5p MIMAT0022946 |
| 88 | AAUCAUACAGGGACAUCCAGUU | >hsa-miR-487a MIMAT0002178 |
| 89 | ACCUGUCUGUGGAAAGGAGCUA | >hsa-miR-4421 MIMAT0018934 |
| 90 | UCACUCCUCUCCUCCCGUCUU | >hsa-miR-483-3p MIMAT0002173 |
| 91 | CGCGCCGGGCCCGGGUU | >hsa-miR-3195 MIMAT0015079 |
| 92 | UUUCUUCUUAGACAUGGCAACG | >hsa-miR-4659a-3p MIMAT0019727 |
| 93 | UGGGUCUUUGCGGGCGAGAUGA | >hsa-miR-193a-5p MIMAT0004614 |
| 94 | GCUGGGCGAGGCUGGCA | >hsa-miR-4486 MIMAT0019020 |
| 95 | UGAGAACUGAAUUCCAUGGGUU | >hsa-miR-146a-5p MIMAT0000449 |
| 96 | UGGAGUCCAGGAAUCUGCAUUUU | >hsa-miR-1289 MIMAT0005879 |
| 97 | GGAUGGAGGAGGGGUCU | >hsa-miR-4534 MIMAT0019073 |
| 98 | AGGUUGACAUACGUUUCCC | >hsa-miR-563 MIMAT0003227 |
| 99 | GAGAGCAGUGUGUGUUGCCUGG | >hsa-miR-2278 MIMAT0011778 |
| 100 | AUCGGGAAUGUCGUGUCCGCCC | >hsa-miR-425-3p MIMAT0001343 |
| 101 | UUGUGGCUGGUCAUGAGGCUAA | >hsa-miR-4474-3p MIMAT0019001 |
| 102 | AAGCAUUCUUUCAUUGGUUGG | >hsa-miR-1179 MIMAT0005824 |
| 103 | UAUUCAGAAAGGUGCCAGUCA | >hsa-miR-892c-5p MIMAT0025857 |
| 104 | AAUUUGGUUUCUGAGGCACUUAGU | >hsa-miR-5002-5p MIMAT0021023 |
| 105 | AUGAGACUCAUGUAAAACAUCUU | >hsa-miR-3672 MIMAT0018095 |
| 106 | CUAUACAAUCUACUGUCUUUC | >hsa-let-7a-3p MIMAT0004481 |
| 107 | UGGUUGACCAUAGAACAUGCGC | >hsa-miR-380-5p MIMAT0000734 |
| 108 | AGGGGGCGGGCUCCGGCG | >hsa-miR-4488 MIMAT0019022 |
| 109 | AGUGGAUGAUGGAGACUCGGUAC | >hsa-miR-3691-5p MIMAT0018120 |
| 110 | AGUUUUGCAGGUUUGCAUCCAGC | >hsa-miR-19b-1-5p MIMAT0004491 |
| 111 | AGUGGCAAAGUCUUUCCAUAU | >hsa-miR-3688-5p MIMAT0019223 |
| 112 | UAAUCCUUGCUACCUGGGUGAGA | >hsa-miR-500a-5p MIMAT0004773 |
| 113 | UGCGGGCUAGGGCUAACAGCA | >hsa-miR-744-5p MIMAT0004945 |
| 114 | CCUCCCACACCCAAGGCUUGCA | >hsa-miR-532-3p MIMAT0004780 |
| 115 | AGGGAAGGAGGCUUGGUCUUAG | >hsa-miR-4747-5p MIMAT0019882 |
| 116 | CCUAUUCUUGAUUACUUGUUUC | >hsa-miR-26a-2-3p MIMAT0004681 |

TABLE 1-continued

| Human microRNA sequences | | |
|---|---|---|
| NO | Sequence(5' to 3') | ID and accession |
| 117 | CCUCCGUGUUACCUGUCCUCUAG | >hsa-miR-3605-3p MIMAT0017982 |
| 118 | UCUGUGAGACCAAAGAACUACU | >hsa-miR-4677-3p MIMAT0019761 |
| 119 | CAAUCAGCAAGUAUACUGCCCU | >hsa-miR-34a-3p MIMAT0004557 |
| 120 | GUUGGGACAAGAGGACGGUCUU | >hsa-miR-3122 MIMAT0014984 |
| 121 | UUUGUGACCUGGUCCACUAACC | >hsa-miR-758-3p MIMAT0003879 |
| 122 | CAGCAGUCCCUCCCCCUG | >hsa-miR-4274 MIMAT0016906 |
| 123 | UGAGGAGAUCGUCGAGGUUGG | >hsa-miR-3150b-3p MIMAT0018194 |
| 124 | UCUCAGUAAGUGGCACUCUGU | >hsa-miR-4797-3p MIMAT0019973 |
| 125 | CUCAAGUAGUCUGACCAGGGGA | >hsa-miR-4465 MIMAT0018992 |
| 126 | UAAAACUGCAGUUAUUUUUGC | >hsa-miR-548ar-3p MIMAT0022266 |
| 127 | GCAGCCCAGCUGAGGCCUCUG | >hsa-miR-4690-3p MIMAT0019780 |
| 128 | UUCCUAUGCAUAUACUUCUUUG | >hsa-miR-202-5p MIMAT0002810 |
| 129 | CUCUCUACUGACUUGCAACAUA | >hsa-miR-4684-5p MIMAT0019769 |
| 130 | ACUCGGCUGCGGUGGACAAGU | >hsa-miR-4638-5p MIMAT0019695 |
| 131 | UGGGAGCUGGACUACUUC | >hsa-miR-4300 MIMAT0016853 |
| 132 | ACUGGACUUGGAGUCAGAAA | >hsa-miR-378d MIMAT0018926 |
| 133 | CAGGCAGAAGUGGGGCUGACAGG | >hsa-miR-6511a-5p MIMAT0025478 |
| 134 | CAGUUAUCACAGUGCUGAUGCU | >hsa-miR-101-5p MIMAT0004513 |
| 135 | AGGUAGAAUGAGGCCUGACAU | >hsa-miR-4650-3p MIMAT0019714 |
| 136 | CCUGUUGAAGUGUAAUCCCCA | >hsa-miR-1267 MIMAT0005921 |
| 137 | AGGGAAAAAAAAAAGGAUUUGUC | >hsa-miR-4668-5p MIMAT0019745 |
| 138 | ACCGAAGACUGUGCGCUAAUCU | >hsa-miR-4671-5p MIMAT0019752 |
| 139 | ACCUUCUUGUAUAAGCACUGUGCUAAA | >hsa-miR-1248 MIMAT0005900 |
| 140 | GGGGAGCUGUGGAAGCAGUA | >hsa-miR-920 MIMAT0004970 |
| 141 | AAUCCACGCUGAGCUUGGCAUC | >hsa-miR-5092 MIMAT0021084 |
| 142 | GAGACUGGGGUGGGGCC | >hsa-miR-4463 MIMAT0018987 |
| 143 | AAAAGUAAUUGUGGUUUUGGCC | >hsa-miR-548b-5p MIMAT0004798 |
| 144 | UGCUUCCUUUCAGAGGGU | >hsa-miR-516a-3p MIMAT0006778 |
| 145 | UAUAGGGAUUGGAGCCGUGGCG | >hsa-miR-135a-3p MIMAT0004595 |
| 146 | CGCCUGCCCAGCCCUCCUGCU | >hsa-miR-4763-5p MIMAT0019912 |
| 147 | AGACUGACGGCUGGAGGCCCAU | >hsa-miR-4513 MIMAT0019050 |
| 148 | AGCAGGGCUGGGGAUUGCA | >hsa-miR-6132 MIMAT0024616 |
| 149 | CUCUAGAGGGAAGCGCUUUCUG | >hsa-miR-518e-5p MIMAT0005450 |
| 150 | ACGUUGGCUCUGGUGGUG | >hsa-miR-1306-3p MIMAT0005950 |
| 151 | GCUCGGACUGAGCAGGUGGG | >hsa-miR-3917 MIMAT0018191 |
| 152 | UCUGCACUGUGAGUUGGCUGGCU | >hsa-miR-4793-3p MIMAT0019966 |
| 153 | UCCUUCAUUCCACCGGAGUCUG | >hsa-miR-205-5p MIMAT0000266 |
| 154 | UGUCUCUGCUGGGGUUUCU | >hsa-miR-593-3p MIMAT0004802 |

TABLE 1-continued

Human microRNA sequences

| NO | Sequence(5' to 3') | ID and accession |
|---|---|---|
| 155 | GAGCCAGUUGGACAGGAGC | >hsa-miR-575 MIMAT0003240 |
| 156 | UGAGUAUUACAUGGCCAAUCUC | >hsa-miR-496 MIMAT0002818 |
| 157 | AAAAGCUGGGUUGAGAGGGU | >hsa-miR-320c MIMAT0005793 |
| 158 | UUGGAGGGUGUGGAAGACAUC | >hsa-miR-6515-5p MIMAT0025486 |
| 159 | GUGUCUUUUGCUCUGCAGUCA | >hsa-miR-511 MIMAT0002808 |
| 160 | AGGUCUGCAUUCAAAUCCCCAGA | >hsa-miR-6503-5p MIMAT0025462 |
| 161 | UCCCUACCCCUCCACUCCCCA | >hsa-miR-3162-3p MIMAT0019213 |
| 162 | UGCCUGGGUCUCUGGCCUGCGCGU | >hsa-miR-661 MIMAT0003324 |
| 163 | UGUUUCGGGGCUCAUGGCCUGUG | >hsa-miR-5705 MIMAT0022499 |
| 164 | UCUGGCUGUGCUGUAAUGCAG | >hsa-miR-6504-5p MIMAT0025464 |
| 165 | GGCAGGAGGGCUGUGCCAGGUUG | >hsa-miR-4722-5p MIMAT0019836 |
| 166 | CUAUUAAGGACAUUUGUGAUUC | >hsa-miR-4477a MIMAT0019004 |
| 167 | UUUGUUCGUUCGGCUCGCGUGA | >hsa-miR-375 MIMAT0000728 |
| 168 | CAAAACGUGAGGCGCUGCUAU | >hsa-miR-424-3p MIMAT0004749 |
| 169 | AACAUCACUGCAAGUCUUAACA | >hsa-miR-499b-3p MIMAT0019898 |
| 170 | AGAGAUUGGUAGAAAUCAGGU | >hsa-miR-5186 MIMAT0021116 |
| 171 | UGUCUACAUUAAUGAAAAGAGC | >hsa-miR-3618 MIMAT0017998 |
| 172 | AAAUAUAUAUAUAUGUACGUAU | >hsa-miR-1277-5p MIMAT0022724 |
| 173 | GUGAGUGGGAGCCCCAGUGUGUG | >hsa-miR-1238-5p MIMAT0022947 |
| 174 | UAAAUUUCACCUUUCUGAGAAGG | >hsa-miR-513a-3p MIMAT0004777 |
| 175 | AUCUAAAUGCAGCAUGCCAGUC | >hsa-miR-4799-5p MIMAT0019976 |
| 176 | GUUCCUGCUGAACUGAGCCAG | >hsa-miR-3074-5p MIMAT0019208 |
| 177 | AGGGAAGGGGACGAGGGUUGGG | >hsa-miR-5196-5p MIMAT0021128 |
| 178 | CCGCCUGAGCUAGCUGUGG | >hsa-miR-6078 MIMAT0023703 |
| 179 | AGCAAGGCGGCAUCUCUCUGAU | >hsa-miR-4708-3p MIMAT0019810 |
| 180 | UGCCCUGCCUGUUUUCUCCUUU | >hsa-miR-3173-5p MIMAT0019214 |
| 181 | GAGGUUUGGGGAGGAUUUGCU | >hsa-miR-4748 MIMAT0019884 |
| 182 | CCAGUGUGGCUCAGCGAG | >hsa-miR-4302 MIMAT0016855 |
| 183 | AAAGGUGCUCAAAUUAGACAU | >hsa-miR-4735-3p MIMAT0019861 |
| 184 | GCAGGACAGGCAGAAGUGGAU | >hsa-miR-4436a MIMAT0018952 |
| 185 | UGUCAGUUUGUCAAAUACCCCA | >hsa-miR-223-3p MIMAT0000280 |
| 186 | CGGCGCGACCGGCCCGGGG | >hsa-miR-4634 MIMAT0019691 |
| 187 | CAUAAAGUAGAAAGCACUACU | >hsa-miR-142-5p MIMAT0000433 |
| 188 | UGGGCUAAGGGAGAUGAUUGGGUA | >hsa-miR-664b-5p MIMAT0022271 |
| 189 | CCUCACCAUCCCUUCUGCCUGC | >hsa-miR-6511a-3p MIMAT0025479 |
| 190 | GGGGGGAUGUGCAUGCUGGUU | >hsa-miR-4525 MIMAT0019064 |
| 191 | CGGGGCAGCUCAGUACAGGAU | >hsa-miR-486-3p MIMAT0004762 |
| 192 | UUUAACAUGGGGGUACCUGCUG | >hsa-miR-302c-5p MIMAT0000716 |

TABLE 1-continued

Human microRNA sequences

| NO | Sequence(5' to 3') | ID and accession |
|---|---|---|
| 193 | AAACUAAUAUACCCAUAUUCUG | >hsa-miR-5583-5p MIMAT0022281 |
| 194 | UUUUGCACCUUUUGGAGUGAA | >hsa-miR-507 MIMAT0002879 |
| 195 | UGGCAGUGUAUUGUUAGCUGGU | >hsa-miR-449a MIMAT0001541 |
| 196 | AGGGCUGGACUCAGCGGCGGAGCU | >hsa-miR-5001-5p MIMAT0021021 |
| 197 | UGAGUGAUUGAUAGCUAUGUUC | >hsa-miR-4765 MIMAT0019916 |
| 198 | UCAGCAGGCAGGCUGGUGCAGC | >hsa-miR-3619-5p MIMAT0017999 |
| 199 | AGAUGUAUGGAAUCUGUAUAUAUC | >hsa-miR-3171 MIMAT0015046 |
| 200 | ACUCCAGCCCCACAGCCUCAGC | >hsa-miR-766-3p MIMAT0003888 |
| 201 | GAGCAAUGUAGGUAGACUGUUU | >hsa-miR-3908 MIMAT0018182 |
| 202 | ACAAGGUGUGCAUGCCUGACC | >hsa-miR-4761-5p MIMAT0019908 |
| 203 | GCAAAGCACACGGCCUGCAGAGA | >hsa-miR-330-3p MIMAT0000751 |
| 204 | GCCCAAAGGUGAAUUUUUGGG | >hsa-miR-186-3p MIMAT0004612 |
| 205 | GGGAGGUGUGAUCUCACACUCG | >hsa-miR-3689d MIMAT0019008 |
| 206 | CCAGAGGUGGGGACUGAG | >hsa-miR-4257 MIMAT0016878 |
| 207 | ACUCAGUCAUGGUCAUU | >hsa-miR-4264 MIMAT0016899 |
| 208 | AGGGACGGGACGCGGUGCAGUG | >hsa-miR-92b-5p MIMAT0004792 |
| 209 | CAAAUUCGUAUCUAGGGGAAUA | >hsa-miR-10a-3p MIMAT0004555 |
| 210 | UCCUGUCUUUCCUUGUUGGAGC | >hsa-miR-5699 MIMAT0022492 |
| 211 | CAGGGAAAUGGGAAGAACUAGA | >hsa-miR-5584-5p MIMAT0022283 |
| 212 | AGAGAUGAAGCGGGGGGGCG | >hsa-miR-6088 MIMAT0023713 |
| 213 | GGGUGAGGGCAGGUGGUU | >hsa-miR-4710 MIMAT0019815 |
| 214 | UGGAAGGGAGAAGAGCUUUAAU | >hsa-miR-3202 MIMAT0015089 |
| 215 | CAUCUUACCGGACAGUGCUGGA | >hsa-miR-200a-5p MIMAT0001620 |
| 216 | CUGACUGUUGCCGUCCUCCAG | >hsa-miR-943 MIMAT0004986 |
| 217 | AAAGGCAUAAAACCAAGACA | >hsa-miR-3910 MIMAT0018184 |
| 218 | UUUGUAUGGAUAUGUGUGUGUAU | >hsa-miR-3149 MIMAT0015022 |
| 219 | CUAUACAACCUACUGCCUUCCC | >hsa-let-7b-3p MIMAT0004482 |
| 220 | UGCCCUGUGGACUCAGUUCUGG | >hsa-miR-146b-3p MIMAT0004766 |
| 221 | CGGCGGGACGGCGAUUGGUC | >hsa-miR-1908 MIMAT0007881 |
| 222 | UCCAUUACACUACCCUGCCUCU | >hsa-miR-885-5p MIMAT0004947 |
| 223 | UAAGUGCUUCCAUGCUU | >hsa-miR-302e MIMAT0005931 |
| 224 | GUGCCACCUUAACUGCAGCCAAU | >hsa-miR-4715-3p MIMAT0019825 |
| 225 | UCGUUUGCCUUUUUCUGCUU | >hsa-miR-1282 MIMAT0005940 |
| 226 | UUCGCGGGCGAAGGCAAAGUC | >hsa-miR-3124-5p MIMAT0014986 |
| 227 | UGCUGGGGGCCACAUGAGUGUG | >hsa-miR-4731-5p MIMAT0019853 |
| 228 | CUCGGGCGGAGGUGGUUGAGUG | >hsa-miR-4750-5p MIMAT0019887 |
| 229 | GCUGCGCUUGGAUUUCGUCCCC | >hsa-miR-191-3p MIMAT0001618 |
| 230 | UUGCCAUACAUAGACUUUAUU | >hsa-miR-5590-5p MIMAT0022299 |

TABLE 1-continued

Human microRNA sequences

| NO | Sequence(5' to 3') | ID and accession |
|---|---|---|
| 231 | CUGUACAGGCCACUGCCUUGC | >hsa-let-7g-3p MIMAT0004584 |
| 232 | GAAAUCAAGCGUGGGUGAGACC | >hsa-miR-551b-5p MIMAT0004794 |
| 233 | UCACGCGGAGAGAUGGCUUUG | >hsa-miR-3186-3p MIMAT0015068 |
| 234 | UGAGACCUCUGGGUUCUGAGCU | >hsa-miR-769-5p MIMAT0003886 |
| 235 | ACUUAAACGUGGAUGUACUUGCU | >hsa-miR-302a-5p MIMAT0000683 |
| 236 | ACUGCAUUAUGAGCACUUAAAG | >hsa-miR-20a-3p MIMAT0004493 |
| 237 | UGUGCAAAUCUAUGCAAAACUGA | >hsa-miR-19a-3p MIMAT0000073 |
| 238 | AGCGAGGUUGCCCUUUGUAUAU | >hsa-miR-381-5p MIMAT0022862 |
| 239 | CCCCAGGGCGACGCGGCGGG | >hsa-miR-1915-3p MIMAT0007892 |
| 240 | ACCUGAGGUUGUGCAUUUCUAA | >hsa-miR-544b MIMAT0015004 |
| 241 | CACACACUGCAAUUACUUUUGC | >hsa-miR-603 MIMAT0003271 |
| 242 | AGGCUGGGCUGGGACGGA | >hsa-miR-4505 MIMAT0019041 |
| 243 | UAUUGCACAUUACUAAGUUGCA | >hsa-miR-32-5p MIMAT0000090 |
| 244 | UUCUGGAUAACAUGCUGAAGCU | >hsa-miR-5706 MIMAT0022500 |
| 245 | AGGAGCUAGCCAGGCAUAUGCA | >hsa-miR-4633-3p MIMAT0019690 |
| 246 | AGGUGUUAUCCUAUCCAUUUGC | >hsa-miR-4694-5p MIMAT0019786 |
| 247 | GGAGAUGGAGGUUGCAGUG | >hsa-miR-1273f MIMAT0020601 |
| 248 | UUCUAGAUGAGAGAUAUAUAUA | >hsa-miR-4777-5p MIMAT0019934 |
| 249 | AAUUCCCUUGUAGAUAACCCGG | >hsa-miR-3938 MIMAT0018353 |
| 250 | CAGUGGCCAGAGCCCUGCAGUG | >hsa-miR-3677-5p MIMAT0019221 |
| 251 | AAUGUGGACUGGUGUGACCAAA | >hsa-miR-4491 MIMAT0019026 |
| 252 | AAGUGCCCCCACAGUUUGAGUGC | >hsa-miR-371b-3p MIMAT0019893 |
| 253 | UGCCCUUAAAGGUGAACCCAGU | >hsa-miR-938 MIMAT0004981 |
| 254 | CACGCUCAUGCACACACCCACA | >hsa-miR-574-3p MIMAT0003239 |
| 255 | UCACAGUGAACCGGUCUCUUU | >hsa-miR-128 MIMAT0000424 |
| 256 | UGUGACUGGUUGACCAGAGGGG | >hsa-miR-134 MIMAT0000447 |
| 257 | AGAGGACCCGUAGCUGCUAGAAGG | >hsa-miR-4751 MIMAT0019888 |
| 258 | GAUAUCAGCUCAGUAGGCACCG | >hsa-miR-3074-3p MIMAT0015027 |
| 259 | UCCGAACUCUCCAUUCCUCUGC | >hsa-miR-6716-3p MIMAT0025845 |
| 260 | UCUCACACAGAAAUCGCACCCGU | >hsa-miR-342-3p MIMAT0000753 |
| 261 | GGGGUUCCUGGGGAUGGGAUUU | >hsa-miR-23a-5p MIMAT0004496 |
| 262 | AUGGUCACCUCCGGGACU | >hsa-miR-5587-5p MIMAT0022289 |
| 263 | UUAUGGUUUGCCUGGGACUGAG | >hsa-miR-584-5p MIMAT0003249 |
| 264 | CGCGCGGCCGUGCUCGGAGCAG | >hsa-miR-4479 MIMAT0019011 |
| 265 | AGCAGAAGCAGGGAGGUUCUCCCA | >hsa-miR-298 MIMAT0004901 |
| 266 | ACGGAUGUUUGAGCAUGUGCUA | >hsa-miR-105-3p MIMAT0004516 |
| 267 | UGUUCCUCUGUCUCCCAGAC | >hsa-miR-4326 MIMAT0016888 |
| 268 | AGGAGGCAUCUUGAGAAAUGGA | >hsa-miR-3612 MIMAT0017989 |

TABLE 1-continued

Human microRNA sequences

| NO | Sequence(5' to 3') | ID and accession |
|---|---|---|
| 269 | UGAGGUAGUAGGUUGUGUGGUU | >hsa-let-7b-5p MIMAT0000063 |
| 270 | UCGGGGAUCAUCAUGUCACGAGA | >hsa-miR-542-5p MIMAT0003340 |
| 271 | GUGUCUGGGCGGACAGCUGC | >hsa-miR-1231 MIMAT0005586 |
| 272 | UGUGCAAAUCCAUGCAAAACUGA | >hsa-miR-19b-3p MIMAT0000074 |
| 273 | CAGUGUUCAGAGAUGGA | >hsa-miR-4255 MIMAT0016885 |
| 274 | UGGUGCGGAGAGGGCCCACAGUG | >hsa-miR-675-5p MIMAT0004284 |
| 275 | GCCUGCUGGGGUGGAACCUGGU | >hsa-miR-370 MIMAT0000722 |
| 276 | CCCAGUGUUCAGACUACCUGUUC | >hsa-miR-199a-5p MIMAT0000231 |
| 277 | GAGAAAUGCUGGACUAAUCUGC | >hsa-miR-5680 MIMAT0022468 |
| 278 | AGGGUGUGUGUGUUUUU | >hsa-miR-4455 MIMAT0018977 |
| 279 | UGUAAACAUCCUCGACUGGAAG | >hsa-miR-30a-5p MIMAT0000087 |
| 280 | UGAUGAUACAGGUGGAGGUAG | >hsa-miR-3682-3p MIMAT0018110 |
| 281 | UGGCAGGGAGGCUGGGAGGGG | >hsa-miR-1207-5p MIMAT0005871 |
| 282 | CACAGGCUUAGAAAAGACAGU | >hsa-miR-4438 MIMAT0018956 |
| 283 | CCCUUGGGUCUGAUGGGGUAG | >hsa-miR-3189-3p MIMAT0015071 |
| 284 | ACUUUAACAUGGAAGUGCUUUC | >hsa-miR-302b-5p MIMAT0000714 |
| 285 | UGCUGGAUCAGUGGUUCGAGUC | >hsa-miR-1287 MIMAT0005878 |
| 286 | AUCCCUUGCAGGGGCUGUUGGGU | >hsa-miR-623 MIMAT0003292 |
| 287 | CCUGGAAACACUGAGGUUGUG | >hsa-miR-875-3p MIMAT0004923 |
| 288 | UAGUGGUCAGAGGGCUUAUGA | >hsa-miR-6718-5p MIMAT0025849 |
| 289 | GGCAGGUUCUCACCCUCUCUAGG | >hsa-miR-657 MIMAT0003335 |
| 290 | UUGAGGAGACAUGGUGGGGCC | >hsa-miR-4689 MIMAT0019778 |
| 291 | CCCUGGGCCUCUGCUCCCCAG | >hsa-miR-939-3p MIMAT0022939 |
| 292 | CAUCAUCGUCUCAAAUGAGUCU | >hsa-miR-136-3p MIMAT0004606 |
| 293 | AAAGUGCAUCCUUUUAGAGUGU | >hsa-miR-519a-3p MIMAT0002869 |
| 294 | UGAGCGCCUCGACGACAGAGCCG | >hsa-miR-339-3p MIMAT0004702 |
| 295 | UACUUUUCUAGGUUGUUGGGG | >hsa-miR-5003-3p MIMAT0021026 |
| 296 | AGAAGGAAAUUGAAUUCAUUUA | >hsa-miR-1252 MIMAT0005944 |
| 297 | UUUAGGAUAAGCUUGACUUUUG | >hsa-miR-651 MIMAT0003321 |
| 298 | AAGGGAGGAGGAGCGGAGGGGCCCU | >hsa-miR-4739 MIMAT0019868 |
| 299 | AGUAUUCUGUACCAGGGAAGGU | >hsa-miR-630 MIMAT0003299 |
| 300 | UUGAGAAUGAUGAAUCAUUAGG | >hsa-miR-580 MIMAT0003245 |
| 301 | AAUGGAUUUUUGGAGCAGG | >hsa-miR-1246 MIMAT0005898 |
| 302 | GGCUGGAGCGAGUGCAGUGGUG | >hsa-miR-3135b MIMAT0018985 |
| 303 | ACUUACAGACAAGAGCCUUGCUC | >hsa-miR-600 MIMAT0003268 |
| 304 | AUUCUAAUUUCUCCACGUCUUU | >hsa-miR-576-5p MIMAT0003241 |
| 305 | AAGUGCCGCCAUCUUUUGAGUGU | >hsa-miR-371a-3p MIMAT0000723 |
| 306 | AAGCCCUUACCCCAAAAAGUAU | >hsa-miR-129-1-3p MIMAT0004548 |

TABLE 1-continued

Human microRNA sequences

| NO | Sequence(5' to 3') | ID and accession |
|---|---|---|
| 307 | GGCUCCUCCUCUCAGGAUGUG | >hsa-miR-4268 MIMAT0016896 |
| 308 | UAUGCAUUGUAUUUUUAGGUCC | >hsa-miR-586 MIMAT0003252 |
| 309 | UGGAUUUCUUUGUGAAUCACCA | >hsa-miR-876-5p MIMAT0004924 |
| 310 | AACUCCAAACACUCAAAACUCA | >hsa-miR-3145-5p MIMAT0019205 |
| 311 | GGCUAGCAACAGCGCUUACCU | >hsa-miR-621 MIMAT0003290 |
| 312 | UGGGGUGCCCACUCCGCAAGUU | >hsa-miR-4664-5p MIMAT0019737 |
| 313 | CAGGGCAGGAAGAAGUGGACAA | >hsa-miR-4436b-3p MIMAT0019941 |
| 314 | CAACCUCGACGAUCUCCUCAGC | >hsa-miR-3150a-5p MIMAT0019206 |
| 315 | GUUCCACACUGACACUGCAGAAGU | >hsa-miR-3692-3p MIMAT0018122 |
| 316 | UUACAGUUGUUCAACCAGUUACU | >hsa-miR-582-5p MIMAT0003247 |
| 317 | AACAAUAUCCUGGUGCUGAGUG | >hsa-miR-338-5p MIMAT0004701 |
| 318 | UUAGGGCCCUGGCUCCAUCUCC | >hsa-miR-1296 MIMAT0005794 |
| 319 | UGAGAGUGGAAUUCACAGUAUUU | >hsa-miR-4693-3p MIMAT0019785 |
| 320 | GCCCUCCGCCCGUGCACCCCG | >hsa-miR-1470 MIMAT0007348 |
| 321 | AAACAUUCGCGGUGCACUUCUU | >hsa-miR-543 MIMAT0004954 |
| 322 | GAGGCUGAAGGAAGAUGG | >hsa-miR-4419b MIMAT0019034 |
| 323 | UUCAGCAGGAACAGCU | >hsa-miR-4291 MIMAT0016922 |
| 324 | AGGAGGAAUUGGUGCUGGUCUU | >hsa-miR-766-5p MIMAT0022714 |
| 325 | UCGAGGAGCUCACAGUCU | >hsa-miR-151b MIMAT0010214 |
| 326 | GCAGGGACAGCAAAGGGGUGC | >hsa-miR-211-3p MIMAT0022694 |
| 327 | AUAAGACGAGCAAAAAGCUUGU | >hsa-miR-208a MIMAT0000241 |
| 328 | AGUGCCUGCUAUGUGCCAGGCA | >hsa-miR-1271-3p MIMAT0022712 |
| 329 | CACGGCAAAAGAAACAAUCCA | >hsa-miR-4445-3p MIMAT0018964 |
| 330 | UAAUACUGCCGGGUAAUGAUGGA | >hsa-miR-200c-3p MIMAT0000617 |
| 331 | CAGUGCAAUGAUAUUGUCAAAGC | >hsa-miR-301b MIMAT0004958 |
| 332 | UUUGGCACUAGCACAUUUUUGCU | >hsa-miR-96-5p MIMAT0000095 |
| 333 | UAUGGUACUCCUUAAGCUAAC | >hsa-miR-5579-5p MIMAT0022269 |
| 334 | AGGCACCAGCCAGGCAUUGCUCAGC | >hsa-miR-593-5p MIMAT0003261 |
| 335 | UGUGAUAUCAUGGUUCCUGGGA | >hsa-miR-3689a-5p MIMAT0018117 |
| 336 | AAACUCUACUUGUCCUUCUGAGU | >hsa-miR-618 MIMAT0003287 |
| 337 | CAUUACAGCACAGCCAUUCU | >hsa-miR-6504-3p MIMAT0025465 |
| 338 | UAAAAUUUGCAUCCAGGA | >hsa-miR-4282 MIMAT0016912 |
| 339 | UCACACCUGCCUCGCCCCCC | >hsa-miR-1228-3p MIMAT0005583 |
| 340 | CUGCAAUGUAAGCACUUCUUAC | >hsa-miR-106a-3p MIMAT0004517 |
| 341 | UGAGGGCUCCAGGUGACGGUGG | >hsa-miR-4721 MIMAT0019835 |
| 342 | UGACAACUAUGGAUGAGCUCU | >hsa-miR-549a MIMAT0003333 |
| 343 | AGUGGGGAACCCUUCCAUGAGG | >hsa-miR-491-5p MIMAT0002807 |
| 344 | UCUCCCUUCCUGCCCUGGCUAG | >hsa-miR-4685-3p MIMAT0019772 |

TABLE 1-continued

Human microRNA sequences

| NO | Sequence(5' to 3') | ID and accession |
|---|---|---|
| 345 | AACGGCAAUGACUUUUGUACCA | >hsa-miR-548a1 MIMAT0019024 |
| 346 | UCUAAAGACUAGACUUCGCUAUG | >hsa-miR-4744 MIMAT0019875 |
| 347 | AGAGCUCACAGCUGUCCUUCUCUA | >hsa-miR-3670 MIMAT0018093 |
| 348 | ACUCCAGUUUUAGUUCUCUUG | >hsa-miR-3925-3p MIMAT0019228 |
| 349 | ACCCCACUCCUGGUACC | >hsa-miR-4286 MIMAT0016916 |
| 350 | ACUGCAGUGAAGGCACUUGUAG | >hsa-miR-17-3p MIMAT0000071 |
| 351 | UGAAGUACCAGCUACUCGAGAG | >hsa-miR-5585-5p MIMAT0022285 |
| 352 | GUUCUGUUAACCCAUCCCCUCA | >hsa-miR-4652-3p MIMAT0019717 |
| 353 | AGUGUGGCUUUCUUAGAGC | >hsa-miR-644a MIMAT0003314 |
| 354 | CGUGUUCACAGCGGACCUUGAU | >hsa-miR-124-5p MIMAT0004591 |
| 355 | CGUCCCGGGGCUGCGCGAGGCA | >hsa-miR-4449 MIMAT0018968 |
| 356 | AAUAUAACACAGAUGGCCUGU | >hsa-miR-410 MIMAT0002171 |
| 357 | UCGACAGCACGACACUGCCUUC | >hsa-miR-196b-3p MIMAT0009201 |
| 358 | CACCUUGCGCUACUCAGGUCUG | >hsa-miR-3200-3p MIMAT0015085 |
| 359 | CGGCAACAAGAAACUGCCUGAG | >hsa-miR-196a-3p MIMAT0004562 |
| 360 | AAAGACAUAGGAUAGAGUCACCUC | >hsa-miR-641 MIMAT0003311 |
| 361 | AAAGCUGGGUUGAGAAGG | >hsa-miR-320e MIMAT0015072 |
| 362 | UGCUUAACCUUGCCCUCGAAA | >hsa-miR-4804-3p MIMAT0019985 |
| 363 | UCUGGGCAACAAAGUGAGACCU | >hsa-miR-1285-3p MIMAT0005876 |
| 364 | GGGAUGGUAGACCGGUGACGUGC | >hsa-miR-1193 MIMAT0015049 |
| 365 | CUGGGAGGUGUGAUAUCGUGGU | >hsa-miR-3689a-3p MIMAT0018118 |
| 366 | GGGGAAAGCGAGUAGGGACAUUU | >hsa-miR-3153 MIMAT0015026 |
| 367 | CUUUCAGUCGGAUGUUUGCAGC | >hsa-miR-30a-3p MIMAT0000088 |
| 368 | CAAAAACCACAGUUUCUUUUGC | >hsa-miR-548d-3p MIMAT0003323 |
| 369 | GGCCUUGUUCCUGUCCCCA | >hsa-miR-4312 MIMAT0016864 |
| 370 | UACCCAGAGCAUGCAGUGUGAA | >hsa-miR-1912 MIMAT0007887 |
| 371 | GGUGAGGCUAGCUGGUG | >hsa-miR-4316 MIMAT0016867 |
| 372 | UUGCCAGGGCAGGAGGUGGAA | >hsa-miR-5006-5p MIMAT0021033 |
| 373 | CUCCAGAGGGAUGCACUUUCU | >hsa-miR-525-5p MIMAT0002838 |
| 374 | UGAAACAUACACGGGAAACCUC | >hsa-miR-494 MIMAT0002816 |
| 375 | UAGGCCACAGCCACCCAUGUGU | >hsa-miR-4717-5p MIMAT0019829 |
| 376 | GAGCAGGCGAGGCUGGGCUGAA | >hsa-miR-4690-5p MIMAT0019779 |
| 377 | CUCCUGGGGCCCGCACUCUCGC | >hsa-miR-1343 MIMAT0019776 |
| 378 | CAAAAGUGAUUGUGGUUUUUGC | >hsa-miR-548az-5p MIMAT0025456 |
| 379 | CGUGUCUUCUGGCUUGAU | >hsa-miR-4711-3p MIMAT0019817 |
| 380 | CUGCAGAGUUUGUACGGACCGG | >hsa-miR-3678-3p MIMAT0018103 |
| 381 | GGCCAGCCACCAGGAGGGCUG | >hsa-miR-3194-5p MIMAT0015078 |
| 382 | AAACACCAUUGUCACACUCCAC | >hsa-miR-3591-3p MIMAT0019877 |

TABLE 1-continued

Human microRNA sequences

| NO | Sequence(5' to 3') | ID and accession |
|---|---|---|
| 383 | CAAAGUGCUCAUAGUGCAGGUAG | >hsa-miR-20b-5p MIMAT0001413 |
| 384 | UGGGGAAGGCGUCAGUGUCGGG | >hsa-miR-4725-3p MIMAT0019844 |
| 385 | AGCGGGGAGGAAGUGGGCGCUGCUU | >hsa-miR-4706 MIMAT0019806 |
| 386 | AUCCCACCUCUGCCACCA | >hsa-miR-1260a MIMAT0005911 |
| 387 | AAUAAUAUCACAGUAGGUGUAC | >hsa-miR-5692c MIMAT0022476 |
| 388 | AAAGACUCUGCAAGAUGCCU | >hsa-miR-4432 MIMAT0018948 |
| 389 | CUGAUAAGAACAGAGGCCCAGAU | >hsa-miR-3161 MIMAT0015035 |
| 390 | UUUAGUGUGAUAAUGGCGUUUGA | >hsa-miR-3591-5p MIMAT0019876 |
| 391 | GGGGUAUUGUUUCCGCUGCCAGG | >hsa-miR-503-3p MIMAT0022925 |
| 392 | ACUCGGCGUGGCGUCGGUCGUG | >hsa-miR-1307-3p MIMAT0005951 |
| 393 | AUCAUAGAGGAAAAUCCACGU | >hsa-miR-376a-3p MIMAT0000729 |
| 394 | AGGUUGGGAUCGGUUGCAAUGCU | >hsa-miR-92a-1-5p MIMAT0004507 |
| 395 | CAGUUCAGAAGUGUUCCUGAGU | >hsa-miR-5000-5p MIMAT0021019 |
| 396 | CAAAAACCGCAAUUACUUUUGCA | >hsa-miR-548h-3p MIMAT0022723 |
| 397 | UGCCUUCCUGUCUGUG | >hsa-miR-4297 MIMAT0016846 |
| 398 | UCAACAAAAUCACUGAUGCUGGA | >hsa-miR-3065-5p MIMAT0015066 |
| 399 | UCACAAGGUAUUGACUGGCGUA | >hsa-miR-4457 MIMAT0018979 |
| 400 | UGGAAUGUAAAGAAGUAUGUAU | >hsa-miR-1 MIMAT0000416 |
| 401 | UCACAAGUCAGGCUCUUGGGAC | >hsa-miR-125b-2-3p MIMAT0004603 |
| 402 | UUUUGCAUGACCCUGGGAGUAGG | >hsa-miR-3680-3p MIMAT0018107 |
| 403 | CUGCCCUGGCCCGAGGGACCGA | >hsa-miR-874 MIMAT0004911 |
| 404 | AAAAGUAAUUGCGGUUUUUGCC | >hsa-miR-548am-5p MIMAT0022740 |
| 405 | UAGGAUGGGGGUGAGAGGUG | >hsa-miR-2392 MIMAT0019043 |
| 406 | AAAAACCACAAUUACUUUUGCACCA | >hsa-miR-548t-3p MIMAT0022730 |
| 407 | CCCAAUACACGGUCGACCCUCUU | >hsa-miR-323b-3p MIMAT0015050 |
| 408 | UGAGGAGAUGCUGGGACUGA | >hsa-miR-4784 MIMAT0019948 |
| 409 | CGCCUCUUCAGCGCUGUCUUCC | >hsa-miR-2682-3p MIMAT0013518 |
| 410 | GGCGACAAAACGAGACCCUGUC | >hsa-miR-1273c MIMAT0015017 |
| 411 | UCAGCUACUACCUCUAUUAGG | >hsa-miR-5690 MIMAT0022482 |
| 412 | GUGCAUGGCUGUAUAUAUAACA | >hsa-miR-5011-3p MIMAT0021046 |
| 413 | UGGGGCUAGUGAUGCAGGACG | >hsa-miR-4489 MIMAT0019023 |
| 414 | GCGACUCUGAAAACUAGAAGGU | >hsa-miR-4431 MIMAT0018947 |
| 415 | CACUGCAGGACUCAGCAG | >hsa-miR-4418 MIMAT0018930 |
| 416 | ACUGGACUUGGAGCCAGAAG | >hsa-miR-378f MIMAT0018932 |
| 417 | GUGAAUUACCGAAGGGCCAUAA | >hsa-miR-183-3p MIMAT0004560 |
| 418 | CCAGUGGGGCUGCUGUUAUCUG | >hsa-miR-194-3p MIMAT0004671 |
| 419 | UCUGCAAGUGUCAGAGGCGAGG | >hsa-miR-2276 MIMAT0011775 |
| 420 | AAAAACUGUAAUUACUUUU | >hsa-miR-548f MIMAT0005895 |

TABLE 1-continued

Human microRNA sequences

| NO | Sequence(5' to 3') | ID and accession |
|---|---|---|
| 421 | UGGCUUUUAACUUUGAUGGC | >hsa-miR-3119 MIMAT0014981 |
| 422 | CGUGUAUUUGACAAGCUGAGUU | >hsa-miR-223-5p MIMAT0004570 |
| 423 | CACCCCCUGUUUCCUGGCCCAC | >hsa-miR-4640-3p MIMAT0019700 |
| 424 | AAAAUUUCUUUCACUACUUAG | >hsa-miR-3606-3p MIMAT0022965 |
| 425 | AGUUAAUGAAUCCUGGAAAGU | >hsa-miR-569 MIMAT0003234 |
| 426 | UAAAGUGCUGACAGUGCAGAU | >hsa-miR-106b-5p MIMAT0000680 |
| 427 | UCCAGUACAGGUCUCUCAUUUC | >hsa-miR-4712-5p MIMAT0019818 |
| 428 | AGAACUCUUGCAGUCUUAGAUGU | >hsa-miR-4680-5p MIMAT0019764 |
| 429 | GUGUGCGGAAAUGCUUCUGCUA | >hsa-miR-147b MIMAT0004928 |
| 430 | GCCCGAGAGGAUCCGUCCCUGC | >hsa-miR-4740-3p MIMAT0019870 |
| 431 | GGAGGGGUCCCGCACUGGGAGG | >hsa-miR-1914-3p MIMAT0007890 |
| 432 | CAAAGCGCUCCCCUUUAGAGGU | >hsa-miR-518b MIMAT0002844 |
| 433 | AGGAGAUCCUGGGUU | >hsa-miR-3676-5p MIMAT0022734 |
| 434 | UGGUAGACUAUGGAACGUAGG | >hsa-miR-379-5p MIMAT0000733 |
| 435 | AAGGUAUUGUUCAGACUUAUGA | >hsa-miR-4678 MIMAT0019762 |
| 436 | UGAGGGACAGAUGCCAGAAGCA | >hsa-miR-3126-5p MIMAT0014989 |
| 437 | GUGAGUGGGAGCCGGUGGGGCUG | >hsa-miR-4758-5p MIMAT0019903 |
| 438 | UUCAAGUAAUUCAGGAUAGGU | >hsa-miR-26b-5p MIMAT0000083 |
| 439 | AGGGAGGGACGGGGGCUGUGC | >hsa-miR-149-3p MIMAT0004609 |
| 440 | GGGCUAGGGCCUGCUGCCCCC | >hsa-miR-6069 MIMAT0023694 |
| 441 | CGGAUGAGCAAAGAAAGUGGUU | >hsa-miR-1255b-5p MIMAT0005945 |
| 442 | AUGAGCGACUGUGCCUGACC | >hsa-miR-5708 MIMAT0022502 |
| 443 | CCAAACCAGUCGUGCCUGUGG | >hsa-miR-6715a-3p MIMAT0025841 |
| 444 | CCUCUUCCCCUUGUCUCUCCAG | >hsa-miR-1236-3p MIMAT0005591 |
| 445 | CUGAAGUGAUGUGUAACUGAUCAG | >hsa-miR-573 MIMAT0003238 |
| 446 | CUCAGUGACUCAUGUGC | >hsa-miR-4276 MIMAT0016904 |
| 447 | UCUGAAUUGUAAGAGUUGUUA | >hsa-miR-4680-3p MIMAT0019765 |
| 448 | GGCGCGCCCAGCUCCCGGGCU | >hsa-miR-4783-5p MIMAT0019946 |
| 449 | AUCUGUAAGAGAAAGUAAAUGA | >hsa-miR-3686 MIMAT0018114 |
| 450 | UGAGGUAGUAGUUUGUACAGUU | >hsa-let-7g-5p MIMAT0000414 |
| 451 | ACCUCCUGUGUGCAUGGAUUA | >hsa-miR-660-3p MIMAT0022711 |
| 452 | CAUGACGUCACAGAGGCUUCGC | >hsa-miR-4757-3p MIMAT0019902 |
| 453 | CACACAAGUGGCCCCCAACACU | >hsa-miR-4731-3p MIMAT0019854 |
| 454 | ACCAGGCAAGAAAUAUUGU | >hsa-miR-4645-5p MIMAT0019705 |
| 455 | UGCUUAAGUUGUACCAAGUAU | >hsa-miR-4720-3p MIMAT0019834 |
| 456 | GCUUGUCGCUGCGGUGUUGCU | >hsa-miR-3655 MIMAT0018075 |
| 457 | GGCUUUCUAGUCUCAGCUCUCC | >hsa-miR-3160-5p MIMAT0019212 |
| 458 | GUGCCAGCUGCAGUGGGGGAG | >hsa-miR-1202 MIMAT0005865 |

TABLE 1-continued

Human microRNA sequences

| NO | Sequence(5' to 3') | ID and accession |
|---|---|---|
| 459 | UGGAGGAGAAGGAAGGUGAUG | >hsa-miR-765 MIMAT0003945 |
| 460 | UCUAGUAAGAGUGGCAGUCGA | >hsa-miR-628-3p MIMAT0003297 |
| 461 | CCGGCAUGUCCAGGGCA | >hsa-miR-4304 MIMAT0016854 |
| 462 | CCCGGACAGGCGUUCGUGCGACGU | >hsa-miR-3687 MIMAT0018115 |
| 463 | GAAGAACUGUUGCAUUUGCCCU | >hsa-miR-4511 MIMAT0019048 |
| 464 | UUUAAGAAAACACCAUGGAGAU | >hsa-miR-3658 MIMAT0018078 |
| 465 | UCGAGGACUGGUGGAAGGGCCUU | >hsa-miR-3131 MIMAT0014996 |
| 466 | CAUGCCUUGAGUGUAGGACCGU | >hsa-miR-532-5p MIMAT0002888 |
| 467 | AGGGCCCCCCCUCAAUCCUGU | >hsa-miR-296-5p MIMAT0000690 |
| 468 | CGGGUAGAGAGGGCAGUGGGAGG | >hsa-miR-197-5p MIMAT0022691 |
| 469 | CUCCUGACUCCAGGUCCUGUGU | >hsa-miR-378a-5p MIMAT0000731 |
| 470 | CAAUCACUAACUCCACUGCCAU | >hsa-miR-34b-3p MIMAT0004676 |
| 471 | UUCUCCAAAAGGGAGCACUUUC | >hsa-miR-519e-5p MIMAT0002828 |
| 472 | UGAGUACCGCCAUGUCUGUUGGG | >hsa-miR-1911-5p MIMAT0007885 |
| 473 | ACUGGAAUUGGAGUCAAAA | >hsa-miR-6128 MIMAT0024611 |
| 474 | UAAAGUGCUUAUAGUGCAGGUAG | >hsa-miR-20a-5p MIMAT0000075 |
| 475 | CUCAAACCGGCUGUGCCUGUGG | >hsa-miR-6715b-3p MIMAT0025843 |
| 476 | UAUCCAGCUUGUUACUAUAUGC | >hsa-miR-5586-5p MIMAT0022287 |
| 477 | AAAAGUGCUUACAGUGCAGGUAG | >hsa-miR-106a-5p MIMAT0000103 |
| 478 | AUCGCUUUACCAUUCAUGUU | >hsa-miR-4790-5p MIMAT0019961 |
| 479 | AACUCUGACCCCUUAGGUUGAU | >hsa-miR-4714-5p MIMAT0019822 |
| 480 | UGUGGGAUCUGGAGGCAUCUGG | >hsa-miR-4654 MIMAT0019720 |
| 481 | CAACACCAGUCGAUGGGCUGU | >hsa-miR-21-3p MIMAT0004494 |
| 482 | CUCCCACAUGCAGGGUUUGCA | >hsa-miR-188-3p MIMAT0004613 |
| 483 | AUGUGCCUGAGGGAGUAAGACA | >hsa-miR-550b-2-5p MIMAT0022737 |
| 484 | UGGUCUGCAAAGAGAUGACUGU | >hsa-miR-4527 MIMAT0019066 |
| 485 | AUUGUCCUUGCUGUUUGGAGAU | >hsa-miR-2355-3p MIMAT0017950 |
| 486 | UGUUCUCUUUGCCAAGGACAG | >hsa-miR-2117 MIMAT0011162 |
| 487 | GUUGUGUCAGUUUAUCAAAC | >hsa-miR-599 MIMAT0003267 |
| 488 | UCAGUGCAUCACAGAACUUUGU | >hsa-miR-148b-3p MIMAT0000759 |
| 489 | UAAUUUUAUGUAUAAGCUAGU | >hsa-miR-590-3p MIMAT0004801 |
| 490 | GGCUGGGUGCUCUUGUGCAGU | >hsa-miR-5589-5p MIMAT0022297 |
| 491 | CAAAGACUGCAAUUACUUUUGCG | >hsa-miR-548u MIMAT0015013 |
| 492 | AACCCGUAGAUCCGAACUUGUG | >hsa-miR-100-5p MIMAT0000098 |
| 493 | UCAAGUAGUUUCAUGAUAAAGG | >hsa-miR-5697 MIMAT0022490 |
| 494 | UCUGAGUUCCUGGAGCCUGGUCU | >hsa-miR-4682 MIMAT0019767 |
| 495 | CCUGCUGGUCAGGAGUGGAUACUG | >hsa-miR-3692-5p MIMAT0018121 |
| 496 | CAGCAGUGCGCAGGGCUG | >hsa-miR-4519 MIMAT0019056 |

TABLE 1-continued

Human microRNA sequences

| NO | Sequence(5' to 3') | ID and accession |
|---|---|---|
| 497 | AUUCUAAGUGCCUUGGCC | >hsa-miR-4263 MIMAT0016898 |
| 498 | AGCUACAGUUACUUUUGCACCA | >hsa-miR-548v MIMAT0015020 |
| 499 | UGACCUGGGACUCGGACAGCUG | >hsa-miR-3661 MIMAT0018082 |
| 500 | UGGAUAUGAUGACUGAAA | >hsa-miR-4791 MIMAT0019963 |
| 501 | CCUGGACACCGCUCAGCCGGCCG | >hsa-miR-4638-3p MIMAT0019696 |
| 502 | UGCCUGUCUACACUUGCUGUGC | >hsa-miR-214-5p MIMAT0004564 |
| 503 | AUACAUGUCAGAUUGUAUGCC | >hsa-miR-4666a-5p MIMAT0019741 |
| 504 | ACACUUGUUGGGAUGACCUGC | >hsa-miR-6500-3p MIMAT0025455 |
| 505 | GAGGGCAGCGUGGGUGUGGCGGA | >hsa-miR-4632-5p MIMAT0022977 |
| 506 | ACUUGGGCACUGAAACAAUGUCC | >hsa-miR-635 MIMAT0003305 |
| 507 | CAGUGCAAUAGUAUUGUCAAAGC | >hsa-miR-301a-3p MIMAT0000688 |
| 508 | UGGCCCUGACUGAAGACCAGCAGU | >hsa-miR-1291 MIMAT0005881 |
| 509 | UGAUAUGUUUGAUAUUGGGUU | >hsa-miR-190b MIMAT0004929 |
| 510 | UCCAGGCAGGAGCCGGACUGGA | >hsa-miR-4673 MIMAT0019755 |
| 511 | CUCCUGAGCCAUUCUGAGCCUC | >hsa-miR-1200 MIMAT0005863 |
| 512 | AGGCAGCGGGGUGUAGUGGAUA | >hsa-miR-885-3p MIMAT0004948 |
| 513 | AGGGACUGCCUUAGGAGAAAGUU | >hsa-miR-3199 MIMAT0015084 |
| 514 | ACGGCCCAGGCGGCAUUGGUG | >hsa-miR-6075 MIMAT0023700 |
| 515 | GAAGUUGCCCAUGUUAUUUUCG | >hsa-miR-495-5p MIMAT0022924 |
| 516 | UAGGACUAGAUGUUGGAAUUA | >hsa-miR-4759 MIMAT0019905 |
| 517 | UAACGCAUAAUAUGGACAUGU | >hsa-miR-3912 MIMAT0018186 |
| 518 | CAUCUUCCAGUACAGUGUUGGA | >hsa-miR-141-5p MIMAT0004598 |
| 519 | AAAAGGCGGGAGAAGCCCCA | >hsa-miR-4484 MIMAT0019018 |
| 520 | ACUUGUAUGCUAGCUCAGGUAG | >hsa-miR-643 MIMAT0003313 |
| 521 | CACUGUUUCACCACUGGCUCUU | >hsa-miR-4676-3p MIMAT0019759 |
| 522 | UAGGACUGUGCUUGGCACAUAG | >hsa-miR-3169 MIMAT0015044 |
| 523 | UUCAUUUGGUAUAAACCGCGAUU | >hsa-miR-579 MIMAT0003244 |
| 524 | CCUAAUUUGAACACCUUCGGUA | >hsa-miR-4735-5p MIMAT0019860 |
| 525 | AAGUGCUUCCUUUUAGAGGGUU | >hsa-miR-520f MIMAT0002830 |
| 526 | UUAUCAGAAUCUCCAGGGGUAC | >hsa-miR-361-5p MIMAT0000703 |
| 527 | CCAGAGAUGGUUGCCUUCCUAU | >hsa-miR-4756-3p MIMAT0019900 |
| 528 | UGACAGCGCCCUGCCUGGCUC | >hsa-miR-2277-3p MIMAT0011777 |
| 529 | UAAAUCCCAUGGUGCCUUCUCCU | >hsa-miR-605 MIMAT0003273 |
| 530 | UUAGGGAGUAGAAGGGUGGGGAG | >hsa-miR-3162-5p MIMAT0015036 |
| 531 | GCGACCCAUACUUGGUUUCAG | >hsa-miR-551b-3p MIMAT0003233 |
| 532 | GCGGAGAGAGAAUGGGGAGC | >hsa-miR-5739 MIMAT0023116 |
| 533 | UGGGAGGGGAGAGGCAGCAAGCA | >hsa-miR-4728-5p MIMAT0019849 |
| 534 | AUCACAUUGCCAGUGAUUACCC | >hsa-miR-23c MIMAT0018000 |

TABLE 1-continued

Human microRNA sequences

| NO | Sequence(5' to 3') | ID and accession |
|---|---|---|
| 535 | ACUGGACUAGGAGUCAGAAGG | >hsa-miR-378i MIMAT0019074 |
| 536 | GCUGAACUGGGCUGAGCUGGGC | >hsa-miR-4539 MIMAT0019082 |
| 537 | AGGUUGUCCGUGGUGAGUUCGCA | >hsa-miR-323b-5p MIMAT0001630 |
| 538 | ACACAUGGGUGGCUGUGGCCU | >hsa-miR-4717-3p MIMAT0019830 |
| 539 | AAAGUGCUUCCUUUUAGAGGGU | >hsa-miR-520c-3p MIMAT0002846 |
| 540 | AUCGUGCAUCCUUUUAGAGUGU | >hsa-miR-517c-3p MIMAT0002866 |
| 541 | GCAGCAUUCAUGUCCC | >hsa-miR-4310 MIMAT0016862 |
| 542 | CUGCAAAGGGAAGCCCUUUC | >hsa-miR-518a-5p MIMAT0005457 |
| 543 | AGGGGUGGUGUUGGGACAGCUCCGU | >hsa-miR-608 MIMAT0003276 |
| 544 | UGGGAGCUAAGCUAUGGGUAU | >hsa-miR-5591-5p MIMAT0022301 |
| 545 | UAUGGAGUGGACUUUCAGCUGGC | >hsa-miR-6514-5p MIMAT0025484 |
| 546 | UCUCUCGGCUCCUCGCGGCUC | >hsa-miR-3615 MIMAT0017994 |
| 547 | UCCAGUACCACGUGUCAGGGCCA | >hsa-miR-770-5p MIMAT0003948 |
| 548 | GCAGUUCUGAGCACAGUACAC | >hsa-miR-4277 MIMAT0016908 |
| 549 | UGAUUGGUACGUCUGUGGGUAG | >hsa-miR-509-3p MIMAT0002881 |
| 550 | CGCGGGUCGGGUCUGCAGG | >hsa-miR-3621 MIMAT0018002 |
| 551 | ACCUGCCAGCACCUCCCUGCAG | >hsa-miR-4722-3p MIMAT0019837 |
| 552 | GCGGGGCUGGGCGCGCG | >hsa-miR-4508 MIMAT0019045 |
| 553 | UUAACUCCUUUCACACCCAUGG | >hsa-miR-4764-3p MIMAT0019915 |
| 554 | GAGGAAACUGAAGCUGAGAGGG | >hsa-miR-4496 MIMAT0019031 |
| 555 | UUCUGGAUAUGAAGACAAUCAA | >hsa-miR-4782-5p MIMAT0019944 |
| 556 | UCAAAAUGUAGAGGAAGACCCCA | >hsa-miR-4698 MIMAT0019793 |
| 557 | UCAAAACUGAGGGGCAUUUUCU | >hsa-miR-1323 MIMAT0005795 |
| 558 | CAACUAGACUGUGAGCUUCUAG | >hsa-miR-708-3p MIMAT0004927 |
| 559 | GCUAAGGAAGUCCUGUGCUCAG | >hsa-miR-4521 MIMAT0019058 |
| 560 | UGAGGUAGUAGUUUGUGCUGUU | >hsa-let-7i-5p MIMAT0000415 |
| 561 | CAAAAACUGCAAUUACUUUCA | >hsa-miR-548ae MIMAT0018954 |
| 562 | GUGCAUUGUAGUUGCAUUGCA | >hsa-miR-33a-5p MIMAT0000091 |
| 563 | CCCCUGGGCCGGCCUUGG | >hsa-miR-4292 MIMAT0016919 |
| 564 | AUUCCUAGAAAUUGUUCAUA | >hsa-miR-384 MIMAT0001075 |
| 565 | GUGUUGAAACAAUCUCUACUG | >hsa-miR-653 MIMAT0003328 |
| 566 | UCAGGCCUCUUUCUACCUU | >hsa-miR-4650-5p MIMAT0019713 |
| 567 | UAGGUUAUCCGUGUUGCCUUCG | >hsa-miR-154-5p MIMAT0000452 |
| 568 | ACCACUGCACUCCAGCCUGAG | >hsa-miR-1273g-3p MIMAT0022742 |
| 569 | CAGCCACAACUACCCUGCCACU | >hsa-miR-449b-3p MIMAT0009203 |
| 570 | AAUUUACUCUGCAAUCUUCUCC | >hsa-miR-4699-3p MIMAT0019795 |
| 571 | CAUCAGCACCCUAUGUCCUUUCU | >hsa-miR-3617-3p MIMAT0022966 |
| 572 | UAUGGAGGUUCUAGACCAUGUU | >hsa-miR-4802-5p MIMAT0019981 |

TABLE 1-continued

Human microRNA sequences

| NO | Sequence(5' to 3') | ID and accession |
|---|---|---|
| 573 | AGUGGGAGGCCAGGGCACGGCA | >hsa-miR-1233-1-5p MIMAT0022943 |
| 574 | ACUAAAGGAUAUAGAAGGUUUU | >hsa-miR-4509 MIMAT0019046 |
| 575 | AGGGCAUGUCCAGGGGGU | >hsa-miR-4253 MIMAT0016882 |
| 576 | GGGGAGCGAGGGGCGGGGC | >hsa-miR-6090 MIMAT0023715 |
| 577 | UCACCAGCCCUGUGUUCCCUAG | >hsa-miR-1226-3p MIMAT0005577 |
| 578 | UCGGAUCCGUCUGAGCUUGGCU | >hsa-miR-127-3p MIMAT0000446 |
| 579 | CUUGGAUUUUCCUGGGCCUCAG | >hsa-miR-5004-3p MIMAT0021028 |
| 580 | GUUUUACCACCUCCAGGAGACU | >hsa-miR-2681-5p MIMAT0013515 |
| 581 | UAUGUCUGCUGACCAUCACCUU | >hsa-miR-654-3p MIMAT0004814 |
| 582 | AUCACAUUGCCAGGGAUUACC | >hsa-miR-23b-3p MIMAT0000418 |
| 583 | UGUUGUACUUUUUUUUUUGUUC | >hsa-miR-3613-5p MIMAT0017990 |
| 584 | GUUUCACCAUGUUGGUCAGGC | >hsa-miR-5096 MIMAT0020603 |
| 585 | UCUGUGAUAGAGAUUCUUUGCU | >hsa-miR-4679 MIMAT0019763 |
| 586 | UAAUACUGUCUGGUAAAACCGU | >hsa-miR-429 MIMAT0001536 |
| 587 | CCACUUGGAUCUGAAGGCUGCCC | >hsa-miR-3614-5p MIMAT0017992 |
| 588 | UCAGUUCCAGGCCAACCAGGCU | >hsa-miR-584-3p MIMAT0022708 |
| 589 | CACCGGGGAUGGCAGAGGGUCG | >hsa-miR-4655-5p MIMAT0019721 |
| 590 | UGAUUGUAGCCUUUUGGAGUAGA | >hsa-miR-508-3p MIMAT0002880 |
| 591 | CCAAAUCUUGAUCAGAAGCCU | >hsa-miR-4762-5p MIMAT0019910 |
| 592 | CUUCCGCCCCGCCGGGCGUCG | >hsa-miR-718 MIMAT0012735 |
| 593 | AGCUGUACCUGAAACCAAGCA | >hsa-miR-4718 MIMAT0019831 |
| 594 | CAUCUUACUGGGCAGCAUUGGA | >hsa-miR-200b-5p MIMAT0004571 |
| 595 | CUGCCCUAGUCUAGCUGAAGCU | >hsa-miR-3157-3p MIMAT0019210 |
| 596 | AAAAGUAAUUGUGGUUUUUGCC | >hsa-miR-548d-5p MIMAT0004812 |
| 597 | CUAUACAACUUACUACUUUCCC | >hsa-miR-98-3p MIMAT0022842 |
| 598 | AAUCCUUGCUACCUGGGU | >hsa-miR-500b MIMAT0016925 |
| 599 | CCUAGUAGGUGUCCAGUAAGUGU | >hsa-miR-325 MIMAT0000771 |
| 600 | CGCAUCCCCUAGGGCAUUGGUGU | >hsa-miR-324-5p MIMAT0000761 |
| 601 | AACCCCUAAGGCAACUGGAUGG | >hsa-miR-5195-5p MIMAT0021126 |
| 602 | GAGUGUAGUUCUGAGCAGAGC | >hsa-miR-4280 MIMAT0016911 |
| 603 | GGUAUCCGUUUGGGAUGGU | >hsa-miR-3713 MIMAT0018164 |
| 604 | CCUAUUCUUGGUUACUUGCACG | >hsa-miR-26a-1-3p MIMAT0004499 |
| 605 | UGUGAGGUUGGCAUUGUUGUCU | >hsa-miR-1294 MIMAT0005884 |
| 606 | AGUUGCCAGGGCUGCCUUUGGU | >hsa-miR-6501-5p MIMAT0025458 |
| 607 | CUCAUUUAAGUAGUCUGAUGCC | >hsa-miR-5696 MIMAT0022489 |
| 608 | CGUCCCACCCCCCACUCCUGU | >hsa-miR-4433-5p MIMAT0020956 |
| 609 | UUCAGCCAGGCUAGUGCAGUCU | >hsa-miR-3157-5p MIMAT0015031 |
| 610 | AAAAACCACAAUUACUUUUGCACCA | >hsa-miR-548aa MIMAT0018447 |

TABLE 1-continued

Human microRNA sequences

| NO | Sequence(5' to 3') | ID and accession |
|---|---|---|
| 611 | AUUGCCUAACAUGUGCCAGAA | >hsa-miR-4774-3p MIMAT0019930 |
| 612 | AACGCCAUUAUCACACUAAAUA | >hsa-miR-122-3p MIMAT0004590 |
| 613 | AAUCAUACACGGUUGACCUAUU | >hsa-miR-154-3p MIMAT0000453 |
| 614 | CUGUGCGUGUGACAGCGGCUGA | >hsa-miR-210 MIMAT0000267 |
| 615 | CUGGAGAUAUGGAAGAGCUGUGU | >hsa-miR-1270 MIMAT0005924 |
| 616 | GAGUUCUACAGUCAGAC | >hsa-miR-3168 MIMAT0015043 |
| 617 | CUGGGAUCUCCGGGGUCUUGGUU | >hsa-miR-769-3p MIMAT0003887 |
| 618 | CCUGCGUGUUUUCUGUCCAA | >hsa-miR-4520b-5p MIMAT0020299 |
| 619 | UGAGAUGAAGCACUGUAGCUC | >hsa-miR-143-3p MIMAT0000435 |
| 620 | CAGCCCCACAGCCUCAGA | >hsa-miR-4323 MIMAT0016875 |
| 621 | CCUGACCCACCCCCUCCCGCAG | >hsa-miR-4750-3p MIMAT0022979 |
| 622 | CUGGGGGACGCGUGAGCGCGAGC | >hsa-miR-4665-5p MIMAT0019739 |
| 623 | UGCUUCCUUUCAGAGGGU | >hsa-miR-516b-3p MIMAT0002860 |
| 624 | UAAGUGCUUCCAUGUUUUGGUGA | >hsa-miR-302a-3p MIMAT0000684 |
| 625 | UUGUUCUUUGGUCUUUCAGCCA | >hsa-miR-4677-5p MIMAT0019760 |
| 626 | UACCCUGUAGAACCGAAUUUGUG | >hsa-miR-10b-5p MIMAT0000254 |
| 627 | AAGUUCUGUUAUACACUCAGGC | >hsa-miR-148b-5p MIMAT0004699 |
| 628 | GCAGUAGUGUAGAGAUUGGUUU | >hsa-miR-3129-5p MIMAT0014992 |
| 629 | GCUGGUGACAUGAGAGGC | >hsa-miR-4299 MIMAT0016851 |
| 630 | CUGCCAGCCCCGUUCCAGGGCA | >hsa-miR-3972 MIMAT0019357 |
| 631 | AAGUGCUGUCAUAGCUGAGGUC | >hsa-miR-512-3p MIMAT0002823 |
| 632 | GGAUCCGAGUCACGGCACCA | >hsa-miR-4454 MIMAT0018976 |
| 633 | CAAUGGCACAAACUCAUUCUUGA | >hsa-miR-5197-5p MIMAT0021130 |
| 634 | AGCUCGGUCUGAGGCCCCUCAGU | >hsa-miR-423-3p MIMAT0001340 |
| 635 | CCAGUCCUGUGCCUGCCGCCU | >hsa-miR-1910 MIMAT0007884 |
| 636 | CUAGGUAUGGUCCCAGGGAUCC | >hsa-miR-331-5p MIMAT0004700 |
| 637 | AAUCGUACAGGGUCAUCCACUU | >hsa-miR-487b MIMAT0003180 |
| 638 | GGCGGCGGCGGAGGCGGGGG | >hsa-miR-3960 MIMAT0019337 |
| 639 | UUCUGAGCUGAGGACAG | >hsa-miR-4303 MIMAT0016856 |
| 640 | UGGGUAGAGAAGGAGCUCAGAGGA | >hsa-miR-3132 MIMAT0014997 |
| 641 | UGAGCUAAAUGUGUGCUGGGA | >hsa-miR-610 MIMAT0003278 |
| 642 | CAAAGUGCCUCCCUUUAGAGUG | >hsa-miR-519d MIMAT0002853 |
| 643 | GGUCCAGAGGGGAGAUAGGUUC | >hsa-miR-198 MIMAT0000228 |
| 644 | UUUAGAUUGAACAUGAAGUUAG | >hsa-miR-4760-5p MIMAT0019906 |
| 645 | UGUGGUAGAUAUAUGCACGAU | >hsa-miR-4536-5p MIMAT0019078 |
| 646 | AGGCAAGAUGCUGGCAUAGCU | >hsa-miR-31-5p MIMAT0000089 |
| 647 | AAUAAUAUCACAGUAGGUGU | >hsa-miR-5692b MIMAT0022497 |
| 648 | AUAUGUAUAUGUGACUGCUACU | >hsa-miR-3924 MIMAT0018199 |

TABLE 1-continued

| Human microRNA sequences | | |
|---|---|---|
| NO | Sequence(5' to 3') | ID and accession |
| 649 | AACAUUCAUUGUUGUCGGUGGGU | >hsa-miR-181d MIMAT0002821 |
| 650 | AGACCCUGGUCUGCACUCUAUC | >hsa-miR-504 MIMAT0002875 |
| 651 | CCAGUUACCGCUUCCGCUACCGC | >hsa-miR-935 MIMAT0004978 |
| 652 | GCUGGGCAGGGCUUCUGAGCUCCUU | >hsa-miR-612 MIMAT0003280 |
| 653 | UGGUGGGCACAGAAUCUGGACU | >hsa-miR-541-3p MIMAT0004920 |
| 654 | GAAAGCGCUUCUCUUUAGAGG | >hsa-miR-518f-3p MIMAT0002842 |
| 655 | UUUAAGCAGGAAAUAGAAUUUA | >hsa-miR-4503 MIMAT0019039 |
| 656 | GGGGCUGGGGCCGGGGCCGAGC | >hsa-miR-762 MIMAT0010313 |
| 657 | CUGGUACAGGCCUGGGGGACAG | >hsa-miR-150-3p MIMAT0004610 |
| 658 | UCACUACCUGACAAUACAGU | >hsa-miR-4999-3p MIMAT0021018 |
| 659 | GAAAGUAAUUGCUGUUUUUGCC | >hsa-miR-548aq-5p MIMAT0022263 |
| 660 | UACCCAGUCUCCGGUGCAGCC | >hsa-miR-3130-5p MIMAT0014995 |
| 661 | CAUUAUUACUUUUGGUACGCG | >hsa-miR-126-5p MIMAT0000444 |
| 662 | CUGGGAGGUGUGAUAUUGUGGU | >hsa-miR-3689c MIMAT0019007 |
| 663 | CAAACCACACUGUGGUGUUAGA | >hsa-miR-497-3p MIMAT0004768 |
| 664 | GUCACUGAUGUCUGUAGCUGAG | >hsa-miR-4420 MIMAT0018933 |
| 665 | AGUUAGGAUUAGGUCGUGGAA | >hsa-miR-1258 MIMAT0005909 |
| 666 | CCCAGAUAAUGGCACUCUCAA | >hsa-miR-488-5p MIMAT0002804 |
| 667 | ACUGGGAUGUCACUGAAUAUGGU | >hsa-miR-6506-5p MIMAT0025468 |
| 668 | CCGCUUUCUGAGCUGGAC | >hsa-miR-4315 MIMAT0016866 |
| 669 | UGUGGACAGUGAGGUAGAGGGAGU | >hsa-miR-3138 MIMAT0015006 |
| 670 | AAAGAUGGACAAUUGGCUAAAU | >hsa-miR-4662b MIMAT0019736 |
| 671 | CUGUCCUAAGGUUGUUGAGUU | >hsa-miR-676-3p MIMAT0018204 |
| 672 | AAGGCCUUUCUGAACCUUCAGA | >hsa-miR-3142 MIMAT0015011 |
| 673 | UGGGCCAUGCAUUUCUAGAACU | >hsa-miR-6508-3p MIMAT0025473 |
| 674 | AUCGGGCCCUCGGCGCCGG | >hsa-miR-3181 MIMAT0015061 |
| 675 | UGGGCAGGGGCUUAUUGUAGGAG | >hsa-miR-6721-5p MIMAT0025852 |
| 676 | CAGGUAGAUAUUUGAUAGGCAU | >hsa-miR-3927-3p MIMAT0018202 |
| 677 | UCCUCCUCUACCUCAUCCCAGU | >hsa-miR-5193 MIMAT0021124 |
| 678 | AUCAUAGAGGAAAAUCCAUGUU | >hsa-miR-376b-3p MIMAT0002172 |
| 679 | CAGUUGGGUCUAGGGGUCAGGA | >hsa-miR-4259 MIMAT0016880 |
| 680 | GGGCGCCUGUGAUCCCAAC | >hsa-miR-566 MIMAT0003230 |
| 681 | UGGAGACGCGGCCCUGUUGGAGU | >hsa-miR-139-3p MIMAT0004552 |
| 682 | GCUAGUCCUGACUCAGCCAGU | >hsa-miR-554 MIMAT0003217 |
| 683 | CCUGCGUGUUUUCUGUCCAA | >hsa-miR-4520a-5p MIMAT0019235 |
| 684 | ACUCAAACUGUGGGGGCACU | >hsa-miR-371a-5p MIMAT0004687 |
| 685 | CUUAUGCAAGAUUCCCUUCUAC | >hsa-miR-491-3p MIMAT0004765 |
| 686 | UCUUCUUCCUUUGCAGAGUUGA | >hsa-miR-4778-3p MIMAT0019937 |

TABLE 1-continued

Human microRNA sequences

| NO | Sequence(5' to 3') | ID and accession |
|---|---|---|
| 687 | CUGCCAUGUCUAAGAAGAAAAC | >hsa-miR-4659a-5p MIMAT0019726 |
| 688 | AUGGCAUCGUCCCCUGGUGGCU | >hsa-miR-4642 MIMAT0019702 |
| 689 | UCUUCUCUGUUUUGGCCAUGUG | >hsa-miR-942 MIMAT0004985 |
| 690 | UCAGUGCAUGACAGAACUUGG | >hsa-miR-152 MIMAT0000438 |
| 691 | ACUGGACUUAGGGUCAGAAGGC | >hsa-miR-422a MIMAT0001339 |
| 692 | AGGAAACAGGGACCCA | >hsa-miR-4261 MIMAT0016890 |
| 693 | AACAUAGAGGAAAUUCCACGU | >hsa-miR-376c-3p MIMAT0000720 |
| 694 | GUACCUUCUGGUUCAGCUAGU | >hsa-miR-4724-3p MIMAT0019842 |
| 695 | UGAGACAGGCUUAUGCUGCUAU | >hsa-miR-4524a-3p MIMAT0019063 |
| 696 | GGAGACUGAUGAGUUCCCGGGA | >hsa-miR-873-3p MIMAT0022717 |
| 697 | UGUAAACAUCCUACACUCAGCU | >hsa-miR-30b-5p MIMAT0000420 |
| 698 | UUAGAACGUUUUAGGGUCAAAU | >hsa-miR-5687 MIMAT0022478 |
| 699 | UGCCCCACCUGCUGACCACCCUC | >hsa-miR-4758-3p MIMAT0019904 |
| 700 | AUAAAGCUAGAUAACCGAAAGU | >hsa-miR-9-3p MIMAT0000442 |
| 701 | AACACACCUAUUCAAGGAUUCA | >hsa-miR-362-3p MIMAT0004683 |
| 702 | AUGGUACCCUGGCAUACUGAGU | >hsa-miR-1263 MIMAT0005915 |
| 703 | AGGGGGCGCAGUCACUGACGUG | >hsa-miR-4697-5p MIMAT0019791 |
| 704 | UAUCAUGGAGUUGGUAAAGCAC | >hsa-miR-2681-3p MIMAT0013516 |
| 705 | UUCCAGCCCUUCUAAUGGUAGG | >hsa-miR-6512-3p MIMAT0025481 |
| 706 | GGUAGUGAGUUAUCAGCUAC | >hsa-miR-6073 MIMAT0023698 |
| 707 | AAAAGCUGGGCUGAGAGGCG | >hsa-miR-4429 MIMAT0018944 |
| 708 | UGUGUGGAUCCUGGAGGAGGCA | >hsa-miR-3911 MIMAT0018185 |
| 709 | UUAGACCUAGUACACGUCCUU | >hsa-miR-3684 MIMAT0018112 |
| 710 | AGUGAAUGAUGGGUUCUGACC | >hsa-miR-1257 MIMAT0005908 |
| 711 | UGCAUCAGGCCAGAAGACAUGAG | >hsa-miR-4711-5p MIMAT0019816 |
| 712 | AAAAUGAAAUGAGCCCAGCCCA | >hsa-miR-3646 MIMAT0018065 |
| 713 | AAGGGGCUGGGGGAGCACA | >hsa-miR-6085 MIMAT0023710 |
| 714 | ACUGGGGAGCAGAAGGAGAACC | >hsa-miR-4667-5p MIMAT0019743 |
| 715 | CCAGGAGGCGGAGGAGGUGGAG | >hsa-miR-4459 MIMAT0018981 |
| 716 | UGAGAACUGAAUUCCAUAGGCU | >hsa-miR-146b-5p MIMAT0002809 |
| 717 | ACUUCACCUGGUCCACUAGCCGU | >hsa-miR-412 MIMAT0002170 |
| 718 | AGGUGUGUCUGUAGAGUCC | >hsa-miR-3650 MIMAT0018070 |
| 719 | ACUGGACUUGGAGUCAGAAGG | >hsa-miR-378a-3p MIMAT0000732 |
| 720 | AACUCACGAAGUAUACCGAAGU | >hsa-miR-4798-3p MIMAT0019975 |
| 721 | GUAUACACCUGAUAUGUGUAUG | >hsa-miR-4789-5p MIMAT0019959 |
| 722 | AACCAGCACCCCAACUUUGGAC | >hsa-miR-634 MIMAT0003304 |
| 723 | UAUCUGCUGGGCUUUCUGGUGUU | >hsa-miR-4686 MIMAT0019773 |
| 724 | UUUGGUCCCCUUCAACCAGCUA | >hsa-miR-133b MIMAT0000770 |

TABLE 1-continued

Human microRNA sequences

| NO | Sequence(5' to 3') | ID and accession |
|---|---|---|
| 725 | GCUGGUCUGCGUGGUGCUCGG | >hsa-miR-3663-5p MIMAT0018084 |
| 726 | CAAAAACUGCAGUUACUUUUGC | >hsa-miR-548ah-3p MIMAT0020957 |
| 727 | AGUAUGUUCUUCCAGGACAGAAC | >hsa-miR-567 MIMAT0003231 |
| 728 | CAUGCUGACCUCCCUCCUGCCCCAG | >hsa-miR-4728-3p MIMAT0019850 |
| 729 | UGGGGACGUAGCUGGCCAGACAG | >hsa-miR-3191-3p MIMAT0015075 |
| 730 | CUUCCGGUCUGUGAGCCCCGUC | >hsa-miR-4664-3p MIMAT0019738 |
| 731 | UUGCCAUGUCUAAGAAGAA | >hsa-miR-4659b-5p MIMAT0019733 |
| 732 | AUAGCAGCAUAAGCCUGUCUC | >hsa-miR-4524b-5p MIMAT0022255 |
| 733 | GUCCGCUCGGCGGUGGCCCA | >hsa-miR-572 MIMAT0003237 |
| 734 | GCUGGUGCAAAAGUAAUGGCGG | >hsa-miR-548q MIMAT0011163 |
| 735 | UAGCAGCACAUCAUGGUUUACA | >hsa-miR-15b-5p MIMAT0000417 |
| 736 | GAGGCUGAGCUGAGGAG | >hsa-miR-4478 MIMAT0019006 |
| 737 | UGUUUUGAUAACAGUAAUGU | >hsa-miR-2052 MIMAT0009977 |
| 738 | AAUGUUUUUCCUGUUUCC | >hsa-miR-4307 MIMAT0016860 |
| 739 | AGCCGCGGGGAUCGCCGAGGG | >hsa-miR-3648 MIMAT0018068 |
| 740 | CCCUGUGCCCGGCCCACUUCUG | >hsa-miR-1914-5p MIMAT0007889 |
| 741 | CUGGCCCUCUCUGCCCUUCCGU | >hsa-miR-328 MIMAT0000752 |
| 742 | UCUCUGGGCCUGUGUCUUAGGC | >hsa-miR-330-5p MIMAT0004693 |
| 743 | GGAGGCGCAGGCUCGGAAAGGCG | >hsa-miR-3197 MIMAT0015082 |
| 744 | UCUACAGUGCACGUGUCUCCAGU | >hsa-miR-139-5p MIMAT0000250 |
| 745 | CACCCGGCUGUGUGCACAUGUGC | >hsa-miR-941 MIMAT0004984 |
| 746 | AGGAGCAGUGCCGGCCAAGGCGCC | >hsa-miR-6081 MIMAT0023706 |
| 747 | AGAAGUGGCUAAUAAUAUUGA | >hsa-miR-4795-5p MIMAT0019968 |
| 748 | CUCACUGAACAAUGAAUGCAA | >hsa-miR-181b-3p MIMAT0022692 |
| 749 | GCUCUGACUUUAUUGCACUACU | >hsa-miR-301a-5p MIMAT0022696 |
| 750 | UUAAUAUCGGACAACCAUUGU | >hsa-miR-889 MIMAT0004921 |
| 751 | GUGAGUCAGGGUGGGGCUGG | >hsa-miR-937-5p MIMAT0022938 |
| 752 | UUGCAGCUGCGGUUGUAAGGU | >hsa-miR-5047 MIMAT0020541 |
| 753 | AAAAACCACAAUUACUUUU | >hsa-miR-548ap-3p MIMAT0021038 |
| 754 | UGAGUUGGCCAUCUGAGUGAG | >hsa-miR-571 MIMAT0003236 |
| 755 | AGGACCUGCGGGACAAGAUUCUU | >hsa-miR-492 MIMAT0002812 |
| 756 | CAGGGAGGCGCUCACUCUCUGCU | >hsa-miR-4756-5p MIMAT0019899 |
| 757 | UCCGUCUCAGUUACUUUAUAGC | >hsa-miR-340-3p MIMAT0000750 |
| 758 | CGGGGAGAGAACGCAGUGACGU | >hsa-miR-3175 MIMAT0015052 |
| 759 | UGUGUCACUCGAUGACCACUGU | >hsa-miR-597 MIMAT0003265 |
| 760 | AGAGCUGAGACUAGAAAGCCCA | >hsa-miR-3160-3p MIMAT0015034 |
| 761 | CCUGCAGAGAGGAAGCCCUUC | >hsa-miR-3158-5p MIMAT0019211 |
| 762 | UCAGGCAAAGGGAUAUUUACAGA | >hsa-miR-4742-5p MIMAT0019872 |

TABLE 1-continued

Human microRNA sequences

| NO | Sequence(5' to 3') | ID and accession |
|---|---|---|
| 763 | UGCCGCCCUCUCGCUGCUCUAG | >hsa-miR-4632-3p MIMAT0019688 |
| 764 | AUUUCCCUGCCAUUCCCUUGGC | >hsa-miR-4446-5p MIMAT0019233 |
| 765 | UCGUACCGUGAGUAAUAAUGCG | >hsa-miR-126-3p MIMAT0000445 |
| 766 | AAACCGUUACCAUUACUGAGUU | >hsa-miR-451a MIMAT0001631 |
| 767 | UCCUUCUGCUCCGUCCCCAG | >hsa-miR-1237-3p MIMAT0005592 |
| 768 | AAAGGUAAUUGUGGUUUCUGC | >hsa-miR-548ag MIMAT0018969 |
| 769 | AGCUCUGCUGCUCACUGGCAGU | >hsa-miR-3194-3p MIMAT0019218 |
| 770 | AAAUAUGAUGAAACUCACAGCUGAG | >hsa-miR-4517 MIMAT0019054 |
| 771 | GGUGGGGCAAUGGGAUCAGGU | >hsa-miR-3151 MIMAT0015024 |
| 772 | CUCCUACAUAUUAGCAUUAACA | >hsa-miR-155-3p MIMAT0004658 |
| 773 | UCUGGCAAGUAAAAAACUCUCAU | >hsa-miR-3128 MIMAT0014991 |
| 774 | ACAACAGUGACUUGCUCUCCAA | >hsa-miR-4709-5p MIMAT0019811 |
| 775 | CAGGAUCCACAGAGCUAGUCCA | >hsa-miR-4661-3p MIMAT0019730 |
| 776 | AGCGCGGGCUGAGCGCUGCCAGUC | >hsa-miR-2277-5p MIMAT0017352 |
| 777 | CGGGCGUGGUGGUGGGGG | >hsa-miR-1268a MIMAT0005922 |
| 778 | CUCUAGAGGGAAGCACUUUCUG | >hsa-miR-526a MIMAT0002845 |
| 779 | CAGGAAGGAUUUAGGGACAGGC | >hsa-miR-4476 MIMAT0019003 |
| 780 | UAGAGGAAGCUGUGGAGAGA | >hsa-miR-3125 MIMAT0014988 |
| 781 | UGGGCUGGCAGGGCAAGUGCUG | >hsa-miR-4498 MIMAT0019033 |
| 782 | CUCGAGUUGGAAGAGGCG | >hsa-miR-4444 MIMAT0018962 |
| 783 | AGCAGCAUUGUACAGGGCUAUGA | >hsa-miR-103a-3p MIMAT0000101 |
| 784 | GGUGGGGGGUGUUGUUUU | >hsa-miR-4472 MIMAT0018999 |
| 785 | CUGCGCAAGCUACUGCCUUGCU | >hsa-let-7i-3p MIMAT0004585 |
| 786 | AAUCCUUUGUCCCUGGGUGAGA | >hsa-miR-501-5p MIMAT0002872 |
| 787 | UGAGUCAGCAACAUAUCCCAUG | >hsa-miR-5702 MIMAT0022495 |
| 788 | CCCAGUGUUUAGACUAUCUGUUC | >hsa-miR-199b-5p MIMAT0000263 |
| 789 | AGGGGUGCUAUCUGUGAUUGA | >hsa-miR-342-5p MIMAT0004694 |
| 790 | UGCAAGACGGAUACUGUCAUCU | >hsa-miR-4696 MIMAT0019790 |
| 791 | AAAGCGCUUCCCUUCAGAGUG | >hsa-miR-518e-3p MIMAT0002861 |
| 792 | CUCUCACCACUGCCCUCCCACAG | >hsa-miR-1229-3p MIMAT0005584 |
| 793 | UGCUGGCUCAUUUCAUAUGUGU | >hsa-miR-5580-5p MIMAT0022273 |
| 794 | UCUAUACAGACCCUGGCUUUUC | >hsa-miR-1284 MIMAT0005941 |
| 795 | AGACACAUUUGGAGAGGGAACC | >hsa-miR-642a-3p MIMAT0020924 |
| 796 | GUGGGUAGGGUUUGGGGGAGAGCG | >hsa-miR-1229-5p MIMAT0022942 |
| 797 | AGAAGAAGGCGGUCGGUCUGCGG | >hsa-miR-3185 MIMAT0015065 |
| 798 | CUGCAAAGGGAAGCCCUUUC | >hsa-miR-527 MIMAT0002862 |
| 799 | UCAGGGAGUCAGGGGAGGGC | >hsa-miR-4270 MIMAT0016900 |
| 800 | AAGACUGAGAGGAGGGA | >hsa-miR-4499 MIMAT0019035 |

TABLE 1-continued

Human microRNA sequences

| NO | Sequence(5' to 3') | ID and accession |
|---|---|---|
| 801 | UAGCGGGGAUUCCAAUAUUGG | >hsa-miR-4781-5p MIMAT0019942 |
| 802 | GAUGAGCUCAUUGUAAUAUGAG | >hsa-miR-556-5p MIMAT0003220 |
| 803 | CAGGGAGGUGAAUGUGAU | >hsa-miR-1321 MIMAT0005952 |
| 804 | UCAAUCACUUGGUAAUUGCUGU | >hsa-miR-4705 MIMAT0019805 |
| 805 | CCUAGACACCUCCAGUUC | >hsa-miR-4305 MIMAT0016857 |
| 806 | AAUCAGUGAAUGCCUUGAACCU | >hsa-miR-5094 MIMAT0021086 |
| 807 | CUAAGAAGUUGACUGAAG | >hsa-miR-3653 MIMAT0018073 |
| 808 | CUCUAGAGGGAAGCGCUUUCUG | >hsa-miR-519a-5p MIMAT0005452 |
| 809 | GCAGAGUGCAAACAAUUUUGAC | >hsa-miR-759 MIMAT0010497 |
| 810 | GGAUUCCUGGAAAUACUGUUCU | >hsa-miR-145-3p MIMAT0004601 |
| 811 | GGUUCUUAGCAUAGGAGGUCU | >hsa-miR-2116-5p MIMAT0011160 |
| 812 | CGGGCUGUCCGGAGGGGUCGGCU | >hsa-miR-4741 MIMAT0019871 |
| 813 | AUAAGACGAACAAAAGGUUUGU | >hsa-miR-208b MIMAT0004960 |
| 814 | ACCUUGCCUUGCUGCCCGGGCC | >hsa-miR-1915-5p MIMAT0007891 |
| 815 | CAAGUCACUAGUGGUUCCGUU | >hsa-miR-224-5p MIMAT0000281 |
| 816 | CAAAAGUGAUCGUGGUUUUUG | >hsa-miR-548t-5p MIMAT0015009 |
| 817 | UAGCACCAUUUGAAAUCGGUUA | >hsa-miR-29c-3p MIMAT0000681 |
| 818 | UCCUCAUCACACUGCACCUUAG | >hsa-miR-6072 MIMAT0023697 |
| 819 | UCCUGCGCGUCCCAGAUGCCC | >hsa-miR-1539 MIMAT0007401 |
| 820 | UGAGGUAGUAGAUUGUAUAGUU | >hsa-let-7f-5p MIMAT0000067 |
| 821 | AAGACGGGAGGAAAGAAGGGAG | >hsa-miR-483-5p MIMAT0004761 |
| 822 | UUGGAAGCUUGGACCAACUAGCUG | >hsa-miR-6079 MIMAT0023704 |
| 823 | UGAGUGGGGCUCCCGGGACGGCG | >hsa-miR-4745-5p MIMAT0019878 |
| 824 | CUGCAGGCAGAAGUGGGGCUGACA | >hsa-miR-6511b-5p MIMAT0025847 |
| 825 | AGAAGUAAUUGCGGUUUUGCCA | >hsa-miR-548ax MIMAT0022474 |
| 826 | CAUCUCUAAGGAACUCCCCCAA | >hsa-miR-3675-3p MIMAT0018099 |
| 827 | UACAGUAUAGAUGAUGUACU | >hsa-miR-144-3p MIMAT0000436 |
| 828 | UCUGGGGAUGAGGACAGUGUGU | >hsa-miR-4700-5p MIMAT0019796 |
| 829 | AGAGGUAGUAGGUUGCAUAGUU | >hsa-let-7d-5p MIMAT0000065 |
| 830 | GCCGGACAAGAGGGAGG | >hsa-miR-4442 MIMAT0018960 |
| 831 | AGGGCAUAGGAGAGGGUUGAUAU | >hsa-miR-3945 MIMAT0018361 |
| 832 | UUCUCCCACUACCAGGCUCCCA | >hsa-miR-4713-5p MIMAT0019820 |
| 833 | AGAUGUCCAGCCACAAUUCUCG | >hsa-miR-2964a-5p MIMAT0019747 |
| 834 | ACAAAGUGCUUCCCUUUAGAGU | >hsa-miR-520h MIMAT0002867 |
| 835 | CGAGGGCAUUUCAUGAUGCAGGC | >hsa-miR-3616-3p MIMAT0017996 |
| 836 | UUAAGACUUGCAGUGAUGUUU | >hsa-miR-499a-5p MIMAT0002870 |
| 837 | CCCCGGGGAGCCCGGCG | >hsa-miR-4532 MIMAT0019071 |
| 838 | GAAAGAGAGCUGAGUGUG | >hsa-miR-4311 MIMAT0016863 |

TABLE 1-continued

Human microRNA sequences

| NO | Sequence(5' to 3') | ID and accession |
|---|---|---|
| 839 | GCAUGUGAUGAAGCAAAUCAGU | >hsa-miR-3607-5p MIMAT0017984 |
| 840 | ACAGGCAGGAUUGGGGAA | >hsa-miR-4514 MIMAT0019051 |
| 841 | UGUAAACAUCCUUGACUGGAAG | >hsa-miR-30e-5p MIMAT0000692 |
| 842 | CUUAUCAGAUUGUAUUGUAAUU | >hsa-miR-374a-3p MIMAT0004688 |
| 843 | CUUGGCACCUAGCAAGCACUCA | >hsa-miR-1271-5p MIMAT0005796 |
| 844 | AGGGUAAGCUGAACCUCUGAU | >hsa-miR-555 MIMAT0003219 |
| 845 | UAACACUGUCUGGUAAAGAUGG | >hsa-miR-141-3p MIMAT0000432 |
| 846 | UGAGGUAGUAGGUUGUAUGGUU | >hsa-let-7c MIMAT0000064 |
| 847 | AACCACUUUCUUUGCUCAUCCA | >hsa-miR-1255b-2-3p MIMAT0022725 |
| 848 | CAAAGAAUUCUCCUUUUGGGCU | >hsa-miR-186-5p MIMAT0000456 |
| 849 | ACUGCCCUAAGUGCUCCUUCUGG | >hsa-miR-18a-3p MIMAT0002891 |
| 850 | UCCCUGUCCUCCAGGAGCUCACG | >hsa-miR-339-5p MIMAT0000764 |
| 851 | ACUGGACUUGGAGGCAGAA | >hsa-miR-378b MIMAT0014999 |
| 852 | UCCUGUACUGAGCUGCCCCGAG | >hsa-miR-486-5p MIMAT0002177 |
| 853 | GCCUAUCACAUAUCUGCCUGU | >hsa-miR-3927-5p MIMAT0022970 |
| 854 | AAAAGUAAUUGUGGUUUUUGC | >hsa-miR-548ay-5p MIMAT0025452 |
| 855 | UAAGGGGUGUAUGGCAGAUGCA | >hsa-miR-3936 MIMAT0018351 |
| 856 | AUCAUAUGAACCAAACUCUAAU | >hsa-miR-5007-3p MIMAT0021036 |
| 857 | UUGAGGAAAAGAUGGUCUUAUU | >hsa-miR-3915 MIMAT0018189 |
| 858 | GGGAUUCUGUAGCUUCCU | >hsa-miR-4320 MIMAT0016871 |
| 859 | UGAUUGUCUUCAUAUCUAGAAC | >hsa-miR-4782-3p MIMAT0019945 |
| 860 | UGACACGGAGGGUGGCUUGGGAA | >hsa-miR-4462 MIMAT0018986 |
| 861 | AGACACUAUACGAGUCAUAU | >hsa-miR-3117-5p MIMAT0019197 |
| 862 | UUGUGCUUGAUCUAACCAUGU | >hsa-miR-218-5p MIMAT0000275 |
| 863 | UUAGGCCAUCAUCCCAUUAUGC | >hsa-miR-5704 MIMAT0022498 |
| 864 | UGAGCCGAGCUGAGCUUAGCUG | >hsa-miR-4537 MIMAT0019080 |
| 865 | GGUGGCCCGGCCGUGCCUGAGG | >hsa-miR-663b MIMAT0005867 |
| 866 | AGAUCGACCGUGUUAUAUUCGC | >hsa-miR-369-5p MIMAT0001621 |
| 867 | UCAUAUUGCUUCUUUCU | >hsa-miR-1279 MIMAT0005937 |
| 868 | UGGGCUGAGGGCAGGAGGCCUGU | >hsa-miR-4656 MIMAT0019723 |
| 869 | UGGGGAUUUGGAGAAGUGGUGA | >hsa-miR-4450 MIMAT0018971 |
| 870 | UUAGCGGUGGACCGCCCUGCG | >hsa-miR-4321 MIMAT0016874 |
| 871 | AAUAUUAUACAGUCAACCUCU | >hsa-miR-656 MIMAT0003332 |
| 872 | UAUGGCUUUUUAUUCCUAUGUGA | >hsa-miR-135a-5p MIMAT0000428 |
| 873 | UCAAGGCCAGAGGUCCCACAGCA | >hsa-miR-3922-5p MIMAT0019227 |
| 874 | CAGGCGUCUGUCUACGUGGCUU | >hsa-miR-3186-5p MIMAT0015067 |
| 875 | AUAGUCCGAGUAACGUCGGGGC | >hsa-miR-6723-5p MIMAT0025855 |
| 876 | ACUGGCAUGCUGCAUUUAUAUA | >hsa-miR-4799-3p MIMAT0019977 |

TABLE 1-continued

Human microRNA sequences

| NO | Sequence(5' to 3') | ID and accession |
|---|---|---|
| 877 | UGGCCCGGCGACGUCUCACGGUC | >hsa-miR-4745-3p MIMAT0019879 |
| 878 | GUGUUAAUUAAACCUCUAUUUAC | >hsa-miR-2053 MIMAT0009978 |
| 879 | UUGGGCUGGGCUGGGUUGGG | >hsa-miR-1587 MIMAT0019077 |
| 880 | CAAAGUGCUGUUCGUGCAGGUAG | >hsa-miR-93-5p MIMAT0000093 |
| 881 | GGUGGAUAUUCCUUCUAUGUU | >hsa-miR-376c-5p MIMAT0022861 |
| 882 | UUGAAUUCUUGGCCUUAAGUGAU | >hsa-miR-4452 MIMAT0018974 |
| 883 | AAAAGUACUUGCGGAUUUUGCU | >hsa-miR-548k MIMAT0005882 |
| 884 | AGACCCUGCAGCCUUCCCACC | >hsa-miR-4725-5p MIMAT0019843 |
| 885 | UGAGUGACAGGGGAAAUGGGGA | >hsa-miR-1236-5p MIMAT0022945 |
| 886 | GCAGGUGCUCACUUGUCCUCCU | >hsa-miR-764 MIMAT0010367 |
| 887 | AACCCAGUGGGCUAUGGAAAUG | >hsa-miR-4482-5p MIMAT0019016 |
| 888 | UGGUGGGCCGCAGAACAUGUGC | >hsa-miR-654-5p MIMAT0003330 |
| 889 | CUCUAGAGGGAAGCACUUUCUC | >hsa-miR-518f-5p MIMAT0002841 |
| 890 | CCUCAGAUCAGAGCCUUGC | >hsa-miR-4330 MIMAT0016924 |
| 891 | CAAGCUCGCUUCUAUGGGUCUG | >hsa-miR-99a-3p MIMAT0004511 |
| 892 | CCUCACCACCCCUUCUGCCUGCA | >hsa-miR-6511b-3p MIMAT0025848 |
| 893 | AGCUGUCUGAAAAUGUCUU | >hsa-miR-626 MIMAT0003295 |
| 894 | UAUGUGACCUCGGAUGAAUCA | >hsa-miR-4501 MIMAT0019037 |
| 895 | ACUCUUUCCCUGUUGCACUAC | >hsa-miR-130b-5p MIMAT0004680 |
| 896 | UAACAUAAUAGUGUGGAUUGA | >hsa-miR-4803 MIMAT0019983 |
| 897 | UUGCCACACUGCAACACCUUACA | >hsa-miR-3064-3p MIMAT0019865 |
| 898 | ACUCUAGCUGCCAAAGGCGCU | >hsa-miR-1251 MIMAT0005903 |
| 899 | UUCCACUGCCACUACCUAAUUU | >hsa-miR-6509-3p MIMAT0025475 |
| 900 | GUCCCUGAGUGUAUGUGGUG | >hsa-miR-670 MIMAT0010357 |
| 901 | UGGCAGUUACUUUUGCACCAG | >hsa-miR-548au-3p MIMAT0022292 |
| 902 | UGGGGAGCUGAGGCUCUGGGGGUG | >hsa-miR-939-5p MIMAT0004982 |
| 903 | CCUGCAACUUUGCCUGAUCAGA | >hsa-miR-4772-3p MIMAT0019927 |
| 904 | AGAGGCUGGCCGUGAUGAAUUC | >hsa-miR-485-5p MIMAT0002175 |
| 905 | CCUGAGAAAAGGGCCAA | >hsa-miR-4251 MIMAT0016883 |
| 906 | GAACGCCUGUUCUUGCCAGGUGG | >hsa-miR-614 MIMAT0003282 |
| 907 | UCCUGCGUAGGAUCUGAGGAGU | >hsa-miR-3193 MIMAT0015077 |
| 908 | CCCCGGUGUUGGGGCGCGUCUGC | >hsa-miR-4783-3p MIMAT0019947 |
| 909 | AAAUGGGUGGUCUGAGGCAA | >hsa-miR-4506 MIMAT0019042 |
| 910 | GGAUAUCAUCAUAUACUGUAAG | >hsa-miR-144-5p MIMAT0004600 |
| 911 | CACUGUGUCCUUUCUGCGUAG | >hsa-miR-892a MIMAT0004907 |
| 912 | UAUGUAACAUGGUCCACUAACU | >hsa-miR-379-3p MIMAT0004690 |
| 913 | UCUCACUGUAGCCUCGAACCCC | >hsa-miR-1304-3p MIMAT0022720 |
| 914 | UGGAGUGUGACAAUGGUGUUUG | >hsa-miR-122-5p MIMAT0000421 |

TABLE 1-continued

Human microRNA sequences

| NO | Sequence(5' to 3') | ID and accession |
|---|---|---|
| 915 | CCCAGCAGGACGGGAGCG | >hsa-miR-4530 MIMAT0019069 |
| 916 | GCCCCGGCGCGGGCGGGUUCUGG | >hsa-miR-4707-5p MIMAT0019807 |
| 917 | UGGAAUGUAAGGAAGUGUGUGG | >hsa-miR-206 MIMAT0000462 |
| 918 | CCUGCGAGUCUCCGGCGGUGG | >hsa-miR-6068 MIMAT0023693 |
| 919 | ACUCCAUUUGUUUUGAUGAUGGA | >hsa-miR-136-5p MIMAT0000448 |
| 920 | AAGUUGGCUGCAGUUAAGGUGG | >hsa-miR-4715-5p MIMAT0019824 |
| 921 | UGCCUACUGAGCUGAUAUCAGU | >hsa-miR-24-1-5p MIMAT0000079 |
| 922 | UGUGAUAUCAUGGUUCCUGGGA | >hsa-miR-3689e MIMAT0019009 |
| 923 | AUCCAGUUCUCUGAGGGGGCU | >hsa-miR-5195-3p MIMAT0021127 |
| 924 | CAGUGCAAUGUUUUCCUU | >hsa-miR-4295 MIMAT0016844 |
| 925 | UAGUUCUUCCCUUUGCCCAAUU | >hsa-miR-5584-3p MIMAT0022284 |
| 926 | AGGGGGAUGGCAGAGCAAAAUU | >hsa-miR-5010-5p MIMAT0021043 |
| 927 | UGUGAUAUCGUGCUUCCUGGGA | >hsa-miR-3689f MIMAT0019010 |
| 928 | GCGGAAGGCGGAGCGGCGGA | >hsa-miR-6125 MIMAT0024598 |
| 929 | AGAGUUAACUCAAAAUGGACUA | >hsa-miR-4424 MIMAT0018939 |
| 930 | CAACCCUAGGAGAGGGUGCCAUUCA | >hsa-miR-652-5p MIMAT0022709 |
| 931 | UCAGGCCAGGCACAGUGGCUCA | >hsa-miR-1972 MIMAT0009447 |
| 932 | UUAUAAAGCAAUGAGACUGAUU | >hsa-miR-340-5p MIMAT0004692 |
| 933 | CCUGUCUGUGCCUGCUGUACA | >hsa-miR-3120-5p MIMAT0019198 |
| 934 | CAUUCAACUAGUGAUUGU | >hsa-miR-4272 MIMAT0016902 |
| 935 | ACCAAGUCUGCGUCAUCCUCUC | >hsa-miR-3691-3p MIMAT0019224 |
| 936 | GCCUCUCUCGGAGUCGCUCGGA | >hsa-miR-3183 MIMAT0015063 |
| 937 | GUCAUACACGGCUCUCCUCUCU | >hsa-miR-485-3p MIMAT0002176 |
| 938 | GUGUCUGCUUCCUGUGGGA | >hsa-miR-632 MIMAT0003302 |
| 939 | UGAUUGUCCAAACGCAAUUCU | >hsa-miR-219-5p MIMAT0000276 |
| 940 | UUUCAGAUAACAGUAUUACAU | >hsa-miR-3942-3p MIMAT0019230 |
| 941 | CAUUGCACUUGUCUCGUCUGA | >hsa-miR-25-3p MIMAT0000081 |
| 942 | AAGUAGUUGGUUUGUAUGAGAUGGUU | >hsa-miR-1244 MIMAT0005896 |
| 943 | UGUUGCAAGUCGGUGGAGACGU | >hsa-miR-4684-3p MIMAT0019770 |
| 944 | AUAUUACCAUUAGCUCAUCUUU | >hsa-miR-556-3p MIMAT0004793 |
| 945 | ACUCAAAAUGGGGGCGCUUUCC | >hsa-miR-373-5p MIMAT0000725 |
| 946 | AAAACCGUCUAGUUACAGUUGU | >hsa-miR-1537 MIMAT0007399 |
| 947 | AGGCACGGUGUCAGCAGGC | >hsa-miR-564 MIMAT0003228 |
| 948 | AAAAGUAAUUGCGGUUUUUGCC | >hsa-miR-548o-5p MIMAT0022738 |
| 949 | AAUUGCACUUUAGCAAUGGUGA | >hsa-miR-367-3p MIMAT0000719 |
| 950 | UCUGGGCACAGGCGGAUGGACAGG | >hsa-miR-5189 MIMAT0021120 |
| 951 | GCAUUGUGCAGGGCUAUCA | >hsa-miR-4289 MIMAT0016920 |
| 952 | UUCAUUCGGCUGUCCAGAUGUA | >hsa-miR-1298 MIMAT0005800 |

TABLE 1-continued

Human microRNA sequences

| NO | Sequence(5' to 3') | ID and accession |
|---|---|---|
| 953 | UGGUCUAGGAUUGUUGGAGGAG | >hsa-miR-601 MIMAT0003269 |
| 954 | AUUGGGGACAUUUUGCAUUCAU | >hsa-miR-450a-3p MIMAT0022700 |
| 955 | GGCUUGCAUGGGGGACUGG | >hsa-miR-4327 MIMAT0016889 |
| 956 | UAUGGAAAGACUUUGCCACUCU | >hsa-miR-3688-3p MIMAT0018116 |
| 957 | CUCGGCCGCGGCGCGUAGCCCCCGCC | >hsa-miR-4665-3p MIMAT0019740 |
| 958 | UGGGCUCAGGGUACAAAGGUU | >hsa-miR-4437 MIMAT0018953 |
| 959 | CAAAAACUGCAAUUACUUUUGC | >hsa-miR-548aq-3p MIMAT0022264 |
| 960 | AGGAUAGGAAGAAUGAAGUGCU | >hsa-miR-5191 MIMAT0021122 |
| 961 | UGAAACUGGAGCGCCUGGAGGA | >hsa-miR-4738-3p MIMAT0019867 |
| 962 | UGGUGGUUUACAAAGUAAUUCA | >hsa-miR-876-3p MIMAT0004925 |
| 963 | UCUGGCCUUGACUUGACUCUUU | >hsa-miR-3922-3p MIMAT0018197 |
| 964 | UGAGGGGCAGAGAGCGAGACUUU | >hsa-miR-423-5p MIMAT0004748 |
| 965 | GCAGUCCAUGGGCAUAUACAC | >hsa-miR-455-3p MIMAT0004784 |
| 966 | AAUGACACGAUCACUCCCGUUGA | >hsa-miR-425-5p MIMAT0003393 |
| 967 | AACAUUCAACCUGUCGGUGAGU | >hsa-miR-181c-5p MIMAT0000258 |
| 968 | AGGCGAUGUGGGGAUGUAGAGA | >hsa-miR-6717-5p MIMAT0025846 |
| 969 | ACAGCCCAGCAGUUAUCACGGG | >hsa-miR-5685 MIMAT0022475 |
| 970 | AAUGUAGAGAUUGAUCAAAAU | >hsa-miR-3668 MIMAT0018091 |
| 971 | GAUGAUGAUGGCAGCAAAUUCUGAAA | >hsa-miR-1272 MIMAT0005925 |
| 972 | UCCAGCAUCAGUGAUUUUGUUG | >hsa-miR-338-3p MIMAT0000763 |
| 973 | ACAGACUUGCUGUGAUGUUCA | >hsa-miR-499b-5p MIMAT0019897 |
| 974 | AGGAGAAGUAAAGUAGAA | >hsa-miR-4434 MIMAT0018950 |
| 975 | UAACACUGUCUGGUAACGAUGU | >hsa-miR-200a-3p MIMAT0000682 |
| 976 | AUGGAAUGUAUAUACGGAAUA | >hsa-miR-3673 MIMAT0018096 |
| 977 | UGUAGUUGUAUUGUAUUGCCAC | >hsa-miR-4703-3p MIMAT0019802 |
| 978 | UUCCCUUUGUCAUCCUUCGCCU | >hsa-miR-211-5p MIMAT0000268 |
| 979 | UACUGCAGACAGUGGCAAUCA | >hsa-miR-509-5p MIMAT0004779 |
| 980 | AGCCCCUGGCCCCAAACCC | >hsa-miR-4313 MIMAT0016865 |
| 981 | UGCACCAUGGUUGUCUGAGCAUG | >hsa-miR-767-5p MIMAT0003882 |
| 982 | AAAUUAUUGUACAUCGGAUGAG | >hsa-miR-944 MIMAT0004987 |
| 983 | AAAGUCUCGCUCUCUGCCCCUCA | >hsa-miR-3184-3p MIMAT0022731 |
| 984 | GCUGGUUUCAUAUGGUGGUUUAGA | >hsa-miR-29b-1-5p MIMAT0004514 |
| 985 | GUCCACUUCUGCCUGCCCUGCC | >hsa-miR-4436b-5p MIMAT0019940 |
| 986 | CAGGAUGUGGUCAAGUGUUGUU | >hsa-miR-1265 MIMAT0005918 |
| 987 | CAAAAACCGGCAAUUACUUUUG | >hsa-miR-548ac MIMAT0018938 |
| 988 | GUUGGGGUGCAGGGGUCUGCU | >hsa-miR-5572 MIMAT0022260 |
| 989 | UCCUUUGCCUAUUCUAUUUAAG | >hsa-miR-3121-5p MIMAT0019199 |
| 990 | GACCGAGAGGGCCUCGGCUGU | >hsa-miR-4523 MIMAT0019061 |

TABLE 1-continued

Human microRNA sequences

| NO | Sequence(5' to 3') | ID and accession |
|---|---|---|
| 991 | AGAAUUGUGGCUGGACAUCUGU | >hsa-miR-219-2-3p MIMAT0004675 |
| 992 | GAGUGCCUUCUUUUGGAGCGUU | >hsa-miR-515-3p MIMAT0002827 |
| 993 | CAGAUCAUGGGACUGUCUCAG | >hsa-miR-5694 MIMAT0022487 |
| 994 | CUUCCCCCCAGUAAUCUUCAUC | >hsa-miR-3679-3p MIMAT0018105 |
| 995 | UGAGUGUUGUCUACGAGGGCA | >hsa-miR-3659 MIMAT0018080 |
| 996 | UACCACAGGGUAGAACCACGG | >hsa-miR-140-3p MIMAT0004597 |
| 997 | CGCAGACAAUGCCUACUGGCCUA | >hsa-miR-3166 MIMAT0015040 |
| 998 | GCUGACAGCAGGGCUGGCCGCU | >hsa-miR-4526 MIMAT0019065 |
| 999 | UGAGGUGGUAGGAUGUAGA | >hsa-miR-6134 MIMAT0024618 |
| 1000 | GUGAACGGGCGCCAUCCCGAGG | >hsa-miR-887 MIMAT0004951 |
| 1001 | AGGGGGAAAGUUCUAUAGUCC | >hsa-miR-625-5p MIMAT0003294 |
| 1002 | UAGUGGUCCUAAACAUUUCACA | >hsa-miR-203b-5p MIMAT0019813 |
| 1003 | AAUAAUACAUGGUUGAUCUUU | >hsa-miR-369-3p MIMAT0000721 |
| 1004 | UAACAGUCUACAGCCAUGGUCG | >hsa-miR-132-3p MIMAT0000426 |
| 1005 | ACAUUGCCAGGGAGUUU | >hsa-miR-4317 MIMAT0016872 |
| 1006 | UGUGACUUUAAGGGAAAUGGCG | >hsa-miR-3164 MIMAT0015038 |
| 1007 | UAAUGCCCCUAAAAAUCCUUAU | >hsa-miR-365b-3p MIMAT0022834 |
| 1008 | UAAUCUCAGCUGGCAACUGUGA | >hsa-miR-216a-5p MIMAT0000273 |
| 1009 | UACUCUGGAGAGUGACAAUCAUG | >hsa-miR-514a-5p MIMAT0022702 |
| 1010 | UCUGGCCAGCUACGUCCCCA | >hsa-miR-3190-5p MIMAT0015073 |
| 1011 | UGACUGCCUCACUGACCACUU | >hsa-miR-5002-3p MIMAT0021024 |
| 1012 | AUCGCUGCGGUUGCGAGCGCUGU | >hsa-miR-639 MIMAT0003309 |
| 1013 | UGGCGGCGGUAGUUAUGGGCUU | >hsa-miR-4467 MIMAT0018994 |
| 1014 | UUAAUGCUAAUCGUGAUAGGGGU | >hsa-miR-155-5p MIMAT0000646 |
| 1015 | CACUGUAGGUGAUGGUGAGAGUGGGCA | >hsa-miR-1183 MIMAT0005828 |
| 1016 | UAAAAACUGCAAUUACUUUC | >hsa-miR-548x-3p MIMAT0015081 |
| 1017 | CUGCCUGUUCUUCCACUCCAG | >hsa-miR-6514-3p MIMAT0025485 |
| 1018 | CAAAUGGACAGGAUAACACCU | >hsa-miR-4694-3p MIMAT0019787 |
| 1019 | AGGGGACCAAAGAGAUAUAUAG | >hsa-miR-3144-5p MIMAT0015014 |
| 1020 | AAAAGUAAUCGCGGUUUUUGUC | >hsa-miR-548h-5p MIMAT0005928 |
| 1021 | CUAUACGACCUGCUGCCUUUCU | >hsa-let-7d-3p MIMAT0004484 |
| 1022 | GAAGUGUGCCGUGGUGUGUCU | >hsa-miR-595 MIMAT0003263 |
| 1023 | UCCCACGUUGUGGCCCAGCAG | >hsa-miR-662 MIMAT0003325 |
| 1024 | CAGUGCAAUGUUAAAAGGGCAU | >hsa-miR-130a-3p MIMAT0000425 |
| 1025 | AGGCAGGUUAUCUGGGCUG | >hsa-miR-4736 MIMAT0019862 |
| 1026 | CGGCUGGAGGUGUGAGGA | >hsa-miR-3652 MIMAT0018072 |
| 1027 | UGAGGACAGGGCAAAUUCACGA | >hsa-miR-5004-5p MIMAT0021027 |
| 1028 | GUGGGGGAGAGGCUGUC | >hsa-miR-1275 MIMAT0005929 |

TABLE 1-continued

Human microRNA sequences

| NO | Sequence(5' to 3') | ID and accession |
|---|---|---|
| 1029 | AUGCACCUGGGCAAGGAUUCUG | >hsa-miR-500a-3p MIMAT0002871 |
| 1030 | UGUAGUGUUUCCUACUUUAUGGA | >hsa-miR-142-3p MIMAT0000434 |
| 1031 | UUAGUCUCAUGAUCAGACACA | >hsa-miR-4474-5p MIMAT0019234 |
| 1032 | CUACAAAGGGAAGCCCUUUC | >hsa-miR-520d-5p MIMAT0002855 |
| 1033 | AAGCUGCCAGUUGAAGAACUGU | >hsa-miR-22-3p MIMAT0000077 |
| 1034 | UCUGCAGGGUUUGCUUUGAG | >hsa-miR-1205 MIMAT0005869 |
| 1035 | AAAGGUAAUUGCAGUUUUUCCC | >hsa-miR-570-5p MIMAT0022707 |
| 1036 | UAGUAGACCGUAUAGCGUACG | >hsa-miR-411-5p MIMAT0003329 |
| 1037 | UAACGGCCGCGGUACCCUAA | >hsa-miR-4485 MIMAT0019019 |
| 1038 | UGCAACUUACCUGAGUCAUUGA | >hsa-miR-891b MIMAT0004913 |
| 1039 | UGGGAUGAGGGAUUGAAGUGGA | >hsa-miR-5187-5p MIMAT0021117 |
| 1040 | AUUGUCCCUCUCCCUUCCCAG | >hsa-miR-4646-3p MIMAT0019708 |
| 1041 | CAAGGAGACGGGAACAUGGAGC | >hsa-miR-4428 MIMAT0018943 |
| 1042 | UUAGUGAAGGCUAUUUUAAUU | >hsa-miR-3606-5p MIMAT0017983 |
| 1043 | GGUUGGGCAGUGAGGAGGGUGUGA | >hsa-miR-3147 MIMAT0015019 |
| 1044 | CCCCGGGAACGUCGAGACUGGAGC | >hsa-miR-1247-3p MIMAT0022721 |
| 1045 | UAAUGCAUUAAAUUAUUGAAGG | >hsa-miR-5700 MIMAT0022493 |
| 1046 | UGGAGUUAAGGGUUGCUUGGAGA | >hsa-miR-4653-3p MIMAT0019719 |
| 1047 | AGGUAGACUGGGAUUUGUUGUU | >hsa-miR-3529-5p MIMAT0019828 |
| 1048 | CCGGGGCAGAUUGGUGUAGGGUG | >hsa-miR-5090 MIMAT0021082 |
| 1049 | UUCAACGGGUAUUUAUUGAGCA | >hsa-miR-95 MIMAT0000094 |
| 1050 | UAAUGCCCCUAAAAAUCCUUAU | >hsa-miR-365a-3p MIMAT0000710 |
| 1051 | UUCACAGUGGCUAAGUUCCGC | >hsa-miR-27a-3p MIMAT0000084 |
| 1052 | AGAAGGGGUGAAAUUUAAACGU | >hsa-miR-3179 MIMAT0015056 |
| 1053 | AUUGCCUCUGUUCUAACACAAG | >hsa-miR-3152-5p MIMAT0019207 |
| 1054 | CUGUUGCCACUAACCUCAACCU | >hsa-miR-744-3p MIMAT0004946 |
| 1055 | AGGAAGCCCUGGAGGGGCUGGAG | >hsa-miR-671-5p MIMAT0003880 |
| 1056 | UAGAGUCUGGCUGAUAUGGUUU | >hsa-miR-5007-5p MIMAT0021035 |
| 1057 | GAUCUCACUUUGUUGCCCAGG | >hsa-miR-1285-5p MIMAT0022719 |
| 1058 | GCAGAGAACAAAGGACUCAGU | >hsa-miR-3919 MIMAT0018193 |
| 1059 | GGAGAAAUUAUCCUUGGUGUGU | >hsa-miR-539-5p MIMAT0003163 |
| 1060 | ACUUCCUCACUCCCGUGAAGU | >hsa-miR-3124-3p MIMAT0019200 |
| 1061 | GCUAUUUCACGACACCAGGGUU | >hsa-miR-138-2-3p MIMAT0004596 |
| 1062 | GUGCAUUGCUGUUGCAUUGC | >hsa-miR-33b-5p MIMAT0003301 |
| 1063 | ACGUUUGAAUGCUGUACAAGGC | >hsa-miR-5707 MIMAT0022501 |
| 1064 | CCAAUUACCACUUCUUU | >hsa-miR-4275 MIMAT0016905 |
| 1065 | AAGAGGAAGAAAUGGCUGGUUCUCAG | >hsa-miR-3916 MIMAT0018190 |
| 1066 | AAUGCACCUGGGCAAGGAUUCA | >hsa-miR-502-3p MIMAT0004775 |

TABLE 1-continued

Human microRNA sequences

| NO | Sequence(5' to 3') | ID and accession |
|---|---|---|
| 1067 | ACAGGCGGCUGUAGCAAUGGGGG | >hsa-miR-3937 MIMAT0018352 |
| 1068 | AGGGACCUGAGUGUCUAAG | >hsa-miR-3649 MIMAT0018069 |
| 1069 | CUGGGGUUCUGAGACAGACAGU | >hsa-miR-3170 MIMAT0015045 |
| 1070 | AUGCGGACCUGGGUUAGCGGAGU | >hsa-miR-4754 MIMAT0019894 |
| 1071 | UACUCAGGAGAGUGGCAAUCAC | >hsa-miR-510 MIMAT0002882 |
| 1072 | CAGAGUGACAAGCUGGUUAAAG | >hsa-miR-5586-3p MIMAT0022288 |
| 1073 | UCUGGCUGUUGUGGUGUGCAA | >hsa-miR-3064-5p MIMAT0019864 |
| 1074 | UACUGCAGACGUGGCAAUCAUG | >hsa-miR-509-3-5p MIMAT0004975 |
| 1075 | CCAUGGAUCUCCAGGUGGGU | >hsa-miR-490-5p MIMAT0004764 |
| 1076 | AGGCAGUGUAGUUAGCUGAUUGC | >hsa-miR-34c-5p MIMAT0000686 |
| 1077 | CCUCAGGGCUGUAGAACAGGGCU | >hsa-miR-1266 MIMAT0005920 |
| 1078 | AAAAUGGUUCCCUUUAGAGUGU | >hsa-miR-522-3p MIMAT0002868 |
| 1079 | ACGGAAUAUGUAUACGGAAUAUA | >hsa-miR-3669 MIMAT0018092 |
| 1080 | UGGAGAGAAAGGCAGUA | >hsa-miR-4306 MIMAT0016858 |
| 1081 | UGUGAUAUCAUGGUUCCUGGGA | >hsa-miR-3689b-5p MIMAT0018180 |
| 1082 | AGGACUGGACUCCCGGCAGCCC | >hsa-miR-4515 MIMAT0019052 |
| 1083 | ACAGGGCCGCAGAUGGAGACU | >hsa-miR-3918 MIMAT0018192 |
| 1084 | GAAGUGCUUCGAUUUUGGGGUGU | >hsa-miR-373-3p MIMAT0000726 |
| 1085 | AGCCUGGAAGCUGGAGCCUGCAGU | >hsa-miR-1254 MIMAT0005905 |
| 1086 | UACAUGGAUGGAAACCUUCAAGC | >hsa-miR-4802-3p MIMAT0019982 |
| 1087 | UUUCCCUUCAGAGCCUGGCUUU | >hsa-miR-4755-5p MIMAT0019895 |
| 1088 | AGGGACUUUCAGGGGCAGCUGU | >hsa-miR-365b-5p MIMAT0022833 |
| 1089 | GGGACCAUCCUGCCUGCUGUGG | >hsa-miR-3619-3p MIMAT0019219 |
| 1090 | CUGCCAAUUCCAUAGGUCACAG | >hsa-miR-192-3p MIMAT0004543 |
| 1091 | UAAAAACUGCAAUUACUUUUA | >hsa-miR-548aj-3p MIMAT0018990 |
| 1092 | AUCAGGGCUUGUGGAAUGGGAAG | >hsa-miR-3127-5p MIMAT0014990 |
| 1093 | UGGAGAGAAAGGCAGUUCCUGA | >hsa-miR-185-5p MIMAT0000455 |
| 1094 | GGGACUAGGAUGCAGACCUCC | >hsa-miR-6503-3p MIMAT0025463 |
| 1095 | AUGUGGGCUCAGGCUCA | >hsa-miR-4296 MIMAT0016845 |
| 1096 | CUUCCAGACGCUCCGCCCCACGUCG | >hsa-miR-3180-5p MIMAT0015057 |
| 1097 | AUCGUGCAUCCCUUUAGAGUGU | >hsa-miR-517a-3p MIMAT0002852 |
| 1098 | GCAGGAACUUGUGAGUCUCCU | >hsa-miR-873-5p MIMAT0004953 |
| 1099 | UGGGGGAGUGCAGUGAUUGUGG | >hsa-miR-5698 MIMAT0022491 |
| 1100 | AUUAAGGACAUUUGUGAUUGAU | >hsa-miR-4477b MIMAT0019005 |
| 1101 | UAGUCCCUUCCUUGAAGCGGUC | >hsa-miR-2114-5p MIMAT0011156 |
| 1102 | AAAAGUGAUUGCAGUGUUUG | >hsa-miR-548ah-5p MIMAT0018972 |
| 1103 | UACUCAAAAAGCUGUCAGUCA | >hsa-miR-888-5p MIMAT0004916 |
| 1104 | CAACAAAUCCCAGUCUACCUAA | >hsa-miR-7-2-3p MIMAT0004554 |

TABLE 1-continued

Human microRNA sequences

| NO | Sequence(5' to 3') | ID and accession |
|---|---|---|
| 1105 | UUUCCGGCUCGCGUGGGUGUGU | >hsa-miR-1180 MIMAT0005825 |
| 1106 | CUCAGUAGCCAGUGUAGAUCCU | >hsa-miR-222-5p MIMAT0004569 |
| 1107 | UGUGACAGAUUGAUAACUGAAA | >hsa-miR-542-3p MIMAT0003389 |
| 1108 | CUCCGUUUGCCUGUUUCGCUG | >hsa-miR-1468 MIMAT0006789 |
| 1109 | GGGAAGAGCUGUACGGCCUUC | >hsa-miR-6077 MIMAT0023702 |
| 1110 | AUACUGUGAAUUUCACUGUCACA | >hsa-miR-4693-5p MIMAT0019784 |
| 1111 | CAGAGAAUUGUUUAAUC | >hsa-miR-3123 MIMAT0014985 |
| 1112 | AUUCUCUCUGGAUCCCAUGGAU | >hsa-miR-4768-5p MIMAT0019920 |
| 1113 | UGGGGCUCAGCGAGUUU | >hsa-miR-4283 MIMAT0016914 |
| 1114 | UGAGAACCACGUCUGCUCUGAG | >hsa-miR-589-5p MIMAT0004799 |
| 1115 | CCAGUAUUAACUGUGCUGCUGA | >hsa-miR-16-1-3p MIMAT0004489 |
| 1116 | GCAGCAGAGAAUAGGACUACGUC | >hsa-miR-922 MIMAT0004972 |
| 1117 | AACCAUCGACCGUUGAGUGGAC | >hsa-miR-181c-3p MIMAT0004559 |
| 1118 | AUCGUGCAUCCCUUUAGAGUGU | >hsa-miR-517b-3p MIMAT0002857 |
| 1119 | CCAAAACUGCAGUUACUUUUGC | >hsa-miR-548o-3p MIMAT0005919 |
| 1120 | CACAAGGUAUUGGUAUUACCU | >hsa-miR-624-3p MIMAT0004807 |
| 1121 | AUACCUCAUCUAGAAUGCUGUA | >hsa-miR-4777-3p MIMAT0019935 |
| 1122 | ACCACUGACCGUUGACUGUACC | >hsa-miR-181a-2-3p MIMAT0004558 |
| 1123 | GCCCUGACCUGUCCUGUUCUG | >hsa-miR-4732-3p MIMAT0019856 |
| 1124 | UUUUUCAUUAUUGCUCCUGACC | >hsa-miR-335-3p MIMAT0004703 |
| 1125 | CACACAUAGCAGGUGUAUAUA | >hsa-miR-4789-3p MIMAT0019960 |
| 1126 | GGGCUCACAUCACCCCAU | >hsa-miR-4284 MIMAT0016915 |
| 1127 | GAAAACGACAAUGACUUUUGCA | >hsa-miR-548ad MIMAT0018946 |
| 1128 | AGAGUUGAGUCUGGACGUCCCG | >hsa-miR-219-1-3p MIMAT0004567 |
| 1129 | AGCCUUCCAGGAGAAAUGGAGA | >hsa-miR-5581-5p MIMAT0022275 |
| 1130 | AGGGCUUAGCUGCUUGUGAGCA | >hsa-miR-27a-5p MIMAT0004501 |
| 1131 | UUCACAGGGAGGUGUCAU | >hsa-miR-513a-5p MIMAT0002877 |
| 1132 | UAUACCUCAGUUUUAUCAGGUG | >hsa-miR-875-5p MIMAT0004922 |
| 1133 | GCAGGCACAGACAGCCCUGGC | >hsa-miR-4269 MIMAT0016897 |
| 1134 | GGUAGAUUUUCCUUCUAUGGU | >hsa-miR-376a-2-5p MIMAT0022928 |
| 1135 | AGGAGGCAGCGCUCUCAGGAC | >hsa-miR-650 MIMAT0003320 |
| 1136 | AAGUGAUCUAAAGGCCUACAU | >hsa-miR-1245a MIMAT0005897 |
| 1137 | AAAGACCCAUUGAGGAGAAGGU | >hsa-miR-3667-5p MIMAT0018089 |
| 1138 | CCUGCAGCGACUUGAUGGCUUCC | >hsa-miR-1184 MIMAT0005829 |
| 1139 | AUCUGACCUGAUGAAGGU | >hsa-miR-4256 MIMAT0016877 |
| 1140 | UUUGGUCCCCUUCAACCAGCUG | >hsa-miR-133a MIMAT0000427 |
| 1141 | CCUCUAGAUGGAAGCACUGUCU | >hsa-miR-517-5p MIMAT0002851 |
| 1142 | UUUUGCGAUGUGUUCCUAAUAU | >hsa-miR-450a-5p MIMAT0001545 |

TABLE 1-continued

Human microRNA sequences

| NO | Sequence(5' to 3') | ID and accession |
|---|---|---|
| 1143 | AGCCAAGUGGAAGUUACUUUA | >hsa-miR-4480 MIMAT0019014 |
| 1144 | UGUGACUGCAUUAUGAAAAUUCU | >hsa-miR-3118 MIMAT0014980 |
| 1145 | AGCAUGACAGAGGAGAGGUGG | >hsa-miR-6076 MIMAT0023701 |
| 1146 | UCUUGAAGUCAGAACCCGCAA | >hsa-miR-4635 MIMAT0019692 |
| 1147 | AUGGAGAAGGCUUCUGA | >hsa-miR-4531 MIMAT0019070 |
| 1148 | UAUAAAAUGAGGGCAGUAAGAC | >hsa-miR-3163 MIMAT0015037 |
| 1149 | UGGAUUUUUGGAUCAGGGA | >hsa-miR-1290 MIMAT0005880 |
| 1150 | GACAGAGUGCCACUUACUGAA | >hsa-miR-4797-5p MIMAT0019972 |
| 1151 | UAAGGUGCAUCUAGUGCAGUUAG | >hsa-miR-18b-5p MIMAT0001412 |
| 1152 | AGGCGGGGCGCCGCGGGACCGC | >hsa-miR-663a MIMAT0003326 |
| 1153 | UAAGGUGCAUCUAGUGCAGAUAG | >hsa-miR-18a-5p MIMAT0000072 |
| 1154 | UUGCAGCUGCCUGGGAGUGACUUC | >hsa-miR-1301 MIMAT0005797 |
| 1155 | UCUUUGGUUAUCUAGCUGUAUGA | >hsa-miR-9-5p MIMAT0000441 |
| 1156 | AAUUCUGUAAAGGAAGAAGAGG | >hsa-miR-4778-5p MIMAT0019936 |
| 1157 | UAGCCCCCAGGCUUCACUUGGCG | >hsa-miR-3943 MIMAT0018359 |
| 1158 | ACUGGACUUGGAGUCAGAAGAGUGG | >hsa-miR-378c MIMAT0016847 |
| 1159 | UCACAGUGGUCUCUGGGAUUAU | >hsa-miR-216a-3p MIMAT0022844 |
| 1160 | CAAAGUCCUUCCUAUUUUUCCC | >hsa-miR-6507-3p MIMAT0025471 |
| 1161 | CAACAAAUCACAGUCUGCCAUA | >hsa-miR-7-1-3p MIMAT0004553 |
| 1162 | ACUGGAUUUGGAGCCAGAA | >hsa-miR-378j MIMAT0024612 |
| 1163 | CACUGUUUCCUUUCUGAGUGGA | >hsa-miR-892c-3p MIMAT0025858 |
| 1164 | UCCCUGAGACCCUUUAACCUGUGA | >hsa-miR-125a-5p MIMAT0000443 |
| 1165 | GAACGGCUUCAUACAGGAGUU | >hsa-miR-337-5p MIMAT0004695 |
| 1166 | ACUGGACUUGGAGUCAGGA | >hsa-miR-378e MIMAT0018927 |
| 1167 | CAUCCGUCCGUCUGUCCAC | >hsa-miR-4800-3p MIMAT0019979 |
| 1168 | AAAGACAUAGUUGCAAGAUGGG | >hsa-miR-3617-5p MIMAT0017997 |
| 1169 | UUAUAAUACAACCUGAUAAGUG | >hsa-miR-374a-5p MIMAT0000727 |
| 1170 | UCAAGUGUCAUCUGUCCCUAG | >hsa-miR-6513-3p MIMAT0025483 |
| 1171 | GAAAAUGAUGAGUAGUGACUGAUG | >hsa-miR-3662 MIMAT0018083 |
| 1172 | AUAGCAGCAUGAACCUGUCUCA | >hsa-miR-4524a-5p MIMAT0019062 |
| 1173 | CUAGGGGGUUUGCCCUUG | >hsa-miR-4278 MIMAT0016910 |
| 1174 | AGGCUGCGGAAUUCAGGAC | >hsa-miR-604 MIMAT0003272 |
| 1175 | CACUAGAUUGUGAGCUCCUGGA | >hsa-miR-28-3p MIMAT0004502 |
| 1176 | UGUCACUCGGCUCGGCCCACUAC | >hsa-miR-668 MIMAT0003881 |
| 1177 | UGGGCCAGGGAGCAGCUGGUGGG | >hsa-miR-4640-5p MIMAT0019699 |
| 1178 | AGCUUUUGGGAAUUCAGGUAGU | >hsa-miR-3140-3p MIMAT0015008 |
| 1179 | UUGUGAAGAAAGAAAUUCUUA | >hsa-miR-3611 MIMAT0017988 |
| 1180 | UUAGUCCUGCCUGUAGGUUUA | >hsa-miR-4540 MIMAT0019083 |

TABLE 1-continued

Human microRNA sequences

| NO | Sequence(5' to 3') | ID and accession |
|---|---|---|
| 1181 | UACCCUGUAGAUCCGAAUUUGUG | >hsa-miR-10a-5p MIMAT0000253 |
| 1182 | UGAGGGAGUGGAUUGUAUG | >hsa-miR-6130 MIMAT0024614 |
| 1183 | AGGUGCUCCAGGCUGGCUCACA | >hsa-miR-3907 MIMAT0018179 |
| 1184 | CUGGUUUCACAUGGUGGCUUAG | >hsa-miR-29b-2-5p MIMAT0004515 |
| 1185 | UGAAGGUCUACUGUGUGCCAGG | >hsa-miR-493-3p MIMAT0003161 |
| 1186 | UCCUAAAUCUGAAAGUCCAAAA | >hsa-miR-5009-3p MIMAT0021042 |
| 1187 | CCUGGUGGCUUCCUUUU | >hsa-miR-4456 MIMAT0018978 |
| 1188 | AACCCGUAGAUCCGAUCUUGUG | >hsa-miR-99a-5p MIMAT0000097 |
| 1189 | UGGCCGGAUGGGACAGGAGGCAU | >hsa-miR-4743-5p MIMAT0019874 |
| 1190 | AUAGUGGGAAGCUGGCAGAUUC | >hsa-miR-4727-3p MIMAT0019848 |
| 1191 | UAGGUAGUUUCAUGUUGUUGGG | >hsa-miR-196a-5p MIMAT0000226 |
| 1192 | CAAAGUUUAAGAUCCUUGAAGU | >hsa-miR-561-3p MIMAT0003225 |
| 1193 | CCCUCUCUGGCUCCUCCCCAAA | >hsa-miR-4723-3p MIMAT0019839 |
| 1194 | UUCUCAAGAGGGAGGCAAUCAU | >hsa-miR-514b-5p MIMAT0015087 |
| 1195 | GGAGGAACCUUGGAGCUUCGGC | >hsa-miR-3928 MIMAT0018205 |
| 1196 | AGGGAUCGCGGGCGGGUGGCGGCCU | >hsa-miR-638 MIMAT0003308 |
| 1197 | ACUGUAAACGCUUUCUGAUG | >hsa-miR-3607-3p MIMAT0017985 |
| 1198 | CAUGCUAGGAUAGAAAGAAUGG | >hsa-miR-3146 MIMAT0015018 |
| 1199 | AGCCCGCCCCAGCCGAGGUUCU | >hsa-miR-4707-3p MIMAT0019808 |
| 1200 | UCCAGCUCGGUGGCAC | >hsa-miR-4267 MIMAT0016893 |
| 1201 | UCCCUCCUUCUGUCCCCACAG | >hsa-miR-4667-3p MIMAT0019744 |
| 1202 | UACUUGGAAAGGCAUCAGUUG | >hsa-miR-890 MIMAT0004912 |
| 1203 | ACCCGUCCCGUUCGUCCCCGGA | >hsa-miR-1247-5p MIMAT0005899 |
| 1204 | UACCAUUAGAAGAGCUGGAAGA | >hsa-miR-6512-5p MIMAT0025480 |
| 1205 | UUGCACUUGUCUCAGUGA | >hsa-miR-4325 MIMAT0016887 |
| 1206 | ACAAAAAAAAAAGCCCAACCCUUC | >hsa-miR-3613-3p MIMAT0017991 |
| 1207 | GCCCCGGGCAGUGUGAUCAUC | >hsa-miR-5587-3p MIMAT0022290 |
| 1208 | AAAAGUAAUUGCGAGUUUUACC | >hsa-miR-548a-5p MIMAT0004803 |
| 1209 | GAAAGUGCUUCCUUUUAGAGGC | >hsa-miR-526b-3p MIMAT0002836 |
| 1210 | AGGGCCAGAGGAGCCUGGAGUGG | >hsa-miR-4726-5p MIMAT0019845 |
| 1211 | UGUGUCCGGGAAGUGGAGGAGG | >hsa-miR-4669 MIMAT0019749 |
| 1212 | CAACCUGGAGGACUCCAUGCUG | >hsa-miR-490-3p MIMAT0002806 |
| 1213 | GUGGCUGCACUCACUUCCUUC | >hsa-miR-647 MIMAT0003317 |
| 1214 | ACCCAGGUUCCCUCUGGCCGCA | >hsa-miR-4726-3p MIMAT0019846 |
| 1215 | CAGCAGCACACUGUGGUUUGU | >hsa-miR-497-5p MIMAT0002820 |
| 1216 | UAAAGUAAAUAUGCACCAAAA | >hsa-miR-559 MIMAT0003223 |
| 1217 | UACAGUACUGUGAUAACUGAA | >hsa-miR-101-3p MIMAT0000099 |
| 1218 | GAAGAUGGACGUACUUU | >hsa-miR-4426 MIMAT0018941 |

TABLE 1-continued

Human microRNA sequences

| NO | Sequence(5' to 3') | ID and accession |
|---|---|---|
| 1219 | UAUAGAGAGCAGGAAGAUUAAUGU | >hsa-miR-3976 MIMAT0019361 |
| 1220 | UGGAGAGAGAAAAGAGACAGAAG | >hsa-miR-4644 MIMAT0019704 |
| 1221 | CGGGGCGGCAGGGGCCUC | >hsa-miR-3196 MIMAT0015080 |
| 1222 | GGUGGUUGAGGCUGCAGUAAGU | >hsa-miR-1273g-5p MIMAT0020602 |
| 1223 | UGGGAAUGGGGGUAAGGGCC | >hsa-miR-6716-5p MIMAT0025844 |
| 1224 | UGAUGGAUAAAAGACUACAUAUU | >hsa-miR-3134 MIMAT0015000 |
| 1225 | CUGAAGCUCAGAGGGCUCUGAU | >hsa-miR-127-5p MIMAT0004604 |
| 1226 | AGCUGAGCUCCAUGGACGUGCAGU | >hsa-miR-4663 MIMAT0019735 |
| 1227 | AGACACAUUUGGAGAGGGACCC | >hsa-miR-642b-3p MIMAT0018444 |
| 1228 | AACUGGCCCUCAAAGUCCCGCU | >hsa-miR-193b-3p MIMAT0002819 |
| 1229 | AAUUGCACGGUAUCCAUCUGUA | >hsa-miR-363-3p MIMAT0000707 |
| 1230 | UCACCCUGCAUCCCGCACCCAG | >hsa-miR-3620-3p MIMAT0018001 |
| 1231 | CUGUGGGCUCAGCUCUGGG | >hsa-miR-4265 MIMAT0016891 |
| 1232 | UCAGAACAAAUGCCGGUUCCCAGA | >hsa-miR-589-3p MIMAT0003256 |
| 1233 | UGAGGGAGGAGACUGCA | >hsa-miR-4419a MIMAT0018931 |
| 1234 | AGGCGCACCCGACCACAUGC | >hsa-miR-6722-5p MIMAT0025853 |
| 1235 | UGAGGGGUUUGGAAUGGGAUGG | >hsa-miR-5194 MIMAT0021125 |
| 1236 | AAAGUGCUUCCCUUUGGACUGU | >hsa-miR-520a-3p MIMAT0002834 |
| 1237 | CAGAAGGGGAGUUGGGAGCAGA | >hsa-miR-3154 MIMAT0015028 |
| 1238 | UGCAAAAGUAAUUGCAGUUUUUG | >hsa-miR-548x-5p MIMAT0022733 |
| 1239 | CCCAGGGCUUGGAGUGGGGCAAGGUU | >hsa-miR-4685-5p MIMAT0019771 |
| 1240 | UGGGCGUAUCUGUAUGCUA | >hsa-miR-585 MIMAT0003250 |
| 1241 | GUGGAAAGCAUGCAUCCAGGGUGU | >hsa-miR-3978 MIMAT0019363 |
| 1242 | UACAGAUGCAGAUUCUCUGACUUC | >hsa-miR-5683 MIMAT0022472 |
| 1243 | UUGUACAUGGUAGGCUUUCAUU | >hsa-miR-493-5p MIMAT0002813 |
| 1244 | GCCCGCGUGUGGAGCCAGGUGU | >hsa-miR-1471 MIMAT0007349 |
| 1245 | GGGGCUGUGAUUGACCAGCAGG | >hsa-miR-4675 MIMAT0019757 |
| 1246 | UGGGUUUACGUUGGGAGAACU | >hsa-miR-629-5p MIMAT0004810 |
| 1247 | AAUAAAGUUCAUGUAUGGCAA | >hsa-miR-5590-3p MIMAT0022300 |
| 1248 | AGUUGCCUUUUUGUUCCCAUGC | >hsa-miR-4423-5p MIMAT0019232 |
| 1249 | UUGGACUUUUCAGAUUUGGGAU | >hsa-miR-5009-5p MIMAT0021041 |
| 1250 | UGGCUCAGUUCAGCAGGAACAG | >hsa-miR-24-3p MIMAT0000080 |
| 1251 | UCAGGUGUGGAAACUGAGGCAG | >hsa-miR-3934-5p MIMAT0018349 |
| 1252 | UCUAGAAAUGCAUGACCCACC | >hsa-miR-6508-5p MIMAT0025472 |
| 1253 | UCAUUAUAUGUAUGAUCUGGAC | >hsa-miR-4528 MIMAT0019067 |
| 1254 | UUGGAGGCGUGGGUUUU | >hsa-miR-4443 MIMAT0018961 |
| 1255 | CUUCCUCGUCUGUCUGCCCC | >hsa-miR-1238-3p MIMAT0005593 |
| 1256 | CCUCCCAUGCCAAGAACUCCC | >hsa-miR-2116-3p MIMAT0011161 |

TABLE 1-continued

Human microRNA sequences

| NO | Sequence(5' to 3') | ID and accession |
|---|---|---|
| 1257 | AAAAGGCAUUGUGGUUUUUG | >hsa-miR-548an MIMAT0019079 |
| 1258 | AGUUCUUCAGUGGCAAGCUUUA | >hsa-miR-22-5p MIMAT0004495 |
| 1259 | UGUGGAAGGUAGACGGCCAGAGA | >hsa-miR-3190-3p MIMAT0022839 |
| 1260 | CAAAGGUAUUUGUGGUUUUUG | >hsa-miR-548m MIMAT0005917 |
| 1261 | CAGGGCCUCACUGUAUCGCCCA | >hsa-miR-4512 MIMAT0019049 |
| 1262 | UGCCCUAAAUGCCCCUUCUGGC | >hsa-miR-18b-3p MIMAT0004751 |
| 1263 | AAGGAGCUCACAGUCUAUUGAG | >hsa-miR-28-5p MIMAT0000085 |
| 1264 | UGGUUCUAGACUUGCCAACUA | >hsa-miR-182-3p MIMAT0000260 |
| 1265 | CCGGUUCCAGUCCCUGGAG | >hsa-miR-6070 MIMAT0023695 |
| 1266 | GACUAUAGAACUUUCCCCCUCA | >hsa-miR-625-3p MIMAT0004808 |
| 1267 | CACAUUACACGGUCGACCUCU | >hsa-miR-323a-3p MIMAT0000755 |
| 1268 | ACUCAAAACCCUUCAGUGACUU | >hsa-miR-616-5p MIMAT0003284 |
| 1269 | AAAGGAGGAAAUAGGCAGGCCA | >hsa-miR-3173-3p MIMAT0015048 |
| 1270 | AGCUGGUGUUGUGAAUCAGGCCG | >hsa-miR-138-5p MIMAT0000430 |
| 1271 | GGCUCCUUGGUCUAGGGGUA | >hsa-miR-4448 MIMAT0018967 |
| 1272 | AGGCUGGAGUGAGCGGAG | >hsa-miR-4430 MIMAT0018945 |
| 1273 | AUAGGACUCAUAUAGUGCCAG | >hsa-miR-3117-3p MIMAT0014979 |
| 1274 | UCAGCACCAGGAUAUUGUUGGAG | >hsa-miR-3065-3p MIMAT0015378 |
| 1275 | AAAGUGCAUCUUUUUAGAGGAU | >hsa-miR-519c-3p MIMAT0002832 |
| 1276 | UUGGAAUAGGGGAUAUCUCAGC | >hsa-miR-6505-5p MIMAT0025466 |
| 1277 | AGGGACUUUUGGGGGCAGAUGUG | >hsa-miR-365a-5p MIMAT0009199 |
| 1278 | CUUUUUGCGGUCUGGGCUUGC | >hsa-miR-129-5p MIMAT0000242 |
| 1279 | UAUGUAAUAUGGUCCACAUCUU | >hsa-miR-380-3p MIMAT0000735 |
| 1280 | AUCAUACAAGGACAAUUUCUUU | >hsa-miR-539-3p MIMAT0022705 |
| 1281 | AGAGCUGGCUGAAGGGCAG | >hsa-miR-4487 MIMAT0019021 |
| 1282 | AAUAGGCCACGGAUCUGGGCAA | >hsa-miR-1295b-3p MIMAT0022294 |
| 1283 | CAAAAGUAAUUGUGGAUUUUGU | >hsa-miR-548n MIMAT0005916 |
| 1284 | AAUCCCAAUGCUAGACCCGGUG | >hsa-miR-4733-5p MIMAT0019857 |
| 1285 | UACUGCAUCAGGAACUGAUUGGA | >hsa-miR-217 MIMAT0000274 |
| 1286 | CACUGGCUCCUUUCUGGGUAGA | >hsa-miR-892b MIMAT0004918 |
| 1287 | UGGCCCAACCUAUUCAGUUAGU | >hsa-miR-3136-3p MIMAT0019203 |
| 1288 | UGGACUGCCCUGAUCUGGAGA | >hsa-miR-1288 MIMAT0005942 |
| 1289 | AAGCAAUACUGUUACCUGAAAU | >hsa-miR-3942-5p MIMAT0018358 |
| 1290 | GGCGGAGGGAAGUAGGUCCGUUGGU | >hsa-miR-658 MIMAT0003336 |
| 1291 | UUUGGCAAUGGUAGAACUCACACU | >hsa-miR-182-5p MIMAT0000259 |
| 1292 | UAGGCCUUUAGAUCACUUAAA | >hsa-miR-1245b-5p MIMAT0019950 |
| 1293 | CUAUACGGCCUCCUAGCUUUCC | >hsa-let-7e-3p MIMAT0004485 |
| 1294 | AGGACCUUCCCUGAACCAAGGA | >hsa-miR-659-5p MIMAT0022710 |

TABLE 1-continued

Human microRNA sequences

| NO | Sequence(5' to 3') | ID and accession |
|---|---|---|
| 1295 | ACUGGCAUUAGUGGGACUUUU | >hsa-miR-5588-5p MIMAT0022295 |
| 1296 | CUCUCUGGCCGUCUACCUUCCA | >hsa-miR-3191-5p MIMAT0022732 |
| 1297 | AAAAGUAACUGCGGUUUUUGA | >hsa-miR-548ak MIMAT0019013 |
| 1298 | UGGGGCGGAGCUUCCGGAGGCC | >hsa-miR-3180-3p MIMAT0015058 |
| 1299 | AUAACAUUGUAAAGCGCUUCUUUCG | >hsa-miR-3143 MIMAT0015012 |
| 1300 | UGAGGCUCUGUUAGCCUUGGCUC | >hsa-miR-2467-5p MIMAT0019952 |
| 1301 | UAACAAACACCUGUAAAACAGC | >hsa-miR-5688 MIMAT0022479 |
| 1302 | UGAGGAUAUGGCAGGGAAGGGGA | >hsa-miR-3679-5p MIMAT0018104 |
| 1303 | CCAGACUGUGGCUGACCAGAGG | >hsa-miR-4494 MIMAT0019029 |
| 1304 | GUGACUGAUACCUUGGAGGCAU | >hsa-miR-4439 MIMAT0018957 |
| 1305 | UAUGUAACACGGUCCACUAACC | >hsa-miR-411-3p MIMAT0004813 |
| 1306 | AAAAGUAAUUGCGGUUUUUGCC | >hsa-miR-548c-5p MIMAT0004806 |
| 1307 | AUUGACACUUCUGUGAGUAGA | >hsa-miR-514a-3p MIMAT0002883 |
| 1308 | CCAACCUAGGUGGUCAGAGUUG | >hsa-miR-4714-3p MIMAT0019823 |
| 1309 | UUACACAGCUGGACAGAGGCA | >hsa-miR-4672 MIMAT0019754 |
| 1310 | UUCUCUUUCUUUAGCCUUGUGU | >hsa-miR-4753-3p MIMAT0019891 |
| 1311 | CGAAUCAUUAUUUGCUGCUCUA | >hsa-miR-15b-3p MIMAT0004586 |
| 1312 | UUCAUUUGCCUCCCAGCCUACA | >hsa-miR-664b-3p MIMAT0022272 |
| 1313 | AAGAGAACUGAAAGUGGAGCCU | >hsa-miR-3925-5p MIMAT0018200 |
| 1314 | UCCAGUGCCCUCCUCUCC | >hsa-miR-1825 MIMAT0006765 |
| 1315 | UGUCAGUGACUCCUGCCCCUUGGU | >hsa-miR-4697-3p MIMAT0019792 |
| 1316 | AGACAGUAGUUCUUGCCUGGUU | >hsa-miR-4645-3p MIMAT0019706 |
| 1317 | AGAGGUAGGUGUGGAAGAA | >hsa-miR-4458 MIMAT0018980 |
| 1318 | UAGGUAGUUUCCUGUUGUUGGG | >hsa-miR-196b-5p MIMAT0001080 |
| 1319 | AACAUUCAUUGCUGUCGGUGGGU | >hsa-miR-181b-5p MIMAT0000257 |
| 1320 | ACCGUGGCUUUCGAUUGUUACU | >hsa-miR-132-5p MIMAT0004594 |
| 1321 | UGCUCAGGUUGCACAGCUGGGA | >hsa-miR-3934-3p MIMAT0022975 |
| 1322 | AUUAGGUAGUGGCAGUGGAAC | >hsa-miR-6509-5p MIMAT0025474 |
| 1323 | AGCGGUGCUCCUGCGGGCCGA | >hsa-miR-4746-3p MIMAT0019881 |
| 1324 | AGAAGAUUGCAGAGUAAGUUCC | >hsa-miR-4699-5p MIMAT0019794 |
| 1325 | AGGUUACCCGAGCAACUUUGCAU | >hsa-miR-409-5p MIMAT0001638 |
| 1326 | GGGCUGGGGCGCGGGGAGGU | >hsa-miR-5787 MIMAT0023252 |
| 1327 | UACUCCAGAGGGCGUCACUCAUG | >hsa-miR-508-5p MIMAT0004778 |
| 1328 | CGCAGGGGCCGGGUGCUCACCG | >hsa-miR-1909-3p MIMAT0007883 |
| 1329 | UGUCCUCUAGGGCCUGCAGUCU | >hsa-miR-3909 MIMAT0018183 |
| 1330 | UGUAAACAUCCUACACUCUCAGC | >hsa-miR-30c-5p MIMAT0000244 |
| 1331 | UGUGACAAUAGAGAUGAACAUG | >hsa-miR-4504 MIMAT0019040 |
| 1332 | UAUGUGCCUUUGGACUACAUCG | >hsa-miR-455-5p MIMAT0003150 |

TABLE 1-continued

Human microRNA sequences

| NO | Sequence(5' to 3') | ID and accession |
|---|---|---|
| 1333 | GAGGGCAUGCGCACUUUGUCC | >hsa-miR-4761-3p MIMAT0019909 |
| 1334 | CUGAAUAGCUGGGACUACAGGU | >hsa-miR-5585-3p MIMAT0022286 |
| 1335 | AAAUUCAUGUUCAAUCUAAACC | >hsa-miR-4760-3p MIMAT0019907 |
| 1336 | UGCGACAUUGGAAGUAGUAUCA | >hsa-miR-3683 MIMAT0018111 |
| 1337 | GUGAAAUGUUUAGGACCACUAG | >hsa-miR-203a MIMAT0000264 |
| 1338 | GACCUGGACAUGUUUGUGCCCAGU | >hsa-miR-619 MIMAT0003288 |
| 1339 | CACCAGGCAUUGUGGUCUCC | >hsa-miR-1911-3p MIMAT0007886 |
| 1340 | CCAAUAUUGGCUGUGCUGCUCC | >hsa-miR-195-3p MIMAT0004615 |
| 1341 | UUUCCAUAGGUGAUGAGUCAC | >hsa-miR-587 MIMAT0003253 |
| 1342 | UUUAGAGACGGGGUCUUGCUCU | >hsa-miR-1303 MIMAT0005891 |
| 1343 | UGCACAUGGCAACCUAGCUCCCA | >hsa-miR-5589-3p MIMAT0022298 |
| 1344 | GGUGGGCUUCCCGGAGGG | >hsa-miR-4417 MIMAT0018929 |
| 1345 | UCUGAGGCCUGCCUCUCCCCA | >hsa-miR-4649-3p MIMAT0019712 |
| 1346 | GCUCCCUCUAGGGUCGCUCGGA | >hsa-miR-4469 MIMAT0018996 |
| 1347 | UGCAAAAGUAAUUGCAGUUUUUG | >hsa-miR-548aj-5p MIMAT0022739 |
| 1348 | UAGUACCAGUACCUUGUGUUCA | >hsa-miR-624-5p MIMAT0003293 |
| 1349 | AAGGCCCGGGCUUUCCUCCCAG | >hsa-miR-4747-3p MIMAT0019883 |
| 1350 | AAAAGUAAUUGCGGUCUUU | >hsa-miR-548ap-5p MIMAT0021037 |
| 1351 | CGGGGUUUUGAGGGCGAGAUGA | >hsa-miR-193b-5p MIMAT0004767 |
| 1352 | UUUGAGGCUACAGUGAGAUGUG | >hsa-miR-1304-5p MIMAT0005892 |
| 1353 | GAUAUUCAGAGGCUAGGUGG | >hsa-miR-6074 MIMAT0023699 |
| 1354 | AAAUCUCUGCAGGCAAAUGUGA | >hsa-miR-216b MIMAT0004959 |
| 1355 | AGUGCCUGAGGGAGUAAGAGCCC | >hsa-miR-550a-5p MIMAT0004800 |
| 1356 | UUAGGCCGCAGAUCUGGGUGA | >hsa-miR-1295a MIMAT0005885 |
| 1357 | CAGCAGGGGAGAGAGAGGAGUC | >hsa-miR-6510-5p MIMAT0025476 |
| 1358 | UGAGGAUGGAUAGCAAGGAAGCC | >hsa-miR-3605-5p MIMAT0017981 |
| 1359 | CGGGCGUGGUGGUGGGGUG | >hsa-miR-1268b MIMAT0018925 |
| 1360 | UACUAACUGCAGAUUCAAGUGA | >hsa-miR-4637 MIMAT0019694 |
| 1361 | CGUGGAUAUUCCUUCUAUGUUU | >hsa-miR-376b-5p MIMAT0022923 |
| 1362 | UAUUCAGGAAGGUGUUACUUAA | >hsa-miR-506-5p MIMAT0022701 |
| 1363 | UGAGGGAGUUGGGUGUAUA | >hsa-miR-6129 MIMAT0024613 |
| 1364 | GAGGGUCUUGGGAGGGAUGUGAC | >hsa-miR-1182 MIMAT0005827 |
| 1365 | UGGUUUACCGUCCCACAUACAU | >hsa-miR-299-5p MIMAT0002890 |
| 1366 | UAGCAAAAACUGCAGUUACUUU | >hsa-miR-548p MIMAT0005934 |
| 1367 | UGGCAAACGUGGAAGCCGAGA | >hsa-miR-4470 MIMAT0018997 |
| 1368 | CUGGGAGGUGGAUGUUUACUUC | >hsa-miR-30b-3p MIMAT0004589 |
| 1369 | UGGCUGUUGGAGGGGCAGGC | >hsa-miR-4687-3p MIMAT0019775 |
| 1370 | CCCGGAGCCAGGAUGCAGCUC | >hsa-miR-1203 MIMAT0005866 |

TABLE 1-continued

Human microRNA sequences

| NO | Sequence(5' to 3') | ID and accession |
|---|---|---|
| 1371 | UCUGUAGCCUGGGAGCAAUGGGGU | >hsa-miR-3137 MIMAT0015005 |
| 1372 | UCCGAGCCUGGGUCUCCCUCUU | >hsa-miR-615-3p MIMAT0003283 |
| 1373 | UUGCUCUGAGCUCCGAGAAAGC | >hsa-miR-5691 MIMAT0022483 |
| 1374 | AUAUACAGGGGGAGACUCUCAU | >hsa-miR-1185-2-3p MIMAT0022713 |
| 1375 | CUACAAAGGGAAGCACUUUCUC | >hsa-miR-524-5p MIMAT0002849 |
| 1376 | UCUGGCUAUCUCACGAGACUGU | >hsa-miR-4794 MIMAT0019967 |
| 1377 | UUUCCUACCCUACCUGAAGACU | >hsa-miR-3685 MIMAT0018113 |
| 1378 | GCGGGGUGGCGGCGGCAUCCC | >hsa-miR-4787-5p MIMAT0019956 |
| 1379 | UUGCUAGUUGCACUCCUCUCUGU | >hsa-miR-449c-3p MIMAT0013771 |
| 1380 | UUCCAUGCCUCCUAGAAGUUCC | >hsa-miR-5581-3p MIMAT0022276 |
| 1381 | UUCUCGAGGAAAGAAGCACUUUC | >hsa-miR-516a-5p MIMAT0004770 |
| 1382 | ACAGAUUCGAUUCUAGGGGAAU | >hsa-miR-10b-3p MIMAT0004556 |
| 1383 | UAGCACCAUUUGAAAUCAGUGUU | >hsa-miR-29b-3p MIMAT0000100 |
| 1384 | UGGGAUCCAGACAGUGGGAGAA | >hsa-miR-4713-3p MIMAT0019821 |
| 1385 | ACCCUAUCAAUAUUGUCUCUGC | >hsa-miR-454-5p MIMAT0003884 |
| 1386 | UUUCUUCUUAGACAUGGCAGCU | >hsa-miR-4659b-3p MIMAT0019734 |
| 1387 | UUUGGGAUUGACGCCACAUGUCU | >hsa-miR-6513-5p MIMAT0025482 |
| 1388 | CAAAACCGCGAUUACUCUUGCA | >hsa-miR-548ay-3p MIMAT0025453 |
| 1389 | UUAGCUUAAGGAGUACCAGAUC | >hsa-miR-5579-3p MIMAT0022270 |
| 1390 | UUCAGAUCCCAGCGGUGCCUCU | >hsa-miR-5100 MIMAT0022259 |
| 1391 | UAUAUAUACAGCCAUGCACUC | >hsa-miR-5011-5p MIMAT0021045 |
| 1392 | UGGUAGAGCUGAGGACA | >hsa-miR-4451 MIMAT0018973 |
| 1393 | UGUCUUGCAGGCCGUCAUGCA | >hsa-miR-431-5p MIMAT0001625 |
| 1394 | UAAUACUGCCUGGUAAUGAUGA | >hsa-miR-200b-3p MIMAT0000318 |
| 1395 | AAAAGUAAUUGCAGUUUUUGC | >hsa-miR-548ar-5p MIMAT0022265 |
| 1396 | GGGAUAUGAAGAAAAAU | >hsa-miR-3201 MIMAT0015086 |
| 1397 | UUGCUUGAACCCAGGAAGUGGA | >hsa-miR-1273e MIMAT0018079 |
| 1398 | UCGGGCGCAAGAGCACUGCAGU | >hsa-miR-6499-5p MIMAT0025450 |
| 1399 | UAUUGCACUUGUCCCGGCCUGU | >hsa-miR-92a-3p MIMAT0000092 |
| 1400 | CUCCUAUAUGAUGCCUUUCUUC | >hsa-miR-337-3p MIMAT0000754 |
| 1401 | UUUUCAACUCUAAUGGGAGAGA | >hsa-miR-1305 MIMAT0005893 |
| 1402 | UACGUCAUCGUUGUCAUCGUCA | >hsa-miR-598 MIMAT0003266 |
| 1403 | AGGCAGGGGCUGGUGCUGGGCGGG | >hsa-miR-4763-3p MIMAT0019913 |
| 1404 | AUCCGCGCUCUGACUCUCUGCC | >hsa-miR-937-3p MIMAT0004980 |
| 1405 | UAAUUGCUUCCAUGUUU | >hsa-miR-302f MIMAT0005932 |
| 1406 | CUGGAUGGCUCCUCCAUGUCU | >hsa-miR-432-3p MIMAT0002815 |
| 1407 | CACCGACUCUGUCUCCUGCAG | >hsa-miR-6510-3p MIMAT0025477 |
| 1408 | AAAAGUAAUUGCGGAUUUUGCC | >hsa-miR-548i MIMAT0005935 |

TABLE 1-continued

Human microRNA sequences

| NO | Sequence(5' to 3') | ID and accession |
|---|---|---|
| 1409 | UACCCAUUGCAUAUCGGAGUUG | >hsa-miR-660-5p MIMAT0003338 |
| 1410 | ACUGACAGGAGAGCAUUUUGA | >hsa-miR-3660 MIMAT0018081 |
| 1411 | GGAGGCCGGGUGGGGCGGGCGG | >hsa-miR-6089 MIMAT0023714 |
| 1412 | UCUUACUCCCUCAGGCACUG | >hsa-miR-550b-3p MIMAT0018445 |
| 1413 | CUCCAGAGGGAAGUACUUUCU | >hsa-miR-520a-5p MIMAT0002833 |
| 1414 | AAACUACUGAAAAUCAAAGAU | >hsa-miR-606 MIMAT0003274 |
| 1415 | UGGGGCGGAGCUUCCGGAG | >hsa-miR-3180 MIMAT0018178 |
| 1416 | AUCAACAGACAUUAAUUGGGCGC | >hsa-miR-421 MIMAT0003339 |
| 1417 | AAGUGCCUCCUUUUAGAGUGUU | >hsa-miR-519e-3p MIMAT0002829 |
| 1418 | UCGAGGAGCUCACAGUCUAGU | >hsa-miR-151a-5p MIMAT0004697 |
| 1419 | ACUGGGCUUGGAGUCAGAAG | >hsa-miR-378g MIMAT0018937 |
| 1420 | UGGAAGGAGGUUGCCGGACGCU | >hsa-miR-4533 MIMAT0019072 |
| 1421 | ACUGAUUUCUUUUGGUGUUCAG | >hsa-miR-29a-5p MIMAT0004503 |
| 1422 | AACGCACUUCCCUUUAGAGUGU | >hsa-miR-521 MIMAT0002854 |
| 1423 | UUACACACAACUGAGGAUCAUA | >hsa-miR-3941 MIMAT0018357 |
| 1424 | CCAGGCUCUGCAGUGGGA | >hsa-miR-3155b MIMAT0019012 |
| 1425 | CUAGACUGAAGCUCCUUGAGG | >hsa-miR-151a-3p MIMAT0000757 |
| 1426 | CGUCUUACCCAGCAGUGUUUGG | >hsa-miR-200c-5p MIMAT0004657 |
| 1427 | CAGGGUCAGCUGAGCAUG | >hsa-miR-1178-5p MIMAT0022940 |
| 1428 | AACACACCUGGUUAACCUCUUU | >hsa-miR-329 MIMAT0001629 |
| 1429 | UCUCUGGAGGGAAGCACUUUCUG | >hsa-miR-518c-5p MIMAT0002847 |
| 1430 | AAGCAGCUGCCUCUGAGGC | >hsa-miR-646 MIMAT0003316 |
| 1431 | UUACGGACCAGCUAAGGGAGGC | >hsa-miR-4788 MIMAT0019958 |
| 1432 | UUGCAUAGUCACAAAAGUGAUC | >hsa-miR-153 MIMAT0000439 |
| 1433 | CCUGUUCUCCAUUACUUGGCUC | >hsa-miR-26b-3p MIMAT0004500 |
| 1434 | GAGCUUAUUCAUAAAAGUGCAG | >hsa-miR-590-5p MIMAT0003258 |
| 1435 | ACAGGCACGACUGGUUUGGCA | >hsa-miR-6715b-5p MIMAT0025842 |
| 1436 | CUCUAGAGGGAAGCGCUUUCUG | >hsa-miR-523-5p MIMAT0005449 |
| 1437 | GGGGUGGUCUGUUGUUG | >hsa-miR-4483 MIMAT0019017 |
| 1438 | UCGCCUCCUCCUCUCCC | >hsa-miR-1281 MIMAT0005939 |
| 1439 | AGGAGAGUGGAUUCCAGGUGGU | >hsa-miR-5192 MIMAT0021123 |
| 1440 | UAAAGUGGCAGAGUAUAGACAC | >hsa-miR-4796-3p MIMAT0019971 |
| 1441 | GACAUUCAGACUACCUG | >hsa-miR-4262 MIMAT0016894 |
| 1442 | UGUGUCCCAUUAUUGGUGAUU | >hsa-miR-3657 MIMAT0018077 |
| 1443 | UAACUGGUUGAACAACUGAACC | >hsa-miR-582-3p MIMAT0004797 |
| 1444 | UCAGUGCACUACAGAACUUUGU | >hsa-miR-148a-3p MIMAT0000243 |
| 1445 | GUCCUCCAGGCCAUGAGCUGCGG | >hsa-miR-4691-5p MIMAT0019781 |
| 1446 | CCGCACUGUGGGUACUUGCUGC | >hsa-miR-106b-3p MIMAT0004672 |

TABLE 1-continued

Human microRNA sequences

| NO | Sequence(5' to 3') | ID and accession |
|---|---|---|
| 1447 | UUUCUAUUUCUCAGUGGGGCUC | >hsa-miR-4482-3p MIMAT0020958 |
| 1448 | CAAUUCUCAAAGGAGCCUCCC | >hsa-miR-5571-5p MIMAT0022257 |
| 1449 | GUGACAUCACAUAUACGGCAGC | >hsa-miR-489 MIMAT0002805 |
| 1450 | AGCUCUAGAAAGAUUGUUGACC | >hsa-miR-6502-5p MIMAT0025460 |
| 1451 | UGGAAAAAACUGGUGUGUGCUU | >hsa-miR-3148 MIMAT0015021 |
| 1452 | AUUUGUGCUUGGCUCUGUCAC | >hsa-miR-2113 MIMAT0009206 |
| 1453 | CGAAAACAGCAAUUACCUUUGC | >hsa-miR-570-3p MIMAT0003235 |
| 1454 | CUUCUGAUCAAGAUUUGUGGUG | >hsa-miR-4762-3p MIMAT0019911 |
| 1455 | CUGGACUGAGCCAUGCUACUGG | >hsa-miR-1269b MIMAT0019059 |
| 1456 | CCCUGAGACCCUAACCUUAA | >hsa-miR-4324 MIMAT0016876 |
| 1457 | AGGCCUCUGUGACGUCACGGUGU | >hsa-miR-4757-5p MIMAT0019901 |
| 1458 | UGCCUAGGCUGAGACUGCAGUG | >hsa-miR-3135a MIMAT0015001 |
| 1459 | AAGCCCUUACCCCAAAAAGCAU | >hsa-miR-129-2-3p MIMAT0004605 |
| 1460 | ACUGCCCCAGGUGCUGCUGG | >hsa-miR-324-3p MIMAT0000762 |
| 1461 | ACAGUCUGCUGAGGUUGGAGC | >hsa-miR-622 MIMAT0003291 |
| 1462 | GUCCUAGGAGGCUCCUCUG | >hsa-miR-5571-3p MIMAT0022258 |
| 1463 | UGUGUACACACGUGCCAGGCGCU | >hsa-miR-3177-5p MIMAT0019215 |
| 1464 | UAGGAGGGAAUAGUAAAAGCAG | >hsa-miR-4779 MIMAT0019938 |
| 1465 | GGGGCUGGGCGCGCGCC | >hsa-miR-4492 MIMAT0019027 |
| 1466 | UCUUGUGUUCUCUAGAUCAGU | >hsa-miR-581 MIMAT0003246 |
| 1467 | UCAGCUGGCCCUCAUUUC | >hsa-miR-1207-3p MIMAT0005872 |
| 1468 | CAUCUGGCAUCCGUCACACAGA | >hsa-miR-3126-3p MIMAT0015377 |
| 1469 | UUCUGCCUCUGUCCAGGUCCUU | >hsa-miR-5001-3p MIMAT0021022 |
| 1470 | AGAUAUUUUGAGUGUUUGGAAUUG | >hsa-miR-3145-3p MIMAT0015016 |
| 1471 | UAAGGCACCCUUCUGAGUAGA | >hsa-miR-506-3p MIMAT0002878 |
| 1472 | AACAGGUGACUGGUUAGACAA | >hsa-miR-552 MIMAT0003215 |
| 1473 | AAGCGACCAUGAUGUAACUUCA | >hsa-miR-4670-5p MIMAT0019750 |
| 1474 | UGCUAUGCCAACAUAUUGCCAU | >hsa-miR-31-3p MIMAT0004504 |
| 1475 | UGAGGUAGUAAGUUGUAUUGUU | >hsa-miR-98-5p MIMAT0000096 |
| 1476 | UCUUCAACCUCAGGACUUGCA | >hsa-miR-676-5p MIMAT0018203 |
| 1477 | CAUCAGAAUUCAUGGAGGCUAG | >hsa-miR-2115-3p MIMAT0011159 |
| 1478 | UAGCACCAUCUGAAAUCGGUUA | >hsa-miR-29a-3p MIMAT0000086 |
| 1479 | AAUCCUUGGAACCUAGGUGUGAGU | >hsa-miR-362-5p MIMAT0000705 |
| 1480 | AUAGUGGUUGUGAAUUUACCUU | >hsa-miR-4460 MIMAT0018982 |
| 1481 | UGCAGGACCAAGAUGAGCCCU | >hsa-miR-1286 MIMAT0005877 |
| 1482 | AGAAAGGGUGGCAAUACCUCUU | >hsa-miR-5681a MIMAT0022469 |
| 1483 | AAAGGUCAUUGUAAGGUUAAUGC | >hsa-miR-3974 MIMAT0019359 |
| 1484 | CUUAUAUCAGAGGCUGUGGG | >hsa-miR-6083 MIMAT0023708 |

TABLE 1-continued

| Human microRNA sequences | | |
|---|---|---|
| NO | Sequence(5' to 3') | ID and accession |
| 1485 | CGUCAACACUUGCUGGUUUCCU | >hsa-miR-505-3p MIMAT0002876 |
| 1486 | UAUGGGGCUUCUGUAGAGAUUUC | >hsa-miR-3675-5p MIMAT0018098 |
| 1487 | UAGCAGCACAUAAUGGUUUGUG | >hsa-miR-15a-5p MIMAT0000068 |
| 1488 | UCAGGCUCAGUCCCCUCCCGAU | >hsa-miR-484 MIMAT0002174 |
| 1489 | AAAAGUAAUUGCGGGUUUUGCC | >hsa-miR-548as-5p MIMAT0022267 |
| 1490 | AAUCAUUCACGGACAACACUU | >hsa-miR-382-3p MIMAT0022697 |
| 1491 | GGUUCCCUCUCCAAAUGUGUCU | >hsa-miR-642b-5p MIMAT0022736 |
| 1492 | AGUGCCUGAGGGAGUAAGAG | >hsa-miR-550a-3-5p MIMAT0020925 |
| 1493 | UUGUGGAUCUCAAGGAUGUGCU | >hsa-miR-4752 MIMAT0019889 |
| 1494 | UUGGCCACCACACCUACCCCUU | >hsa-miR-4701-5p MIMAT0019798 |
| 1495 | AGGCAUGGGAGGUCAGGUGA | >hsa-miR-3622b-5p MIMAT0018005 |
| 1496 | GUGUGUGGAAAUGCUUCUGC | >hsa-miR-147a MIMAT0000251 |
| 1497 | ACUUUAACAUGGAGGCACUUGC | >hsa-miR-302d-5p MIMAT0004685 |
| 1498 | GGGCGACAAAGCAAGACUCUUUCUU | >hsa-miR-1273a MIMAT0005926 |
| 1499 | UCUUGGAGUAGGUCAUUGGGUGG | >hsa-miR-432-5p MIMAT0002814 |
| 1500 | GCUGGGAAGGCAAAGGGACGU | >hsa-miR-204-3p MIMAT0022693 |
| 1501 | CUGGGCCCGCGGCGGGCGUGGGG | >hsa-miR-6724-5p MIMAT0025856 |
| 1502 | UGAGCACCACACAGGCCGGGCGC | >hsa-miR-3663-3p MIMAT0018085 |
| 1503 | UAAGGCACGCGGUGAAUGCC | >hsa-miR-124-3p MIMAT0000422 |
| 1504 | AACUAGUAAUGUUGGAUUAGGG | >hsa-miR-3923 MIMAT0018198 |
| 1505 | AGGAAAUGAGGCUGGCUAGGAGC | >hsa-miR-5093 MIMAT0021085 |
| 1506 | AAAAGCAUCAGGAAGUACCCA | >hsa-miR-4422 MIMAT0018935 |
| 1507 | AAUCAUGUGCAGUGCCAAUAUG | >hsa-miR-96-3p MIMAT0004510 |
| 1508 | ACAGGGAGGAGAUUGUA | >hsa-miR-4441 MIMAT0018959 |
| 1509 | UCUGCCCCUCCGCUGCUGCCA | >hsa-miR-1913 MIMAT0007888 |
| 1510 | UUGCAUGUCAGAUUGUAAUUCCC | >hsa-miR-4666b MIMAT0022485 |
| 1511 | AGGCCAUCAGCAGUCCAAUGAA | >hsa-miR-4529-5p MIMAT0019236 |
| 1512 | GUGGACCUGGCUGGGAC | >hsa-miR-4535 MIMAT0019075 |
| 1513 | CUGGAGUCUAGGAUUCCA | >hsa-miR-4309 MIMAT0016859 |
| 1514 | UGAGGGGCCUCAGACCGAGCUUUU | >hsa-miR-3184-5p MIMAT0015064 |
| 1515 | AUAUGCCUGGCUAGCUCCUC | >hsa-miR-4633-5p MIMAT0019689 |
| 1516 | GAGCCAGUGGUGAGACAGUGA | >hsa-miR-4676-5p MIMAT0019758 |
| 1517 | AAAAGCUGGGUUGAGAGGA | >hsa-miR-320d MIMAT0006764 |
| 1518 | CCAGACAGAAUUCUAUGCACUUUC | >hsa-miR-1324 MIMAT0005956 |
| 1519 | UGCCCUCCUUUCUUCCCUC | >hsa-miR-4290 MIMAT0016921 |
| 1520 | CUCUUGAGGGAAGCACUUUCUGU | >hsa-miR-526b-5p MIMAT0002835 |
| 1521 | GUGGGCUGGGCUGGGCUGGGCC | >hsa-miR-3620-5p MIMAT0022967 |
| 1522 | UGGCCAAAAAGCAGGCAGAGA | >hsa-miR-3926 MIMAT0018201 |

TABLE 1-continued

Human microRNA sequences

| NO | Sequence(5' to 3') | ID and accession |
|---|---|---|
| 1523 | UAGGGGCAGCAGAGGACCUGGG | >hsa-miR-4688 MIMAT0019777 |
| 1524 | AGCUACAUCUGGCUACUGGGU | >hsa-miR-222-3p MIMAT0000279 |
| 1525 | GCCCUGAACGAGGGGUCUGGAG | >hsa-miR-345-3p MIMAT0022698 |
| 1526 | AGACUUCCCAUUUGAAGGUGGC | >hsa-miR-617 MIMAT0003286 |
| 1527 | GCGGCGAGUCCGACUCAU | >hsa-miR-4285 MIMAT0016913 |
| 1528 | ACUGGCCUGGGACUACCGG | >hsa-miR-3176 MIMAT0015053 |
| 1529 | UUGCUCACUGUUCUUCCCUAG | >hsa-miR-1178-3p MIMAT0005823 |
| 1530 | UGUCUAUACUCUGUCACUUUAC | >hsa-miR-4796-5p MIMAT0019970 |
| 1531 | AUCCUUGCUAUCUGGGUGCUA | >hsa-miR-502-5p MIMAT0002873 |
| 1532 | ACUGAAUCCUCUUUUCCUCAG | >hsa-miR-5187-3p MIMAT0021118 |
| 1533 | AAGGUUUGGAUAGAUGCAAUA | >hsa-miR-4464 MIMAT0018988 |
| 1534 | UUCAAGUAAUUCAGGUG | >hsa-miR-1297 MIMAT0005886 |
| 1535 | UGUGCAGCAGGCCAACCGAGA | >hsa-miR-3944-5p MIMAT0019231 |
| 1536 | AAAAGUUAUUGCGGUUUUGGCU | >hsa-miR-548at-5p MIMAT0022277 |
| 1537 | UAUUCAUUUAUCCCCAGCCUACA | >hsa-miR-664a-3p MIMAT0005949 |
| 1538 | GGUGCAGUGCUGCAUCUCUGGU | >hsa-miR-143-5p MIMAT0004599 |
| 1539 | AGACCAUGGGUUCUCAUUGU | >hsa-miR-591 MIMAT0003259 |
| 1540 | UCACUGUUCAGACAGGCGGA | >hsa-miR-1208 MIMAT0005873 |
| 1541 | AUGACCUAUGAAUUGACAGAC | >hsa-miR-215 MIMAT0000272 |
| 1542 | CAAGGCCAAAGGAAGAGAACAG | >hsa-miR-4753-5p MIMAT0019890 |
| 1543 | UGACUCUGCCUGUAGGCCGGU | >hsa-miR-4522 MIMAT0019060 |
| 1544 | AAUCACUAACCACACGGCCAGG | >hsa-miR-34c-3p MIMAT0004677 |
| 1545 | UAGCAGCGGGAACAGUUCUGCAG | >hsa-miR-503-5p MIMAT0002874 |
| 1546 | UCUGCUCAUACCCCAUGGUUUCU | >hsa-miR-767-3p MIMAT0003883 |
| 1547 | UCGGCCUGACCACCCACCCCAC | >hsa-miR-1234-3p MIMAT0005589 |
| 1548 | AGUUUUGCAUAGUUGCACUACA | >hsa-miR-19a-5p MIMAT0004490 |
| 1549 | AGAGAAGAAGAUCAGCCUGCA | >hsa-miR-1253 MIMAT0005904 |
| 1550 | UGGAUGUGGAAGGAGUUAUCU | >hsa-miR-4764-5p MIMAT0019914 |
| 1551 | ACAGUAGAGGGAGGAAUCGCAG | >hsa-miR-936 MIMAT0004979 |
| 1552 | CUAGUGAGGGACAGAACCAGGAUUC | >hsa-miR-921 MIMAT0004971 |
| 1553 | UGAGCCCUGUCCUCCCGCAG | >hsa-miR-1233-3p MIMAT0005588 |
| 1554 | AACUGGCCUACAAAGUCCCAGU | >hsa-miR-193a-3p MIMAT0000459 |
| 1555 | AGAGGAUACCCUUUGUAUGUU | >hsa-miR-1185-5p MIMAT0005798 |
| 1556 | GGGGCCUGGCGGUGGGCGG | >hsa-miR-2861 MIMAT0013802 |
| 1557 | CCAGAGCAGCCUGCGGUAACAGU | >hsa-miR-6501-3p MIMAT0025459 |
| 1558 | AUCCCACCACUGCCACCAU | >hsa-miR-1260b MIMAT0015041 |
| 1559 | ACCCUCGUCAGGUCCCCGGGG | >hsa-miR-4655-3p MIMAT0019722 |
| 1560 | UCGUGCAUAUAUCUACCACAU | >hsa-miR-4536-3p MIMAT0020959 |

TABLE 1-continued

Human microRNA sequences

| NO | Sequence(5' to 3') | ID and accession |
|---|---|---|
| 1561 | AGGGGCUGGCUUUCCUCUGGUC | >hsa-miR-185-3p MIMAT0004611 |
| 1562 | AUUGGACUGCUGAUGGCCCGU | >hsa-miR-4529-3p MIMAT0019068 |
| 1563 | GAACCCAUGAGGUUGAGGCUGCAGU | >hsa-miR-1273d MIMAT0015090 |
| 1564 | UACGUAGAUAUAUAUGUAUUUU | >hsa-miR-1277-3p MIMAT0005933 |
| 1565 | CUUGCCAUCCUGGUCCACUGCAU | >hsa-miR-4776-3p MIMAT0019933 |
| 1566 | CGGCCCGGGCUGCUGCUGUUCCU | >hsa-miR-1538 MIMAT0007400 |
| 1567 | UGCCUGGAACAUAGUAGGGACU | >hsa-miR-3116 MIMAT0014978 |
| 1568 | CUGGGAGAAGGCUGUUUACUCU | >hsa-miR-30c-2-3p MIMAT0004550 |
| 1569 | AACUGGAUCAAUUAUAGGAGUG | >hsa-miR-1243 MIMAT0005894 |
| 1570 | ACCAGCGCGUUUUCAGUUUCAU | >hsa-miR-4738-5p MIMAT0019866 |
| 1571 | CUUUCAGUCGGAUGUUUACAGC | >hsa-miR-30e-3p MIMAT0000693 |
| 1572 | GCAGCAGGGUGAAACUGACACA | >hsa-miR-761 MIMAT0010364 |
| 1573 | UCUGGCUCCGUGUCUUCACUCCC | >hsa-miR-149-5p MIMAT0000450 |
| 1574 | ACUGGGAAGAGGAGCUGAGGGA | >hsa-miR-4646-5p MIMAT0019707 |
| 1575 | GUGGAGUCCUGGGGAAUGGAGA | >hsa-miR-3198 MIMAT0015083 |
| 1576 | CCAGUGACUGAGCUGGAGCCA | >hsa-miR-5190 MIMAT0021121 |
| 1577 | AGCUACAUUGUCUGCUGGGUUUC | >hsa-miR-221-3p MIMAT0000278 |
| 1578 | AAUGAGAGACCUGUACUGUAU | >hsa-miR-4712-3p MIMAT0019819 |
| 1579 | UAGGAGCUCAACAGAUGCCUGUU | >hsa-miR-3139 MIMAT0015007 |
| 1580 | UGCUGUAUUGUCAGGUAGUGA | >hsa-miR-4999-5p MIMAT0021017 |
| 1581 | GGAGUGGGCUGGUGGUU | >hsa-miR-4481 MIMAT0019015 |
| 1582 | ACUGUAGUAUGGGCACUUCCAG | >hsa-miR-20b-3p MIMAT0004752 |
| 1583 | AACUCGUGUUCAAAGCCUUUAG | >hsa-miR-4636 MIMAT0019693 |
| 1584 | AGGCAGUGUAUUGUUAGCUGGC | >hsa-miR-449b-5p MIMAT0003327 |
| 1585 | UCUGACAUCAGUGAUUCUCCUG | >hsa-miR-6719-3p MIMAT0025850 |
| 1586 | AAUCGGACCCAUUUAAACCGGAG | >hsa-miR-5188 MIMAT0021119 |
| 1587 | AGGGGACUGGUUAAUAGAACUA | >hsa-miR-4652-5p MIMAT0019716 |
| 1588 | AAUGGCGCCACUAGGGUUGUG | >hsa-miR-652-3p MIMAT0003322 |
| 1589 | AUGCGAGGAUGCUGACAGUG | >hsa-miR-4737 MIMAT0019863 |
| 1590 | GGCGGGUGCGGGGGUGG | >hsa-miR-3656 MIMAT0018076 |
| 1591 | UUUCAAGCCAGGGGGCGUUUUUC | >hsa-miR-498 MIMAT0002824 |
| 1592 | GCUGCGGGCUGCGGUCAGGGCG | >hsa-miR-4734 MIMAT0019859 |
| 1593 | CACUGUGGGUACAUGCU | >hsa-miR-4318 MIMAT0016869 |
| 1594 | CUCGGCGCGGGGCGCGGGCUCC | >hsa-miR-1469 MIMAT0007347 |
| 1595 | UCUGGUAAGAGAUUUGGGCAUA | >hsa-miR-4490 MIMAT0019025 |
| 1596 | CUUGGGGCAUGGAGUCCCA | >hsa-miR-4260 MIMAT0016881 |
| 1597 | AUGGGUGAAUUUGUAGAAGGAU | >hsa-miR-1262 MIMAT0005914 |
| 1598 | AGCUUCCAUGACUCCUGAUGGA | >hsa-miR-2115-5p MIMAT0011158 |

TABLE 1-continued

Human microRNA sequences

| NO | Sequence(5' to 3') | ID and accession |
|---|---|---|
| 1599 | AGGUAUUGCCACCCUUUCUAGU | >hsa-miR-5681b MIMAT0022480 |
| 1600 | AUAUUAUUAGCCACUUCUGGAU | >hsa-miR-4795-3p MIMAT0019969 |
| 1601 | UUAGCCAAUUGUCCAUCUUUAG | >hsa-miR-4662a-5p MIMAT0019731 |
| 1602 | CUAAUAGUAUCUACCACAAUAAA | >hsa-miR-633 MIMAT0003303 |
| 1603 | UUCCGCCAGUCGGUGGCCGG | >hsa-miR-6084 MIMAT0023709 |
| 1604 | CCGUGUUUCCCCCACGCUUU | >hsa-miR-3676-3p MIMAT0018100 |
| 1605 | AUAUAAUACAACCUGCUAAGUG | >hsa-miR-374b-5p MIMAT0004955 |
| 1606 | UGACCGAUUUCUCCUGGUGUUC | >hsa-miR-29c-5p MIMAT0004673 |
| 1607 | UGGGAACUUAGUAGAGGUUUAA | >hsa-miR-4471 MIMAT0018998 |
| 1608 | CUGGGAGAGGGUUGUUUACUCC | >hsa-miR-30c-1-3p MIMAT0004674 |
| 1609 | AAAAGUAACUGCGGUUUUUGCCU | >hsa-miR-548w MIMAT0015060 |
| 1610 | AGUCAUUGGAGGGUUUGAGCAG | >hsa-miR-616-3p MIMAT0004805 |
| 1611 | UAACAGUCUCCAGUCACGGCC | >hsa-miR-212-3p MIMAT0000269 |
| 1612 | AGAUUGUUUCUUUUGCCGUGCA | >hsa-miR-4445-5p MIMAT0018963 |
| 1613 | AUCAAGGAUCUUAAACUUUGCC | >hsa-miR-561-5p MIMAT0022706 |
| 1614 | GUGAGGACUCGGGAGGUGG | >hsa-miR-1224-5p MIMAT0005458 |
| 1615 | UAUCGUAUCGUAUUGUAUUGU | >hsa-miR-5686 MIMAT0022477 |
| 1616 | UGAUCAGGCAAAAUUGCAGACU | >hsa-miR-4772-5p MIMAT0019926 |
| 1617 | UGAAGCCAGCUCUGGUCUGGGC | >hsa-miR-4786-3p MIMAT0019955 |
| 1618 | AAGGGCUUCCUCUCUGCAGGAC | >hsa-miR-3158-3p MIMAT0015032 |
| 1619 | UCUGAAUAGAGUCUGAAGAGU | >hsa-miR-4427 MIMAT0018942 |
| 1620 | UGGGUUCCUGGCAUGCUGAUUU | >hsa-miR-23b-5p MIMAT0004587 |
| 1621 | UUUGGGACUGAUCUUGAUGUCU | >hsa-miR-3913-5p MIMAT0018187 |
| 1622 | AAAACGGUGAGAUUUUGUUUU | >hsa-miR-553 MIMAT0003216 |
| 1623 | AUGUAUAAAUGUAUACACAC | >hsa-miR-568 MIMAT0003232 |
| 1624 | CAGUAACAAAGAUUCAUCCUUGU | >hsa-miR-802 MIMAT0004185 |
| 1625 | GAAGGCAGCAGUGCUCCCCUGU | >hsa-miR-3714 MIMAT0018165 |
| 1626 | UCCCUGAGACCCUAACUUGUGA | >hsa-miR-125b-5p MIMAT0000423 |
| 1627 | UUGUGUCAAUAUGCGAUGAUGU | >hsa-miR-592 MIMAT0003260 |
| 1628 | AAGCCUGCCCGGCUCCUCGGG | >hsa-miR-596 MIMAT0003264 |
| 1629 | UGCCCCAUCUGUGCCCUGGGUAGGA | >hsa-miR-3189-5p MIMAT0019217 |
| 1630 | CAUAGCCCGGUCGCUGGUACAUGA | >hsa-miR-3651 MIMAT0018071 |
| 1631 | AUGAAGUGCACUCAUGAUAUGU | >hsa-miR-3616-5p MIMAT0017995 |
| 1632 | CAGGGCUCAGGGAUUGGAUGGAG | >hsa-miR-5088 MIMAT0021080 |
| 1633 | UCAGUAAAUGUUUAUUAGAUGA | >hsa-miR-545-5p MIMAT0004785 |
| 1634 | CAGAACAGGAGCAUAGAAAGGC | >hsa-miR-4773 MIMAT0019928 |
| 1635 | ACUCAAAAGAUGGCGGCACUUU | >hsa-miR-371b-5p MIMAT0019892 |
| 1636 | AGAGCAGAAGGAUGAGAU | >hsa-miR-4468 MIMAT0018995 |

TABLE 1-continued

Human microRNA sequences

| NO | Sequence(5' to 3') | ID and accession |
|---|---|---|
| 1637 | AAGGCAGGGCCCCCGCUCCCC | >hsa-miR-940 MIMAT0004983 |
| 1638 | CAGUGCCUCGGCAGUGCAGCCC | >hsa-miR-33b-3p MIMAT0004811 |
| 1639 | UCUCUGAGCAAGGCUUAACACC | >hsa-miR-4653-5p MIMAT0019718 |
| 1640 | GAAAAUCCUUUUUGUUUUUCCAG | >hsa-miR-4668-3p MIMAT0019746 |
| 1641 | UUGGCCACAAUGGGUUAGAAC | >hsa-miR-588 MIMAT0003255 |
| 1642 | UAAGUGCUUCCAUGUUUCAGUGG | >hsa-miR-302c-3p MIMAT0000717 |
| 1643 | AUCUGGAGGUAAGAAGCACUUU | >hsa-miR-516b-5p MIMAT0002859 |
| 1644 | UCCGGUUCUCAGGGCUCCACC | >hsa-miR-671-3p MIMAT0004819 |
| 1645 | UCAGCAAACAUUUAUUGUGUGC | >hsa-miR-545-3p MIMAT0003165 |
| 1646 | AUGGAUAAGGCUUUGGCUU | >hsa-miR-1261 MIMAT0005913 |
| 1647 | AGGAGAAGUCGGGAAGGU | >hsa-miR-5703 MIMAT0022496 |
| 1648 | UGGACGGAGAACUGAUAAGGGU | >hsa-miR-184 MIMAT0000454 |
| 1649 | CCUCUGAAAUUCAGUUCUUCAG | >hsa-miR-146a-3p MIMAT0004608 |
| 1650 | UAGGCAGUGUAUUGCUAGCGGCUGU | >hsa-miR-449c-5p MIMAT0010251 |
| 1651 | GGGUUUGUAGCUUUGCUGGCAUG | >hsa-miR-5087 MIMAT0021079 |
| 1652 | ACUGCUGAGCUAGCACUUCCCG | >hsa-miR-93-3p MIMAT0004509 |
| 1653 | UAUGGCUUUUCAUUCCUAUGUGA | >hsa-miR-135b-5p MIMAT0000758 |
| 1654 | AGACAUCAAGAUCAGUCCCAAA | >hsa-miR-3913-3p MIMAT0019225 |
| 1655 | UAGCAGCACAGAAAUAUUGGC | >hsa-miR-195-5p MIMAT0000461 |
| 1656 | UCGCGCCCCGGCUCCCGUUC | >hsa-miR-1292-3p MIMAT0022948 |
| 1657 | ACAGGUGAGGUUCUUGGGAGCC | >hsa-miR-125a-3p MIMAT0004602 |
| 1658 | AAAACUGCAGUUACUUUUGC | >hsa-miR-548av-3p MIMAT0022304 |
| 1659 | UUAUUGUCACGUUCUGAUU | >hsa-miR-5701 MIMAT0022494 |
| 1660 | UUGGGAUCAUUUUGCAUCCAUA | >hsa-miR-450b-3p MIMAT0004910 |
| 1661 | CUCCGGGACGGCUGGGC | >hsa-miR-4497 MIMAT0019032 |
| 1662 | CCCCGCCACCGCCUUGG | >hsa-miR-4258 MIMAT0016879 |
| 1663 | CCUGGGCAGCGUGUGGCUGAAGG | >hsa-miR-3187-5p MIMAT0019216 |
| 1664 | CUGUACAGCCUCCUAGCUUUCC | >hsa-let-7a-2-3p MIMAT0010195 |
| 1665 | CCGUCGCCGCCACCCGAGCCG | >hsa-miR-1181 MIMAT0005826 |
| 1666 | AAAAUGGUGCCCUAGUGACUACA | >hsa-miR-224-3p MIMAT0009198 |
| 1667 | UAAAUAGAGUAGGCAAAGGACA | >hsa-miR-3121-3p MIMAT0014983 |
| 1668 | AAAGUGCUUCUCUUUGGUGGGU | >hsa-miR-520d-3p MIMAT0002856 |
| 1669 | GGUGGGGGCUGUUGUUU | >hsa-miR-4447 MIMAT0018966 |
| 1670 | GACACUAGGCAUGUGAGUGAUU | >hsa-miR-4704-5p MIMAT0019803 |
| 1671 | GCUUCUGUAGUGUAGUC | >hsa-miR-3182 MIMAT0015062 |
| 1672 | UUUUGCAAUAUGUUCCUGAAUA | >hsa-miR-450b-5p MIMAT0004909 |
| 1673 | CGGUGAGCGCUCGCUGGC | >hsa-miR-4792 MIMAT0019964 |
| 1674 | GGGGGAAGAAAAGGUGGGG | >hsa-miR-4271 MIMAT0016901 |

TABLE 1-continued

Human microRNA sequences

| NO | Sequence(5' to 3') | ID and accession |
|---|---|---|
| 1675 | UGGAGAUCCAGUGCUCGCCCGAU | >hsa-miR-4683 MIMAT0019768 |
| 1676 | UGAAUGGUAAAGCGAUGUCACA | >hsa-miR-4790-3p MIMAT0019962 |
| 1677 | AACUGUUUGCAGAGGAAACUGA | >hsa-miR-452-5p MIMAT0001635 |
| 1678 | GAAUACGUCUGGUUGAUCC | >hsa-miR-6082 MIMAT0023707 |
| 1679 | CCAGCCACGGACUGAGAGUGCAU | >hsa-miR-4691-3p MIMAT0019782 |
| 1680 | GACUGGACAAGCUGAGGAA | >hsa-miR-3654 MIMAT0018074 |
| 1681 | GUGGGCGGGGGCAGGUGUGUG | >hsa-miR-1228-5p MIMAT0005582 |
| 1682 | GUCCCUCUCCAAAUGUGUCUUG | >hsa-miR-642a-5p MIMAT0003312 |
| 1683 | UCGUGGCCUGGUCUCCAUUAU | >hsa-miR-1204 MIMAT0005868 |
| 1684 | AAAGAUCUGGAAGUGGGAGACA | >hsa-miR-3156-5p MIMAT0015030 |
| 1685 | UAUGUGGGAUGGUAAACCGCUU | >hsa-miR-299-3p MIMAT0000687 |
| 1686 | CGGGUGGAUCACGAUGCAAUUU | >hsa-miR-363-5p MIMAT0003385 |
| 1687 | UGUGCUUGCUCGUCCCGCCCGCA | >hsa-miR-636 MIMAT0003306 |
| 1688 | AAAAGUAAUUGCGGUCUUUGGU | >hsa-miR-548j MIMAT0005875 |
| 1689 | GCCUGGAGCUACUCCACCAUCUC | >hsa-miR-4254 MIMAT0016884 |
| 1690 | UGUGUUAGAAUAGGGGCAAUAA | >hsa-miR-3152-3p MIMAT0015025 |
| 1691 | AAAGUGCUUCCUUUUUGAGGG | >hsa-miR-520e MIMAT0002825 |
| 1692 | GUUCAAAUCCAGAUCUAUAAC | >hsa-miR-607 MIMAT0003275 |
| 1693 | CUCUAGAGGGAAGCACUUUCUG | >hsa-miR-520c-5p MIMAT0005455 |
| 1694 | CUUCUUGUGCUCUAGGAUUGU | >hsa-miR-578 MIMAT0003243 |
| 1695 | UCUGAAAGAGCAGUUGGUGUU | >hsa-miR-4766-5p MIMAT0019917 |
| 1696 | CAACCUCGAGGAUCUCCCCAGC | >hsa-miR-3150b-5p MIMAT0019226 |
| 1697 | AGAUCAGAAGGUGAUUGUGGCU | >hsa-miR-383 MIMAT0000738 |
| 1698 | AAGGGGGAAGGAAACAUGGAGA | >hsa-miR-4716-3p MIMAT0019827 |
| 1699 | UAGUGAGUUAGAGAUGCAGAGCC | >hsa-miR-3174 MIMAT0015051 |
| 1700 | AGGCGGAGACUUGGGCAAUUG | >hsa-miR-25-5p MIMAT0004498 |
| 1701 | UGUUCAUGUAGAUGUUUAAGC | >hsa-miR-1206 MIMAT0005870 |
| 1702 | UGUCUACUACUGGAGACACUGG | >hsa-miR-934 MIMAT0004977 |
| 1703 | UACGCGCAGACCACAGGAUGUC | >hsa-miR-3939 MIMAT0018355 |
| 1704 | CAAAAACUGCAGUUACUUUUGU | >hsa-miR-548am-3p MIMAT0019076 |
| 1705 | CAGCAGCAAUUCAUGUUUUGAA | >hsa-miR-424-5p MIMAT0001341 |
| 1706 | UAGACCAUCUUUCUAGAGUAU | >hsa-miR-6502-3p MIMAT0025461 |
| 1707 | GGGGCGCGGCCGGAUCG | >hsa-miR-3178 MIMAT0015055 |
| 1708 | UGUAACAGCAACUCCAUGUGGA | >hsa-miR-194-5p MIMAT0000460 |
| 1709 | CAAGAACCUCAGUUGCUUUUGU | >hsa-miR-548b-3p MIMAT0003254 |
| 1710 | ACCUUCCUCUCCAUGGGUCUUU | >hsa-miR-3667-3p MIMAT0018090 |
| 1711 | CGGGGUGGGUGAGGUCGGGC | >hsa-miR-4651 MIMAT0019715 |
| 1712 | GAUGAUGCUGCUGAUGCUG | >hsa-miR-1322 MIMAT0005953 |

TABLE 1-continued

Human microRNA sequences

| NO | Sequence(5' to 3') | ID and accession |
|---|---|---|
| 1713 | UUCGGUAUACUUUGUGAAUUGG | >hsa-miR-4798-5p MIMAT0019974 |
| 1714 | UCUGUAUUCUCCUUUGCCUGCAG | >hsa-miR-4742-3p MIMAT0019873 |
| 1715 | AAAGUUCUGAGACACUCCGACU | >hsa-miR-148a-5p MIMAT0004549 |
| 1716 | AAUGUUGGAAUCCUCGCUAGAG | >hsa-miR-4781-3p MIMAT0019943 |
| 1717 | AAUGUAAACAGGCUUUUUGCU | >hsa-miR-4495 MIMAT0019030 |
| 1718 | GAGCUUGGAUGAGCUGGGCUGA | >hsa-miR-4538 MIMAT0019081 |
| 1719 | GCUCAGGGAUGAUAACUGUGCUGAGA | >hsa-miR-4518 MIMAT0019055 |
| 1720 | UUCGGGCUGGCCUGCUGCUCCGG | >hsa-miR-3944-3p MIMAT0018360 |
| 1721 | CAAAGUGAUGAGUAAUACUGGCUG | >hsa-miR-3609 MIMAT0017986 |
| 1722 | GUGCAAAAGUCAUCACGGUU | >hsa-miR-548aw MIMAT0022471 |
| 1723 | AGGGUGUUUCUCUCAUCUCU | >hsa-miR-609 MIMAT0003277 |
| 1724 | UGCAGGGGUCGGGUGGGCCAGG | >hsa-miR-6722-3p MIMAT0025854 |
| 1725 | UCCAUGUUUCCUUCCCCCUUCU | >hsa-miR-4716-5p MIMAT0019826 |
| 1726 | CAAAACUGGCAAUUACUUUUGC | >hsa-miR-548a-3p MIMAT0003251 |
| 1727 | GUGAAGGCCCGGCGGAGA | >hsa-miR-6126 MIMAT0024599 |
| 1728 | UGUCGUGGGGCUUGCUGGCUUG | >hsa-miR-4440 MIMAT0018958 |
| 1729 | ACUGGACUUGGUGUCAGAUGG | >hsa-miR-378h MIMAT0018984 |
| 1730 | AGGAUGAGCAAAGAAAGUAGAUU | >hsa-miR-1255a MIMAT0005906 |
| 1731 | ACAAAGUACAGCAUUAGCCUUAG | >hsa-miR-3973 MIMAT0019358 |
| 1732 | CACCCGUAGAACCGACCUUGCG | >hsa-miR-99b-5p MIMAT0000689 |
| 1733 | AAAAGUAAUUGCGGUUUUUGC | >hsa-miR-548au-5p MIMAT0022291 |
| 1734 | CUCAUCUGCAAAGAAGUAAGUG | >hsa-miR-452-3p MIMAT0001636 |
| 1735 | UCACAAAUCUAUAAUAUGCAGG | >hsa-miR-4719 MIMAT0019832 |
| 1736 | AGUUUUGCAGGUUUGCAUUUCA | >hsa-miR-19b-2-5p MIMAT0004492 |
| 1737 | AUCUGCCAGCUUCCACAGUGG | >hsa-miR-4727-5p MIMAT0019847 |
| 1738 | ACCUGGCAUACAAUGUAGAUUU | >hsa-miR-221-5p MIMAT0004568 |
| 1739 | CUGUGGGCUCAGCGCGUGGGG | >hsa-miR-4322 MIMAT0016873 |
| 1740 | AUGGAGAUAGAUAUAGAAAU | >hsa-miR-620 MIMAT0003289 |
| 1741 | CCUGAGACCCUAGUUCCAC | >hsa-miR-4329 MIMAT0016923 |
| 1742 | CAAAACCGCAGUAACUUUUGU | >hsa-miR-548at-3p MIMAT0022278 |
| 1743 | UCAGUCACAUAUCUAGUGUCUA | >hsa-miR-4704-3p MIMAT0019804 |
| 1744 | UCUCAGGAGUAAAGACAGAGUU | >hsa-miR-3664-3p MIMAT0019220 |
| 1745 | UAGCAAGAGAACCAUUACCAUU | >hsa-miR-451b MIMAT0019840 |
| 1746 | UGUGGGACUGCAAAUGGGAG | >hsa-miR-4648 MIMAT0019710 |
| 1747 | CUAUACAGUCUACUGUCUUUCC | >hsa-let-7f-2-3p MIMAT0004487 |
| 1748 | GCGACCCACUCUUGGUUUCCA | >hsa-miR-551a MIMAT0003214 |
| 1749 | UGCGGGGACAGGCCAGGGCAUC | >hsa-miR-4749-5p MIMAT0019885 |
| 1750 | AGGAUUUCAGAAAUACUGGUGU | >hsa-miR-3167 MIMAT0015042 |

TABLE 1-continued

| Human microRNA sequences | |
|---|---|
| NO Sequence(5' to 3') | ID and accession |
| 1751 CACCCAGAUCUGCGGCCUAAU | >hsa-miR-1295b-5p MIMAT0022293 |
| 1752 UGCAGCUCUGGUGGAAAAUGGAG | >hsa-miR-4660 MIMAT0019728 |
| 1753 AGAAUUGCGUUUGGACAAUCAGU | >hsa-miR-2964a-3p MIMAT0019748 |
| 1754 UGAGGGAGUGGGUGGGAGG | >hsa-miR-6127 MIMAT0024610 |
| 1755 UGGGAACGGGUUCCGGCAGACGCUG | >hsa-miR-1292-5p MIMAT0005943 |
| 1756 UGAAGUUACAUCAUGGUCGCUU | >hsa-miR-4670-3p MIMAT0019751 |
| 1757 UGUCUUACUCCCUCAGGCACAU | >hsa-miR-550a-3p MIMAT0003257 |
| 1758 CCUGGCAUAUUUGGUAUAACUU | >hsa-miR-4720-5p MIMAT0019833 |
| 1759 AUAUACCUGUUCGGUCUCUUUA | >hsa-miR-3144-3p MIMAT0015015 |
| 1760 AACUCUAGCCUGAGCAACAG | >hsa-miR-5684 MIMAT0022473 |
| 1761 UCUCCCAACCCUUGUACCAGUG | >hsa-miR-150-5p MIMAT0000451 |
| 1762 UCCCCCAGGUGUGAUUCUGAUUU | >hsa-miR-361-3p MIMAT0004682 |
| 1763 UGAGGGAGGAGGUUGGGUA | >hsa-miR-6133 MIMAT0024617 |
| 1764 CAGGGCUGGCAGUGACAUGGGU | >hsa-miR-4446-3p MIMAT0018965 |
| 1765 GGGUCCCGGGGAGGGGGG | >hsa-miR-4281 MIMAT0016907 |
| 1766 UCCCCUUCUGCAGGCCUGCUGG | >hsa-miR-3127-3p MIMAT0019201 |
| 1767 UGAGGUAGGAGGUUGUAUAGUU | >hsa-let-7e-5p MIMAT0000066 |
| 1768 UGAGGGAGUAGGAUGUAUGGUU | >hsa-miR-4510 MIMAT0019047 |
| 1769 AUGCUGACAUAUUUACUAGAGG | >hsa-miR-628-5p MIMAT0004809 |
| 1770 AGAGAUGCCGCCUUGCUCCUU | >hsa-miR-4708-5p MIMAT0019809 |
| 1771 UCCCACUACUUCACUUGUGA | >hsa-miR-4301 MIMAT0016850 |
| 1772 UCUGGGAGGUUGUAGCAGUGGAA | >hsa-miR-3192 MIMAT0015076 |
| 1773 GUGGGGCCAGGCGGUGG | >hsa-miR-1227-5p MIMAT0022941 |
| 1774 CUAUACAAUCUAUUGCCUUCCC | >hsa-let-7f-1-3p MIMAT0004486 |
| 1775 CAAGCUUGUAUCUAUAGGUAUG | >hsa-miR-100-3p MIMAT0004512 |
| 1776 UAAAGAACUCUUAAAACCCAAU | >hsa-miR-3133 MIMAT0014998 |
| 1777 CAAAGAGGAAGGUCCCAUUAC | >hsa-miR-583 MIMAT0003248 |
| 1778 CGGCUCUGGGUCUGUGGGGA | >hsa-miR-760 MIMAT0004957 |
| 1779 CUGGGACAGGAGGAGGAGGCAG | >hsa-miR-4298 MIMAT0016852 |
| 1780 AGGUGGUCCGUGGCGCGUUCGC | >hsa-miR-323a-5p MIMAT0004696 |
| 1781 UUGAACUGUUAAGAACCACUGGA | >hsa-miR-203b-3p MIMAT0019814 |
| 1782 GCGAGGACCCCUCGGGGUCUGAC | >hsa-miR-611 MIMAT0003279 |
| 1783 GCUGACUCCUAGUCCAGGGCUC | >hsa-miR-345-5p MIMAT0000772 |
| 1784 GUAGAGGAGAUGGCGCAGGG | >hsa-miR-877-5p MIMAT0004949 |
| 1785 AACUGAACCAGGAGUGAGCUUCG | >hsa-miR-4724-5p MIMAT0019841 |
| 1786 UAGCAAUACAGUACAAAUAUAGU | >hsa-miR-4703-5p MIMAT0019801 |
| 1787 UGAGGCCCUUGGGGCACAGUGG | >hsa-miR-5008-5p MIMAT0021039 |
| 1788 CACAGGACUGACUCCUCACCCCAGUG | >hsa-miR-4700-3p MIMAT0019797 |

TABLE 1-continued

Human microRNA sequences

| NO | Sequence(5' to 3') | ID and accession |
|---|---|---|
| 1789 | AGAGCUUAGCUGAUUGGUGAAC | >hsa-miR-27b-5p MIMAT0004588 |
| 1790 | UCAGGACACUUCUGAACUUGGA | >hsa-miR-5000-3p MIMAT0021020 |
| 1791 | UCUCCCUUGAGGGCACUUU | >hsa-miR-4287 MIMAT0016917 |
| 1792 | GUGGACCAGGAUGGCAAGGGCU | >hsa-miR-4776-5p MIMAT0019932 |
| 1793 | CGUGCCACCCUUUUCCCCAG | >hsa-miR-1227-3p MIMAT0005580 |
| 1794 | CUUGGUUCAGGGAGGGUCCCCA | >hsa-miR-659-3p MIMAT0003337 |
| 1795 | GGGUGGGGAUUUGUUGCAUUAC | >hsa-miR-92a-2-5p MIMAT0004508 |
| 1796 | GAGGCUGAUGUGAGUAGACCACU | >hsa-miR-3929 MIMAT0018206 |
| 1797 | AGGCAUUGACUUCUCACUAGCU | >hsa-miR-1256 MIMAT0005907 |
| 1798 | UCAAAUGCUCAGACUCCUGUGGU | >hsa-miR-105-5p MIMAT0000102 |
| 1799 | AGCCAGGCUCUGAAGGGAAAGU | >hsa-miR-4755-3p MIMAT0019896 |
| 1800 | AUGAUCCAGGAACCUGCCUCU | >hsa-miR-640 MIMAT0003310 |
| 1801 | AGACCUGGCCCAGACCUCAGC | >hsa-miR-631 MIMAT0003300 |
| 1802 | ACAGUAGUCUGCACAUUGGUUA | >hsa-miR-199a-3p MIMAT0000232 |
| 1803 | CCCCACCUCCUCUCUCCUCAG | >hsa-miR-1224-3p MIMAT0005459 |
| 1804 | UCUCUGAGUACCAUAUGCCUUGU | >hsa-miR-3921 MIMAT0018196 |
| 1805 | UCUGGUAUGUAGUAGGUAAUAA | >hsa-miR-4774-5p MIMAT0019929 |
| 1806 | CUUUCAGUCAGAUGUUUGCUGC | >hsa-miR-30d-3p MIMAT0004551 |
| 1807 | ACGGGUUAGGCUCUUGGGAGCU | >hsa-miR-125b-1-3p MIMAT0004592 |
| 1808 | UGAUAUGUUUGAUAUAUUAGGU | >hsa-miR-190a MIMAT0000458 |
| 1809 | CAAUUUAGUGUGUGUGAUAUUU | >hsa-miR-32-3p MIMAT0004505 |
| 1810 | UCGACCGGACCUCGACCGGCU | >hsa-miR-1307-5p MIMAT0022727 |
| 1811 | UGAGGUAGUAGUUUCUU | >hsa-miR-4500 MIMAT0019036 |
| 1812 | AUGGCCAGAGCUCACACAGAGG | >hsa-miR-4435 MIMAT0018951 |
| 1813 | CUAGGAGGCCUUGGCC | >hsa-miR-4266 MIMAT0016892 |
| 1814 | GUGUUCUCUGAUGGACAG | >hsa-miR-4273 MIMAT0016903 |
| 1815 | GAAGGCGCUUCCCUUUAGAGCG | >hsa-miR-525-3p MIMAT0002839 |
| 1816 | AAGGAGCUUACAAUCUAGCUGGG | >hsa-miR-708-5p MIMAT0004926 |
| 1817 | UUGAAAGGCUAUUUCUUGGUC | >hsa-miR-488-3p MIMAT0004763 |
| 1818 | GGGUGCGGGCCGGCGGGG | >hsa-miR-4466 MIMAT0018993 |
| 1819 | AGCAGAGGCAGAGAGGCUCAGG | >hsa-miR-2467-3p MIMAT0019953 |
| 1820 | UCUGCCAUCCUCCCUCCCCUAC | >hsa-miR-4769-3p MIMAT0019923 |
| 1821 | AAAGUAAUUGUGGAUUUUGCU | >hsa-miR-548ab MIMAT0018928 |
| 1822 | AAAGUAAUCACUGUUUUUGCC | >hsa-miR-548y MIMAT0018354 |
| 1823 | AAGGAACCAGAAAAUGAGAAGU | >hsa-miR-3914 MIMAT0018188 |
| 1824 | ACCAUCGACCGUUGAUUGUACC | >hsa-miR-181a-3p MIMAT0000270 |
| 1825 | ACUGGCUAGGGAAAAUGAUUGGAU | >hsa-miR-664a-5p MIMAT0005948 |
| 1826 | UGGCAGUGUCUUAGCUGGUUGU | >hsa-miR-34a-5p MIMAT0000255 |

TABLE 1-continued

Human microRNA sequences

| NO | Sequence(5' to 3') | ID and accession |
|---|---|---|
| 1827 | CUCUCCUCCCGGCUUC | >hsa-miR-4279 MIMAT0016909 |
| 1828 | AUACACAUACACGCAACACACAU | >hsa-miR-466 MIMAT0015002 |
| 1829 | UCAAGAGCAAUAACGAAAAAUGU | >hsa-miR-335-5p MIMAT0000765 |
| 1830 | GGGACCCAGGGAGAGACGUAAG | >hsa-miR-711 MIMAT0012734 |
| 1831 | AAGUCCCACUAAUGCCAGC | >hsa-miR-5588-3p MIMAT0022296 |
| 1832 | UGUUGGGAUUCAGCAGGACCAU | >hsa-miR-4425 MIMAT0018940 |
| 1833 | ACGGAGACGACAAGACUGUGCUG | >hsa-miR-5091 MIMAT0021083 |
| 1834 | UUCAAGUAAUCCAGGAUAGGCU | >hsa-miR-26a-5p MIMAT0000082 |
| 1835 | CAAGCUCGUGUCUGUGGGUCCG | >hsa-miR-99b-3p MIMAT0004678 |
| 1836 | ACAUCCUGCUCCACAGGGCAGAGG | >hsa-miR-4793-5p MIMAT0019965 |
| 1837 | AAAAGCUGGGUUGAGAGGGCGA | >hsa-miR-320a MIMAT0000510 |
| 1838 | CCAAUAUUACUGUGCUGCUUUA | >hsa-miR-16-2-3p MIMAT0004518 |
| 1839 | GUGGGUACGGCCCAGUGGGGGG | >hsa-miR-1225-5p MIMAT0005572 |
| 1840 | UUGUCUGCUGAGUUUCC | >hsa-miR-4288 MIMAT0016918 |
| 1841 | AACAUUCAACGCUGUCGGUGAGU | >hsa-miR-181a-5p MIMAT0000256 |
| 1842 | AAAGAUAGACAAUUGGCUAAAU | >hsa-miR-4662a-3p MIMAT0019732 |
| 1843 | AUAGCAAUUGCUCUUUUGGAA | >hsa-miR-4766-3p MIMAT0019918 |
| 1844 | UCAGAUGAUCUAAAGGCCUAUA | >hsa-miR-1245b-3p MIMAT0019951 |
| 1845 | ACGCCCUUCCCCCCCUUCUUCA | >hsa-miR-1249 MIMAT0005901 |
| 1846 | GAAGAUGGUGCUGUGCUGAGGAA | >hsa-miR-4647 MIMAT0019709 |
| 1847 | AUUGUAGAACCUAAGAUUGGCC | >hsa-miR-3674 MIMAT0018097 |
| 1848 | ACUCCAAGAAGAAUCUAGACAG | >hsa-miR-5695 MIMAT0022488 |
| 1849 | AGGUGGAUGCAAUGUGACCUCA | >hsa-miR-3165 MIMAT0015039 |
| 1850 | UGAGGCAGUAGAUUGAAU | >hsa-miR-1827 MIMAT0006767 |
| 1851 | CAAAAAUCUCAAUUACUUUUGC | >hsa-miR-548c-3p MIMAT0003285 |
| 1852 | UUCUGGAAUUCUGUGUGAGGGA | >hsa-miR-1299 MIMAT0005887 |
| 1853 | UCCCUGGAGUUUCUUCUU | >hsa-miR-4308 MIMAT0016861 |
| 1854 | AUGGGUGAUGGGUGUGGUGU | >hsa-miR-4701-3p MIMAT0019799 |
| 1855 | CACUUAGCAGGUUGUAUUAUAU | >hsa-miR-374c-3p MIMAT0022735 |
| 1856 | GGCUGGUCAGAUGGGAGUG | >hsa-miR-6131 MIMAT0024615 |
| 1857 | GCUGCACCGGAGACUGGGUAA | >hsa-miR-3130-3p MIMAT0014994 |
| 1858 | CAGUGCAAGUGUAGAUGCCGA | >hsa-miR-3666 MIMAT0018088 |
| 1859 | AAAAGCUGGGUUGAGAGGGCAA | >hsa-miR-320b MIMAT0005792 |
| 1860 | GGGAGCCAGGAAGUAUUGAUGU | >hsa-miR-505-5p MIMAT0004776 |
| 1861 | UUGCUAAGUAGGCUGAGAUUGA | >hsa-miR-4639-5p MIMAT0019697 |
| 1862 | AUGUAUGUGUGCAUGUGCAUG | >hsa-miR-297 MIMAT0004450 |
| 1863 | CAAGUCUUAUUUGAGCACCUGUU | >hsa-miR-1264 MIMAT0005791 |
| 1864 | UCAUUUAUCUGUUGGGAAGCUA | >hsa-miR-4729 MIMAT0019851 |

TABLE 1-continued

Human microRNA sequences

| NO | Sequence(5' to 3') | ID and accession |
|---|---|---|
| 1865 | GAAUAUGGGUAUAUUAGUUUGG | >hsa-miR-5583-3p MIMAT0022282 |
| 1866 | AGAGGCUUUGUGCGGAUACGGGG | >hsa-miR-3188 MIMAT0015070 |
| 1867 | AACUCUGUCUUCACUCAUGAGU | >hsa-miR-3664-5p MIMAT0018086 |
| 1868 | UGAGGUAGUAGGUUGUAUAGUU | >hsa-let-7a-5p MIMAT0000062 |
| 1869 | CUGACCUAUGAAUUGACAGCC | >hsa-miR-192-5p MIMAT0000222 |
| 1870 | UCUAGUGCGGGCGUUCCCG | >hsa-miR-6080 MIMAT0023705 |
| 1871 | UGGAAGACUAGUGAUUUUGUUGU | >hsa-miR-7-5p MIMAT0000252 |
| 1872 | AAAAGUAUUUGCGGGUUUUGUC | >hsa-miR-5481 MIMAT0005889 |
| 1873 | ACAGGAGUGGGGUGGGACAU | >hsa-miR-4433-3p MIMAT0018949 |
| 1874 | CUGACUGAAUAGGUAGGGUCAUU | >hsa-miR-3136-5p MIMAT0015003 |
| 1875 | UCUACAAAGGAAAGCGCUUUCU | >hsa-miR-1283 MIMAT0005799 |
| 1876 | AACAUCACAGCAAGUCUGUGCU | >hsa-miR-499a-3p MIMAT0004772 |
| 1877 | AAAAACUGAGACUACUUUUGCA | >hsa-miR-548e MIMAT0005874 |
| 1878 | GUUCUCCCAACGUAAGCCCAGC | >hsa-miR-629-3p MIMAT0003298 |
| 1879 | AGCAUACACCUGUAGUCCUAGA | >hsa-miR-5689 MIMAT0022481 |
| 1880 | UUUCCCUUUCCAUCCUGGCAG | >hsa-miR-5006-3p MIMAT0021034 |
| 1881 | AGCAGACUUGACCUACAAUUA | >hsa-miR-4771 MIMAT0019925 |
| 1882 | CAGUGCAAUGAUGAAAGGGCAU | >hsa-miR-130b-3p MIMAT0000691 |
| 1883 | CAAAAACCGCAAUUACUUUUGCA | >hsa-miR-548z MIMAT0018446 |
| 1884 | AUAAUACAUGGUUAACCUCUUU | >hsa-miR-655 MIMAT0003331 |
| 1885 | CAAAGCGCUUCCCUUUGGAGC | >hsa-miR-518d-3p MIMAT0002864 |
| 1886 | AUCACACAAAGGCAACUUUUGU | >hsa-miR-377-3p MIMAT0000730 |
| 1887 | UCCCUGAGCAAAGCCAC | >hsa-miR-4319 MIMAT0016870 |
| 1888 | UGCAACGAACCUGAGCCACUGA | >hsa-miR-891a MIMAT0004902 |
| 1889 | AUAAUACAACCUGCUAAGUGCU | >hsa-miR-374c-5p MIMAT0018443 |
| 1890 | UUCACAUUGUGCUACUGUCUGC | >hsa-miR-130a-5p MIMAT0004593 |
| 1891 | UUAUUGCUUAAGAAUACGCGUAG | >hsa-miR-137 MIMAT0000429 |
| 1892 | ACAGUAGUCUGCACAUUGGUUA | >hsa-miR-199b-3p MIMAT0004563 |
| 1893 | CAGCAGGAGGUGAGGGGAG | >hsa-miR-6165 MIMAT0024782 |
| 1894 | UCACUCUCACCUUGCUUUGC | >hsa-miR-4639-3p MIMAT0019698 |
| 1895 | UAGUGCAAUAUUGCUUAUAGGGU | >hsa-miR-454-3p MIMAT0003885 |
| 1896 | GCCCCUGGGCCUAUCCUAGAA | >hsa-miR-331-3p MIMAT0000760 |
| 1897 | UAGUACUGUGCAUAUCAUCUAU | >hsa-miR-1278 MIMAT0005936 |
| 1898 | UCGUGUCUUGUGUUGCAGCCGG | >hsa-miR-187-3p MIMAT0000262 |
| 1899 | CUGGGGAGAUCCUCGAGGUUGG | >hsa-miR-3150a-3p MIMAT0015023 |
| 1900 | CGCGCCUGCAGGAACUGGUAGA | >hsa-miR-6720-3p MIMAT0025851 |
| 1901 | AGAGUCUUGUGAUGUCUUGC | >hsa-miR-924 MIMAT0004974 |
| 1902 | GAACGCGCUUCCCUAUAGAGGGU | >hsa-miR-523-3p MIMAT0002840 |

TABLE 1-continued

Human microRNA sequences

| NO | Sequence(5' to 3') | ID and accession |
|---|---|---|
| 1903 | UGACUUCUACCUCUUCCAAAG | >hsa-miR-6505-3p MIMAT0025467 |
| 1904 | UAGAUAAAAUAUUGGUACCUG | >hsa-miR-577 MIMAT0003242 |
| 1905 | GAAGUUGUUCGUGGUGGAUUCG | >hsa-miR-382-5p MIMAT0000737 |
| 1906 | UGAGAUGACACUGUAGCU | >hsa-miR-4770 MIMAT0019924 |
| 1907 | CUAGUGCUCUCCGUUACAAGUA | >hsa-miR-4473 MIMAT0019000 |
| 1908 | ACCGUGCAAAGGUAGCAUA | >hsa-miR-1973 MIMAT0009448 |
| 1909 | GGGGGGGGGGGGGGGGCCG | >hsa-miR-1234-5p MIMAT0022944 |
| 1910 | AUGGUUCCGUCAAGCACCAUGG | >hsa-miR-218-1-3p MIMAT0004565 |
| 1911 | AAACUAAUCUCUACACUGCUGC | >hsa-miR-3129-3p MIMAT0019202 |
| 1912 | GACUGACACCUCUUUGGGUGAA | >hsa-miR-888-3p MIMAT0004917 |
| 1913 | AUAUGGGUUUACUAGUUGGU | >hsa-miR-3115 MIMAT0014977 |
| 1914 | CCGGUCCCAGGAGAACCUGCAGA | >hsa-miR-4746-5p MIMAT0019880 |
| 1915 | AGCAGCAUUGUACAGGGCUAUCA | >hsa-miR-107 MIMAT0000104 |
| 1916 | UUUUGUGUCUCCCAUUCCCAG | >hsa-miR-5010-3p MIMAT0021044 |
| 1917 | UCACAACAACCUUGCAGGGUAGA | >hsa-miR-5003-5p MIMAT0021025 |
| 1918 | UUGGACGGUAAGGUUAAGCAA | >hsa-miR-4804-5p MIMAT0019984 |
| 1919 | GUAGAUUCUCCUUCUAUGAGUA | >hsa-miR-376a-5p MIMAT0003386 |
| 1920 | UAUACAAGGGCAGACUCUCUCU | >hsa-miR-300 MIMAT0004903 |
| 1921 | CAUCCCUUGCAUGGUGGAGGG | >hsa-miR-188-5p MIMAT0000457 |
| 1922 | GAAGAAUAGGAGGGACUUUGU | >hsa-miR-6507-5p MIMAT0025470 |
| 1923 | UCCGUACAAACUCUGCUGUG | >hsa-miR-3678-5p MIMAT0018102 |
| 1924 | CCACCAGGUCUAGCAUUGGGAU | >hsa-miR-4733-3p MIMAT0019858 |
| 1925 | UUAAUUUUUUGUUUCGGUCACU | >hsa-miR-4775 MIMAT0019931 |
| 1926 | CUGGGUUGGGCUGGGCUGGG | >hsa-miR-4507 MIMAT0019044 |
| 1927 | CUCCCACUUCCAGAUCUUUCU | >hsa-miR-3156-3p MIMAT0019209 |
| 1928 | AAACAAACAUGGUGCACUUCUU | >hsa-miR-495-3p MIMAT0002817 |
| 1929 | UUAGUGCAUAGUCUUUGGUCU | >hsa-miR-4671-3p MIMAT0019753 |
| 1930 | GUGAGUGUGGAUCCUGGAGGAAU | >hsa-miR-4658 MIMAT0019725 |
| 1931 | UGUGCGCAGGGAGACCUCUCCC | >hsa-miR-933 MIMAT0004976 |
| 1932 | CAGCCUGACAGGAACAG | >hsa-miR-4293 MIMAT0016848 |
| 1933 | GGGAGAAGGGUCGGGGC | >hsa-miR-4516 MIMAT0019053 |
| 1934 | CAAGGGACCAAGCAUUCAUUAU | >hsa-miR-4475 MIMAT0019002 |
| 1935 | CAAAGCGCUUCUCUUUAGAGUGU | >hsa-miR-518c-3p MIMAT0002848 |
| 1936 | AACGGGAAUGCAGGCUGUAUCU | >hsa-miR-4681 MIMAT0019766 |
| 1937 | GAAUGUUGCUCGGUGAACCCCU | >hsa-miR-409-3p MIMAT0001639 |
| 1938 | UUCCCUUUGUCAUCCUAUGCCU | >hsa-miR-204-5p MIMAT0000265 |
| 1939 | GUGAGUCUCUAAGAAAAGAGGA | >hsa-miR-627 MIMAT0003296 |
| 1940 | CAUACAAUCUGACAUGUAUUU | >hsa-miR-4666a-3p MIMAT0019742 |

TABLE 1-continued

Human microRNA sequences

| NO | Sequence(5' to 3') | ID and accession |
|---|---|---|
| 1941 | CAGCCCGGAUCCCAGCCCACUU | >hsa-miR-3940-3p MIMAT0018356 |
| 1942 | GAUGCGCCGCCCACUGCCCCGCGC | >hsa-miR-4787-3p MIMAT0019957 |
| 1943 | UUCUGCUGCCGGCCAAGGC | >hsa-miR-6071 MIMAT0023696 |
| 1944 | CAUGGUUCUGUCAAGCACCGCG | >hsa-miR-218-2-3p MIMAT0004566 |
| 1945 | ACUGAUUAUCUUAACUCUCUGA | >hsa-miR-3920 MIMAT0018195 |
| 1946 | UAAAUUUCACCUUUCUGAGAAGA | >hsa-miR-513c-3p MIMAT0022728 |
| 1947 | ACCUUGGCUCUAGACUGCUUACU | >hsa-miR-212-5p MIMAT0022695 |
| 1948 | CUCUAGAGGGAAGCGCUUUCUG | >hsa-miR-519b-5p MIMAT0005454 |
| 1949 | AAAAACUGCAAUCACUUUUGC | >hsa-miR-548az-3p MIMAT0025457 |
| 1950 | CUGUAAUAUAAAUUUAAUUUAUU | >hsa-miR-2054 MIMAT0009979 |
| 1951 | UAUGGCACUGGUAGAAUUCACU | >hsa-miR-183-5p MIMAT0000261 |
| 1952 | AUUCUGCAUUUUUAGCAAGUUC | >hsa-miR-544a MIMAT0003164 |
| 1953 | CAGGCCAUAUUGUGCUGCCUCA | >hsa-miR-15a-3p MIMAT0004488 |
| 1954 | AUGUAGGGCUAAAAGCCAUGGG | >hsa-miR-135b-3p MIMAT0004698 |
| 1955 | UAGCCUUCAGAUCUUGGUGUUUU | >hsa-miR-3614-3p MIMAT0017993 |
| 1956 | AAAGGUAAUUGCAGUUUUUCCC | >hsa-miR-548ai MIMAT0018989 |
| 1957 | UUGGACAGAAAACACGCAGGAA | >hsa-miR-4520a-3p MIMAT0019057 |
| 1958 | AAUGCACCCGGGCAAGGAUUCU | >hsa-miR-501-3p MIMAT0004774 |
| 1959 | UGAGUGUGUGUGUGUGAGUGUGU | >hsa-miR-574-5p MIMAT0004795 |
| 1960 | CAGGAGGCAGUGGGCGAGCAGG | >hsa-miR-4695-5p MIMAT0019788 |
| 1961 | CAAUGUUUCCACAGUGCAUCAC | >hsa-miR-33a-3p MIMAT0004506 |
| 1962 | UGAGUGCCGGUGCCUGCCCUG | >hsa-miR-1909-5p MIMAT0007882 |
| 1963 | AAAACUGUAAUUACUUUUGUAC | >hsa-miR-548g-3p MIMAT0005912 |
| 1964 | CACAUAUGAAGUGAGCCAGCAC | >hsa-miR-5580-3p MIMAT0022274 |
| 1965 | UCAGGCAGUGUGGGUAUCAGAU | >hsa-miR-4692 MIMAT0019783 |
| 1966 | GAUUGAGACUAGUAGGGCUAGGC | >hsa-miR-4461 MIMAT0018983 |
| 1967 | UCAUAGCCCUGUACAAUGCUGCU | >hsa-miR-103b MIMAT0007402 |
| 1968 | AGAAGUAACUACGGUUUUUGCA | >hsa-miR-548ao-5p MIMAT0021029 |
| 1969 | GUGAGGGCAUGCAGGCCUGGAUGGGG | >hsa-miR-1226-5p MIMAT0005576 |
| 1970 | AAUGUGGAAGUGGUCUGAGGCAU | >hsa-miR-4657 MIMAT0019724 |
| 1971 | AGCAGGUGCGGGCGGCG | >hsa-miR-3665 MIMAT0018087 |
| 1972 | GAAUCGGAAAGGAGGCGCCG | >hsa-miR-3610 MIMAT0017987 |
| 1973 | UUACAGGCGUGAACCACCGCG | >hsa-miR-5095 MIMAT0020600 |
| 1974 | CGCGGGCGCUCCUGGCCGCCGCC | >hsa-miR-4767 MIMAT0019919 |
| 1975 | GAGGGUUGGGUGGAGGCUCUCC | >hsa-miR-296-3p MIMAT0004679 |
| 1976 | GAAGGCGCUUCCCUUUGGAGU | >hsa-miR-524-3p MIMAT0002850 |
| 1977 | AUAGGCACCAAAAAGCAACAA | >hsa-miR-4423-3p MIMAT0018936 |
| 1978 | ACAGCAGGCACAGACAGGCAGU | >hsa-miR-214-3p MIMAT0000271 |

TABLE 1-continued

Human microRNA sequences

| NO | Sequence(5' to 3') | ID and accession |
|---|---|---|
| 1979 | CUCUAGAGGGAAGCGCUUUCUG | >hsa-miR-519c-5p MIMAT0002831 |
| 1980 | UCCUCUUCUCCCUCCUCCCAG | >hsa-miR-877-3p MIMAT0004950 |
| 1981 | UAGGACACAUGGUCUACUUCU | >hsa-miR-1197 MIMAT0005955 |
| 1982 | UGAGGCGGGGGGCGAGC | >hsa-miR-6087 MIMAT0023712 |
| 1983 | CCUGUGCUCCCAGGGCCUCGC | >hsa-miR-5008-3p MIMAT0021040 |
| 1984 | GAGGGCGGGUGGAGGAGGA | >hsa-miR-3141 MIMAT0015010 |
| 1985 | UGUCUGCCCGCAUGCCUGCCUCU | >hsa-miR-346 MIMAT0000773 |
| 1986 | UUCACAGUGGCUAAGUUCUGC | >hsa-miR-27b-3p MIMAT0000419 |
| 1987 | UAGCUUAUCAGACUGAUGUUGA | >hsa-miR-21-5p MIMAT0000076 |
| 1988 | UUCACCACCUUCUCCACCCAGC | >hsa-miR-197-3p MIMAT0000227 |
| 1989 | AAAGUGCUGCGACAUUUGAGCGU | >hsa-miR-372 MIMAT0000724 |
| 1990 | AAACCUGUGUUGUUCAAGAGUC | >hsa-miR-649 MIMAT0003319 |
| 1991 | CCUCUGGGCCCUUCCUCCAG | >hsa-miR-326 MIMAT0000756 |
| 1992 | UAAAACUUUAAGUGUGCCUAGG | >hsa-miR-5582-3p MIMAT0022280 |
| 1993 | UGAGACCAGGACUGGAUGCACC | >hsa-miR-4786-5p MIMAT0019954 |
| 1994 | GAUUUCAGUGGAGUGAAGUUC | >hsa-miR-205-3p MIMAT0009197 |
| 1995 | UGCCUACUGAGCUGAAACACAG | >hsa-miR-24-2-5p MIMAT0004497 |
| 1996 | UGCAAAAGUAAUUGCAGUUUUUG | >hsa-miR-548g-5p MIMAT0022722 |
| 1997 | AUAUACAGGGGGAGACUCUUAU | >hsa-miR-1185-1-3p MIMAT0022838 |
| 1998 | UUCUCAAGGAGGUGUCGUUUAU | >hsa-miR-513c-5p MIMAT0005789 |
| 1999 | AUCAUGAUGGGCUCCUCGGUGU | >hsa-miR-433 MIMAT0001627 |
| 2000 | GGAGGUUGGGAAGGGCAGAG | >hsa-miR-6086 MIMAT0023711 |
| 2001 | AGUGGACCGAGGAAGGAAGGA | >hsa-miR-4800-5p MIMAT0019978 |
| 2002 | GUCCAGUUUUCCCAGGAAUCCCU | >hsa-miR-145-5p MIMAT0000437 |
| 2003 | GCAGUGGCUCUGAAAUGAACUC | >hsa-miR-5693 MIMAT0022486 |
| 2004 | UACACAAGAAAACCAAGGCUCA | >hsa-miR-4801 MIMAT0019980 |
| 2005 | ACCCUUGAGCCUGAUCCCUAGC | >hsa-miR-4780 MIMAT0019939 |
| 2006 | UGUAGAUACGAGCACCAGCCAC | >hsa-miR-3935 MIMAT0018350 |
| 2007 | GACACGGGCGACAGCUGCGGCCC | >hsa-miR-602 MIMAT0003270 |
| 2008 | AACAACAAAAUCACUAGUCUUCCA | >hsa-miR-3529-3p MIMAT0022741 |
| 2009 | AACUAGCUCUGUGGAUCCUGAC | >hsa-miR-4661-5p MIMAT0019729 |
| 2010 | AUCCCCAGAUACAAUGGACAA | >hsa-miR-2355-5p MIMAT0016895 |
| 2011 | UAAAACCCACAAUUAUGUUUGU | >hsa-miR-548as-3p MIMAT0022268 |
| 2012 | GGCCACUGAGUCAGCACCA | >hsa-miR-4252 MIMAT0016886 |
| 2013 | AGGAGCUAUCCACUCCAGGUGUCC | >hsa-miR-6500-5p MIMAT0025454 |
| 2014 | CCAGGAGAUCCAGAGAGAAU | >hsa-miR-4768-3p MIMAT0019921 |
| 2015 | ACGGUGCUGGAUGUGGCCUUU | >hsa-miR-1250 MIMAT0005902 |
| 2016 | AUACCCAUAGCUUAGCUCCCA | >hsa-miR-5591-3p MIMAT0022302 |

TABLE 1-continued

Human microRNA sequences

| NO | Sequence(5' to 3') | ID and accession |
|---|---|---|
| 2017 | UAGGCACACUUAAAGUUAUAGC | >hsa-miR-5582-5p MIMAT0022279 |
| 2018 | UAGCAGCACGUAAAUAUUGGCG | >hsa-miR-16-5p MIMAT0000069 |
| 2019 | GGGAAAAGGAAGGGGGAGGA | >hsa-miR-6124 MIMAT0024597 |
| 2020 | GAGCUUGGUCUGUAGCGGUU | >hsa-miR-4453 MIMAT0018975 |
| 2021 | CUGGGAGGUGUGAUAUUGUGGU | >hsa-miR-3689b-3p MIMAT0018181 |
| 2022 | UAGGAUUACAAGUGUCGGCCAC | >hsa-miR-3159 MIMAT0015033 |
| 2023 | UUGGGACAUACUUAUGCUAAA | >hsa-miR-1302 MIMAT0005890 |
| 2024 | GGCUACAACACAGGACCCGGGC | >hsa-miR-187-5p MIMAT0004561 |
| 2025 | UGAGCUGCUGUACCAAAAU | >hsa-miR-558 MIMAT0003222 |
| 2026 | AUUGACACCUCUGUGAGUGGA | >hsa-miR-514b-3p MIMAT0015088 |
| 2027 | AGGAAUGUUCCUUCUUUGCC | >hsa-miR-613 MIMAT0003281 |
| 2028 | UGGGUGGUCUGGAGAUUUGUGC | >hsa-miR-1293 MIMAT0005883 |
| 2029 | AGAGUCGGCGACGCCGCCAGC | >hsa-miR-4785 MIMAT0019949 |
| 2030 | UGGGGGAGCCAUGAGAUAAGAGCA | >hsa-miR-4723-5p MIMAT0019838 |
| 2031 | AUCAAAUAAGGACUAGUCUGCA | >hsa-miR-3671 MIMAT0018094 |
| 2032 | CGCCCCUCCUGCCCCCACAG | >hsa-miR-4749-3p MIMAT0019886 |
| 2033 | UGAGCCCCUGUGCCGCCCCCAG | >hsa-miR-1225-3p MIMAT0005573 |
| 2034 | GCUGAUGAUGAUGGUGCUGAAG | >hsa-miR-4502 MIMAT0019038 |
| 2035 | GGGAGUCUACAGCAGGG | >hsa-miR-4294 MIMAT0016849 |
| 2036 | CACUCAGCCUUGAGGGCACUUUC | >hsa-miR-512-5p MIMAT0002822 |
| 2037 | GACACAUGACCAUAAAUGCUAA | >hsa-miR-4643 MIMAT0019703 |
| 2038 | UAAGUGCUUCCAUGUUUGAGUGU | >hsa-miR-302d-3p MIMAT0000718 |
| 2039 | UGCACGGCACUGGGGACACGU | >hsa-miR-3177-3p MIMAT0015054 |
| 2040 | CCUCCUGCCCUCCUUGCUGU | >hsa-miR-1976 MIMAT0009451 |
| 2041 | CAACGGAAUCCCAAAAGCAGCUG | >hsa-miR-191-5p MIMAT0000440 |
| 2042 | CAGCCCUCCUCCCGCACCCAAA | >hsa-miR-4687-5p MIMAT0019774 |

In one embodiment, the oligomer does not comprise a lower affinity region that can bind to a RNA sequence that is complementary to position 2-7 of SEQ ID NO:1051.

In yet another embodiment, the oligomer is not complementary to any of SEQ ID NOs: 1-2041 (over its full length).

Particular preferred oligomers of the invention have a length of 10-20 monomers, and consists of
  a higher affinity region that comprise at least 25% BNA monomers
  a lower affinity region of 6-10 contiguous monomers that comprise less than 25% BNA monomers and wherein the two monomers at the 5' end of the lower affinity region and the two monomers at the 3'end of the lower affinity region are non-BNA monomers
  and wherein the oligomer does not comprise a region of 5 contiguous DNA monomers In this embodiment, different affinities of the higher affinity region and the lower affinity region (as defined above) is ensured by a higher density of BNA monomers in the higher affinity region as compared to the density of BNA monomers in the lower affinity region.

It is preferred that the higher affinity region consist of at least 4 monomers, more preferably, at least 5, 6, 7 or 8 monomers.

Preferably, the density of BNA monomers in the higher affinity region is at least 2-fold higher than the density of BNA monomers in the lower affinity region. Even more preferably, the density it at least 3-fold higher such as 4 or 5 fold higher.

In a preferred embodiment, the lower affinity region does not comprise any BNA monomers at all.

The higher affinity region preferably comprise at least 33% (1 BNA monomer/3 monomers in the higher affinity region), 50% (1 BNA/2 monomers), 67% (2 BNA/3 monomers), (3 BNA/4 monomers) 75% or 100% BNA monomers.

Preferably, at least one internucleotide linkage is a phosphorothioate linkage. In another embodiment, all internucleotide linkages are phosphorothioate linkages.

In a related embodiment, the oligomer the lower affinity region consists of 8-10 contiguous monomers and the remaining monomers of the oligomer are BNA monomers.

Typically, both the 5'end of the oligomer and the 3'end of the oligomer is a BNA monomer.

The oligomer may even be of 12-18 monomers or 13-17 monomers.

Preferably, the lower affinity region can base pair to the seed sequence of a microRNA or can base pair to the RNA complement of the seed sequence of a microRNA. Human microRNAs are preferred.

EXAMPLES

Example 1

In the present example, the affinity of various oligomers toward an intended target, as well as to an off-target RNA was measured. Finally, the affinity of the oligomers toward a target RNA consisting of the consensus sequence was measured.

The employed target RNA first was:

(135-Hcvtarg)
5' GAUGGGGGCGACACUCCACCAUGAAU wherein a consensus sequence is underlined.

The sequence of the oligomers complementary to this target RNA:

CUGUGAGGUGGUAC-5'

And when bound to each other:

Target:        5'GAUGGGGGCGACACUCCACCAUGAAU
                         ||||||||||||||
HCV Oligomer             CUGUGAGGUGGUAC5'

First, the following oligomers were employed, wherein lower affinity regions are underlined:
(123-HCVtm, uniformly modified)
lClAmUmGlGmUlGlGmAlGmUmGlTlC
(124-HCVtm, lower affinity region complementary to consensus sequence)
lClAlTlGlGlTmGmGmAmGmUmGlUlC
(125-HCV, tm lower affinity region complementary to consensus sequence)
lClAlTlGlGmUmGmGmAmGmUmGmUlC
(126-HCVtm, lower affinity region complementary to consensus sequence)
lClAlTlGlGmUmGmGuAmGmUmGmUlC
(127-HCVtm, lower affinity region complementary to consensus sequence)
lClAmUmGlGmUmGmGmAmGmUmGlTlC
(128-HCVtm, higher affinity region complementary to consensus sequence)
mCmAmUmGmGlTlGlGlAlGlTlGlTmC
m indicates 2'O-methyl RNA
l indicate LNA (BNA)
u indicate unlocked Nucleic Acid (UNA)

The melting temperatures were measured in medium salt concentration, i.e. 100 mM NaCl, 0.1 mM EDTA, 10 mM NaH2PO4, 5 mM Na2HPO4, pH 7.0), using 1.0 µM concentrations of both oligomer and complementary RNA and in low salt concentration, i.e. in 10 mM NaCl instead of 100 mM NaCl.

TABLE 2

| Oligomer | Tm, 100 mM NaCl | Tm, 10 mM NaCl |
|---|---|---|
| 123-HCVtm | >90 | 86 |
| 124-HCVtm | >90 | 84 |
| 125-HCVtm | >90 | 80 |
| 126-HCVtm | 79 | 65 |
| 127-HCVtm | >90 | 79 |
| 128-HCVtm | >85 | 83 |

For the measurements in high salt, only 126HCVtm sticks out with a lower tm value, which is in line with the presence of a UNA monomer that decreases affinity.

For the measurements in low salt, the tm values correlate well with the content of LNA monomer and again it is seen that one UNA monomer decreases affinity significantly.

Next, the affinity of another oligomer sequence (Aldo A) toward the same target RNA was measured. This other oligomer is complementary to the same consensus sequence of the target RNA, but differs in the remaining part of the sequence:

Target:        5'GAUGGGGGCGACACUCCACCAUGAAU
                         |1||||||||
Aldo Oligomer:           GUUGUGAGGUCCGG 1 indicate a potential G:U base pair.

The oligomers used in these measurements were:
Lower Affinity Regions are Underlined
(129-Aldo, uniformly modified)
lGlGmClCmUlGmGlAmGmUlGmUlTlG
(130-Aldotm, lower affinity region complementary to consensus sequence)
lGlGlClClTmGmGmAmGmUmGlTlTlG
(131-Aldotm, lower affinity region complementary to consensus sequence)
lGlGlClCmUmGmGmAmGmUmGmUlTlG
(133-Aldotm, higher affinity region complementary to consensus sequence)
mGmGmCmClTlGlGlAlGlTlGlTmUmG

TABLE 3

| Oligomer | Tm, 100 mM NaCl |
|---|---|
| 129-Aldotm | 77 |
| 130-Aldotm | 70 |
| 131-Aldotm | 66 |
| 133-Aldotm | 83 |

In this set of measurements, the HCV target may be seen as an off-target that shares the consensus target with the intended target of the oligomer. Again the melting temperature correlates overall with the content of LNA. Moreover, it is seen that affinity increases when the content of LNA increases in the complementary region. When the LNA density is higher in the non-complementary region, the melting temperature decreases, see oligomer 131.

Next, the affinity of the oligomers toward a complementary 8 nucleotide consensus RNA was measured. The affinity of the oligomers toward this 8 nucleotide consensus RNA may be seen as a measure of the affinity of the oligomer toward to off-targets comprising the consensus sequence, but which are not complementary to the oligomer in the regions adjacent to the consensus sequence.

The consensus RNA was:

```
5'ACACUCCA
```

TABLE 4

| Oligomer | Tm, 100 mM NaCl |
|---|---|
| 123-HCVtm | 77 |
| 124-HCVtm | 59 |
| 125-HCVtm | 48 |
| 126-HCVtm | No transition |
| 127-HCVtm | 60 |
| 128-HCVtm | 82 |
| 129-Aldotm | 73 |
| 130-Aldotm | 66 |

TABLE 4-continued

| Oligomer | Tm, 100 mM NaCl |
|---|---|
| 131-Aldotm | 55 |
| 132-Aldotm | 84 |

As seen, less off-target binding (more specific oligomers) can be designed by reducing the LNA content in the complementary region.

If the same design principles are used to design antisense oligomers toward other target sequences comprising a consensus sequence, generally improved specificity can be achieved.

Thus, the teachings of the present invention, including the findings in the above experiments, should be generally applicable and not limited to certain sequences/targets.

The invention claimed is:

1. An oligomer of 10-20 monomers that binds RNA that consists of
   a higher affinity region of at least 4 monomers that comprise at least 25% BNA monomers;
   a lower affinity region of 6-10 contiguous monomers that comprise no BNA monomers and wherein the oligomer does not comprise a region of 5 contiguous DNA monomers,
   wherein the oligomer comprises at least 30% BNA monomers and wherein the lower affinity region can base pair to the seed sequence of a microRNA or can base pair to the RNA complement of the seed sequence of a microRNA.

2. The oligomer of claim 1, wherein the higher affinity region comprise at least 50% BNA monomers.

3. The oligomer of claim 1, wherein at least one internucleotide linkage is a phosphorothioate linkage.

4. The oligomer of claim 1, wherein the lower affinity region consists of 8-10 contiguous monomers and wherein the remaining monomers of the oligomer are BNA monomers.

5. The oligomer of claim 1, wherein both the 5'end of the oligomer and the 3'end of the oligomer is a BNA monomer.

6. The oligomer of claim 1, consisting of 12-18 monomers.

7. The microRNA of claim 1, wherein the microRNA is a human microRNA.

* * * * *